US009751851B2

(12) United States Patent
Bassler et al.

(10) Patent No.: US 9,751,851 B2
(45) Date of Patent: Sep. 5, 2017

(54) MOLECULES AND COMPOSITIONS THAT INHIBIT GRAM NEGATIVE BACTERIA AND THEIR USES

(71) Applicants: THE TRUSTEES OF PRINCETON UNIVERSITY, Princeton, NJ (US); Bonnie L. Bassler, Princeton, NJ (US); Martin F. Semmelhack, Princeton, NJ (US); Knut Drescher, Princeton, NJ (US); Albert Siryaporn, Princeton Junction, NJ (US); Laura C. Miller, Princeton, NJ (US); Colleen T. O'Loughlin, San Francisco, CA (US)

(72) Inventors: Bonnie L. Bassler, Princeton, NJ (US); Martin F. Semmelhack, Princeton, NJ (US); Knut Drescher, Princeton, NJ (US); Albert Siryaporn, Princeton Junction, NJ (US); Laura C. Conrad-Miller, Princeton, NJ (US); Colleen T. O'Loughlin, San Francisco, CA (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 15/023,279

(22) PCT Filed: Sep. 19, 2014

(86) PCT No.: PCT/US2014/056497
§ 371 (c)(1),
(2) Date: Mar. 18, 2016

(87) PCT Pub. No.: WO2015/042363
PCT Pub. Date: Mar. 26, 2015

(65) Prior Publication Data
US 2016/0368892 A1 Dec. 22, 2016

Related U.S. Application Data

(60) Provisional application No. 61/880,610, filed on Sep. 20, 2013, provisional application No. 61/881,204, filed on Sep. 23, 2013.

(51) Int. Cl.
*C07D 333/32* (2006.01)
*A61K 45/06* (2006.01)
*C07D 213/75* (2006.01)
*C07D 239/42* (2006.01)
*C07D 239/47* (2006.01)
*C07D 307/33* (2006.01)

(52) U.S. Cl.
CPC .......... *C07D 333/32* (2013.01); *A61K 45/06* (2013.01); *C07D 213/75* (2013.01); *C07D 239/42* (2013.01); *C07D 239/47* (2013.01); *C07D 307/33* (2013.01)

(58) Field of Classification Search
CPC .................................................. C07D 333/32
USPC .......................................................... 514/352
See application file for complete search history.

(56) References Cited

U.S. PATENT DOCUMENTS

| 8,247,443 B2 * | 8/2012 | Bassler .......... A01N 43/08 514/445 |
| 2009/0163545 A1 * | 6/2009 | Goldfarb .......... A61K 31/122 514/312 |
| 2011/0046195 A1 | 2/2011 | Blackwell et al. |
| 2012/0135925 A1 | 5/2012 | Meijler et al. |

FOREIGN PATENT DOCUMENTS

WO 2013/143597 * 10/2013

OTHER PUBLICATIONS

International Search Report of PCT/US2014/056497, Dec. 4, 2014.
Written Opinion of the International Searching Authority (PCT/US20141056497), Dec. 4, 2014.
Ng W-L, Bassler, Bonnie L. (2009) Bacterial Quorum-Sensing Network Architectures. Annual Review of Genetics 43(1 ): 197-222.
Rutherford ST, Bassler, Bonnie L. (2012) Bacterial Quorum Sensing: Its Role in Virulence and Possibilities for Its Control. Cold Spring Harbor Perspectives in Medicine 2(11 ).
Zhu J, Winans, Stephen C. (1999) Autoinducer binding by the quorum-sensing regulator TraR increases affinity for target promoters in vitro and decreases TraR turnover rates in whole cells. Proceedings of the National Academy of Sciences 96(9):4832-4837.
Zhu J, Winans, Stephen C. (2001) The quorum-sensing transcriptional regulator TraR requires its cognate signaling ligand for protein folding, protease resistance, and dimerization. Proceedings of the National Academy of Sciences 98( 4 ): 1507-1512.
Sadikot RT, Blackwell, Timothy S., Christman, John W., Prince, Alice S. (2005) Pathogen-Host Interactions in Pseudomonas aeruginosa Pneumonia. American Journal of Respiratory and Critical Care Medicine 171 ( 11 ): 1209-1223.
Pesci EC, Pearson, J P, Seed, P C, Iglewski, B H (1997) Regulation of las and rhl quorum sensing in *Pseudomonas aeruginosa*. Journal of Bacteriology 179(1 0):3127-3132.
Schuster M, Lostroh, C. Phoebe, Ogi, Tomoo, Greenberg, E. P. (2003) Identification, Timing, and Signal Specificity of *Pseudomonas aeruginosa* Duorum-Controlled Genes: a Transcriptome Analysis. Journal of Bacteriology 185(7):2066-2079.

(Continued)

*Primary Examiner* — Taofiq A Solola
(74) *Attorney, Agent, or Firm* — Meagher Emanuel Laks Goldberg & Liao, LLP

(57) ABSTRACT

Antivirulence strategies to combat *Pseudomonas aeruginosa*, are described. One strategy encompasses synthesis of a series of compounds that inhibit the production of pyocyanin, a redox-active virulence factor produced by this pathogen. A related strategy encompasses synthesis of compounds that inhibit the two *P. aeruginosa* quorum-sensing receptors, LasR and RhlR, inhibit production of pyocyanin, and inhibit biofilm formation.

25 Claims, 17 Drawing Sheets

(56) References Cited

OTHER PUBLICATIONS

Tan M-W, Rahme, Laurence G., Sternberg, Jeffrey A , Tompkins, Ronald G., Ausubel, Frederick M. (1999) Pseudomonas aeruginosa killing of Caenorhabditis elegans used to identify P. aeruginosa virulence factors. Proceedings of the National Academy of Sciences 96(5):2408-2413.
Gambello MJ, Iglewski, B H (1991) Cloning and characterization of the Pseudomonas aeruginosa lasR gene, a transcriptional activator of elastase expression. Journal of Bacteriology 173(9):3000-3009.
Pearson JP, et.al. (1994) Structure of the autoinducer required for expression of Pseudomonas aeruginosa virulence genes. Proceedings of the National Academy of Sciences 91(1 ):197-201.
Wagner VE, Bushnell, Daniel, Passador, Luciano, Brooks, Andrew 1., Iglewski, Barbara H. (2003) Microarray Analysis of Pseudomonas aeruginosa QuorumSensing Regulons: Effects of Growth Phase and Environment. Journal of Bacteriology 185(7):2080-2095.
Gilbert KB, Kim, Tae Hoon, Gupta, Rashmi, Greenberg, E. Peter, Schuster, Martin (2009) Global position analysis of the Pseudomonas aeruginosa quorumsensing transcription factor LasR. Molecular Microbiology 73(6): 1072-1085.
Pearson JP, Passador, L., Iglewski, B. H., Greenberg, E P. (1995) A Second Nacylhomoserine Lactone Signal Produced by Pseudomonas aeruginosa. Proceedings of the National Academy of Sciences 92(5):1490-1494.
Ochsner UA, Fiechter, A, Reiser, J (1994) Isolation, characterization, and expression in Escherichia coli of the Pseudomonas aeruginosa rhIAB genes encoding a rhamnosyltransferase involved in rhamnolipid biosurfactant synthesis. Journal of Biological Chemistry 269(31 ): 19787-19795.
Latifi A, Winson, M. K., Foglino, M., Bycroft, B. W., Stewart, G. S. A B., Lazdunski, A , et. al (1995) Multiple Homologues of LuxR and LuxI Control Expression of Virulence Determinants and Secondary Metabolites through Quorum Sensing in Pseudomonas aeruginosa PA01. Molecular Microbiology 17(2):333-343.
Brint JM, Ohman, D E (1995) Synthesis of multiple exoproducts in Pseudomonas aeruginosa is under the control of RhIR-RhII, another set of regulators in strain PA01 with homology to the autoinducer-responsive LuxR-LuxI family. Journal of Bacteriology 177(24):7155-7163.
Parsek MR, Greenberg, E Peter (2000) Acyl-homoserine lactone quorum sensing in Gram-negative bacteria: A signaling mechanism involved in associations with higher organisms. Proceedings of the National Academy of Sciences 97 ( 16 ):8789-8793.
Müh U, Schuster, M., Heim, R., Singh, A., Olson, E. R., Greenberg, E. P. (2006) Novel Pseudomonas aeruginosa Quorum-Sensing Inhibitors Identified in an Ultra-High-Throughput Screen. Antimicrobial Agents and Chemotherapy 50( 11 ):3674-3679.
Geske Go, O'Neill, Jennifer C., Miller, David M., Mattmann, Margrith E., Blackwell, Helen E. (2007) Vlodulation of Bacterial Quorum Sensing with Synthetic Ligands: Systematic Evaluation of N-Acylated Homoserine Lactones in Multiple Species and New Insights into Their Mechanisms of Action. Journal of the American Chemical Society 129( 44 ): 13613-13625.
Amara N, et.al. (2009) Covalent Inhibition of Bacterial Quorum Sensing. Journal of the American Chemical Society 131(30):10610-10619.

Swem LR, Swem, D. L, O'Loughlin, C. T., Gatmaitan, R., Zhao, B., Ulrich, S. M., et. al. (2009) A Quorum-Sensing Antagonist Targets Both Membrane-Bound and Cytoplasmic Receptors and Controls Bacterial Pathogenicity. Molecular Cell 35(2):143-153.
Lau GW, Hassett, Daniel J., Ran, Huimin, Kong, Fansheng (2004) The role of pyocyanin in Pseudomonas aeruginosa infection. Trends in Molecular Medicine 10(12):599-606.
Mahajan-Miklos S, Tan, Man-Wah, Rahme, Laurence G., Ausubel, Frederick M. (1999) Molecular Mechanisms of Bacterial Virulence Elucidated Using a Pseudomonas aeruginosa- Caenorhabditis elegans Pathogenesis Model. sell 96(1 ):47-56.
Dietrich LEP, Price-Whelan, Alexa, Petersen, Ashley, Whiteley, Marvin, Newman, Dianne K. (2006) The phenazine pyocyanin is a terminal signalling factor in the quorum sensing network of Pseudomonas aeruginosa. Molecular Microbiology 61 (5 ): 1308-1321.
Cezairliyan B. VN, Grenfell-Lee D., Yuen G.J., Saghatelian A, Ausubel, F.M. (2013) Identification of Pseudomonas aeruginosa Phenazines that Kill Caenorhabditis elegans. PLoS Pathog 9(1 ).
Drescher K, Shen, Y., Bassler, B. L., Stone, H. A. (2013) Biofilm Streamers Cause Catastrophic Disruption of Flow with Consequences for Environmental and Medical Systems. Proceedings of the National Academy of Sciences 110( 11 ):4345-4350.
Kalia VC (2013) Quorum sensing inhibitors: An overview. Biotechnology Advances 31 (2):224-245.
Limmer S, Haller, S., Drenkard, E., Lee, J., Yu, S., Kooks, C., et. al. (2011) Pseudomonas aeruginosa RhIR is Required to Neutralize the Cellular Immune Response in a Drosophila melanogaster Oral Infection Model. Proceedings of the National Academy of Sciences 108(42): 17378-17383.
Lazenby JJ GP, Kyd J, Whitchurch CB, Cooley MA (2013) A Quadruple Knockout of lasIR and rhiiR of Pseudomonas aeruginosa PA01 That Retains Wild-Type Twitching Motility Has Equivalent Infectivity and Persistence to PA01 in a Mouse Model of Lung Infection. PLoS ONE 8(4): e60973.
Liberati NT, Urbach, Jonathan M., Miyata, Sachiko, Lee, Daniel G., Drenkard, Eliana, Wu, Gang, et.al. (2006) An ordered, nonredundant library of Pseudomonas aeruginosa strain PA14 transposon insertion mutants. Proceedings of the National Academy of Sciences of the United States of America 103(8 ):2833-2838.
Dunn AK, Millikan OS, Adin OM, Bose JL, & Stabb EV (2006) New rfp- and pES213-Derived Tools for Analyzing Symbiotic Vibrio fischeri Reveal Patterns of Infection and lux Expression In Situ. Applied and Environmental Microbiology 72(1 ):802-810.
Shen Y, Siryaporn, Albert, Lecuyer, Sigolene, Gitai, Zemer, Stone, Howard A (2012) Flow Directs Surface-Attached Bacteria to Twitch Upstream. Biophysical Journal103(1 ):146-151.
Lesic B, Rahme, Laurence (2008) Use of the lambda Red recombinase system to rapidly generate mutants in Pseudomonas aeruginosa. BMC Molecular Biology 9(1 ):20.
Hoang TT, Karkhoff-Schweizer, RoxAnn R., Kutchma, Alecksandr J., Schweizer, Herbert P. (1998) A broad-host-range Flp-FRT recombination system for sitespecific excision of chromosomally-located DNA sequences: application for solation of unmarked Pseudomonas aeruginosa mutants. Gene 212(1 ):77-86.
Morkunas B, Galloway, Warren R. J. D., Wright, Megan, Ibbeson, Brett M., Hodgkinson, James T., O'Connell, Kieron M. G., et. al. (2012) Inhibition of the production of the Pseudomonas aeruginosa virulence factor pyocyanin in wildtype cells by quorum sensing autoinducer-mimics. Organic & Biomolecular Chemistry 10(42):8452-8464.

* cited by examiner

Head Group Library

4

5

Hybrid Library

6

14
63% efficacy
$IC_{50}$ = 0.16 µM 15
70% efficacy
$IC_{50}$ = 4.4 µM 16
99% efficacy
$IC_{50}$ = 2.7 µM 1
84% efficacy 17
103% efficacy
$IC_{50}$ = 6.3 µM 18
68% efficacy

MOLECULES AND COMPOSITIONS THAT INHIBIT GRAM NEGATIVE BACTERIA AND THEIR USES

CROSS-REFERENCE TO RELATED APPLICATIONS

This application claims priority to U.S. Provisional Application No. 61/880,610, filed Sep. 20, 2013 and U.S. Provisional Application No. 61/881,204, filed Sep. 23, 2013, all of which are herein incorporated by reference in their entirety.

STATEMENT REGARDING FEDERALLY SPONSORED RESEARCH OR DEVELOPMENT

This invention was made with government support under Grant No. GM065859 awarded by the National Institutes of Health, Grant No. MCB-0343821 awarded by the National Science Foundation, and Grant No. FA9550-12-1-0368 awarded by the Air Force Office of Scientific Research. The government has certain rights in the invention.

BACKGROUND

In a process referred to as quorum sensing, bacteria communicate using chemical signal molecules called autoinducers. By monitoring increases and decreases in autoinducer concentration, quorum-sensing bacteria track changes in cell-population density and synchronously switch into and out of group behaviors. Quorum sensing allows bacteria to collectively carry out tasks that would be unsuccessful if carried out by an individual bacterium acting alone.

Both Gram-positive and Gram-negative infectious bacteria, which include human, animal, plant, and marine pathogens, use quorum sensing strategies to control virulence. Typically, bacterial infections are treated with bactericidal or bacteriostatic molecules that impede four major processes: DNA replication, transcription, translation or tetrahydrofolic acid synthesis. Existing methods for treating bacterial infection unfortunately exacerbate the growing antibiotic resistance problem because they inherently select for growth of bacteria that in turn can resist the drug. What is needed are new treatments that avoid selecting for drug resistant bacteria.

Quorum sensing also controls biofilm formation. Biofilms are communities of bacterial cells adhered to surfaces and are highly problematic, for example in industrial processes (e.g., clogging of cooling towers in manufacturing plants) and in hospital or other clinical settings (e.g., catheter and implant infections). Initial studies with *Staphylococcus aureus* and *Staphylococcus epidermidis* indicated that manipulation of a form of quorum sensing that is peptide-mediated would not have successful results. Most notably, disruption of the peptide quorum-sensing circuit in *S. epidermidis* by deleting necessary quorum sensing genes led unexpectedly to increased biofilm formation on implanted medical devices. Therefore what is needed are new treatments for bacterial infection that can more subtly manipulate bacterial behaviors that promote health problems.

The bacterium *Pseudomonas aeruginosa* is the major pathogen associated with cystic fibrosis lung infection, keratitis eye infection, and third-degree burn-associated skin infections. *P. aeruginosa* has a complex signaling pathway that governs quorum sensing and virulence (FIG. 1B). The signaling pathway includes LasI, a synthase enzyme that makes the native acyl-homoserine lactone (AHL) signal, 3OC12-HSL. The native signal is detected by the transcriptional regulator LasR, forming a LasR:3OC12-HSL complex. The LasR:3OC12-HSL complex affects gene transcription, turning on virulence factors, the Rhl system and additional quorum-sensing circuits.

Another synthase, RhlI, produces another AHL (C4-HSL), which is detected by the transcriptional regulator RhlR. The RhlR:C4-HSL complex also regulates virulence genes and other components of the signaling pathway. Virulence production is impacted by multiple other factors, including the transcription factor QscR and the PQS system that produces and detects quinolone signals.

This tandem regulatory arrangement allows LasI/R to control the first wave of quorum-sensing-controlled gene expression and RhlI/R to control the second. Because LasR activates expression of rhlR, deletion of lasR reduces expression of both LasR- and RhlR-regulated target genes.

Additionally one key factor in pathogenicity of a bacterial infection is the production of virulence factor produced at high cell density, such as pyocyanin. This small molecule is redox active and is important for maintaining the redox balance in *P. aeruginosa*, particularly under low oxygen or anaerobic conditions. RhlR is a key transcriptional regulator controlling the up-regulation of the pyocyanin biosynthetic pathway, which in turn is induced by the LasR:3OC12-HSL complex (FIG. 1B). Thus, new compounds and methods of treating bacterial infection and/or contamination are needed.

SUMMARY OF THE INVENTION

The inventive concept is for anti-infective and prophylactic therapies to protect humans against gram negative bacteria, such as, for example, *P. aeruginosa*. This includes methods to block gram negative bacteria virulence and biofilm formation.

In one aspect, the invention is a compound having the formula:

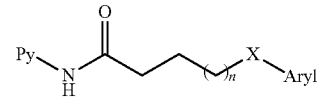

wherein
Py is a pyridine ring attached in the 2, 3, or 4 position and substituted with one or more additional substituents selected from the group consisting of alkyl, trifluoromethyl, methoxy, F, Cl and Br;
Aryl is a benzene ring with one or more additional substituents selected from the group consisting of methyl, trifluoromethyl, cyano, nitro, F, Cl, Br and methoxy;
X is O, NH, S or —$CH_2$—; and
n is 0 to 4 —$CH_2$— units.

In one embodiment of this aspect, the compound has the formula:

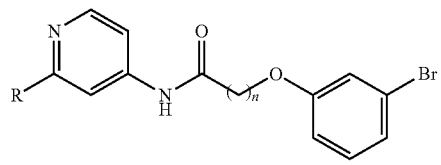

wherein
R is a substituent selected from the group consisting of alkyl, trifluoromethyl, methoxy, and Cl; and
n is 4 to 5 —$CH_2$— units.

In yet another embodiment, the compound has the formula:

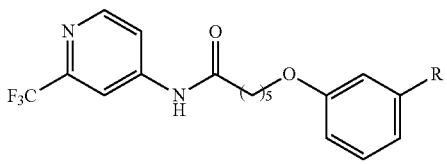

wherein

R is a substituent selected from the group consisting of I, F, and Cl.

In another aspect, the invention is a compound having the formula:

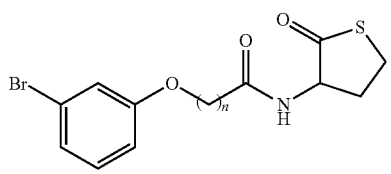

where n=1, 2, 4 or 5
and a compound having the formula:

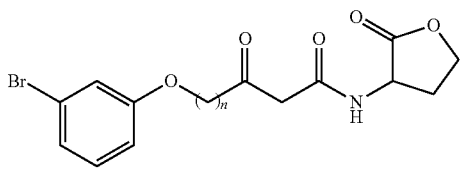

where n=1 or 3.

In the aspect of the invention which is inventive compounds, the compound is not meta-bromothiolactone (mBTL); is not chlorolactone (CL); and is not chlorothiolactone (CTL).

Another embodiment is a composition comprising the inventive compound.

Another aspect of the invention is the use of the compounds or the composition of the invention to inhibit gram negative bacteria. In the present invention, preferred examples of gram negative bacteria that can be inhibited by molecules of the invention, include, but are not limited to Burkholderia cepaci, C. violaceum, V harveyi, Pseudomonas, including, but not limited to Pseudomonas aeruginosa, Neisseria gonorrhoeae, Neisseria meningitidis, Bordetell pertussis, Haemophilus influenzae, Legionella pneuinophila, Brucella, Francisella, Xanthomonas, Agrobacterium, enteric bacteria, such as Escherichia coli and its relatives, the members of the family Enterobacteriaceae, such as Salmonella and Shigella, Proteus, and Yersinia pestis.

It is contemplated that the use of the compounds or the composition of the invention inhibits quorum sensing and production of a biofilm or virulence factor, preferably pyocyanin. It is also contemplated that the use of the compounds of the invention inhibit LasR/RhlR receptor signaling.

Another aspect of the invention is the use wherein an effective amount of the compounds or composition is administered to a subject. Preferably the subject is a cow, pig, horse, chicken, cat, or dog, and even more preferably, a human. It is contemplated that the subject may have an infection, which may be, for example, opportunistic, antibiotic resistant, or have respiratory illness, dental plaque, gingivitis, chronic sinusitis, endocarditis, burn, wound, or may be immunosuppressed, immunocompromised, or may have bacterial invasion of a device in contact with the subject such as coating of contact lenses, medical device or other implanted device. The medical device may be a catheter, stent, joint prosthesis, prosthetic cardiac valve, ventilator or intrauterine device. The infection may be of the pulmonary tract and may be pneumonia. The respiratory illness may be cystic fibrosis and it may be in conjunction with pneumonia.

It is contemplated that the administration is therapeutic or prophylactic. Some of the preferable prophylactic uses are when the subject is undergoing surgery, a dental procedure or implantation of a medical device. It is also contemplated that the administration may be a co-administration with one or more drugs, preferably antibiotics. It is contemplated that administration may be topical, intravenous or intranasal.

Another aspect the invention is use of the compound or composition on or within a medical instrument or device, a filtration device, a tubing, a pipe, a pipeline, a sewage system, water tower cooling system, or a work surface. Preferably the medical device is a joint prosthesis, a prosthetic cardiac valve, a ventilator, a stent, or an intrauterine device.

The use of the compounds is also contemplated as a method comprising contacting the bacteria with the compound or composition of the invention. Preferably, the method comprises administering the inventive compound or composition to a subject. Alternatively the compound or composition is applied to surfaces, tubes, pipes or devices in a fluid, aerosol, gel or cream formulation.

DETAILED DESCRIPTION OF THE INVENTION

Figure 1:
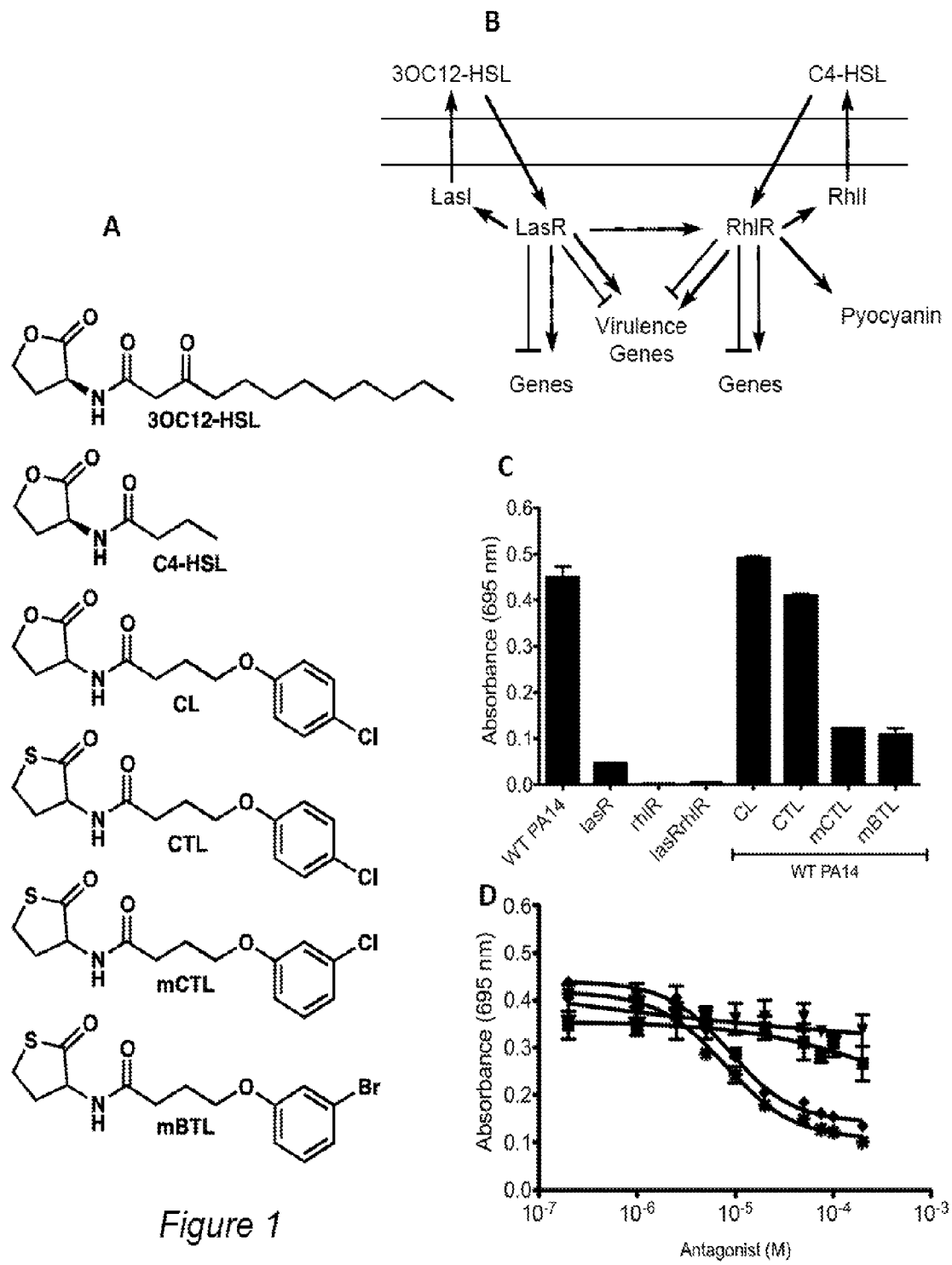
FIG. 1. Small molecule control of pyocyanin production in P. aeruginosa PA14. A. Structures of autoinducers and inhibitors. B. Simplified schematic of the major components of the P. aeruginosa quorum-sensing circuit. C. Pyocyanin production measured at $OD_{600}$=695 nm in cell-free culture fluids prepared from WT P. aeruginosa PA14, lasR and rhlR single and double mutants, and in WT treated with 100 µM CL, CTL, mCTL, and mBTL. Error bars represent S.D. for two replicates. D. Pyocyanin inhibition titrations performed with WT P. aeruginosa PA14 in triplicate with CL (inverted triangles), CTL (squares), mCTL (diamonds) and mBTL, (asterisks). Error bars represent S.D. of three replicates.

One aspect of the invention is directed to a class of molecules that have the ability to inhibit gram negative bacteria, whether by inhibiting quorum sensing, pathogenicity, virulence factor, and/or pyrocyanin production, and/or biofilm production, For example, disabling quorum-sensing circuits with small molecules is one strategy to prevent bacterial pathogenicity. Synthetic molecules were prepared and assayed for inhibition of the two P. aeruginosa quorum-sensing receptors, LasR and RhlR. The most effective compound, the small molecule meta-bromothiolactone (mBTL) inhibits both the production of the virulence factor pyocyanin and biofilm formation in our assays. In tissue culture and in an animal model, mBTL protects cells from P. aeruginosa. mBTL partially inhibited both the LasR and RhlR receptors in vivo and in vitro. In the tested assays, more potent antagonists did not exhibit superior function in impeding virulence which may be because mBTL displays a more appropriate tuning of the two receptors. In the present invention, one strategy described herein for blocking pathogenesis in vivo comprises developing inhibitors that appropriately tune the two P. aeruginosa receptors, as well as the corresponding receptors found in other gram negative bacteria. These findings are the basis for the inventive concept of anti-infective and prophylactic therapies to protect humans against gram negative bacteria, such as, for example, Burkholderia cepaci, C. violaceum, harveyi, Pseudomonas, including, but not limited to Pseudomonas

*aeruginosa, Neisseria gonorrhoeae, Neisseria meningitidis, Bordetella pertussis, Haemophilus influenzae, Legionella pneumophila, Brucella, Francisella, Xanthomonas, Agrobacterium*, enteric bacteria, such as *Escherichia coli* and its relatives, the members of the family Enterobacteriaceae, such as *Salmonella* and *Shigella, Proteus*, and *Yersinia pestis*.

Moreover, the gram negative bacteria, such as the pathogen *P. aeroginosa* owes its virulence to virulence factors, such as, for example, pyocyanin that it produces under the control of a quorum-sensing system. Compounds of the invention have been designed that attenuate the virulence of gram negative bacteria (for example, *P. aeroginosa*, working by means of a regulator of the quorum-sensing system.

The native QS autoinducers in *P. aeroginosa* are 3OC12-HSL and C4-HSL which form complexes with the LuxR-type proteins LasR and RhlR, respectively. With the lactone moiety as a starting point for the design of substitute compounds that bind these proteins, a library of candidates was synthesized and inhibitory compounds were identified.

In the present tested assays, the most potent of these compounds as an inhibitor of pyocyanin production is meta-bromo thiolactone (mBTL) (FIG. 1a). mBTL was used as a lead compound to design other inhibitors, either retaining the thiolactone moiety or substituting a lactone moiety. Of the thiolactone derivatives of mBTL, C5-mBTL was the most effective inhibitor of pyocyanin production in the assays tested. Of the lactone derivatives of mBTL, C4-mBL was the most effective inhibitor of pyocyanin production in the assays tested. The S enantiomer of mBTL is active as an inhibitor of pyocyanin production (IC50=4 µM) and the R enantiomer has residual activity (IC50=100 µM).

mBTL was found to be an effective as an attenuator of virulence in P. aeroginosa in the assays tested. mBTL or derivatives of mBTL find use as compounds as described herein. They can act through the quorum sensing system by binding to a QS LuxR-type protein.

In a broader context, what is contemplated is the use of the compounds of the invention to attenuate bacterial virulence. In one embodiment, the compound or compounds are a component of a composition and have efficacy to inhibit the bacterial virulence, preferably of gram negative bacteria, such as, for example, *P. aeroginosa*. Preferably these compositions comprise mBTL or derivatives of mBTL. In another embodiment procedures are contemplated comprising administering mBTL, derivatives of mBTL, or the compositions to an individual who is free of bacterial disease. Preferably, administration is in advance of an anticipated health-related procedure known to increase susceptibility to a gram negative bacteria, and preferably, *P. aeroginosa* pathogenicity, for example, in advance of a surgical procedure, including dental procedures, especially procedures involving implants, or insertion of catheters or other devices. In yet another embodiment, it is contemplated to contact surfaces of work areas, medical instruments, medical devices and the like with the compositions of the invention in order to attenuate the virulence of a gram negative bacteria, such as *P. aeroginosa*, that might come into contact with these surfaces.

In another aspect of the invention, what is contemplated is deploying the compounds of the invention to prevent the failure of devices that are prone to fouling by biofilms. These compounds are useful in industrial settings and in contexts requiring medical implants. The compounds of the invention may be administered in the liquid phase, may be embedded in materials used for production of such devices, or may coat such devices resulting in products that are innately resistant to biofilms. These compounds also may be used to inhibit biofilms from forming in situations where liquids are flowing, as, for example, through pipes, pipelines, tubing, water cooling systems, stents or filtration devices.

Indications

Gram negative bacteria are typically free-living organisms often found in soil and water, and play an important role in decomposition, biodegradation, and the C and N cycles. However, many gram negative bacteria are pathogenic. Examples of gram negative bacteria that can be inhibited by compounds of the invention, include, but are not limited to *Burkholderia cepaci, C. violaceum, harveyi, Pseudomonas*, including, but not limited to *Pseudomonas aeruginosa, Neisseria gonorrhoeae, Neisseria meningitidis, Bordetella pertussis, Haemophilus influenzae, Legionella pneurnophila, Brucella, Francsella, Xanthomonas, Agrobacterium*, enteric bacteria, such as *Escherichia coli* and its relatives, the members of the family Enterobacteriaceae, such as *Salmonella* and *Shigella, Proteus*, and *Yersinia pestis*.

For example, gram negative bacteria often cause opportunistic infections in immunocompromised or immunosuppressed individuals. One example of such a bacteria is *P. aeruginosa*. These infections are spread by heath care workers or patients to surfaces, machinery or instruments in health care facilities. *P. aeruginosa* typically infects the pulmonary tract, urinary tract, burns, and wounds. *P. aeruginosa* also causes catheter-associated infections, blood infections, middle ear infections, formation of dental plaque, gingivitis, chronic sinusitis, endocarditis, coating of contact lenses, and infections associated with implanted devices, for example, catheters, joint prostheses, prosthetic cardiac valves and intrauterine devices. *P. aeruginosa* causes infections of the central nervous system, gastrointestinal tract, bones, joints, ears and eyes. The compounds or compound compositions of the invention can be used to treat these infections and conditions.

Specifically, the compound or compound compositions of the invention can be administered to treat, inhibit, and/or ameliorate infections including opportunistic infections and/or antibiotic resistant bacterial infections caused by gram negative bacteria. Examples of such opportunistic infections, include, but are not limited to *P. aeruginosa*. or poly-microbial infections of *P. aeruginosa* with, for example, *Staphylococcus aureus* or *Burkholderia cepacia*. Examples of patients who may acquire such opportunistic and/or resistant infections include, but are not limited to patients who are immunocompromised or immunosuppressed, who have cystic fibrosis or HIV. who have implanted medical devices, subcutaneous devices or who are on ventilators, patients who have been intubated or who have catheters, nosocomial infections, patients who are undergoing bone marrow transplant or other types of surgery, including, but not limited to dental surgery and patients who are TV drug users, especially with regard to heart valve infection.

Burns and/or other traumatic wounds as well as common or uncommon infections can also be prophylactically treated and/or ameliorated by administration of the compound or compound compositions. Examples of such wounds and infection disorders include, but are not limited to puncture wounds, radial keratotomy, ecthyma gangrenosum, osteomyelitis, external otitis or dermatitis.

In one embodiment, the compound or compound compositions of the invention can be administered to treat, prevent, and/or ameliorate pulmonary infections. More preferably, the compound or compound compositions of the invention can be administered to treat, prevent, diagnose, and/or ameliorate pneumonia. More preferably, the compound or compound compositions of the invention can be administered to treat, prevent, and/or ameliorate lung infections, such as pneumonia, in cystic fibrosis patients. More preferably, the compound or compound compositions of the invention can be administered to treat, prevent, and/or ameliorate gram negative infections such as by *P. aeruginosa* in cystic fibrosis patients. Pneumonia can be caused by colonization of medical devices, such. as ventilator-associated pneumonia, and other nosocomial pneumonia, and the compound or compound compositions of the invention can be administered to treat and/or prevent these types of pneumonia or bacterial infections as well.

Additionally, the compound or compound compositions of the invention can be administered to treat and prevent septic shock. More preferably, the compound or compound compositions of the invention can be administered to treat, prevent, and/or ameliorate septic shock in neutropenic, immunocompromised, and/or immunosuppressed patients or patients infected with antibiotic resistant bacteria, such as, for example, antibiotic resistant P. aeruginosa.

Additionally, the compound or compound compositions of the invention can be administered to treat, prevent, and/or ameliorate urinary tract or pelvic infections. In another preferred embodiment, the compound or compound compositions of the invention can be administered to treat, prevent, and/or ameliorate gastrointestinal infections, such as necrotizing enterocolitis, often seen in premature infants and/or neutropenic cancer patients.

Additionally, the compound or compound compositions of the invention can be administered to treat, prevent, and/or ameliorate urinary dysenteriae (for example, dysenteria caused by bacillary dysentery), food poisoning and/or gastroenteritis (for example, caused by *Salmonella enterica*), typhoid fever (for example, caused by *Salmonella typhi*), whooping cough (or pertussis) as is caused by *Bordetella pertussis*, Legionnaires' pneumonia, caused by *Legionella pneumophila*, sexually transmitted diseases, such as gonorrhea, caused by *Neisseria gonorrhoeae*, or meningitis, caused by, for example, *Neisseria meningitidis* or *Haemophilus influenzae*, brucellosis which is caused by brucellae, and more specifically, *Brucella abortus*.

Formulations and Methods of Administration

The invention provides methods of treatment, inhibition and prophylaxis by administration to a subject of an effective amount of the compound or a pharmaceutical composition of the invention. In a preferred aspect, the compound is substantially purified (i.e., substantially free from substances that limit its effect or produce undesired side-effects). The subject is preferably an animal, including but not limited to mammals, amphibians, birds, and fish. The subject is more preferably either a mammal, including but not limited to animals such as cows, pigs, horses, cats, dogs, etc., or an avian species, including but not limited to chickens, ducks and other domestic poultry. The subject is most preferably a human.

Formulations and methods of administration that can be employed with the compound or compound compositions, additional appropriate formulations and routes of administration can be selected from among those described herein below. The compound or compound compositions of the invention may be administered therapeutically, such as, for example, in the case of infection of a susceptible patient with burn or other traumatic wound injury or lung infection, such as in a cystic fibrosis patient infected with *P. aeruginosa* or *Burkholderia cepacia* separately or in combination. Alternatively, the compound or compound compositions may be administered prophylactically, such as, for example, to prevent opportunistic gram negative bacterial infection, such as by *P. aeruginosa*, prior to surgery, dental work, or implantation of a medical device such as a catheter or ventilator tube continuously, such as, for example in the case of an immunosuppressed or immunocompromised patient.

Various delivery systems are known and can be used to administer compound, e.g., encapsulation in liposomes, microp articles, microcapsules. Methods of introduction include, but are not limited to, topical, intradermal, intramuscular, intraperitoneal, intravenous, subcutaneous, inhalation, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In one embodiment the compound of the invention is formulated in 10 mM sodium citrate, 1.9% glycine, 0.5% sucrose, 0.01% polysorbate 80, pH 6.5 (±0.3). In another embodiment, the compound of the invention is formulated in 10 mM sodium citrate, 1.9% glycine, 0.5% sucrose, 0.01% polysorbate 80, pH 6.5 (±0.3) for intravenous administration.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the composition can be delivered in a vesicle, in particular a liposome (see Langer, Science 249:1527-1533 (1990); Treat et al, in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition can be delivered in a controlled release system. In one embodiment, a pump may be used (see Langer, supra; Sefton, CRC Crit, Ref Biomed. Eng. 14:20 1 (1987); Buchwald et al, Surgery 88:507 (1980); Saudek et al, N. Engl. J. Med. 321:574 (1989)), In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, Macromol. Sci. Rev. Macromol. Chem. 2.3:61 (1983); see also Levy et al, Science 2.28:190 (1985); During et al, Ann. Neurol. 25:35 1 (1989); Howard et al, J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The present invention also provides pharmaceutical compositions. Such compositions comprise a therapeutically effective amount of compound and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a. suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc, Examples of suitable pharmaceutical carriers are described in "Remington's Pharmaceutical Sciences" by E. W. Martin. Such compositions will contain a therapeutically effective amount of the compound together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous, topical or pulmonary administration to human beings. Typically, compositions for such administration are solutions in sterile isotonic aqueous buffer. Where necessary, the composition may also include a solubilizing agent and a local anesthetic such as lignocanme to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms, Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention that will be effective in the treatment, inhibition and prevention of a disease or disorder can be determined by standard clinical techniques. Additionally, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For example, the dosage administered to a patient should typically be 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. In preferred embodiments, a dose of 1, 4, 10, or 20 mg/kg is administered intravenously to a patient. Further, the dosage and frequency of administration, of therapeutic or pharmaceutical compositions of the invention may be reduced by enhancing uptake and tissue penetration (e.g., into the skin and/or lungs) of by modifications such as, for example, lipidation.

The compound or compound compositions of the invention may be administered alone or in combination with other compounds, such as adjuvants. In one embodiment the compounds may be administered in combination with one or more antibiotics, for example, gentamicin, tobramycin, colistin, and fluoroquinolins. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In the treatment of burns or other traumatic wound injuries that are susceptible to bacterial infection such as, for example, P. aeruginosa infection, the presently described compound can be prepared in a medicament and the preparation applied generously (e.g., topically) to the entire burn area as quickly as possible. Repeated applications are made, if necessary and as needed to relieve pain, increase healing and decrease infection. If necessary, resuscitation is started by the introduction of the conventional intravenous fluids. Pain killers, toxin neutralizers, vitamins and antibiotics may be employed as indicated. Moreover, intravenous treatment of the compound or compound composition may also be needed to treat the burn or other traumatic wound injury.

The wound to which the compound or compound compositions have been applied may be covered with gauze and sheet wadding and thereafter dressed daily. At the time of dressing, all devitalized tissue and crusts Which can be removed readily should be removed. Tissue which is attached firmly is permitted to separate normally, In the use of the compound or compound compositions for the treatment of lung infections, preferably, for example, in patients suffering from cystic fibrosis, pneumonia (regardless of the etiology), and/or antibiotic resistant bacterial pulmonary infection, the compound will generally be administered for symptomatic treatment in the form of a conventional pharmaceutical composition, for example, as generally described in U.S. Pat. No. 4,910,190, and preferably as an aerosol. A formulation providing a solution containing a concentration, for example, of 10 mg/mL, 20 mg/ml, or 30 mg/ml of the compound and suitable for use with a. nebulizer (preferably) or as an injectable solution. A suitable nebulizer for use is, for example, a RETEC™ nebulizer, in which the solution is nebulized with compressed air.

In general, the compound or compound compositions will be administered to humans at a daily dose in the range of, for example, 5 to 100 mg of the compound by aerosol or 50 to 1000 mg intravenously, or a combination of the two. However, it readily will be understood that it may be necessary to vary the dose of therapeutic product administered in accordance with well-known medical practice to take account of the nature and severity of the lung disease (for example, cystic fibrosis) under treatment, concurrent therapy, and the age, weight and sex of the patient receiving treatment. it similarly will be understood that generally equivalent amounts of a pharmaceutically acceptable salt of the compound also may be used.

Industrial Uses

Compounds of the invention can be used in industrial settings to inhibit biofilm production and/or to remove antibiotic resistant bacteria, such as in a hospital or other public setting. For example, the compounds of the invention can be used to remove biofilms that have grown in moist and warm environments, such as showers, water and sewage pipes, cooling or heating water systems, (e.g., cooling towers), marine engineering systems, such as, for example, pipelines of the offshore oil and gas industry. The compounds of the invention can also be used, for example, to remove and/or prevent bacterial adhesion to boat hulls, since once a biofilm of bacteria forms, it is easier for other marine organisms such as barnacles to attach. The compounds of the invention can be used to reduce, for example, the time a boat is in dry dock for refitting and repainting, thereby increasing productivity of shipping assets, and useful life of the ships. The compounds of the invention can also be used to remove biofilm production intentionally used to eliminate petroleum oil from contaminated oceans or marine systems, once the contamination is removed.

Additionally, the compound of the invention can be used to wash, rinse or swab floors and counters, such as in food preparation areas or medical facilities, as well as medical devices, including but not limited to, stents, catheters, intubation tubes, or ventilator equipment. Still further the compounds can be used as a handwash to help eliminate spread of virulent bacteria by health workers, patients and others.

Particular species of bacteria may be especially problematic. For example, *Pseudomonas aeruginosa* is a pathogen that can survive in a wide range of environments. The bacterium is a public health threat because it causes a variety of secondary infections in humans, where those with burn wounds, cystic fibrosis, and implanted medical devices are particularly at risk. With an outer membrane of low permeability, a multitude of efflux pumps, and various degradative enzymes to disable antibiotics, *P. aeruginosa* is difficult to treat. As with other common pathogenic bacteria, antibiotic-resistant strains are an increasing problem.

Blocking virulence is one of the strategies contemplated to combat these bacteria. This approach provides less selective pressure for the spread of resistant mutants and leads to drug therapies that are effective over a greater time span compared to traditional antibiotics. Rather than preventing growth or killing the bacteria, an antivirulence approach prevents the expression of virulence traits. The bacteria that have been treated and are thus benign should then be more easily cleared by the host immune system.

In yet another embodiment, another series of potent molecules were designed that inhibit pyocyanin production. The invention encompasses the design, synthesis, and evaluation of these inhibitors. In a preferred embodiment, the structures of these molecules were evolved from the native signal, 3OC12-HSL, and a thiolactone inhibitor mBTL (FIG. 15, 1). The structures of the inhibitors substitute the lactone moiety of the native signal with a chemically stable moiety that was chosen to maintain native binding contacts with LasR, according to modeling based on the LasR crystal structure.

In considering the natural QS components (FIG. 1A), the homoserine lactone (HSL) head group is the common feature of a series of AHL quorum sensing signals and this head group takes part in key hydrogen-bonding interactions with the receptor binding pocket (2, FIG. 12), while the tails generally have only van der Waals interactions in a hydrophobic pocket of the protein. A replacement for the HSL should maintain the key hydrogen-bond interactions with the receptor and perhaps find additional opportunities for enhanced binding. Using the LasR crystal structure as a template for HSL binding, a set of head group candidates was identified in a virtual screen using AutoDock. Heterocycles, including aminopyridine (3, FIG. 12) were identified as good candidates that could maintain the native binding contacts and could have potential for additional hydrogen-bonding interactions. In addition to its chemical stability, the aminopyridine moiety was attractive as the platform for the synthesis of a focused library to explore structure-activity relationships.

Despite having been designed to bind the LasR and/or RhlR receptors of *P. aeruginosa*, subsequent studies suggest that the inhibitor compounds reduce pyocyanin levels by a pathway different from the LasR or RHLR receptors.

The compounds of the present invention can be described according to the following formula:

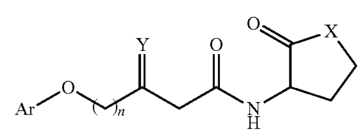

A where X═O, S, or NH;

Y═O; H, H; or H, OH, n=2-8;

Ar=a phenyl group or a substituted phenyl group, wherein the substituted phenyl group is represented by:

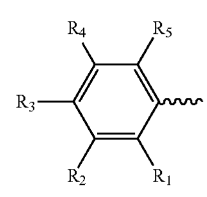

where $R_1$-$R_5$ can be Cl, Br, F, $NO_2$, CN, alkyl, or phenyl.

The following examples set forth the general procedures involved in practicing the present invention. To the extent that specific materials are mentioned, it is merely for purposes of illustration and is not intended to limit the invention.

EXAMPLE 1

Strains and Media

*E. coli* strains were grown at 37° C. in Luria broth (LB) (Fisher). Plasmid pET23b (Novagen) was used to express lasR and rhlR in *E. coli* strain BL21-Gold (DE3) (Stratagene). Plasmids were maintained with 100 μg/mL ampicillin. Plasmid pEVS141 was used for rhlA-gfp or rsaL-gfp expression and maintained with 50 mg/mL of kanamycin. *P. aeruginosa* strains were grown with shaking at 37° C. in LB. *C. elegans* wild-type strain N2 was propagated on NGM with an *E. coli* HB101 lawn as the food source at 20° C. A549 human lung carcinoma cells (ATCC #CCL-185) were grown in DMEM medium (Gibco) plus 20% fetal bovine serum and 1× PenStep (Sigma) at 37° C.

The *P. aeruginosa* rhlR strain (rhlR::MAR2xT7) and the rhlI strain (rhlI::MAR2xT7) come from the *P. aeruginosa* PA14 ordered transposon library. The *P. aeruginosa* lasR and lasR, rhlR double mutant strains were constructed using red recombination. The region spanning approximately 600 bp upstream of lasR and including the start codon (called lasR') and the sequence encoding the C-terminal 6 amino acids of LasR and approximately 600 bp downstream (called 'lasR) were amplified by PCR. The FRT-aacCl-FRT region in pAS03 was amplified using primers that span sequences in lasR' or 'lasR. The lasR', FRT-aacCl-FRT and lasR PCR products were combined through overlap extension PCR and amplified. The resulting lasR'-FRT-aacCl-FRT-'lasR product was transformed into *P. aeruginosa* PA14 harboring pUCP18-RedS. Gentamicin resistance was selected to yield lasR::aacCl in the chromosome. Following excision of the gentamicin resistance gene, the lasR, rhlR double mutant strain was constructed by inserting rhlR::MAR2xT7 into the lasR strain background followed by selection for gentamicin resistance. This strategy yielded the lasR::FRT, rhlR::MAR2xT7 strain.

EXAMPLE 2

Chemistry, Materials and Methods

Unless otherwise stated, reactions were performed in flame-dried glassware fitted with rubber septa under a nitrogen atmosphere and were stirred with Teflon-coated magnetic stirring bars. Liquid reagents and solvents were transferred via syringe using standard Schlenk techniques. Reaction solvents were dried by passage over a column of activated alumina. All other solvents and reagents were used as received unless otherwise noted. Reaction temperatures above 23° C. refer to the oil bath temperature, which was controlled by an OptiCHEM temperature modulator. Thin layer chromatography was performed using SiliCycle silica gel 60 F-254 precoated plates (0.25 mm) and visualized by UV irradiation and anisaldehyde, ceric ammonium molybdate, or potassium permanganate stain. Sorbent standard silica gel (particle size 40-63 μm) was used for flash chromatography. $^1H$ and $^{13}C$ NMR spectra were recorded on Bruker Avance II (500 MHz for 1H; 125 MHz for $^{13}C$) spectrometer fitted with either a $^1H$-optimized TCI (H/C/N) cryoprobe or a $^{13}C$-optimized dual C/H cryoprobe. Chemical shifts (δ) are reported in ppm relative to the residual solvent signal (δ=7.26 for $^1H$ NMR and δ=77.0 for $^{13}C$ NMR). Data for $^1H$ NMR spectra are reported as follows: chemical shift (multiplicity, coupling constants, number of hydrogens). Abbreviations are as follows: s (singlet), d (doublet), t (triplet), m (multiples). High-resolution mass spectral analysis was performed using an Agilent 1200-series electrospray ionization—time-of-flight (ESI-TOF) mass spectrometer in the positive ESI mode. The following compounds were synthesized as previously described: CL, CTL, mBTL, mCTL, itc-13, PD-12. Methods used to prepare and evaluate molecules described above are described in example 14 and in Swem et al. (2009) (Reference 4, below).

EXAMPLE 3

Pyocyanin Analyses

Methods. The oxidized form of pyocyanin imparts a green color to *P. aeruginosa* cultures, making the production of pyocyanin convenient to monitor by UV/Vis absorbance. Overnight *P. aeruginosa* cultures were subcultured into 5 mL fresh medium at 1:1000 dilution. Synthetic compounds were assayed at 100 μM for end point assays and at concentrations ranging from 200 nM to 200 μM for titrations following 17 hr of aerobic growth with shaking at 37° C. Cells were separated from culture fluids via centrifugation at 13,000 rpm for 15 min. Culture fluids were passed through 0.22 μm syringe driven filters (Millipore). Cell-free culture fluids were analyzed for pyocyanin using wavelength scans on a Beckman Coulter DU-800 spectrophotometer from 200 nm to 800 nm 695 nm was chosen for graphical representation. Titration data were fit with a variable-slope sigmoidal dose-response curve using GraphPad Prism to determine the $IC_{50}$ values.

Results. The molecule CL (FIG. 1a) is an inhibitor of the LasR/RhlR homolog CviR from *Chromobacterium violaceum*. Based on the CL structure, design and synthesis of a focused library of approximately 30 molecules was completed. Analyses for CL and three additional molecules are provided as examples (CTL, mCTL, and mBTL; FIG. 1a). The first experiment was of the molecules for inhibition of quorum sensing in wild-type *P. aeruginosa* PA14 using the quorum-sensing-regulated production of the virulence factor pyocyanin as the readout (FIG. 1c). Following activation by LasR:3OC12-HSL, the RhlR:C4-HSL complex activates expression of the pyocyanin operon (FIG. 1b). Therefore, *P. aeruginosa* PA14 produces pyocyanin at high cell density, and limited pyocyanin production occurs in a lasR or a rhlR null mutant and in the lasR, rhlR double mutant (FIG. 1c).

Figure 5:
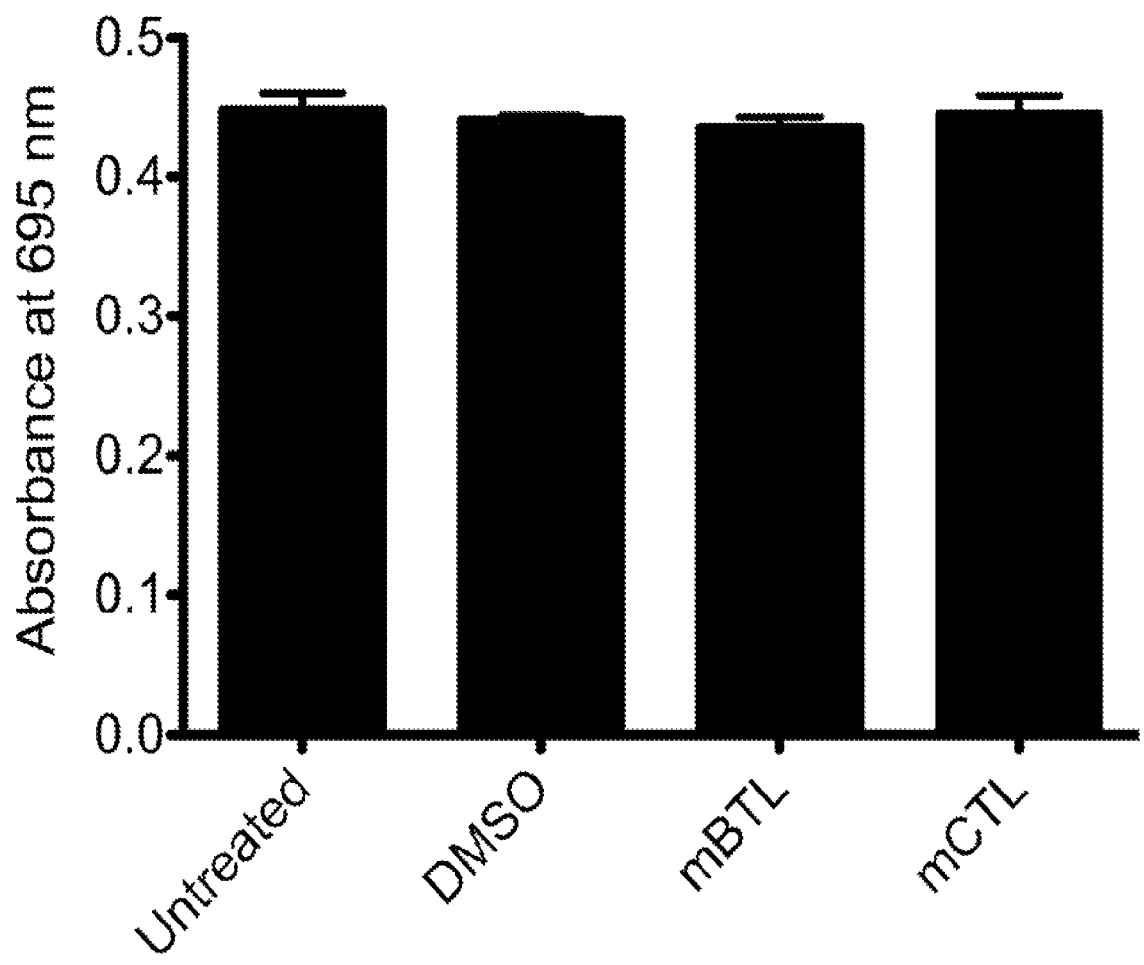
FIG. 5. Treatment of cell-free culture fluids with mBTL or mCTL does not alter pyocyanin levels. Cell-free culture fluids from WT P. aeruginosa PA14 following 17 hr growth were left untreated or supplied with 100 mM mCTL, mBTL, or an equivalent amount of DMSO. Subsequently, the fluids were incubated shaking at 37° C. for 17 hr. Pyocyanin levels were assessed by absorption. Error bars indicate S.D. of three replicates.
Figure 6:
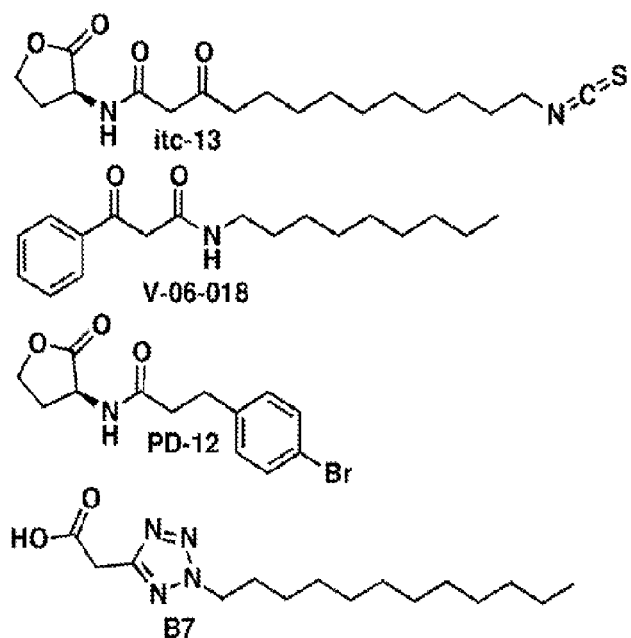
FIG. 6. Inhibition of pyocyanin production in P. aeruginosa PA14 by previously reported LasR inhibitors. a. Structures of four previously published LasR inhibitors. b. Pyocyanin inhibition assays were performed with 100 mM of each of the four molecules in panel a. on WT P. aeruginosa PA14. c. Pyocyanin inhibition titration assays were performed with itc-13 (circles) and V-06-018 (squares) at the concentrations shown using WT P. aeruginosa PA14. Error bars represent S.D. of three replicates.
Figure 6:
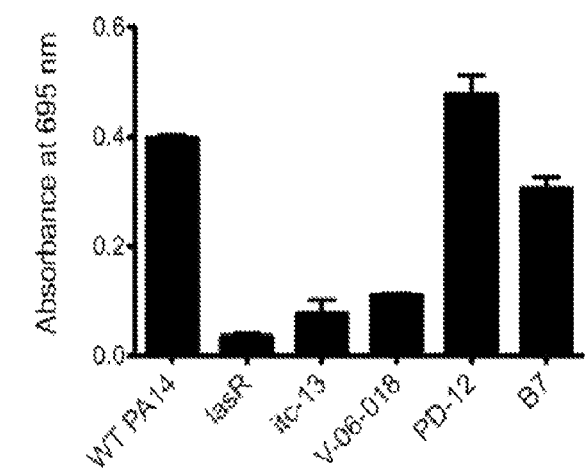
Figure 6:
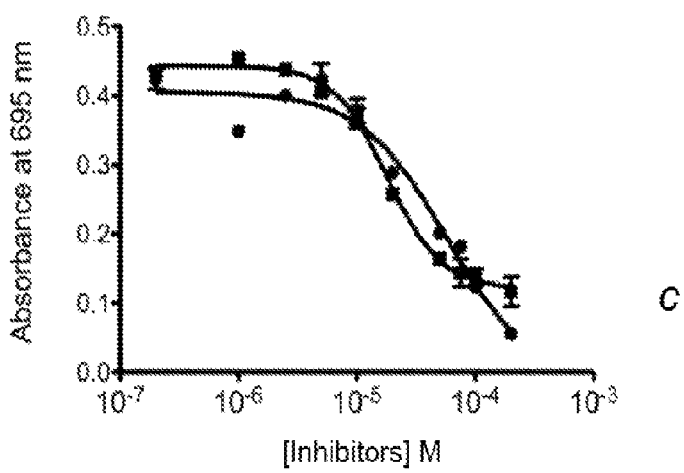

Neither CL nor CTL inhibited pyocyanin production in vivo (FIG. 1c). By contrast, mCTL and mBTL showed potent inhibition of pyocyanin (FIG. 1c) while not affecting *P. aeruginosa* PA14 growth. Calculated $IC_{50}$ values were 8 μM (±2) for mBTL and 9 μM (±2) for mCTL (FIG. 1d). Inhibition was not due to interaction of these molecules with pyocyanin, as incubation of pyocyanin-containing cell-free culture fluids from untreated *P. aeruginosa* PA14 with 100 μM mBTL or mCTL did not alter pyocyanin levels (FIG. 5). The next experiment involved synthesis of four previously reported LasR inhibitors for comparison in the pyocyanin assay (FIG. 6a). Two compounds, itc-13 and V-06-018, inhibited pyocyanin production in *P. aeruginosa* PA14 with higher $IC_{50}$ values (56 μM (±10) and 18 μM (±2), respectively) than mBTL and mCTL (FIG. 6b,c). The other molecules (PD-12 and B7) showed limited or no inhibition in vivo. (FIG. 6b). Thus, mBTL is more potent than mCTL and these previously identified inhibitors.

EXAMPLE 4

Chiral Resolution of mBTL

Methods. mBTL enantiomers were resolved using a Berger Multigram II SFC system equipped with two Varian SD-1 pumps, a Knauer K-2501 multi-wavelength detector set at 220 nm, a Knauer K-1900 pump, a Vatran SGP-50-100 condenser, and using a Chiralpak IC (2×15 cm) column. An isocratic method using a mixture of 30% MeOH/CO$_2$ (100 bar) at 60 mL/min was employed. The two peaks eluted at 1.66 min and 2.13 min. The identity of the enantiomers was determined through comparison of the HPLC trace with that of authentic (S)-mBTL synthesized from L-homocysteine thiolactone hydrochloride. Based on this analysis, peak 1 (>99:1 er) is (S)-mBTL and peak 2 (>99:1 er) is (R)-mBTL.

Figure 7A:
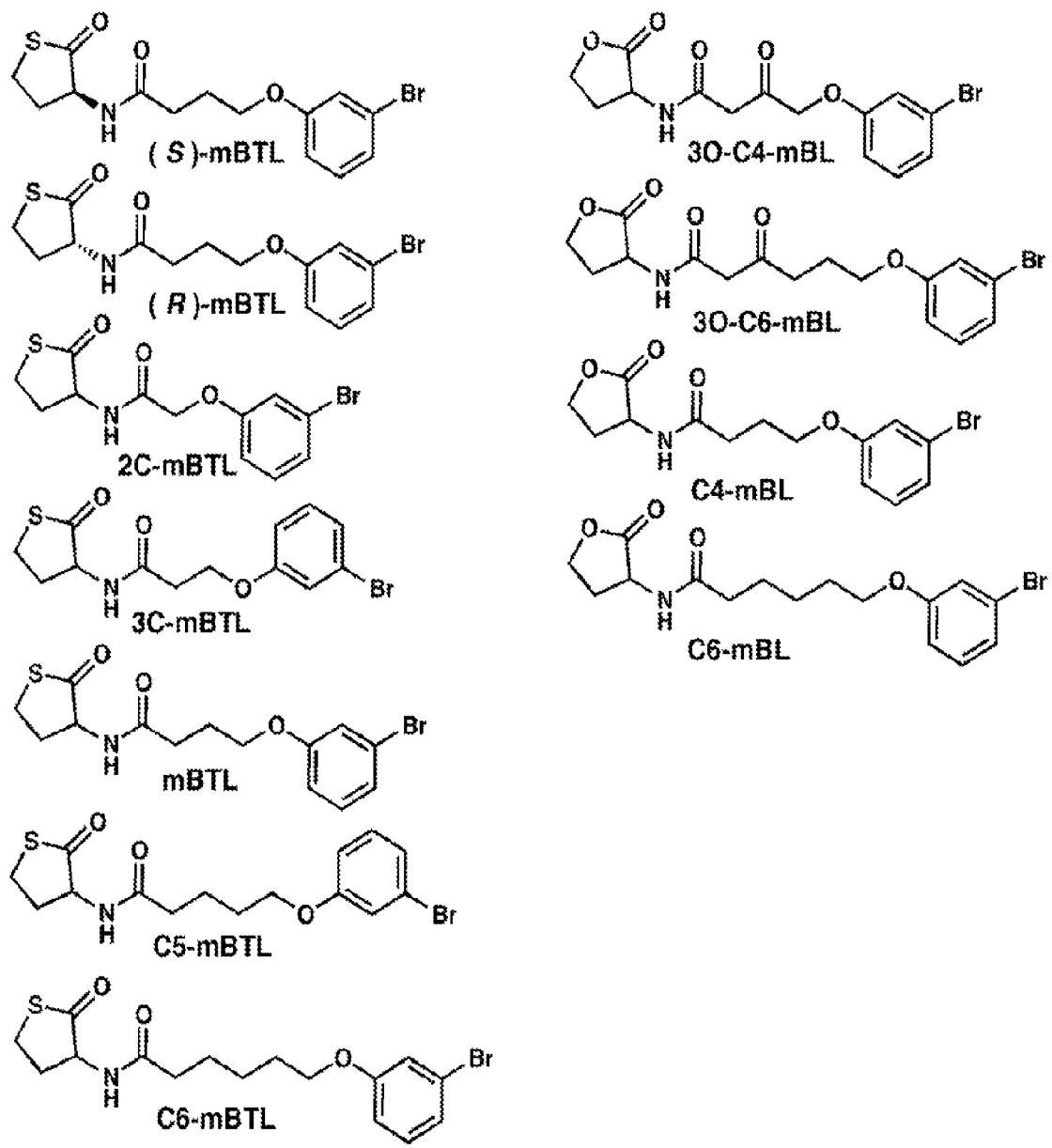
FIG. 7. Structure-function analysis of mBTL and closely related derivatives. a. Structures of mBTL and derivatives tested for inhibition of pyocyanin production. b. Pyocyanin inhibition titrations were performed with the (R) (squares) and (S) (circles) enantiomers of mBTL and the racemic mixture (asterisks). c. mBTL derivatives containing 2-6 carbon chains were tested at 100 mM. d. Lactone variants were examined at 100 mM. In all panels, error bars indicate S.D. of three replicates.
Figure 7B:
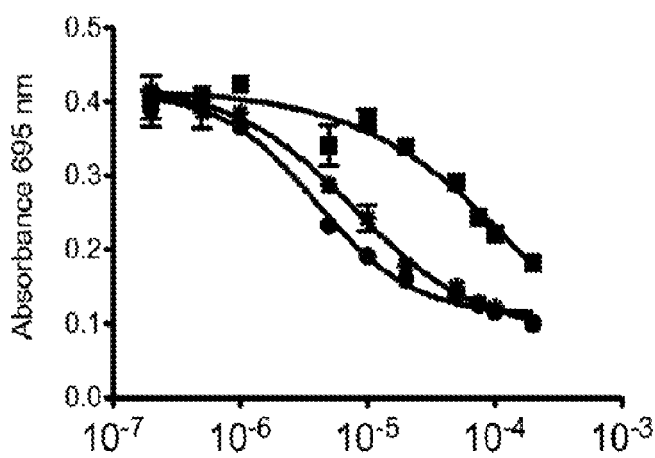
Figure 7C:
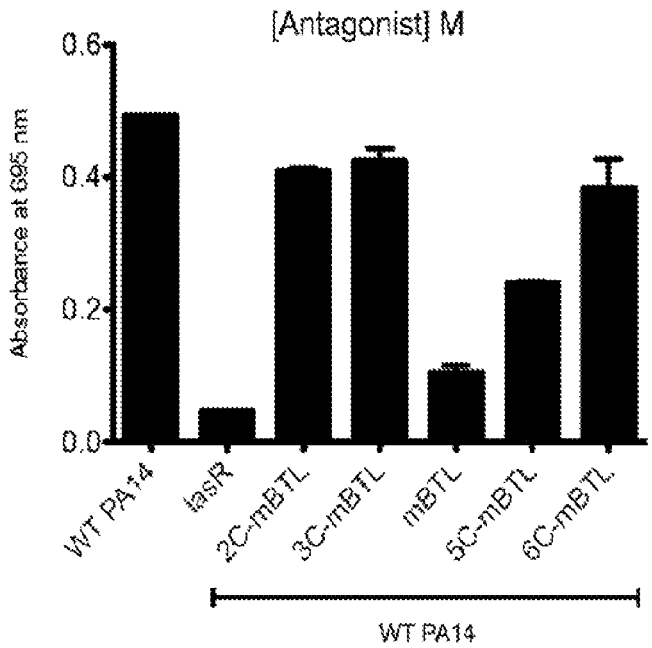
Figure 7D:
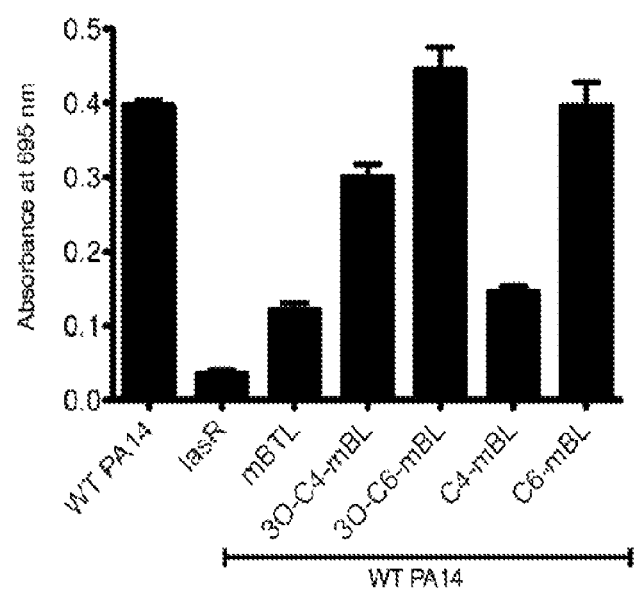

Results. To determine the enantiomer of mBTL responsible for inhibition, a chiral separation was performed. The S enantiomer is active (IC$_{50}$=4 μM) while the R enantiomer displays residual activity (IC$_{50}$=100 μM) (FIG. 7a,b). Because the racemic mixture has an IC$_{50}$ value only 2-fold higher than the isolated S enantiomer, we conclude that the R enantiomer does not influence inhibition. For ease of synthesis, racemic mixtures of mBTL were used for the other examples.

EXAMPLE 5

LasR and RhlR GFP Assays

Methods. The LasR-GFP assays were performed in *E. coli* strain BL21 DE3 Gold (Agilent) carrying pET23b (Novagen) containing lasR (maintained with 100 μg/mL ampicillin) and carrying plasmid pEVS141 (31) containing the rsaL promoter driving expression of gfp (maintained with 50 mg/mL of kanamycin.) The RhlR-GFP assays were performed in *E. coli* strain BL21 DE3 Gold (Agilent) carrying pET23b (Novagen) containing rhlR (maintained with 100 μg/mL ampicillin) and carrying plasmid pEVS141 containing the rhlA promoter driving expression of gfp (maintained with 50 μg/mL of kanamycin.) These *E. coli* strains were grown overnight and subcultured into fresh medium with appropriate antibiotics at a 1:100 dilution and grown shaking for 8 hr at 37° C. for the LasR-GFP strain and 12 hr for the RhlR-GFP construct. 50 nM 3OC12-HSL or 20 μM C4-HSL was added to the LasR-GFP and RhlR-GFP preparations, respectively. Compounds were tested at 1 mM for antagonism and at 100 nM or 20 μM for agonism. These concentrations were chosen for agonism studies to match the concentrations of autoinducers used in the experiments. For antagonism studies, the EC$_{95}$ concentration was used for each receptor. GFP was measured on an Envision plate reader.

Figure 2:
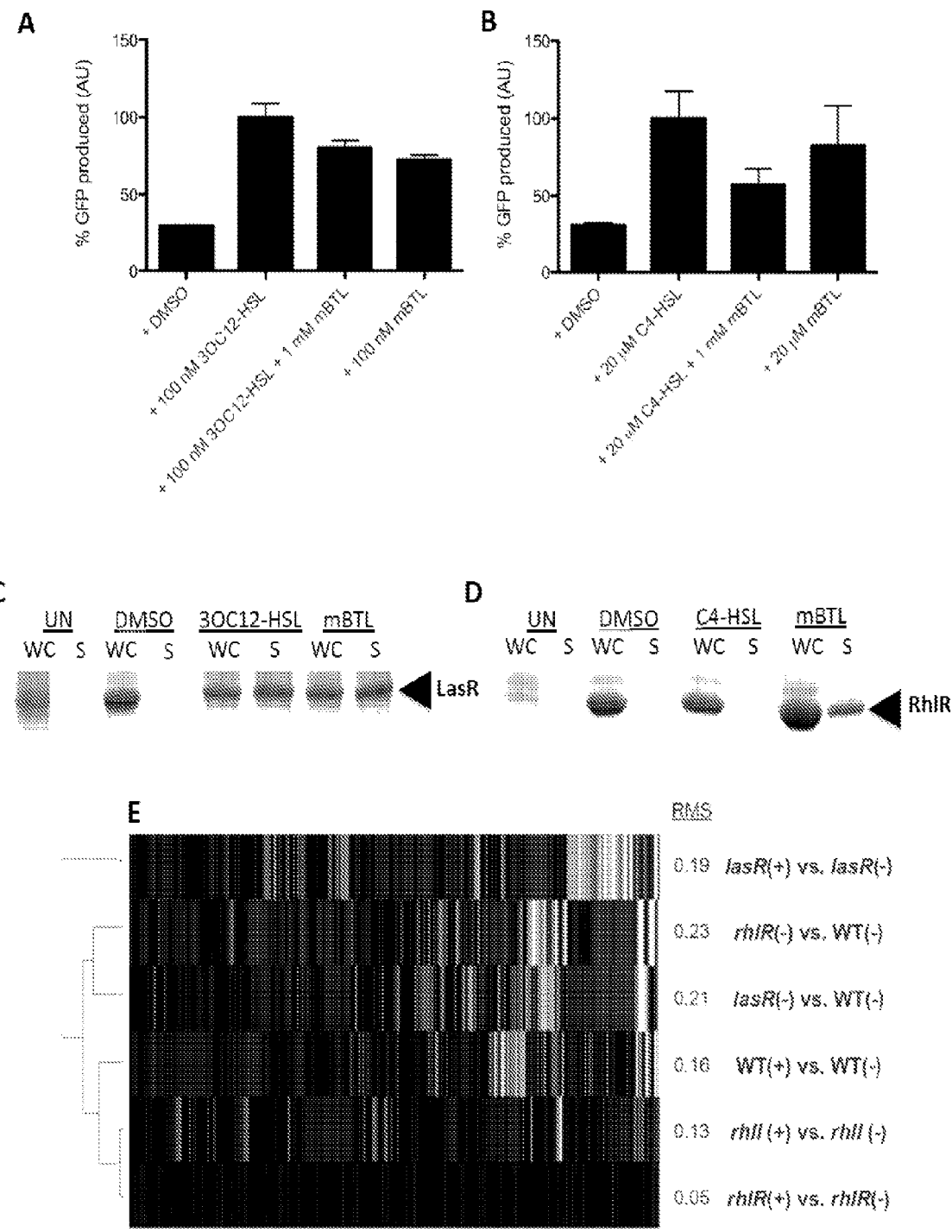
FIG. 2. mBTL binds and inhibits LasR and RhlR. A. LasR activation of expression of rsaL-gfp in E. coli. B. RhlR activation of expression of rhlA-gfp in E. coli. In each panel, gfp expression in the presence of the cognate autoinducer (100 nM 3OC12-HSL or 20 µM C4-HSL) is set to 100%. mBTL was tested for inhibition at 1 mM. Agonism was examined at 100 nM for LasR and 20 µM for RhlR. Error bars represent S.D. of three replicates. C. SDS-PAGE analysis of whole cell (WC) and soluble (S) extracts from E. coli cultures expressing LasR in the presence of DMSO, 100 µM 3OC12-HSL, or 100 µM mBTL. An uninduced control is shown for comparison. D. Same as panel c with RhlR in the presence of DMSO, 100 µM C4-HSL, or 100 µM mBTL. E. Hierarchical clustering, heat maps and the root mean square (RMS) of the fold-change ($log_{in}$) of mBTL treated (+) or DMSO treated (−) WT P. aeruginosa, lasR, rhlR, and rhlI mutants. Dendrogram to the left of the map indicates average Euclidean linkage distances between the gene expression profiles. Data are the average of three independent biological experiments, one in which the Cy3 and Cy5 dyes were swapped.
Figure 10:
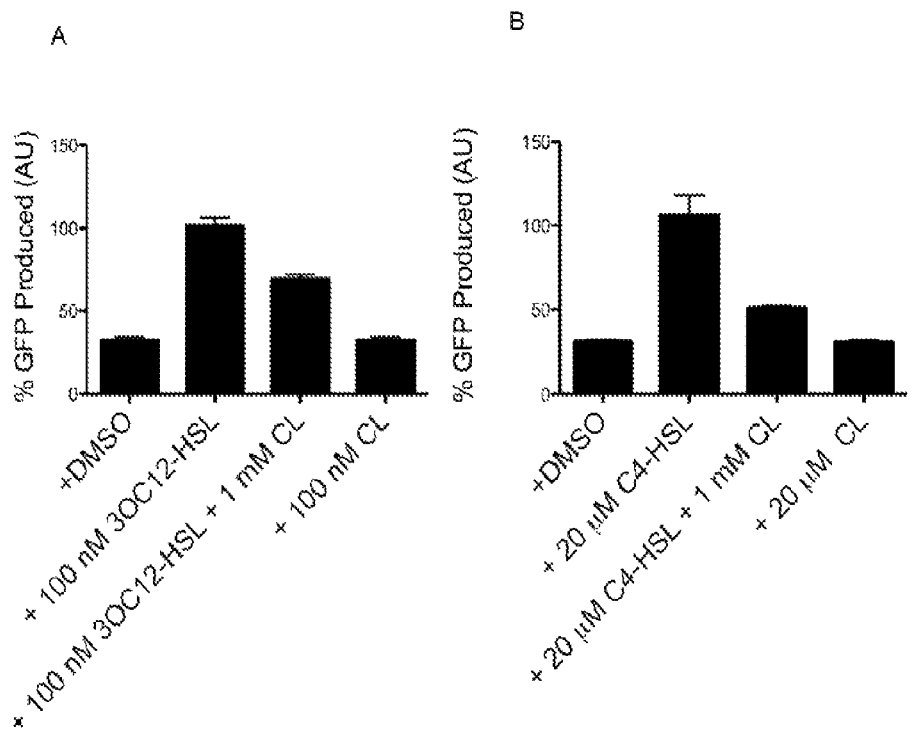
FIG. 10. CL inhibits LasR- and RhlR-controlled transcription in E. coli. A. LasR activation of expression of rsaL-gfp in E. coli. B. RhlR activation of expression of rhlA-gfp in E. coli. In each panel, gfp expression in the presence of the cognate autoinducer (100 nM 3OC12-HSL or 20 μM C4-HSL) is set to 100%. CL was tested for inhibition at 1 mM and agonism at 100 nM for LasR and 20 μM for RhlR. Error bars represent S.D. of three replicates.

Results. Investigation of whether mBTL interacts with LasR, RhlR, or both receptors proceeded using recombinant *E. coli* strains producing the receptor proteins and containing target gfp reporter fusions (rsaL-gfp for LasR and rhlA-gfp for RhlR). In the absence of ligand, neither receptor activates expression of the target-gfp fusion (FIG. 2a,b). When autoinducer is supplied at the EC$_{95}$, LasR and RhlR activate gene expression. mBTL partially antagonizes this effect (22%±4 and 43%±10 inhibition, respectively, FIG. 2a,b). In the absence of autoinducer, mBTL, when provided at the EC$_{95}$ of the native ligand for each receptor, acts as a partial agonist of both LasR and RhlR (72%±3 and 80%±25, respectively). Molecules such as mBTL, that resemble autoinducers, induce conformational changes in LuxR-type receptors that impair their ability to interact with RNA polymerase which lowers their transcriptional activation potential. In the presence of autoinducer, this reduction in transcription potential manifests as antagonism. In the absence of autoinducer, some transcription activation can still occur. Thus, without autoinducer present, molecules such as mBTL appear as partial agonists.

mBTL, the most potent in vivo inhibitor, is a partial agonist/partial antagonist of RhlR and LasR in the recombinant *E. coli* assay (FIG. 2a,b) and according to *P. aeruginosa* microarrays (Table 7). This feature of mBTL may be critical for its ability to function in vivo. Because LasR and RhlR act reciprocally to control key virulence genes (FIG. 1b), molecules that function as pure antagonists of both receptors might not be superior anti-virulence therapies. Consistent with this notion, CL is a more potent inhibitor of both LasR- and RhlR-directed transcription in *E. coli* than is mBTL, and CL does not agonize either receptor (FIG. 10). Nevertheless, CL exhibits no in vivo inhibition of pyocyanin production (FIG. 1b,c) and it does not attenuate killing of A549 lung cells by *P. aeruginosa*. This might be termed that a "sweet spot" exists in terms of antagonist potency for inhibitors of LasR and/or RhlR, and that mBTL has the appropriate level of potency to be effective in vivo. Consider a case in which LasR activates and RhlR represses a particular virulence factor (see FIG. 1b).

EXAMPLE 6

Binding of LuxR-Type Proteins LasR and RhlR to mBTL and to Cognate Autoinducers

Methods. Overnight cultures of *E. coli* BL21-Gold (DE3) carrying the LasR and RhlR overexpression constructs were diluted 1:100 into fresh LB supplemented with antibiotics and grown shaking at 37° C. to an OD$_{600}$ of 0.4. Autoinducer or antagonist molecules were added at 100 μM and incubated an additional 30 min at 20° C., after which protein production was induced by the addition of 1 mM IPTG for 6 hr at 20° C. Cells were harvested by centrifugation and resuspended in 1 mL of 20 mM Tris (pH 7.5), 0.5 mM EDTA, 300 mM NaCl, 1 mM DTT, and 5% glycerol and 100 μM of the appropriate ligand. Resuspended pellets were sonicated twice for 15 seconds to produce lysates containing all of the cell contents. This preparation is referred to as the whole cell (WC) fraction. The WC fraction was subjected to centrifugation at 4° C. at 13,300 RPM for 15 min to remove insoluble material and the membrane fraction. The supernatant from this pellet is referred to as the soluble (S) fraction. SDS-PAGE gels (4% stacking and 12% resolving) were used followed by Coomassie blue (BioRad) staining to visualize protein. Contrast was uniformly adjusted for both gels.

Results. LuxR-type proteins require cognate autoinducers to fold. Consistent with this, LasR and RhlR are insoluble in the absence of autoinducer, and are present in the whole cell (WC) fraction but not the soluble (S) fraction following SDS-PAGE (FIG. 2c,d). Addition of 100 μM 3OC12-HSL or mBTL solubilizes LasR (FIG. 2c). mBTL also solubilizes RhlR; surprisingly, C4-HSL, its native autoinducer, does not (FIG. 2d). It appears that autoinducer-bound RhlR is not particularly soluble when over-produced in *E. coli* and the protein likely aggregates. mBTL appears to protect the protein from aggregation. Similar protection occurs with CviR bound to CL.

EXAMPLE 7

RNA Extraction and Microarray Analysis

Methods. Overnight *P. aeruginosa* PA14 cultures were back-diluted 1:1000 into 5 mL of fresh LB. 100 μM mBTL, or an equivalent amount of DMSO, was added to cultures which were grown aerobically with shaking at 37° C. for 17 hr. 9 ODs of cells were harvested for each treatment. Lysozyme (1 mg/mL in TE buffer) (Sigma) was added for 10 min at room temperature. Total RNA was prepared using the RNeasy Midi Kit (Qiagen). RNA was treated with RNase-Free DNaseI (Ambion) for 1 hr at 37° C., inactivated using DNaseI Inactivation Reagent Resin (Ambion), and re-purified using the RNeasy Mini Kit. A cDNA library containing Cy3- or Cy5-labeled dUTP (Enzo Life Sciences) was synthesized from the purified RNA using SuperScript III Reverse Transcriptase (Invitrogen). Sodium hydroxide was added to degrade RNA, and the reaction was subsequently neutralized by addition of hydrochloric acid. The library was purified using the PCR Purification kit (Qiagen) and assessed for Cy3 and Cy5 incorporation using a Nanodrop ND-1000 Spectrophotometer (Nanodrop Technologies). Libraries were normalized for cDNA concentration and hybridized using the Gene Expression Hybridization Kit (Agilent) to a custom microarray (Agilent design number 43307), which was designed using the Agilent eArray tool with 2 probes for most genes. Samples were hybridized for 22 hr at 65° C. with continuous rotation at 10 rpm. Microarrays were scanned using an Agilent G2505C scanner and analyzed using Agilent Feature Extract software version 9.5. Resulting microarray intensity data were submitted to the PUMA Database (http://puma.princeton.edu) for archiving and analyzed using Matlab R2013a.

Results. To verify that mBTL functions by inhibiting quorum sensing in vivo, microarrays were used to examine the consequences of administering mBTL to wild-type *P. aeruginosa* and to the lasR and rhlR mutants. Treatment of wild-type *P. aeruginosa* PA14 caused alterations in expression of many of the known quorum-sensing targets (Table 7). For example, LasR-regulon genes including rpoS and nor were down-regulated (Tables S1 and S2). RhlR-controlled virulence genes, for example those encoding rhamnolipids (rhlA and rhlB), and phenazine (phzA2, phzB1, and phzB2, were also repressed (Table 7 and S3). Indeed, the profile of wild-type cells treated with mBTL matches well with the combined profiles of the lasR and rhlR mutants (Table 7). However, the fold-activation and fold-repression is not as dramatic in the mBTL-treated wild-type as in the mutants, confirming that mBTL does not fully inhibit either regulator (Tables S1, S2 and S3). Thirteen genes are activated 2-fold or more in wild-type *P. aeruginosa* PA14 when treated with mBTL (Table 10). By contrast, two hundred and thirteen genes are down-regulated 2-fold or more when wild-type is treated with mBTL (Table 7). These data indicate that the major role of mBTL in wild-type *P. aeruginosa* PA14 is as an antagonist that exerts control over virulence through partial-inhibition of LasR and RhlR not via up-regulation of other genes. Both the LasR and RhlR quorum-sensing receptors are partially inhibited by mBTL, however, as shown in the following experiment, in the contexts that we have examined, RhlR, not LasR, is the relevant in vivo target.

EXAMPLE 8

Analysis of lasR and rhlR Mutants Gene Expression

Results. The most important comparisons for defining the target of mBTL are the mBTL-treated and untreated lasR and rhlR mutants (Tables 11 and 12 and FIG. 2e). In the absence of LasR, mBTL treatment still alters expression of some genes. By contrast, there is essentially no difference between the untreated and mBTL-treated rhlR mutant profiles. Thus, while some of the mBTL effects occur through LasR, all of the mBTL effects depend on RhlR (Tables 11 and 12 and FIG. 2e). Thus, mBTL functions in vivo by inhibiting quorum sensing via RhlR.

EXAMPLE 9 mBTL Agonism of RhlR In Vivo

Given that mBTL acts as a partial agonist of RhlR in recombinant *E. coli* when the cognate autoinducer C4-HSL is not present (FIG. 2b), further examination was made of the extent of mBTL agonism of RhlR in vivo. To do this, a *P. aeruginosa* rhl1 null strain was treated with mBTL and microarrays were performed. mBTL activated 2-fold or higher expression of forty-four genes. For comparison, RhlR bound to C4-HSL activated nearly 300 genes (Tables 13 and 9). In every case in which a gene could be activated by C4-HSL or by mBTL, C4-HSL was a much more potent activator. Importantly, only one gene that was activated by mBTL in the rhl1 mutant was activated by mBTL in wild-type *P. aeruginosa* (Tables 13 and 10). These data indicate that mBTL can act as a weak RhlR agonist in vivo, but only when the native autoinducer is absent; a situation that is not likely to occur in wild-type bacteria.

EXAMPLE 10 mBTL Limits Virulence in an Animal Model

Methods. *C. elegans* fast killing assays were conducted with 90 wild-type N2 worms for each condition (30 worms/replicate, 3 replicates performed). *C. elegans* were propagated on NGM plates prior to eggs being harvested from gravid adults using a standard bleaching protocol (30 mL 5% bleach, 15 mL 5 M KOH, 55 mL $dH_2O$). Harvested eggs were placed on lawns of fresh *E. coli* HB101 and allowed to grow for 48 hr (to reach the L4 stage) at 20° C. prior to being moved to lawns of *P. aeruginosa* and placed at 25° C. on sorbitol, glucose, cholesterol plates. Nematodes were scored for survival every hr for 5 hr and again at 24 hr. The % living worms was calculated in triplicate for each time point. 50 μM mBTL or an equivalent volume of DMSO was added to plates and to the bacterial cultures during growth.

Figure 8:
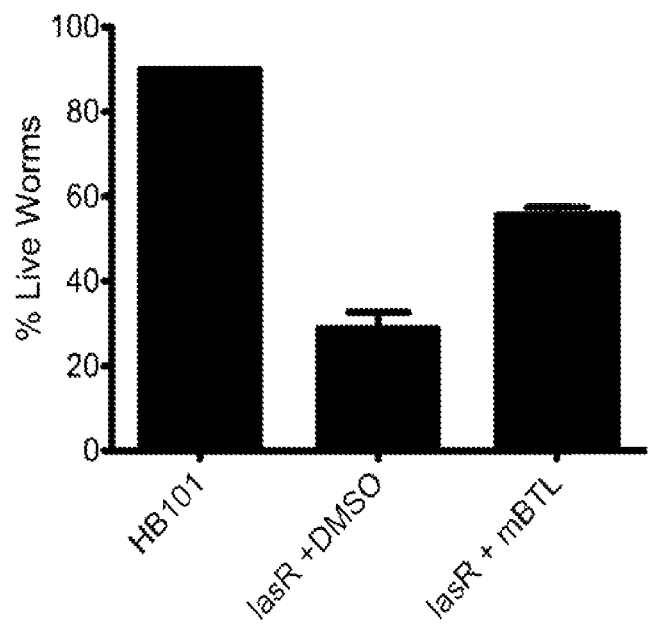
FIG. 8. mBTL rescues C. elegans from killing by the P. aeruginosa PA14 lasR strain. The % living worms was scored on plates containing the lasR P. aeruginosa mutant in the presence of 100 mM mBTL and compared to plates containing DMSO after 5 hr. HB101 denotes the E. coli control strain. Error bars represent S.E.M. of three replicates.

Results. To determine if mBTL can limit virulence, a *C. elegans* fast-kill infection assay was used. Wild-type *P. aeruginosa* PA14 and the lasR mutant rapidly kill *C. elegans*: 77% and 90% of worms die after 24 hr, respectively (FIG. 3a), indicating that LasR is not required for pathogenesis in this assay. Much less killing occurs when the nematodes are exposed to the rhlR or the lasR, rhlR double null strain (31% and 17%, respectively, died in 24 hr, FIG. 3a) showing that RhlR is required for virulence in this assay. Treatment of wild-type and the lasR mutant *P. aeruginosa* PA14 strains with 50 μM mBTL protects *C. elegans* from killing (23% and 50% death, respectively, FIG. 3b and FIG. 8). Together, these results confirm that the relevant in vivo target of mBTL is RhlR and, importantly, that inhibiting RhlR could form the basis of an anti-bacterial therapeutic strategy.

The double lasR, rhlR null mutant is not hyper-virulent in the nematode assay. The quorum-sensing-controlled virulence factors required for pathogenicity in mammalian cells are not precisely identical to those that are essential for virulence in nematodes which presumably accounts for this discrepancy.

EXAMPLE 11

A549 Human Lung Cell Infections

Methods. Human A549 cells were grown in CellStar tissue culture flasks. Prior to infection, the A549 cells were treated with trypsin-EDTA (CellGro), split, counted, and aliquotted into 96 well plates at 20,000 mammalian cells/well (cell counts were estimated using Trypan Blue (CellGro) exclusion). Cells were grown for 20 hr at 37° C. in DMEM (Invitrogen). Cells were washed 3× with warm PBS (Gibco). 100 µL of "master mix" was added to each well for each condition. Master mix contained 1 mL pre-warmed-PBS, 5 µL of 2 mg/mL propidium iodide (Bioprobes), 1 µL of a 100 mM inhibitor stock or DMSO, and 10 µL of $OD_{600}=2$ P. aeruginosa PA14 grown in the presence of mBTL or DMSO. Infections were monitored using an EnVision plate reader every 2 hr with the RFP filter supplied by GE.

Figure 3:
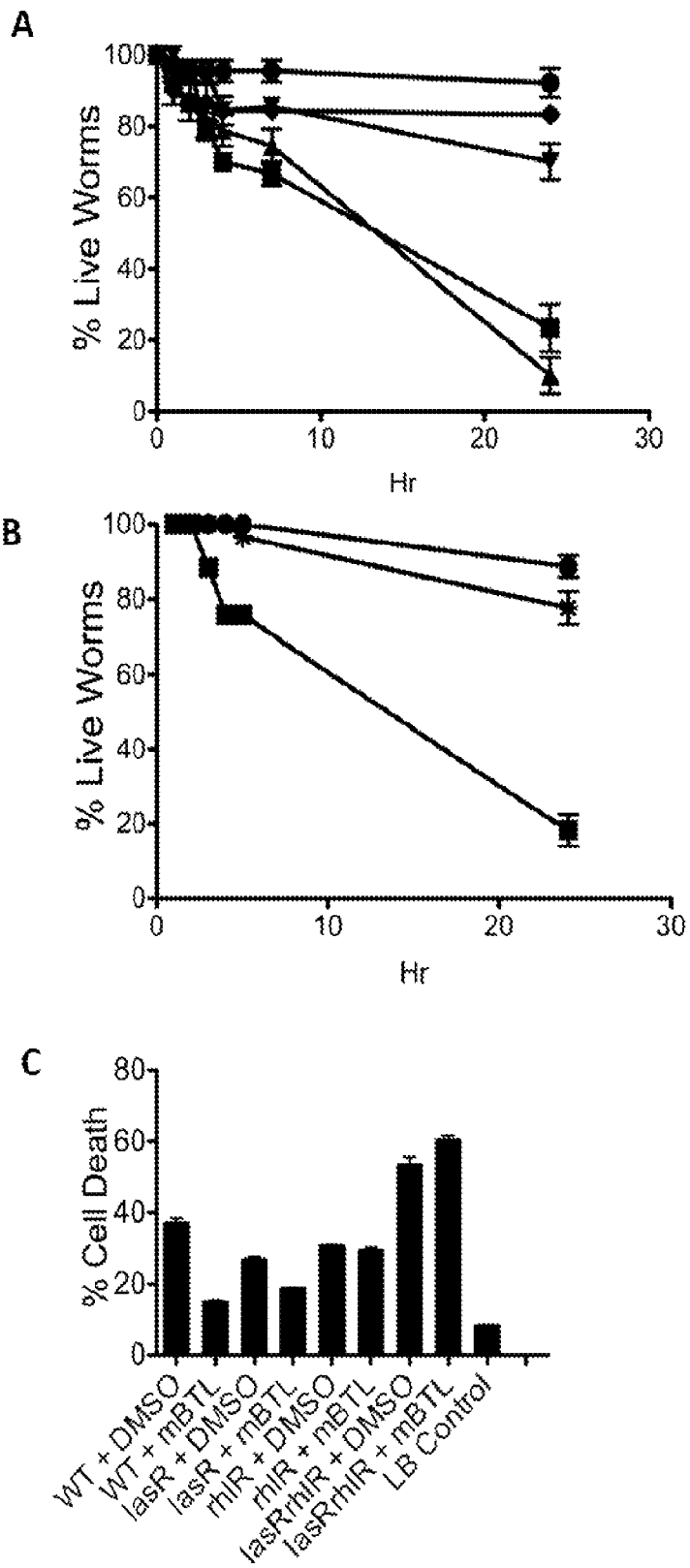
FIG. 3. mBTL inhibits P. aeruginosa PA14 virulence toward C. elegans and human A549 lung cells. A. C. elegans were applied to lawns of E. coli HB101 (circles), WT P. aeruginosa PA14 (squares), lasR mutant (triangles), rhlR mutant (inverted triangles), and lasR, rhlR double mutant (diamonds) strains. The % live worms was calculated every hr for the first 5 hr and again at 24 hr. Error bars represent S.E.M. of three replicates. B. Same as panel a. E. coli HB101 (circles), WT P. aeruginosa PA14 (squares), and WT P. aeruginosa in the presence of 50 μM mBTL (asterisks). C. The % cell death was calculated using propidium iodide uptake into A549 lung cells after 8 hr and normalized to cells lysed with detergent. Error bars represent S.E.M. of three replicates.
Figure 9:
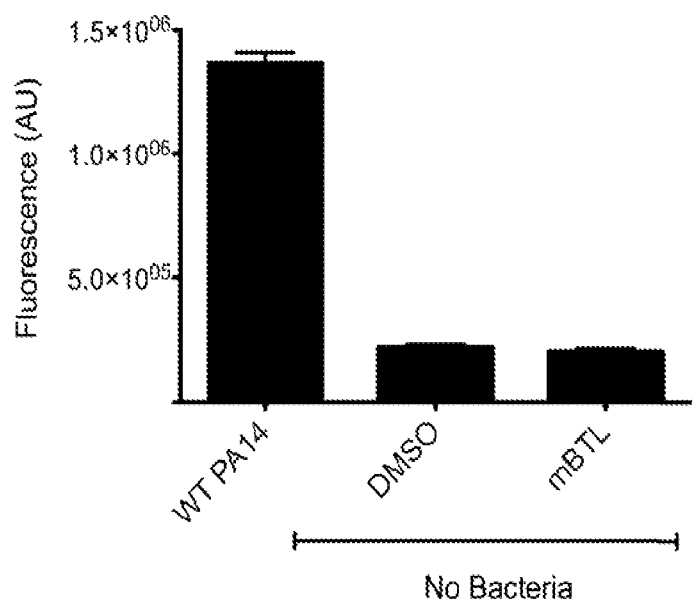
FIG. 9. mBTL is not cytotoxic to A549 human lung cells. A549 human lung cells were treated with 100 mM mBTL or an equivalent amount of DMSO in the absence of bacteria. Fluorescence from propidium iodide uptake was measured after 8 hr. Error bars represent S.E.M. of six replicates. Lung cells treated with WT P. aeruginosa PA14 show the maximum level of propidium iodide uptake.

Results. To test whether mBTL could improve the outcome for mammalian cells during infection the human lung carcinoma cell line A549 was used. mBTL at 100 µM is not toxic to A549 cells (FIG. 9). Wild-type, lasR and rhlR single mutants, and the lasR, rhlR double mutant P. aeruginosa are all capable of killing A549 cells (FIG. 3c). Treatment with mBTL reduces killing by the wild-type and the lasR mutant strain but not by the rhlR or the lasR, rhlR double mutant strains (FIG. 3c). These results validate the conclusion reached on the basis of the microarray data presented above. Specifically, the relevant target of mBTL is present in the wild-type and the lasR mutant but is not in the rhlR single and lasR, rhlR double mutant strains. Thus, RhlR appears to be the major in vivo target.

Figure 11:
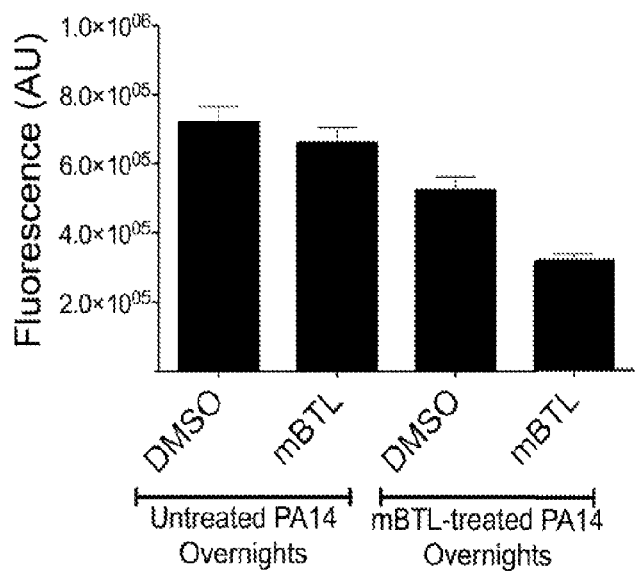
FIG. 11. mBTL functions as a prophylactic. Pelleted P. aeruginosa PA14 cells that had been grown for 17 hr in the presence of 100 mM mBTL or an equivalent amount of DMSO were washed, resuspended in PBS, and added to human lung A549 cells. An additional 100 μM mBTL or an equivalent amount of DMSO was added at the start of infection. Cell death was measured using fluorescence from propidium iodide uptake. Error bars indicate S.E.M. of six replicates.

In the nematode and lung cell experiments shown here, the bacteria were pregrown with mBTL and supplied a dose of inhibitor at the start of infection. Virulence was not reduced when P. aeruginosa PA14 was pre-grown in the absence of inhibitor (FIG. 11), indicating that mBTL may also function prophylactically.

It is noteworthy that, in the lung cell assay, the lasR, rhlR double mutant causes more cell death than does the wild-type (FIG. 3c). This result may stem from mis-regulation of virulence factors that are controlled in opposing directions by RhlR and LasR (FIG. 1b). The phenotype of the double mutant in the lung cell assay supports the proposition that potent inhibition of both LasR and RhlR could result in increased pathogenicity. Complete inhibition of LasR and RhlR would yield the same phenotype as deletion of both receptors. Apparently, that phenotype is high virulence.

EXAMPLE 12 mBTL Inhibits P. aeruginosa Biofilms

Microfluidic Flow Cells. Methods. Overnight P. aeruginosa PA14 cultures were back-diluted 1:1000 into 800 mL of tryptone broth (1% tryptone in $H_2O$) with or without 100 µM mBTL and grown to mid-logarithmic phase ($OD_{600}=0.5$). These cultures were used to fill 100 mL reservoirs that fed into microfluidic flow channels via Tygon tubing with an inner diameter of 2.4 mm. Similar tubing connected the outlet of the microfluidic channel to a collection dish on an analytical balance controlled via LabVIEW. The elevation of the culture reservoir above the collection dish on the balance set the constant pressure difference that drove the flow through the microfluidic channel. The microfluidic channel is 200 µm wide, 90 µm high, and contains a sequence of 37 bends that mimic corners in porous materials. The weight of the effluent culture was measured as a function of time t with measurement intervals of 4 s, and the data were converted into a flow rate Q(t) via the equation $$Q(t) = \frac{w(t+\Delta t) - w(t-\Delta t)}{1 \min} \frac{1}{density},$$

where $\Delta t=30$ s and the density is assumed to be that of water, 1 kg/L. To the resulting flow rate time series Q(t), the function $$Q_0 / \left[1 + \exp\left(\frac{t+T}{\tau/2}\right)\right]$$

was fitted which yields the measurement of the time until clogging (corresponding to the time at which the flow rate declined to 50% of its baseline value $Q_0$).

Figure 4:
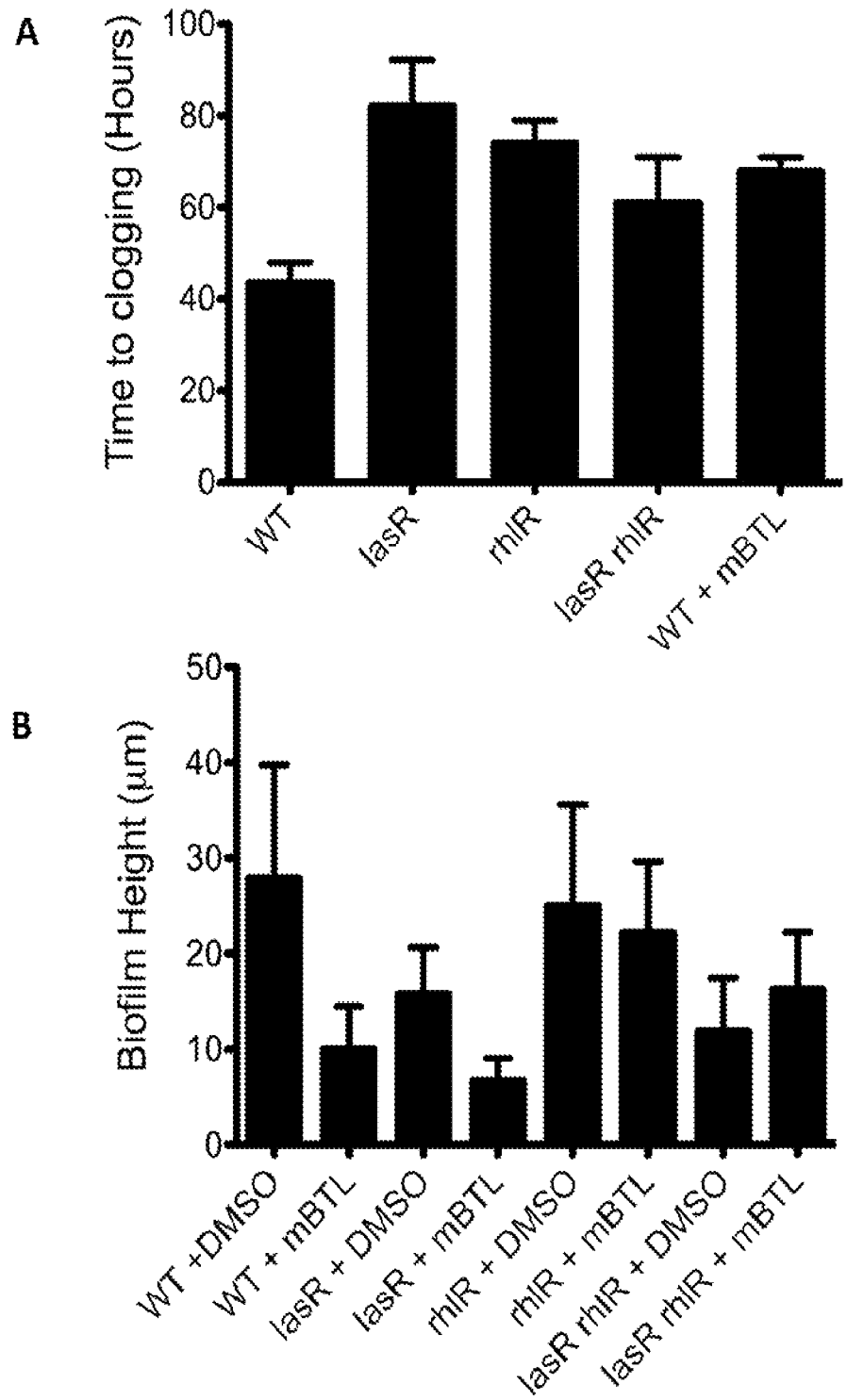
FIG. 4. mBTL inhibits quorum-sensing-regulated clogging of microfludic chambers and biofilm formation in static cultures. A. Time to clogging was measured for the designated P. aeruginosa PA14 strains and for the WT in the presence of 100 μM mBTL. Error bars represent S.D. of six replicates. B. Biofilms were grown in static cultures at the base of a glass-bottom microtiter plate in the presence or absence of 100 μM mBTL. Biofilm thickness was measured using confocal microscopy. Error bars indicate S.D. of 5-8 biological replicates.

Results. Beyond being a clinically-relevant pathogen, P. aeruginosa is an industrial and medical nuisance because it causes blockages in filtration devices and stents. P. aeruginosa PA14 also clogs microfluidic chambers that model such devices. Clogging is due to biofilms that produce exopolysaccharide-containing streamers that act as sieves to catch passing cells. Compared to wild-type, lasR and rhlR single and double null mutants exhibit dramatically delayed clogging, demonstrating that quorum sensing is required to form blockages (FIG. 4a). In the presence of 100 µm mBTL, wild-type P. aeruginosa PA14 exhibits a phenotype indistinguishable from the mutants (FIG. 4a).

The results showing that mBTL prevents biofilm formation and clogging in microfluidic devices (FIG. 4) suggest that, in addition to the implications of mBTL as an anti-infective, deploying anti-quorum-sensing molecules could prevent the failure of devices that are prone to fouling by biofilms.

Static culture. Methods. Overnight P. aeruginosa cultures were back-diluted 1:1000 into tryptone broth with 100 µM mBTL, or an equivalent concentration of DMSO, and grown to mid-logarithmic phase ($OD_{600}=0.5$). A 96-well plate with glass bottom (Thermo Fisher), which was filled with 200 µL of tryptone broth containing 100 µM mBTL or DMSO, was then inoculated with 2 µL of the mid-logarithmic culture. The 96-well plates were incubated for 24 h, prior to adding 5 µM SYTO 9 nucleic acid stain (Invitrogen). Biofilm thickness was measured using confocal microscopy (Nikon).

Results. The ability of mBTL to influence static biofilm formation in P. aeruginosa PA14 was examined. Wild-type P. aeruginosa PA14 forms biofilms with an average height of 27.5+/−11.5 µm (FIG. 4b). Treatment of wild-type with 100 µM mBTL results in a decrease in the average height to 10+/−4 µm (FIG. 4b). Treatment of the lasR null strain with mBTL also decreases the average height of the biofilm (15.7+/−4.9 µm to 6.6+/−2.3 µm). However, treatment of the rhlR null strain (25+/−10.6 µm untreated vs. 22.1+/−7.5 µm treated) or the lasR, rhlR double null strain (11.9+/−5.5 µm untreated vs. 16.2+/−5.9 µm treated) did not influence the height of the biofilm, indicating that the action of mBTL relies on the presence of RhlR (FIG. 4b). Taken together these findings show that mBTL inhibits quorum-sensing-controlled biofilm formation in P. aeruginosa PA14.

EXAMPLE 13

Synthetic Compounds Evolved from mBTL

Methods. Synthesis of the compounds is described in Example 14. The pyocyanin production assay is described in Example 3.

Results. mBTL contains a four-carbon linker (FIG. 1a). Synthesis and testing was performed of mBTL derivatives with two- to six-carbon linkers, and lactone versions of mBTL harboring four- or six-carbon linkers, containing or lacking a 3-oxo-moiety. Of the thiolactone derivatives of mBTL, C5-mBTL was the most effective inhibitor of pyocyanin production. Of the lactone derivatives of mBTL, C4-mBL was the most effective inhibitor of pyocyanin production. None of these compounds exhibited increased potency over mBTL (FIG. 7a, c, d). Thus, mBTL remains the most potent in vivo inhibitor in our collection.

EXAMPLE 14

Synthetic Chemistry General Procedures

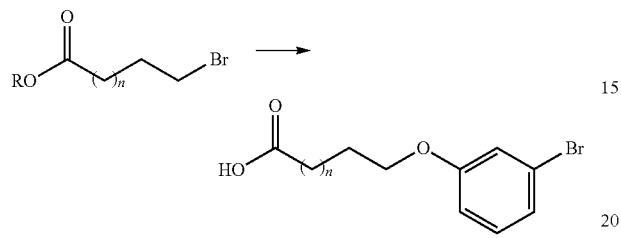

General Procedure A. Synthesis of acids: To a flame-dried flask was added the 3-bromophenol (1.0 equiv), the appropriate bromo-ester (1.0 equiv), potassium carbonate (1.2 equiv), and DMF (0.50 M). The reaction was stirred for 3 d or until complete by TLC. After completion, $H_2O$ was added, and the aqueous layer was extracted 3× with $Et_2O$. The combined organic layer was washed 3× with $H_2O$ and 1× with 1 M NaOH. The solution was dried over $Na_2SO_4$, filtered, and concentrated. The product was purified by column chromatography to remove excess 3-bromophenol if necessary. The resulting ester (1.0 equiv) was added to a solution of sodium hydroxide (5.0 equiv) in 3:1 $THF/H_2O$ (0.30 M). The reaction was heated to 65° C. for 12 hr, or until complete by TLC. The reaction was cooled and acidified with 1 M HCl. The aqueous layer was extracted 3× with EtOAc. The combined organic layer was washed with brine, dried over $Na_2SO_4$, filtered, and concentrated. The product was carried forward crude.

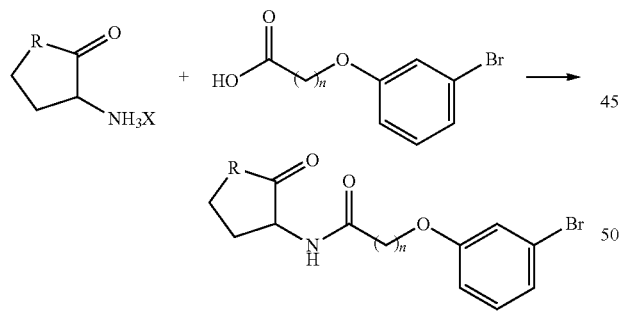

General Procedure B. Synthesis of amides: To a flame-dried flask were added the acid (1.0 equiv), N-(3-dimethylaminopropyl)-N'-ethylcarbodiimide hydrochloride (1.1 equiv), 1-hydroxybenzotriazole (0.25 equiv), triethylamine (2.2 equiv), the appropriate (thio)lactone (1.0 equiv), and $CH_2Cl_2$ (0.10 M). After the mixture was stirred at room temperature for 24 hr, $H_2O$ was added, and the aqueous layer was extracted 3× with EtOAc. The combined organic layer was washed sequentially with 1 M $NaHSO_4$, saturated aqueous $NaHCO_3$, and brine. The solution was dried over $Na_2SO_4$, filtered, and concentrated. The crude product was purified by column chromatography with a hexanes/EtOAc gradient.

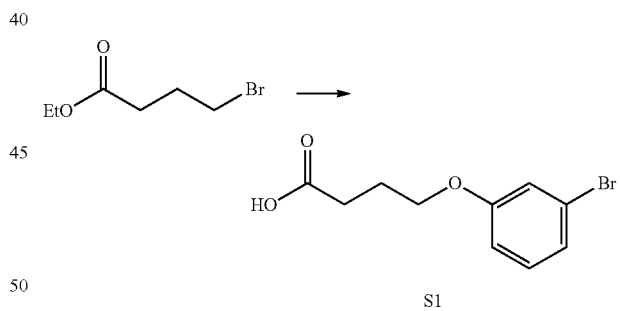

General Procedure C. Synthesis of β-keto amides: The acid (1.0 equiv) was combined with $CH_2Cl_2$ (0.5 M) and cooled to 0° C. N,N-dicyclohexylcarbodiimide (1.0 equiv) was added, and the reaction was stirred at 0° C. for 30 min. Meldrum's acid (1.0 equiv) and 4-(dimethylamino)pyridine (1.0 equiv) were added, and the reaction mixture was stirred at room temperature overnight. The solution was filtered through a Celite plug and concentrated. The residue was dissolved in $CH_3CN$ (0.10 M). After L-homoserine lactone hydrobromide (1.0 equiv) and trifluoroacetic acid (1.0 equiv) were added, the reaction was heated to 65° C. for 4 hr. The reaction mixture was cooled, diluted with EtOAc, and washed sequentially with 1 M $NaHSO_4$, saturated aqueous $NaHCO_3$, and brine. The solution was dried over $Na_2SO_4$, filtered, and concentrated. The crude product was purified by column chromatography with a hexanes/EtOAc gradient.

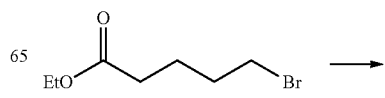

S1

C4 acid (S1): Prepared from ethyl 4-bromobutyrate using general procedure A to give S1 in 90% yield over two steps. $^1$H NMR (500 MHz, $CDCl_3$) δ 7.16-7.01 (m, 3H), 6.84-6.79 (m, 1H), 4.00 (t, J=6.0 Hz, 2H), 2.59 (t, J=7.2 Hz, 2H), 2.16-2.08 (m, 2H); $^{13}$C NMR (125 MHz, $CDCl_3$) δ 179.1, 159.4, 130.5, 123.9, 122.8, 117.6, 113.4, 66.6, 30.4, 24.2; HRMS (ESI-TOF) calculated for $C_{10}H_{12}BrO_3$ [M+H]$^+$: m/z 258.9971, found 258.9967.

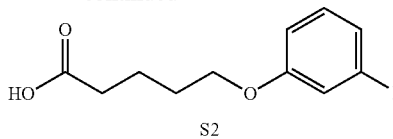

S2

C5 acid (S2): Prepared from ethyl 5-bromovalerate using general procedure A to give S2 in 93% yield over two steps. $^1$H NMR (500 MHz, CDCl$_3$) δ 7.18-7.01 (m, 3H), 6.85-6.77 (m, 1H), 3.96 (t, J=5.6 Hz, 2H), 2.50-2.41 (m, 2H), 1.89-1.80 (m, 4H); $^{13}$C NMR (125 MHz, CDCl$_3$) δ 178.6, 159.6, 130.5, 123.7, 122.8, 117.6, 113.5, 67.5, 33.4, 28.4, 21.3; HRMS (ESI-TOF) calculated for C$_{11}$H$_{14}$BrO$_3$ [M+H]$^+$: m/z 273.0127. found 273.0135.

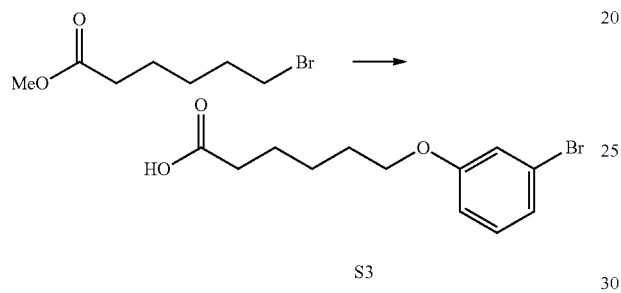

S3

C6 acid (S3): Prepared from methyl 6-bromohexanoate using general procedure A to give S3 in 80% yield over two steps. $^1$H NMR (500 MHz, CDCl$_3$) δ 7.16-7.01 (m, 3H), 6.85-6.78 (m, 1H), 3.94 (t, J=6.4 Hz, 2H), 2.40 (t, J=7.4 Hz, 2H), 1.84-1.76 (m, 2H), 1.76-1.67 (m, 2H), 1.60-1.49 (m, 2H); $^{13}$C NMR (125 MHz, CDCl$_3$) δ 179.0, 159.7, 130.5, 123.6, 122.8, 117.6, 113.5, 67.8, 33.7, 28.8, 25.5, 24.3; HRMS (ESI-TOF) calculated for C$_{12}$H$_{16}$BrO$_3$ [M+H]$^+$: m/z 287.0283. found 287.0277.

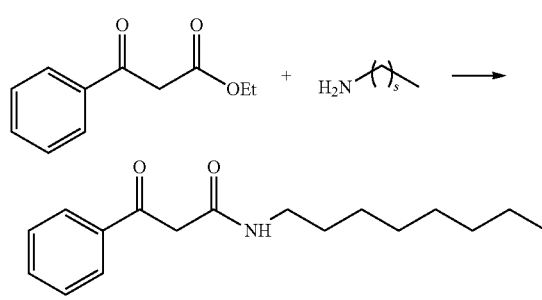

V-06-018

V-06-018: Ethyl benzylacetate (0.10 mL, 0.58 mmol, 1.0 equiv) was combined with ethanol (5.8 mL, 10 M). Nonylamine (0.11 mL, 0.58 mmol, 1.0 equiv) was added dropwise, and the mixture was heated to reflux for 6 hr. The reaction mixture was concentrated, and the residue was dissolved in EtOAc. The solution was washed sequentially 2× with 1 M HCl, 1× with brine, then dried over Na$_2$SO$_4$, filtered, and concentrated. The crude material was purified by column chromatography (hexanes/EtOAc gradient) to afford 8.3 mg of V-06-018 in a 5.0% yield. $^1$H NMR (500 MHz, CDCl$_3$) δ 8.00 (d, J=7.5 Hz, 2H), 7.62 (t, J=7.4 Hz, 1H), 7.50 (t, J=7.8 Hz, 2H), 7.15 (s, 1H), 3.95 (s, 2H), 3.31-3.27 (m, 2H), 1.55-1.50 (m, 2H), 1.38-1.17 (m, 12H), 0.87 (t, J=6.9 Hz, 3H); $^{13}$C NMR (125 MHz, CDCl$_3$) δ 196.4, 165.5, 136.1, 134.1, 128.9, 128.6, 45.2, 39.7, 31.8, 29.5, 29.4, 29.2, 29.2, 26.9, 22.7, 14.1; HRMS (ESI-TOF) calculated for C$_{18}$H$_{28}$NO$_2$ [M+H]$^+$: m/z 290.2120. found 290.2120.

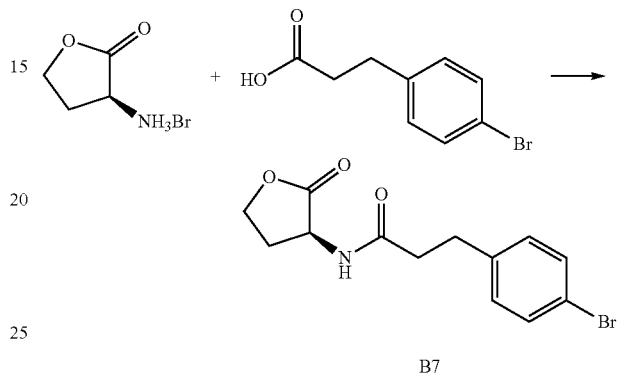

B7

B7: Prepared with L-homoserine lactone and 3-(4-bromophenyl)propionic acid using general procedure B to give B7 in a 52% yield. The spectral data agreed with that reported for B7 (17). $^1$H NMR (500 MHz, CDCl$_3$) δ 7.41 (d, J=8.3 Hz, 2H), 7.07 (t, J=9.1 Hz, 2H), 5.86 (s, 1H), 4.57-4.41 (m, 2H), 4.30-4.25 (m, 1H), 2.93 (t, J=7.5 Hz, 2H), 2.89-2.78 (m, 1H), 2.61-2.43 (m, 2H), 2.09-2.00 (m, 1H).; $^{13}$C NMR (125 MHz, CDCl$_3$) δ 175.2, 172.2, 139.3, 131.6, 130.1, 120.2, 66.1, 49.3, 37.5, 30.6, 30.6; HRMS (ESI-TOF) calculated for C$_{13}$H$_{15}$BrNO$_3$ [M+H]$^+$: m/z 312.0236. found 312.0239.

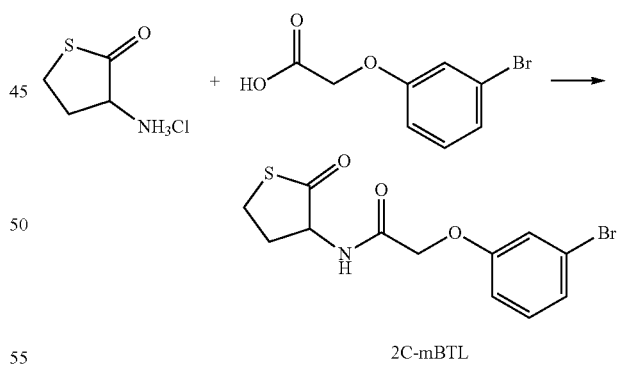

2C-mBTL 2C-mBTL: Prepared with homocysteine thiolactone hydrochloride and (3-bromophenoxy)acetic acid using general procedure B to give 2C-mBTL in a 50% yield. $^1$H NMR (500 MHz, CDCl$_3$) δ 7.22-7.09 (m, 3H), 6.95 (s, 1H), 6.89-6.84 (m, 1H), 4.68-4.58 (m, 1H), 4.57-4.46 (m, 2H), 3.44-3.35 (m, 1H), 3.34-3.26 (m, 1H), 3.00-2.91 (m, 1H), 2.08-1.95 (m, 1H); $^{13}$C NMR (125 MHz, CDCl$_3$) δ 204.6, 168.1, 157.5, 130.9, 125.5, 123.0, 118.3, 113.4, 67.2, 58.9, 31.6, 27.5; HRMS (ESI-TOF) calculated for C$_{12}$H$_{13}$BrNO$_3$S [M+H]$^+$: m/z 329.9800. found 329.9830.

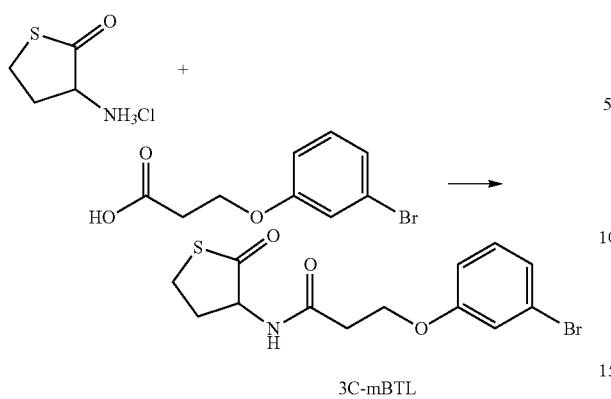

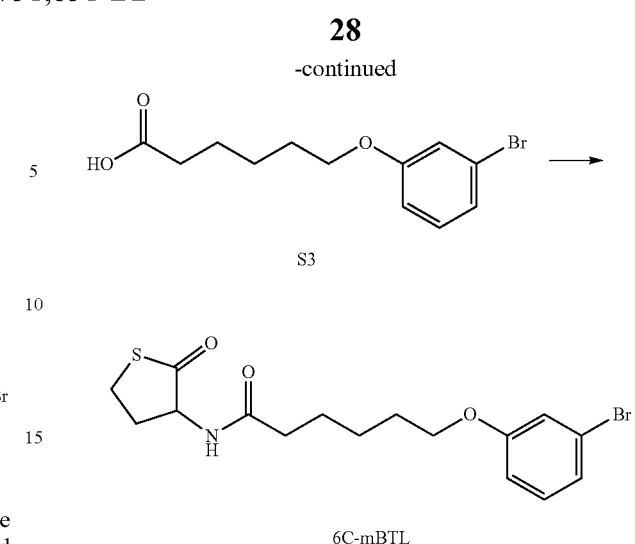

3C-mBTL: Prepared with homocysteine thiolactone hydrochloride and 3-(3-bromo-phenoxy)-propionic acid using general procedure B to give 3C-mBTL in a 42% yield. $^1$H NMR (500 MHz, CDCl$_3$) δ 7.21-7.07 (m, 3H), 6.90-6.84 (m, 1H), 6.32 (s, 1H), 4.57-4.49 (m, 1H), 4.30-4.21 (m, 2H), 3.43-3.33 (m, 1H), 3.32-3.24 (m, 1H), 3.04-2.96 (m, 1H), 2.80-2.67 (m, 2H), 2.01-1.87 (m, 1H); $^{13}$C NMR (125 MHz, CDCl$_3$) δ 205.3, 170.7, 158.9, 130.6, 124.4, 122.8, 117.9, 113.6, 64.0, 59.6, 36.2, 32.0, 27.7; HRMS (ESI-TOF) calculated for C$_{13}$H$_{15}$BrNO$_3$S [M+H]$^+$: m/z 343.9956. found 343.9984.

6C-mBTL: Prepared with homocysteine thiolactone hydrochloride and S3 using general procedure B to give 6C-mBTL in a 74% yield. $^1$H NMR (500 MHz, CDCl$_3$) δ 7.16-7.00 (m, 3H), 6.85-6.76 (m, 1H), 5.89 (s, 1H), 4.57-4.45 (m, 1H), 3.93 (t, J=6.4 Hz, 2H), 3.41-3.31 (m, 1H), 3.30-3.20 (m, 1H), 3.03-2.91 (m, 1H), 2.35-2.21 (m, 2H), 1.98-1.83 (m, 1H), 1.83-1.66 (m, 4H), 1.54-1.44 (m, 2H); $^{13}$C NMR (125 MHz, CDCl$_3$) δ 205.7, 173.3, 159.7, 130.5, 123.6, 122.7, 117.6, 113.4, 67.8, 59.5, 36.2, 32.1, 28.8, 27.6, 25.6, 25.1; HRMS (ESI-TOF) calculated for C$_{16}$H$_{21}$BrNO$_3$S [M+H]$^+$: m/z 386.0426. found 386.0427.

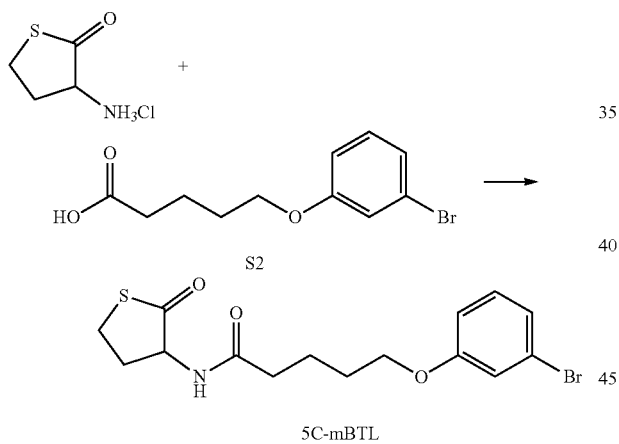

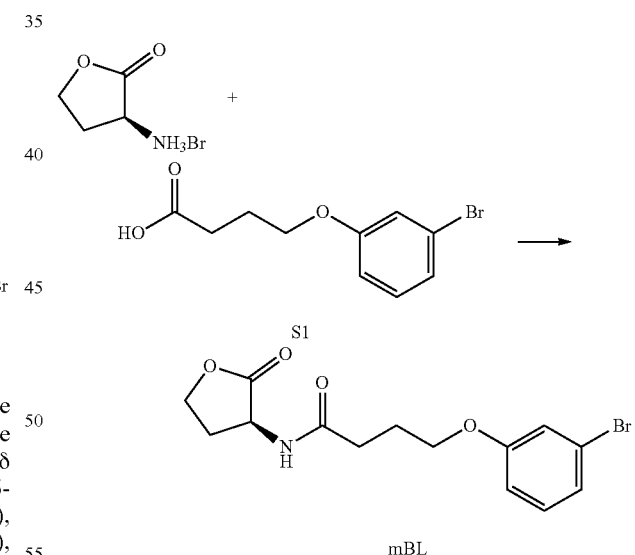

5C-mBTL: Prepared with homocysteine thiolactone hydrochloride and S2 using general procedure B to give 5C-mBTL in a 68% yield. $^1$H NMR (500 MHz, CDCl$_3$) δ 7.16-6.99 (m, 3H), 6.85-6.77 (m, 1H), 5.91 (s, 1H), 4.56-4.46 (m, 1H), 3.95 (t, J=5.5 Hz, 2H), 3.42-3.31 (m, 1H), 3.30-3.22 (m, 1H), 3.01-2.90 (m, 1H), 2.37-2.29 (m, 2H), 1.97-1.78 (m, 5H); $^{13}$C NMR (125 MHz, CDCl$_3$) δ 205.6, 173.0, 159.6, 130.5, 123.7, 122.8, 117.6, 113.4, 67.6, 59.5, 35.8, 32.1, 28.5, 27.6, 22.1; HRMS (ESI-TOF) calculated for C$_{15}$H$_{19}$BrNO$_3$S [M+H]$^+$: m/z 372.0269. found 372.0300.

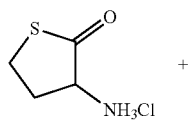

mBL: Prepared with L-homoserine lactone hydrobromide and S1 using general procedure B to give mBL in a 62% yield. $^1$H NMR (500 MHz, CDCl$_3$) δ 7.14-6.98 (m, 3H), 6.83-6.76 (m, 1H), 5.98 (s, 1H), 4.56-4.47 (m, 1H), 4.44 (t, J=9.0 Hz, 1H), 4.30-4.21 (m, 1H), 3.97 (t, J=5.9 Hz, 2H), 2.87-2.78 (m, 1H), 2.44 (t, J=6.8 Hz, 2H), 2.17-2.02 (m, 3H); $^{13}$C NMR (125 MHz, CDCl$_3$) δ 175.3, 172.7, 159.5, 130.6, 123.9, 122.8, 117.7, 113.4, 66.9, 66.1, 49.3, 32.2, 30.6, 24.7; HRMS (ESI-TOF) calculated for C$_{14}$H$_{17}$BrNO$_4$ [M+H]$^+$: m/z 342.0341. found 342.0345.

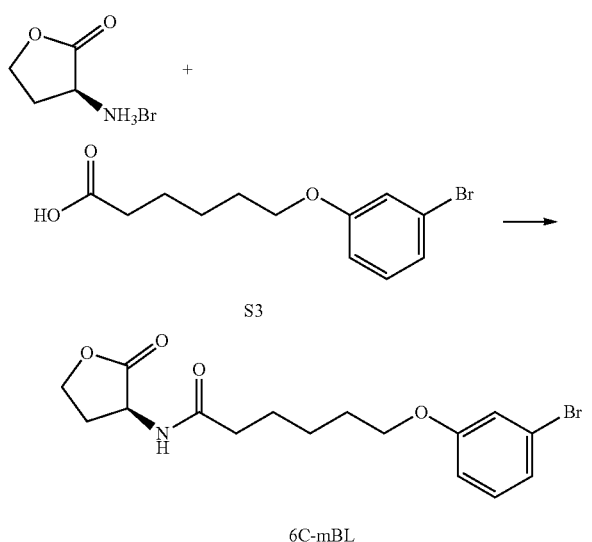

S3

6C-mBL

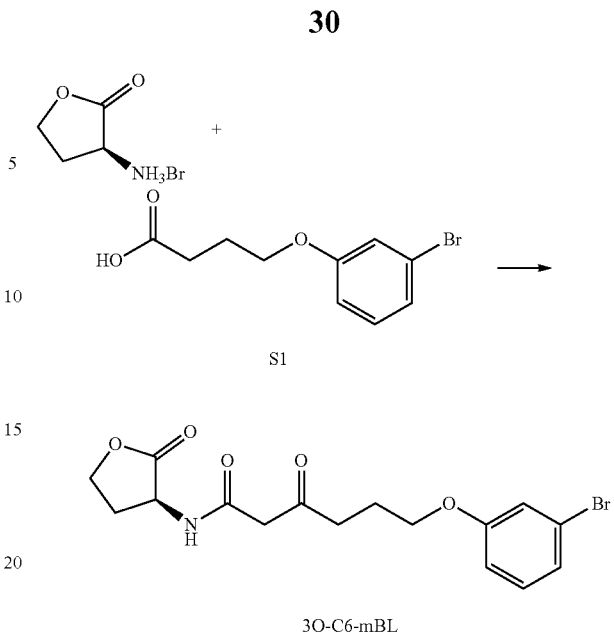

S1

3O-C6-mBL

C6-mBL: Prepared with L-homoserine lactone hydrobromide and S3 using general procedure B to give C6-mBL in a 61% yield. $^1$H NMR (500 MHz, CDCl$_3$) δ 7.17-7.01 (m, 3H), 6.85-6.77 (m, 1H), 5.95 (s, 1H), 4.59-4.50 (m, 1H), 4.48 (t, J=9.0 Hz, 1H), 4.34-4.25 (m, 1H), 3.93 (t, J=6.3 Hz, 2H), 2.93-2.82 (m, 1H), 2.35-2.23 (m, 2H), 2.19-2.06 (m, 1H), 1.86-1.68 (m, 4H), 1.55-1.46 (m, 2H); $^{13}$C NMR (125 MHz, CDCl$_3$) δ 175.4, 173.3, 159.7, 130.5, 123.6, 122.8, 117.6, 113.4, 67.7, 66.1, 49.3, 36.0, 30.7, 28.8, 25.6, 25.0; HRMS (ESI-TOF) calculated for C$_{16}$H$_{21}$BrNO$_4$ [M+H]$^+$: m/z 370.0654. found 370.0666.

3O—C6-mBL: Prepared with L-homoserine lactone hydrobromide and S1 using general procedure C to give 3O-C6-mBL in a 34% yield. $^1$H NMR (500 MHz, CDCl$_3$) δ 7.59 (s, 1H), 7.18-6.99 (m, 3H), 6.85-6.76 (m, 1H), 4.63-4.55 (m, 1H), 4.48 (t, J=8.6 Hz, 1H), 4.32-4.23 (m, 1H), 3.96 (t, J=5.9 Hz, 2H), 3.51 (s, 2H), 2.83-2.70 (m, 3H), 2.23-2.15 (m, 1H), 2.14-2.02 (m, 2H); $^{13}$C NMR (125 MHz, CDCl$_3$) δ 205.6, 174.7, 166.1, 159.3, 130.6, 124.0, 122.8, 117.6, 113.4, 66.6, 65.9, 49.1, 48.2, 40.1, 29.9, 22.9; HRMS (ESI-TOF) calculated for C$_{16}$H$_{19}$BrNO$_5$ [M+H]$^+$: m/z 384.0447. found 384.0455.

Chiral Resolution of mBTL: mBTL enantiomers were resolved using a Berger Multigram II SFC system equipped with two Varian SD-1 pumps, a Knauer K-2501 multi-wavelength detector set at 220 nm, a Knauer K-1900 pump, a Vatran SGP-50-100 condenser, and using a Chiralpak IC (2×15 cm) column. An isocratic method using a mixture of 30% MeOH/CO$_2$ (100 bar) at 60 mL/min was employed. The two peaks eluted at 1.66 min and 2.13 min. The identity of the enantiomers was determined through comparison of the HPLC trace with that of authentic (S)-mBTL synthesized from L-homocysteine thiolactone hydrochloride. Based on this analysis, peak 1 (>99:1 er) is (S)-mBTL and peak 2 (>99:1 er) is (R)-mBTL.

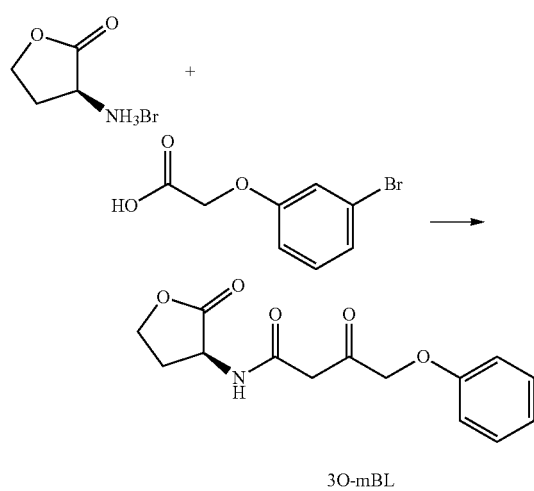

3O-mBL 3O-mBL: Prepared with L-homoserine lactone hydrobromide and (3-bromophenoxy)acetic acid using general procedure C to give 3O-mBL in a 46% yield. $^1$H NMR (500 MHz, CDCl$_3$) δ 7.20-7.03 (m, 3H), 6.87-6.80 (m, 1H), 4.68 (s, 2H), 4.64-4.56 (m, 1H), 4.48 (t, J=8.9 Hz, 1H), 4.35-4.24 (m, 1H), 3.66 (s, 2H), 2.93-2.88 (m, 1H), 2.81-2.75 (m, 1H), 2.29-2.15 (m, 1H); $^{13}$C NMR (125 MHz, CDCl$_3$) δ 201.7, 174.8, 165.6, 157.9, 130.9, 125.3, 123.0, 118.0, 113.3, 72.6, 66.0, 49.3, 45.5, 29.9; HRMS (ESI-TOF) calculated for C$_{14}$H$_{15}$BrNO$_5$ [M+H]$^+$: m/z 356.0134. found 356.0127.

REFERENCES

1. Müh U, Schuster, M., Heim, R., Singh, A., Olson, E. R., Greenberg, E. P. (2006) Novel *Pseudomonas aeruginosa* Quorum-Sensing Inhibitors Identified in an Ultra-High-Throughput Screen. *Antimicrobial Agents and Chemotherapy* 50(11):3674-3679.
2. Geske G D, O'Neill, Jennifer C., Miller, David M., Mattmann, Margrith E., Blackwell, Helen E. (2007) Modulation of Bacterial Quorum Sensing with Synthetic Ligands: Systematic Evaluation of N-Acylated Homoserine Lactones in Multiple Species and New Insights into Their Mechanisms of Action. *Journal of the American Chemical Society* 129(44):13613-13625.

3. Amara N, et. al. (2009) Covalent Inhibition of Bacterial Quorum Sensing. *Journal of the American Chemical Society* 131(30):10610-10619.

4. Swem L R, Swem, D. L., O'Loughlin, C. T., Gatmaitan, R., Zhao, B., Ulrich, S. M., et. al. (2009) A Quorum-Sensing Antagonist Targets Both Membrane-Bound and Cytoplasmic Receptors and Controls Bacterial Pathogenicity. *Molecular Cell* 35(2):143-153.

5. Morkunas B, Galloway, Warren R. J. D., Wright, Megan, Ibbeson, Brett M., Hodgkinson, James T., O'Connell, Kieron M. G., et. al. (2012) Inhibition of the production of the *Pseudomonas aeruginosa* virulence factor pyocyanin in wild-type cells by quorum sensing autoinducer-mimics *Organic & Biomolecular Chemistry* 10(42): 8452-8464.

EXAMPLE 15

Synthesis of Surrogate Head Groups with 3OC12 Tail

Figure 13:
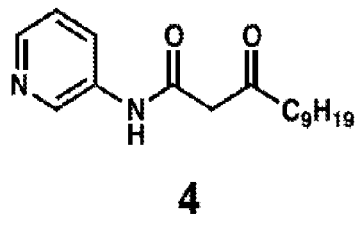
FIG. 13. Library design and representative examples.
Figure 13:
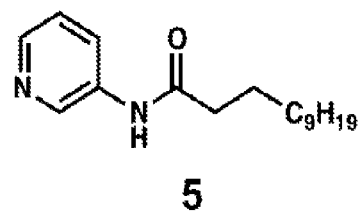
Figure 13:
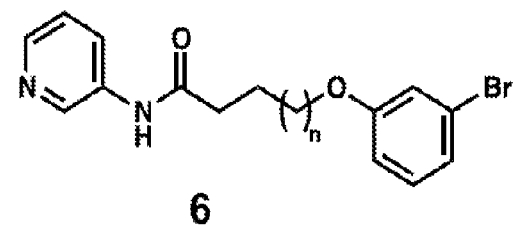

The initial investigation focused on the binding of surrogate head groups using the native 3OC12 tail of the LasR signal or a simplified C12 tail (e.g., 4-5, FIG. 13) to evaluate the effectiveness of the head group as a replacement for the HSL. In principle, any head group that binds LasR is of interest, even if the compound were an agonist.

Based on previous work, the working hypothesis was that the addition of the appropriately functionalized tail could transform an agonist into an antagonist. Nonetheless, a new head group structure with inherent antagonistic activity is particularly interesting. Hits from the initial head group study are then combined with a functionalized tail to form hybrid analogs (e.g., 6, FIG. 13) that are designed to have higher potency as antagonists and better stability in vivo.

Figure 14:
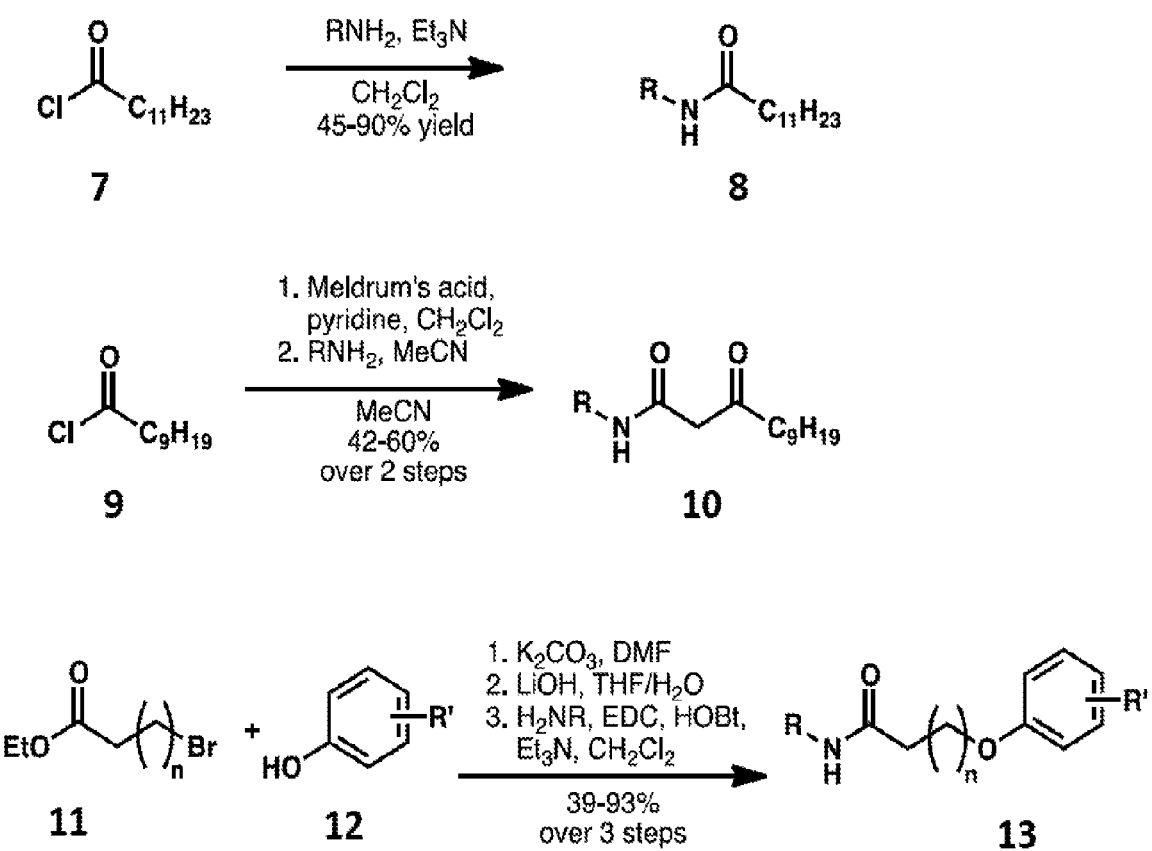
FIG. 14. Synthesis of head group library and hybrid library.

For the first library, acylation of an amino-heterocycle furnished the C12 tail analogs (8, FIG. 14). To install the β-ketoamide of the 3OC12 tail, the Meldrum's acid adduct was first made and then an amino-heterocycle was added to furnish 10. Hybrids (13) were generally synthesized via an $S_N2$ displacement of an alkyl halide with a phenol to incorporate the tail functionality and an amide formation to append the head group.

EXAMPLE 16

Bioassay of Compounds of the First Library

The compounds of the first library were assayed in wild-type (WT) *P. aeruginosa* PA14. Pyocyanin was used as a read-out for quorum sensing activity based on its absorbance at 695 nm. The efficacy of the compounds at reducing pyocyanin levels was calculated with respect to WT levels of pyocyanin, where WT levels of pyocyanin would lead to a 0% efficacy, and an absorbance equal to the background medium would lead to a 100% efficacy. Agonists that increase pyocyanin production have negative efficacy values. The growth of *P. aeruginosa* was also monitored by absorbance at 600 nm in the presence of the compounds to ensure that the potential inhibitors did not impact growth.

Figure 12:
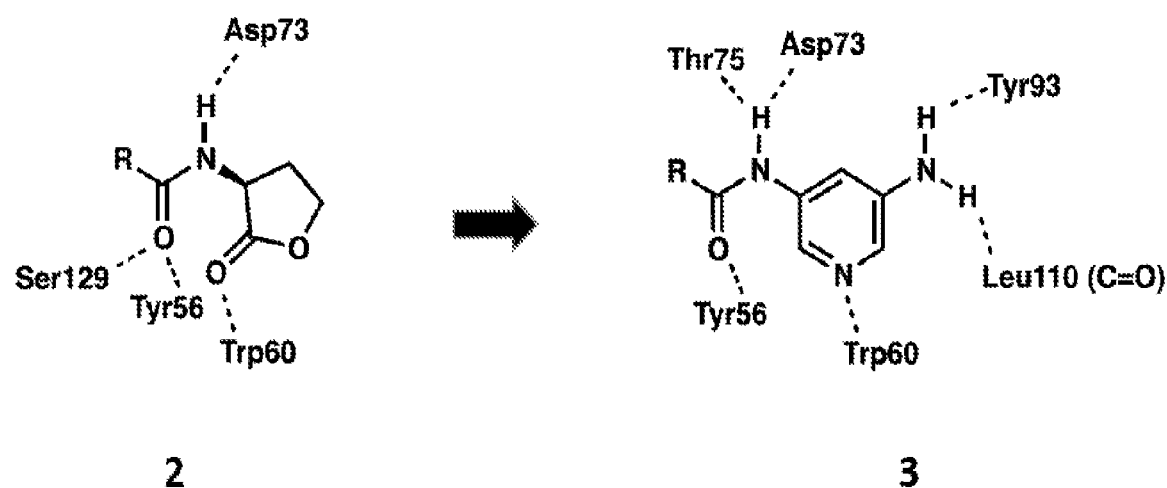
FIG. 12. Key interactions of the homoserine lactone with LasR and modeled interactions of 3 with LasR.

Since the modeled interactions of compound 3 were promising (FIG. 12), it was followed by a systematic examination of a series of pyridine, pyrimidine and pyrazine head groups with a 3OC12 or C12 tail (entries 1-6, 7-12, respectively; Table 1). The 4-aminopyridine (entry 3) and 4-aminopyrimidine (entry 4) were the most active compounds. The 2-aminopyridine (entry 1) was a less effective inhibitor, suggesting that the nitrogen in the heterocycle para to the amine is key to activity and a second nitrogen in the ortho-position is also tolerated.

TABLE 1

Pyridine, pyrimidine, and pyrazine head groups.

| Entry | Substrate | Efficacy (%) |
|---|---|---|
| 1 | [2-pyridyl-NH-C(O)-CH2-C(O)-C9H19] | 44 ± 13 |
| 2 | [3-pyridyl-NH-C(O)-CH2-C(O)-C9H19] | 10 ± 9 |
| 3 | [4-pyridyl-NH-C(O)-CH2-C(O)-C9H19] | 63 ± 2 |
| 4 | [4-pyrimidinyl-NH-C(O)-CH2-C(O)-C9H19] | 64 ± 0.8 |
| 5 | [2-pyrazinyl-NH-C(O)-CH2-C(O)-C9H19] | 21 ± 13 |
| 6 | [2-pyrimidinyl-NH-C(O)-CH2-C(O)-C9H19] | −0.51 ± 4 |
| 7 | [2-pyridyl-NH-C(O)-CH2-CH2-C9H19] | 55 ± 3 |
| 8 | [3-pyridyl-NH-C(O)-CH2-CH2-C9H19] | 34 ± 3 |
| 9 | [4-pyridyl-NH-C(O)-CH2-CH2-C9H19] | 28 ± 11 |
| 10 | [4-pyrimidinyl-NH-C(O)-CH2-CH2-C9H19] | 55 ± 8 |
| 11 | [2-pyrazinyl-NH-C(O)-CH2-CH2-C9H19] | −38 ± 3 |

TABLE 1-continued

Pyridine, pyrimidine, and pyrazine head groups.

| Entry | Substrate | Efficacy (%) |
|---|---|---|
| 12 | 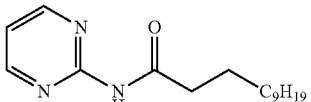 | 23 ± 3 |

EXAMPLE 17

Bioassay of Aminopyridine and other Head Group Compounds

The 4-aminopyridine scaffold was further explored, incorporating a variety of substituents about the pyridine ring (e.g., entries 1-10, Table 2). The exploration included related pyridines (entries 11-14), as well as indole and benzofuran motifs (entries 15-23). Most analogs were less effective than the parent 4-aminopyridine. However, the incorporation of a fluoride at the 2-position along with the removal of the ketone in the tail led to a compound that decreased pyocyanin levels by 70% (entry 7).

TABLE 2

4-Aminopyridine and other head groups

| Entry | Substrate | Efficacy (%) |
|---|---|---|
| 1 | 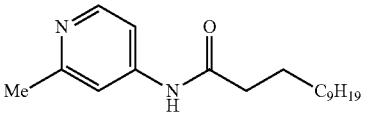 | −19 ± 3 |
| 2 | 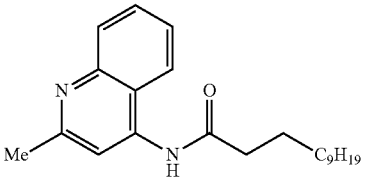 | −24 ± 2 |
| 3 | 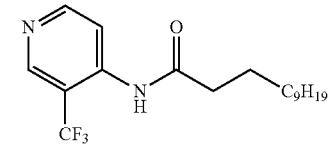 | −17 ± 2 |
| 4 | 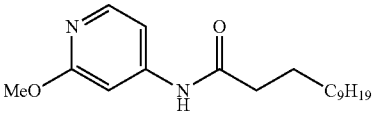 | −5.1 ± 1 |
| 5 | 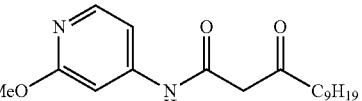 | 24 ± 1 |
| 6 | 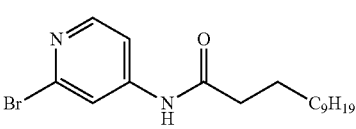 | 34 ± 5 |
| 7 | 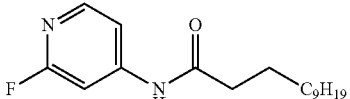 | 70 ± 2 |
| 8 | 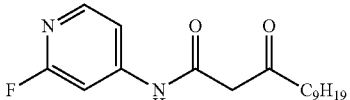 | −8.5 ± 3 |
| 9 | 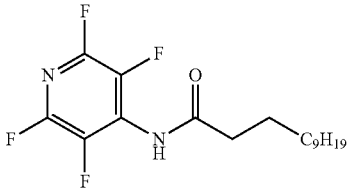 | −12 ± 3 |
| 10 | 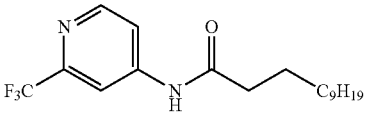 | 27 ± 3 |
| 11 | 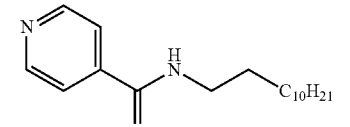 | 13 ± 3 |
| 12 | 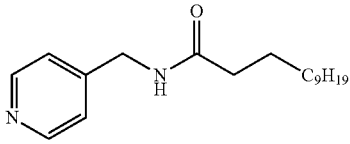 | 7.7 ± 5 |
| 13 | 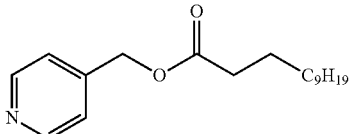 | −15 ± 4 |
| 14 | 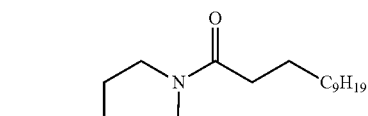 | −42 ± 2 |
| 15 |  | −11 ± 3 |

TABLE 2-continued

4-Aminopyridine and other head groups

| Entry | Substrate | Efficacy (%) |
|---|---|---|
| 16 | 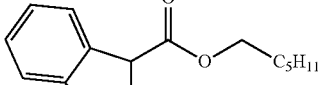 | 1.5 ± 8 |
| 17 | 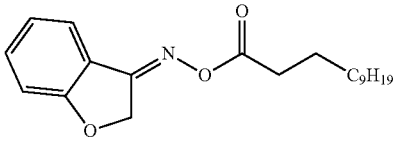 | 12 ± 3 |
| 18 | 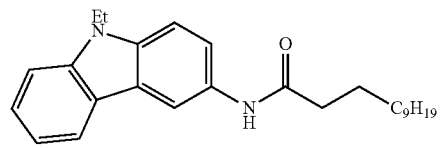 | −1.0 ± 3 |
| 19 | 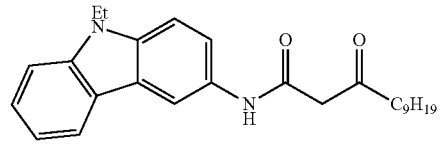 | 9.3 ± 4 |
| 20 | 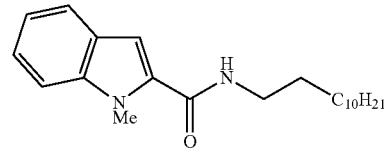 | −9.2 ± 4 |
| 21 | 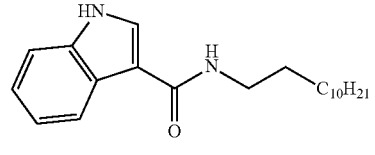 | 4.4 ± 3 |
| 22 | 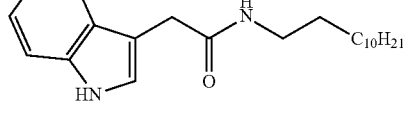 | 0.60 ± 4 |
| 23 | 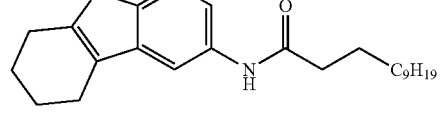 | 6.1 ± 4 |

EXAMPLE 18

Bioassay of Head Group/Tail Group Hybrids

The next library of compounds (Table 3) encompassed an initial study of the combination of 4-aminopyridine head group analogs with the 3-bromophenol tail group from previously identified inhibitor 1, examining two linker lengths (entries 1-5, 7, Table 3). For this initial set of hybrid compounds, a methoxy group in the 2-position of the head group along with the longer linker was the most effective, reducing pyocyanin levels by 73% (entry 7). A subsequent set of compounds allowed more extensive study of the importance of the linker (entries 5-10). The four-methylene linker is the most active (81%, entry 6). Increasing to a 5- or 6-methylene linker drops the activity to 73-75% (entries 7 and 9), and an additional methylene group leads to further deterioration of activity (60%, entry 10). The incorporation of a ketone at C3 in the linker also decreases activity to 40% (entry 7 vs. entry 8).

In the initial head group studies, the 4-aminopyrimidine was as efficacious as the 4-aminopyridine (Table 1, entries 3-4). This motif was revisited in the hybrid studies (entries 11-14, Table 3). The addition of a methoxy group to the 6-position increased activity (entry 11 vs. entry 12), but a methoxy group in the 2-position or a second methoxy group was not tolerated (entries 13-14). The best analog of this series had an efficacy of only 41% (entry 12), so further investigation returned to the 4-aminopyridine scaffold.

Other inductively withdrawing groups at the 2-position in the head group were more effective, with a chloride substituent (entry 15) affording 89% efficacy and a trifluoromethyl group (entry 18) effectively shutting down pyocyanin production completely (99% efficacy). Exploration of the importance of chain length on this potent analog (entries 16-19) revealed that the five-methylene linker was the most active (entry 18), followed by nearly equal activity with the four-methylene linker (95% efficacy, entry 17). The pyridine nitrogen is important for activity, as its removal led to a compound with only 62% efficacy (entry 20), and an additional trifluoromethyl group fails to rescue activity (44%, entry 21). While the electronics of the 2-position substituents are important, an analog with a simple methyl group is still fairly active (80%, entry 22). Moving the trifluoromethyl group to the 3-position was not tolerated, leading to a compound with only 15% efficacy (entry 23).

TABLE 3

Head group study of hybrids.

| Entry | Substrate | Efficacy (%) |
|---|---|---|
| 1 | 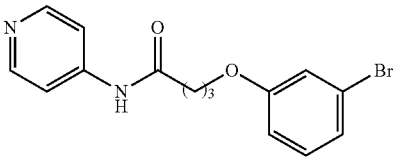 | 21 ± 5 |

TABLE 3-continued

Head group study of hybrids.

| Entry | Substrate | Efficacy (%) |
|---|---|---|
| 2 | 4-pyridyl-NH-C(O)-CH2-(CH2)5-O-(3-bromophenyl) | 53 ± 1 |
| 3 | 2-fluoro-4-pyridyl-NH-C(O)-CH2-(CH2)3-O-(3-bromophenyl) | 32 ± 4 |
| 4 | 2-fluoro-4-pyridyl-NH-C(O)-CH2-(CH2)5-O-(3-bromophenyl) | 31 ± 6 |
| 5 | 2-methoxy-4-pyridyl-NH-C(O)-CH2-(CH2)3-O-(3-bromophenyl) | 20 ± 1 |
| 6 | 2-methoxy-4-pyridyl-NH-C(O)-CH2-(CH2)4-O-(3-bromophenyl) | 81 ± 6 |
| 7 | 2-methoxy-4-pyridyl-NH-C(O)-CH2-(CH2)5-O-(3-bromophenyl) | 73 ± 2 |
| 8 | 2-methoxy-4-pyridyl-NH-C(O)-CH2-C(O)-(CH2)3-O-(3-bromophenyl) | 40 ± 6 |
| 9 | 2-methoxy-4-pyridyl-NH-C(O)-CH2-(CH2)6-O-(3-bromophenyl) | 75 ± 3 |
| 10 | 2-methoxy-4-pyridyl-NH-C(O)-CH2-(CH2)7-O-(3-bromophenyl) | 60 ± 2 |

TABLE 3-continued

Head group study of hybrids.

| Entry | Substrate | Efficacy (%) |
|---|---|---|
| 11 | pyrimidin-4-yl-NH-C(O)-(CH2)5-O-C6H4-Br (3-position) | 27 ± 7 |
| 12 | 6-MeO-pyrimidin-4-yl-NH-C(O)-(CH2)5-O-C6H4-Br | 41 ± 9 |
| 13 | 2-MeO-pyrimidin-4-yl-NH-C(O)-(CH2)5-O-C6H4-Br | 16 ± 5 |
| 14 | 2,6-diMeO-pyrimidin-4-yl-NH-C(O)-(CH2)5-O-C6H4-Br | 15 ± 7 |
| 15 | 2-Cl-pyridin-4-yl-NH-C(O)-(CH2)5-O-C6H4-Br | 89 ± 5 |
| 16 | 2-F3C-pyridin-4-yl-NH-C(O)-(CH2)3-O-C6H4-Br | 43 ± 8 |
| 17 | 2-F3C-pyridin-4-yl-NH-C(O)-(CH2)4-O-C6H4-Br | 95 ± 5 |
| 18 | 2-F3C-pyridin-4-yl-NH-C(O)-(CH2)5-O-C6H4-Br | 99 ± 0.3 |

TABLE 3-continued

Head group study of hybrids.

| Entry | Substrate | Efficacy (%) |
|-------|-----------|--------------|
| 19 | 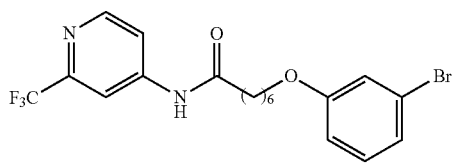 | 23 ± 7 |
| 20 | 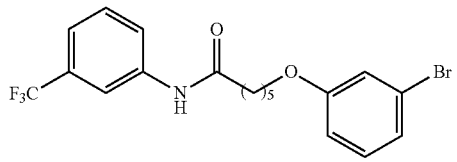 | 62 ± 6 |
| 21 | 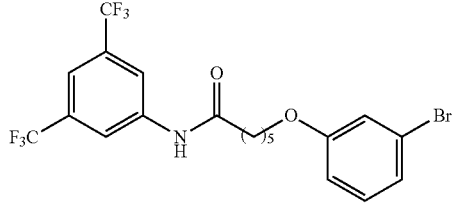 | 44 ± 8 |
| 22 | 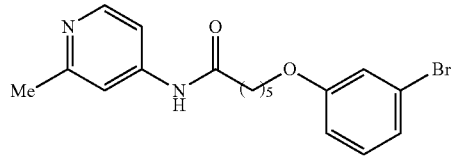 | 80 ± 8 |
| 23 | 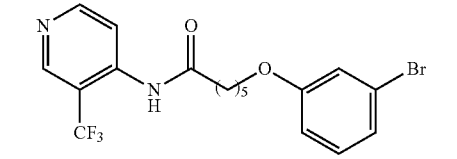 | 15 ± 7 |

EXAMPLE 19

Optimizing Tail Group for Trifluoromethylpyridine Head Group

Working with the 4-amino-2-trifluoromethylpyridine head group, optimization of the tail group was studied. Moving the bromide to the 2-position of the aryl tail group (94%, entry 1, Table 4) was better than a move to the 4-position (88%, entry 2), but both modifications led to a decrease in activity in comparison to the parent compound (99%, Table 3, entry 18). Evaluating other halides in the 3-position also gave potent analogs: an iodide was slightly less active (95%, entry 3, Table 4), while the chloride (101%, entry 4) and fluoride derivatives (103%, entry 5) were very effective at inhibiting pyocyanin production. Moving the fluoride around the ring led to similar trends as in the bromide case (entries 6-7 vs. entries 1-2), where substitution at the 4-position was the least active (54%, entry 7), and the 3-position was superior overall (entry 5). The incorporation of additional fluorides only decreased activity (entries 8-10).

Substrates with other inductively withdrawing groups at the 3-position were less effective inhibitors (entries 11-13). A methyl group is still effective (81%, entry 14), but less so than the halides at the 3-position. A hydroxyl group at this position also had moderate activity (70%, entry 15), but was more potent at the 2-position (95%, entry 16).

The importance of the ether linkage between the aryl tail and the rest of the substrate was examined. Substituting the oxygen with a sulfur or carbon lead to a small decrease in activity (94%, entry 17 and 96%, entry 18) and suggested that the electronic character of this linker atom was not significant to the activity. A nitrogen displayed similar efficacy as the parent oxygen (100%, entry 19). An alkyne was also tolerated in the linker (97%, entry 20).

TABLE 4
Hybrid tail group optimization
| Entry | Substrate | Efficacy (%) |
|---|---|---|
| 1 | 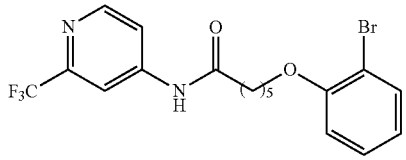 | 94 ± 4 |
| 2 | 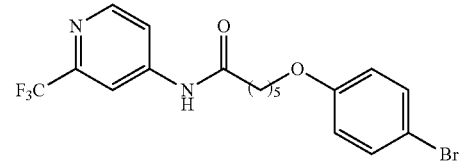 | 88 ± 4 |
| 3 | 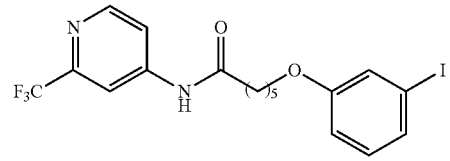 | 95 ± 3 |
| 4 | 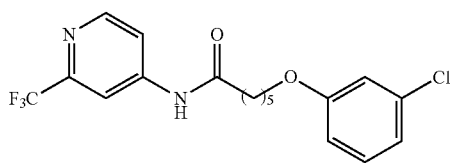 | 101 ± 3 |
| 5 | 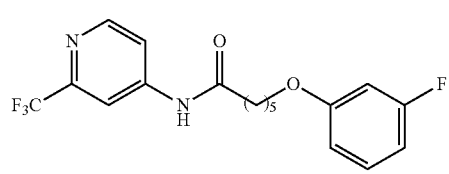 | 103 ± 3 |
| 6 | 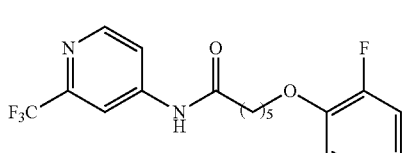 | 78 ± 3 |
| 7 | 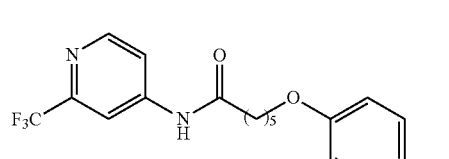 | 54 ± 4 |
| 8 | 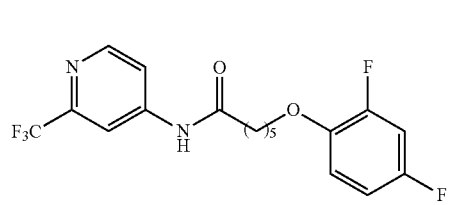 | 49 ± 3 |

TABLE 4-continued
Hybrid tail group optimization
| Entry | Substrate | Efficacy (%) |
|---|---|---|
| 9 | 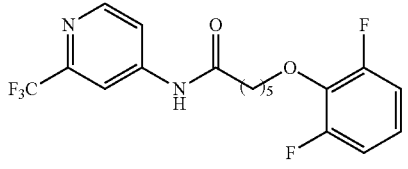 | 66 ± 4 |
| 10 | 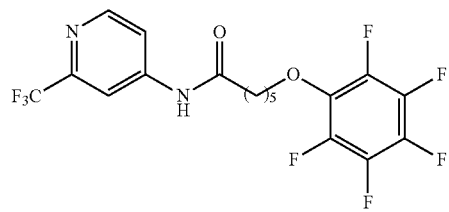 | 21 ± 14 |
| 11 | 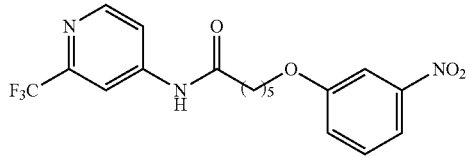 | 39 ± 36 |
| 12 | 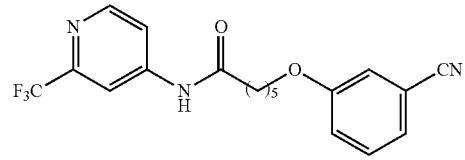 | 0.48 ± 7 |
| 13 | 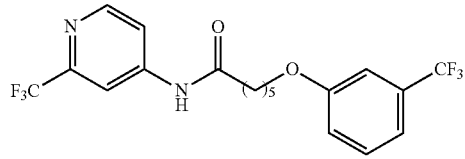 | 59 ± 3 |
| 14 | 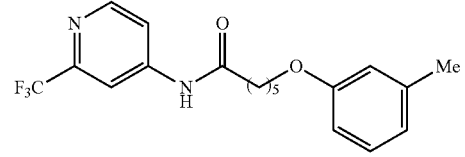 | 81 ± 4 |
| 15 | 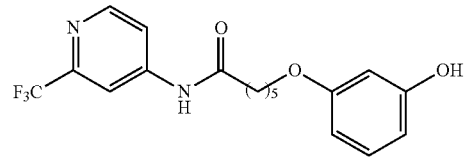 | 70 ± 7 |
| 16 | 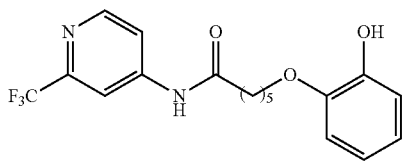 | 95 ± 4 |

TABLE 4-continued

Hybrid tail group optimization

| Entry | Substrate | Efficacy (%) |
|-------|-----------|--------------|
| 17 | F₃C-pyridine-NH-C(O)-(CH₂)₅-S-C₆H₄-F (3-fluorophenyl) | 94 ± 4 |
| 18 | F₃C-pyridine-NH-C(O)-(CH₂)₅-C₆H₄-F (3-fluorophenyl) | 96 ± 4 |
| 19 | F₃C-pyridine-NH-C(O)-(CH₂)₅-NH-C₆H₄-F (3-fluorophenyl) | 100 ± 4 |
| 20 | F₃C-pyridine-NH-C(O)-(CH₂)₃-C≡C-C₆H₄-F (3-fluorophenyl) | 97 ± 4 |

EXAMPLE 20

Inhibitory Activity of the Synthetic Compounds

Figure 15:
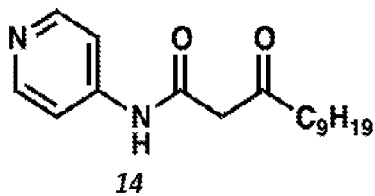
FIG. 15. Activities of selected hits and previously reported compounds.
Figure 15:
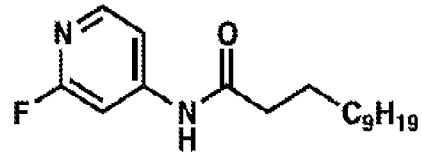
Figure 15:
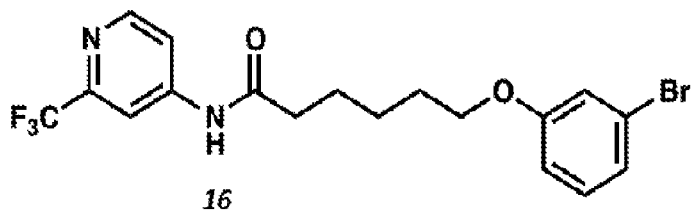
Figure 15:
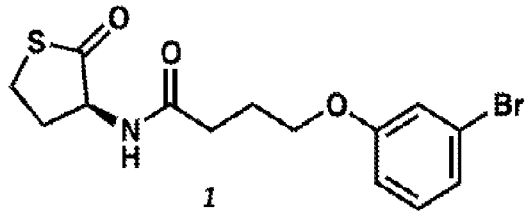
Figure 15:
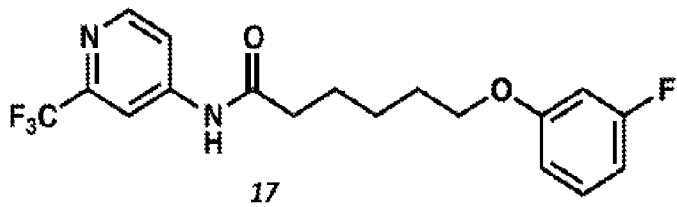
Figure 15:
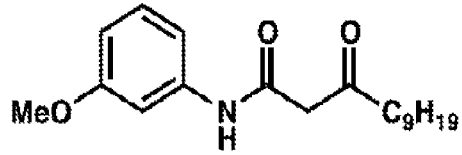
Figure 16:
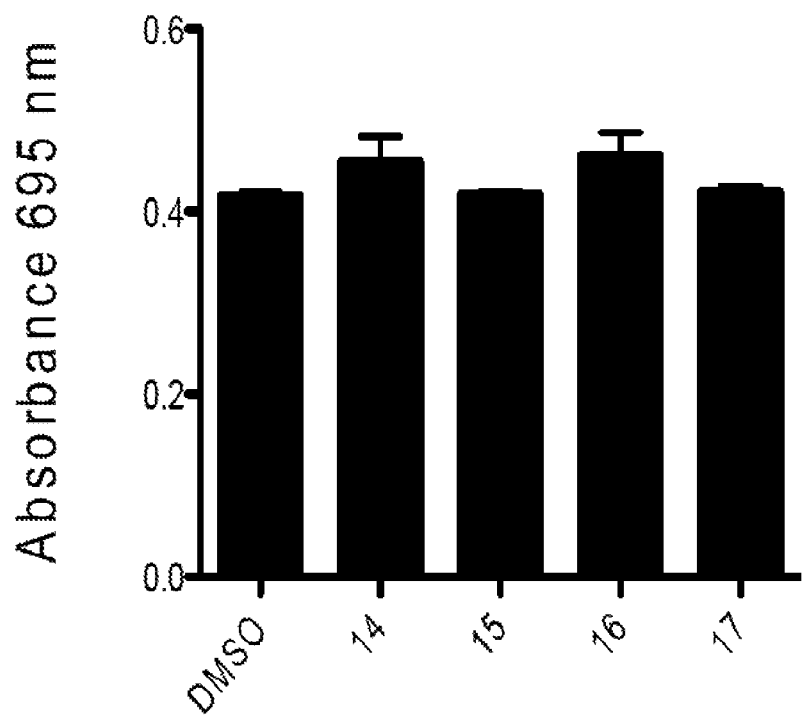
FIG. 16. Inhibitors do not affect the redox state of pyocyanin. Incubation of cell-free supernatant with DMSO or inhibitor leads to no change in pyocyanin absorbance.

The $IC_{50}$ values for top hits from each of the libraries was determined (FIG. 15). Most of the inhibitors had low micromolar activities, while 14 was an order of magnitude more active ($IC_{50}$=0.16 μM). Strikingly, the hybrid compounds (16-17) were highly effective at blocking pyocyanin production and are superior to inhibitor 1 or compound 18, a very effective pyocyanin inhibitor in *P. aeruginosa* PAO1. To ensure that the observed activity in the compounds was not due to the alteration of the oxidation state of pyocyanin, cell-free supernatant containing pyocyanin was incubated with the inhibitors. No change in absorbance occurred over 17 hours (FIG. 16).

EXAMPLE 21

Biological Targets of the Synthetic Compounds

Figure 17:
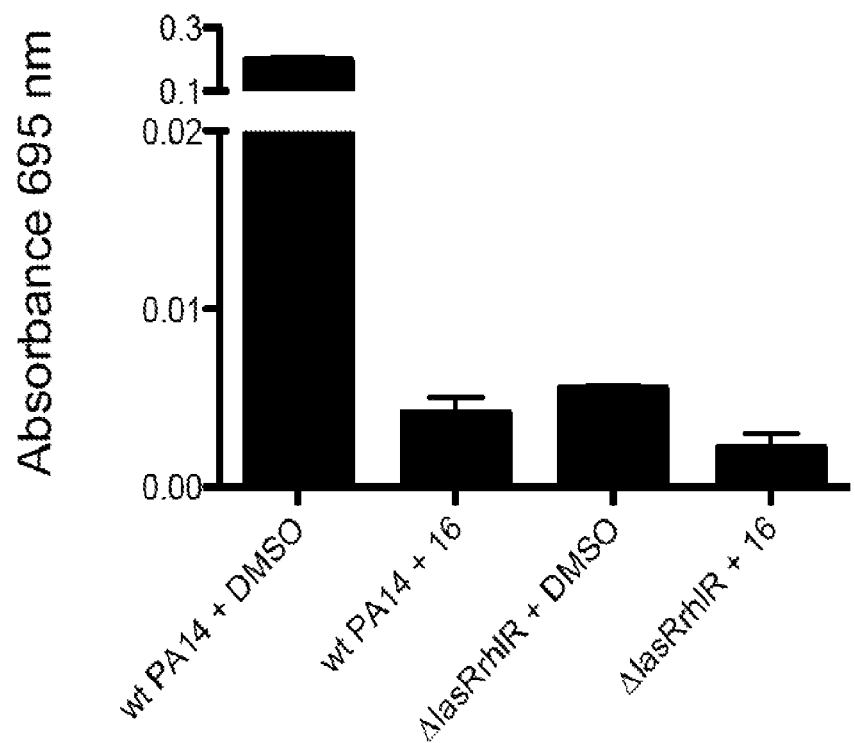
FIG. 17. Pyocyanin production of WT P. aeruginosa and ΔlasRrhlR mutant after treatment with DMSO or 16. P<0.05 of DMSO versus 16-treated (Student's t test).
Figure 18A:
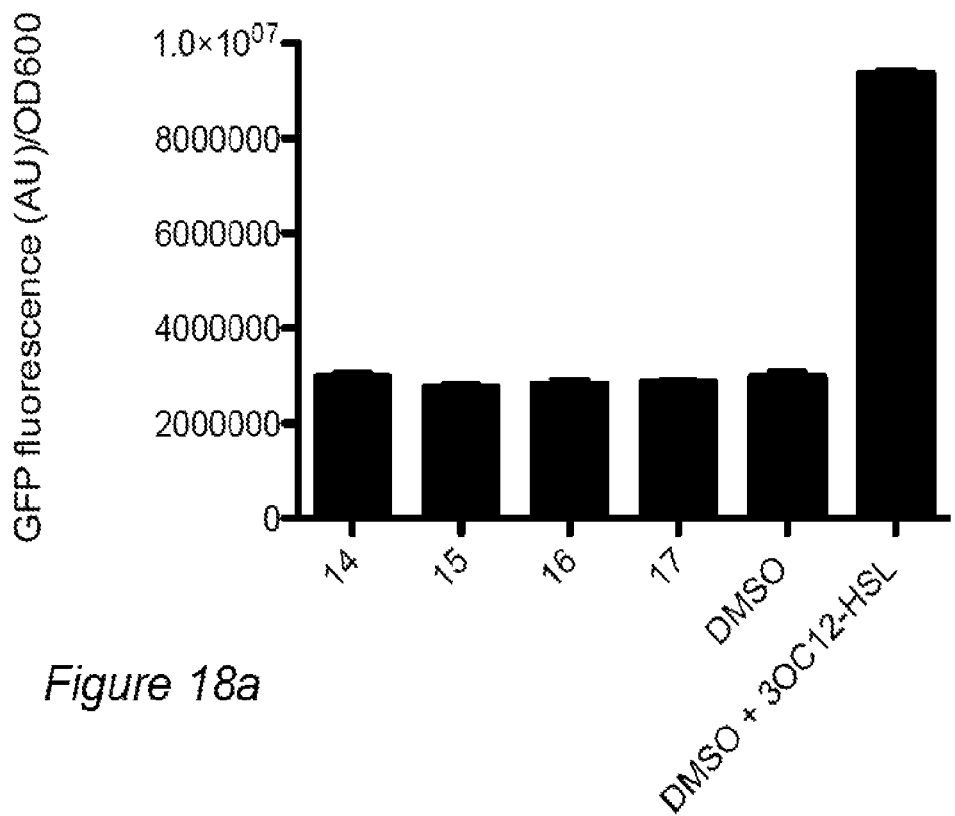
FIG. 18. LasR and RhlR assays in E. coli with gfp reporter. Compounds tested at 100 μM. For antagonism assays, the native AHL was also added at its $EC_{95}$. a) LasR agonism b) LasR antagonism c) RhlR agonism d) RhlR antagonism.
Figure 18B:
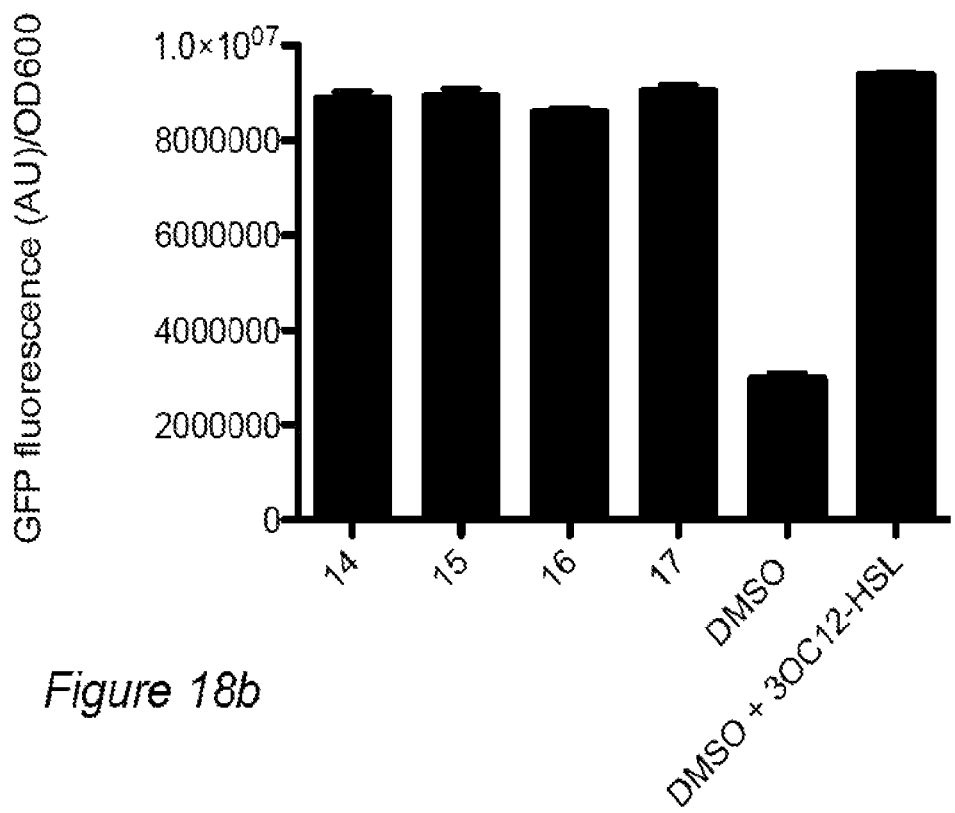
Figure 18C:
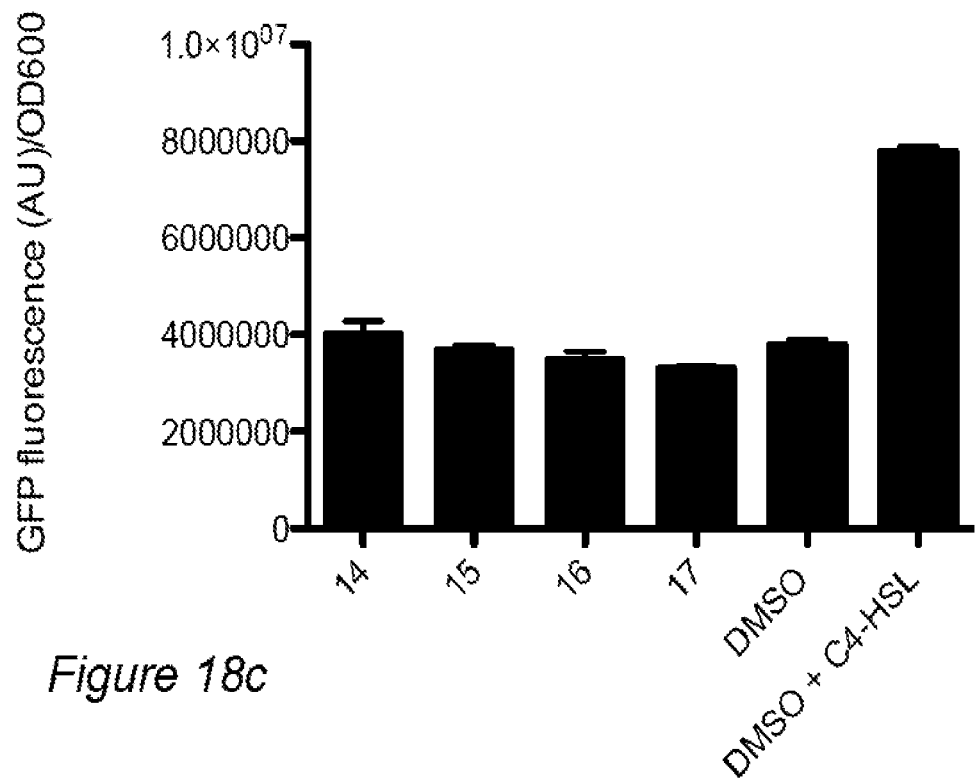
Figure 18D:
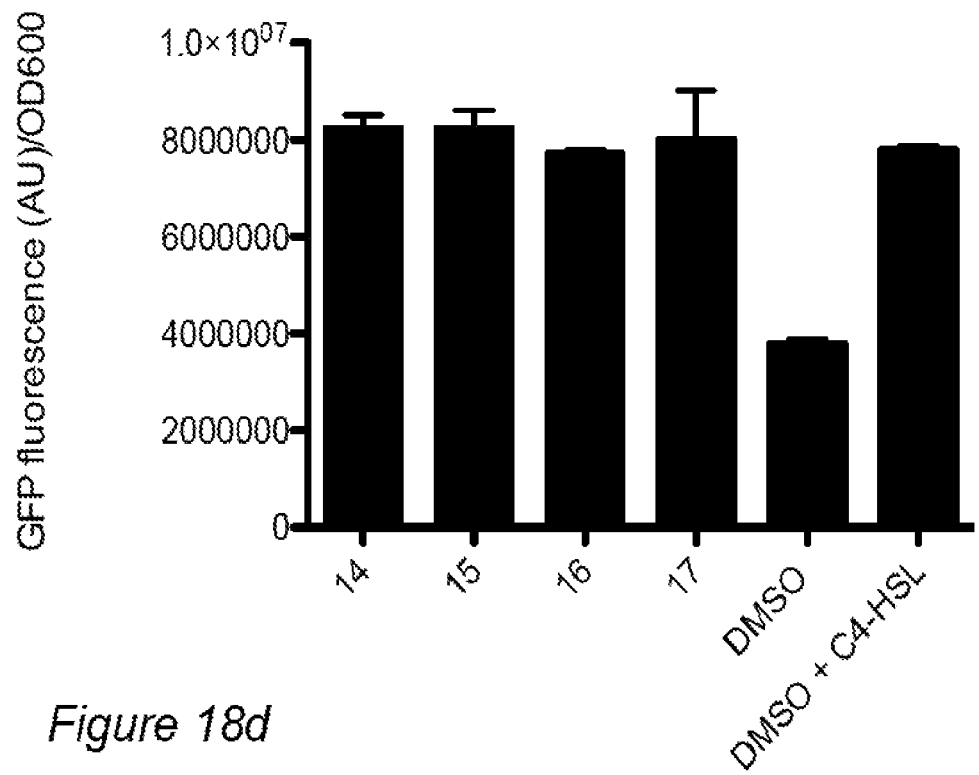

The compounds were designed to be AHL analogs that bind and antagonize LasR and/or RhlR. If either receptor were the target, a ΔlasRrhlR strain of *P. aeruginosa* would not be expected to have a further reduction of pyocyanin when treated with an inhibitor. Instead, in a mutant *P. aeruginosa* strain that lacks LasR and RhlR, pyocyanin levels are further reduced upon treatment with hybrid 16 (FIG. 17).

EXAMPLE 22

LasR and RhlR GFP Assays of Synthetic Compounds

The LasR-GFP assays were performed in *E. coli* strain BL21 DE3 Gold (Agilent) carrying pET23b (Novagen) containing lasR (maintained with 100 μg/mL ampicillin) and carrying plasmid pEVS141 (31) containing the rsaL promoter driving expression of gfp (maintained with 50 μg/mL of kanamycin.) The RhlR-GFP assays were performed in *E. coli* strain BL21 DE3 Gold (Agilent) carrying pET23b (Novagen) containing rhlR (maintained with 100 μg/mL ampicillin) and carrying plasmid pEVS141 (31) containing the rhlA promoter driving expression of gfp (maintained with 50 μg/mL of kanamycin.) These *E. coli* strains were grown overnight and subcultured into fresh medium with appropriate antibiotics at a 1:100 dilution and grown shaking for 8 hr at 37° C. for the LasR-GFP strain and 12 hr for the RhlR-GFP construct. 50 nM 3OC12-HSL or 20 μM C4-HSL was added to the LasR-GFP and RhlR-GFP preparations, respectively. Compounds were tested at 1 mM for antagonism and at 100 nM or 20 μM for agonism. These concentrations were chosen for agonism studies to match the concentrations of autoinducers used in our experiments. For antagonism studies, we used the $EC_{95}$ concentration for each receptor. GFP was measured on an Envision plate reader.

The activity of the pyocyanin inhibitors was investigated in a heterologous *E. coli* system, where the relevant transcriptional regulator and target-gfp fusions are present on plasmids. Upon addition of an agonist such as the native AHL, GFP is produced. None of the compounds acted as agonists for LasR or RhlR at 100 μM (FIG. 18). In the presence of the native AHL, an inhibitor should decrease the production of GFP. None of the compounds acted as antagonists for LasR or RhlR at 100 μM. Despite having been designed to hit the LasR and/or RhlR receptors of *P. aeruginosa*, clearly the inhibitors are reducing pyocyanin levels by influencing a different pathway, in a more effective manner than the LasR/RhlR inhibitors 1 and 18.

Due to the importance of pyocyanin to maintain the redox balance of *P. aeruginosa*, it is reasonable that an environmental response regulator could also control pyocyanin production.

EXAMPLE 23

RNA Extraction and Microarray Analysis

Overnight *P. aeruginosa* PA14 cultures were back-diluted 1:1000 into 5 mL of fresh LB. 100 μM inhibitor compound, or an equivalent amount of DMSO, was added to cultures which were grown aerobically with shaking at 37° C. for 17 hr. 9 ODs of cells were harvested for each treatment. Lysozyme (1 mg/mL in TE buffer) (Sigma) was added for 10 min at room temperature. Total RNA was prepared using the RNeasy Midi Kit (Qiagen). RNA was treated with RNase-Free DNaseI (Ambion) for 1 hr at 37° C., inactivated using DNaseI Inactivation Reagent Resin (Ambion), and re-purified using the RNeasy Mini Kit. A cDNA library containing Cy3- or Cy5-labeled dUTP (Enzo Life Sciences) was synthesized from the purified RNA using SuperScript III Reverse Transcriptase (Invitrogen). Sodium hydroxide was added to degrade RNA, and the reaction was subsequently neutralized by addition of hydrochloric acid. The library was purified using the PCR Purification kit (Qiagen) and assessed for Cy3 and Cy5 incorporation using a Nanodrop ND-1000 Spectrophotometer (Nanodrop Technologies). Libraries were normalized for cDNA concentration and hybridized using the Gene Expression Hybridization Kit (Agilent) to a custom microarray (Agilent design number 43307), which was designed using the Agilent eArray tool with 2 probes for most genes. Samples were hybridized for 22 hr at 65° C. with continuous rotation at 10 rpm. Microarrays were scanned using an Agilent G2505C scanner and analyzed using Agilent Feature Extract software version 9.5. Resulting microarray intensity data were submitted to the PUMA Database (http://puma.princeton.edu) for archiving and analyzed using Matlab R2013a.

Microarray analysis allows observation of the effects of the inhibitor in vivo. WT *P. aeruginosa* PA14 was treated with hybrid 16 and compared with the untreated bacterium. Pyocyanin acts as a terminal signal in *P. aerguinosa*, upregulating the production of putative monooxygenase PA14_35160 as well as transporters through SoxR. [24] If there were no pyocyanin produced, decreased expression of the genes controlled by SoxR would be expected. Treatment with inhibitor 16 does lead to the expected down-regulation of the SoxR-regulated genes (Table 5).

TABLE 5

Changes in the SoxR regulon after treatment with 16.

| Gene Locus | Gene Name | Description | Fold Down-Regulated |
|---|---|---|---|
| PA14_35160 | | hypothetical protein | 4.93 |
| PA14_16310 | | MFS permease | 3.27 |

TABLE 5-continued

Changes in the SoxR regulon after treatment with 16.

| Gene Locus | Gene Name | Description | Fold Down-Regulated |
|---|---|---|---|
| PA14_09530 | mexH | RND efflux membrane fusion protein | 2.93 |
| PA14_09520 | mexI | RND efflux transporter | 2.84 |
| PA14_09540 | mexG | hypothetical protein | 2.68 |
| PA14_09500 | opmD | outer membrane protein | 2.50 |

Examining the rest of the microarray data, none of the pyocyanin biosynthetic genes are impacted by hybrid 16, suggesting a post-transcriptional regulation of the virulence factor. Indeed, few genes of the quorum-sensing regulon as a whole were affected. Instead, the majority of genes with the greatest down-regulation are associated with the oxidative stress response (Table 6).

TABLE 6

Oxidative stress genes impacted by 16.

| Gene Locus | Gene Name | Description | Fold Down-regulated |
|---|---|---|---|
| PA14_21530 | | ankyrin domain-containing protein | 44.39 |
| PA14_22320 | | hypothetical protein | 35.99 |
| PA14_01720 | ahpF | alkyl hydroperoxide reductase | 33.03 |
| PA14_53290 | trxB2 | thioredoxin reductase 2 | 27.79 |
| PA14_09150 | katA | catalase | 20.80 |
| PA14_03090 | | hypothetical protein | 14.35 |
| PA14_58040 | | hypothetical protein | 5.67 |
| PA14_51830 | | DNA-binding stress protein | 5.60 |
| PA14_61040 | katB | catalase | 4.15 |
| PA14_58030 | fumC | fumarate hydratase | 2.71 |

EXAMPLE 24

Chemistry Materials and Methods

Unless otherwise stated, reactions were performed in flame-dried glassware fitted with rubber septa under a nitrogen atmosphere and were stirred with Teflon-coated magnetic stirring bars. Liquid reagents and solvents were transferred via syringe using standard Schlenk techniques. Reaction solvents were dried by passage over a column of activated alumina. All other solvents and reagents were used as received unless otherwise noted. Reaction temperatures above 23° C. refer to oil bath temperature, which was controlled by an OptiCHEM temperature modulator. Thin layer chromatography was performed using SiliCycle silica gel 60 F-254 precoated plates (0.25 mm) and visualized by UV irradiation and anisaldehyde or potassium permanganate stain. Sorbent standard silica gel (particle size 40-63 μm) was used for flash chromatography. $^1$H and $^{13}$C NMR spectra were recorded on Bruker Avance III (500 MHz for $^1$H; 125 MHz for $^{13}$C) spectrometer fitted with either a $^1$H-optimized TCI (H/C/N) cryoprobe or a $^{13}$C-optimized dual C/H cryoprobe or a Bruker NanoBay (300 MHz). Chemical shifts (δ) are reported in ppm relative to the residual solvent signal (δ=7.26 for $^1$H NMR and δ=77.0 for $^{13}$C NMR for CDCl$_3$, δ=3.31 for $^1$H NMR and δ=49.0 for $^{13}$C NMR for CD$_3$OD, δ=2.05 for $^1$H NMR and δ=29.8 for $^{13}$C NMR for acetone-d6). Data for $^1$H NMR spectra are reported as follows: chemical shift (multiplicity, coupling constants, number of hydrogens). Abbreviations are as follows: s (singlet), bs (broad singlet), d (doublet), t (triplet), q (quartet), p (pentet), dd (doublet of doublets), ddd (doublet of doublet of doublets), dt (doublet of triplets), td (triplet of doublets), m (multiplet). High-resolution mass spectral analysis was performed using an Agilent 1200-series electrospray ionization—time-of-flight (ESI-TOF) mass spectrometer in the positive ESI mode.

General Procedures:

Synthesis of β-keto Amide Compounds

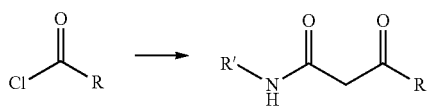

General procedure A: To a flame-dried flask was added Meldrum's acid (1 equiv) and $CH_2Cl_2$ (0.34 M). The reaction mixture was cooled to 0° C., and pyridine (2 equiv) was added over 20 min. Decanoyl chloride (1 equiv) was then added dropwise. The reaction mixture was stirred at 0° C. for 2 h and was allowed to return to room temperature over 1 h. The reaction was diluted with $CH_2Cl_2$ and a 2 M HCl/ice mixture. After stirring for 10 min., the phases were separated. The organic phase was washed sequentially with 2 M HCl and brine, dried over $Na_2SO_4$ and concentrated. The residue was dissolved in $CH_3CN$ (0.1 M) and the amino-heterocycle (1 equiv) was added. The reaction was heated to 65° C. for 4 h. The reaction mixture was then concentrated and the crude product was purified by column chromatography.

Synthesis of Amide Compounds:

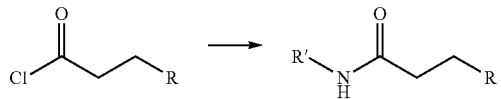

General procedure B: The amino-heterocycle (1 equiv), $CH_2Cl_2$ (0.15 M), and $Et_3N$ (2 equiv) were combined in a flame-dried flask. The reaction mixture was cooled to 0° C., and dodecanoyl chloride (1 equiv) was added dropwise. The reaction mixture was allowed to warm to room temperature over 3 h. The reaction was then quenched with saturated aqueous $NaHCO_3$ solution. The layers were separated, and the aqueous layer was extracted 3× with $CH_2Cl_2$. The combined organic layer was washed with brine, dried over $Na_2SO_4$, and concentrated. The crude product was purified by column chromatography.

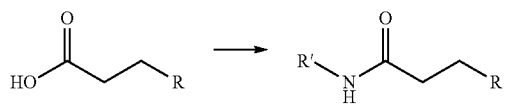

General procedure C: To a flame-dried flask were added the carboxylic acid (1.0 equiv), dicyclohexylcarbodiimide (1.1 equiv), dimethylaminopyridine (1.1 equiv), dodecylamine (1.0 equiv), and $CH_2Cl_2$ (0.40 M). After stirring at room temperature for 24 h, the reaction mixture was filtered through a Celite plug and concentrated. The crude product was purified by column chromatography.

Synthesis of 4-amino-2-trifluoromethylpyridine analogs:

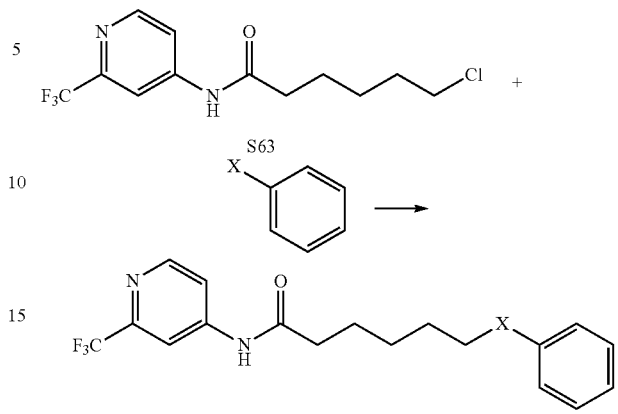

General procedure D: S63 (1 equiv), anhydrous potassium iodide (12 equiv), anhydrous potassium carbonate (7.5 equiv), and the corresponding aryl nucleophile (3.8 equiv) were dissolved in isopropanol (0.68 M) in a vial. The vial was sealed, and the reaction mixture was heated to 100° C. behind a blast shield for at least 60 hours, or until done. After cooling, the reaction was quenched with water and extracted with $CH_2Cl_2$. The combined organic layer was washed sequentially with saturated aqueous $NaHCO_3$ (2×), 1 M HCl, and brine. The solution was dried over $Na_2SO_4$ and concentrated. The crude product was purified by column chromatography.

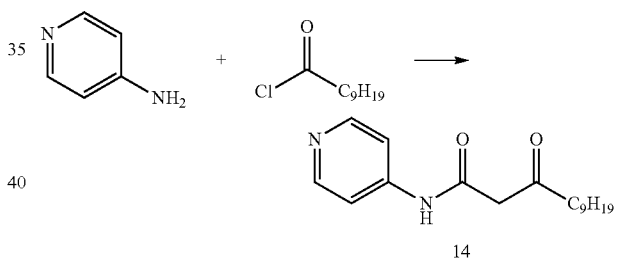

3OC12-4-aminopyridine (14): Prepared from 4-aminopyridine using general procedure A to furnish 14 in a 51% yield. HRMS (ESI-TOF) calculated for $C_{17}H_{27}N_2O_2$ [M+H]$^+$: m/z 291.2073. found 291.2077; $^1$H NMR (500 MHz, CDCl$_3$) δ 9.61 (s, 1H), 8.51 (d, J=5.7 Hz, 2H), 7.58-7.48 (m, 2H), 3.59 (s, 2H), 2.58 (t, J=7.3 Hz, 2H), 1.62 (p, J=6.7 Hz, 2H), 1.44-1.15 (m, 12H), 0.87 (t, J=6.8 Hz, 3H); $^{13}$C NMR (125 MHz, CDCl$_3$) δ 208.0, 164.2, 150.8, 144.3, 113.9, 48.3, 44.3, 31.8, 29.3, 29.3, 29.2, 28.9, 23.3, 22.6, 14.1.

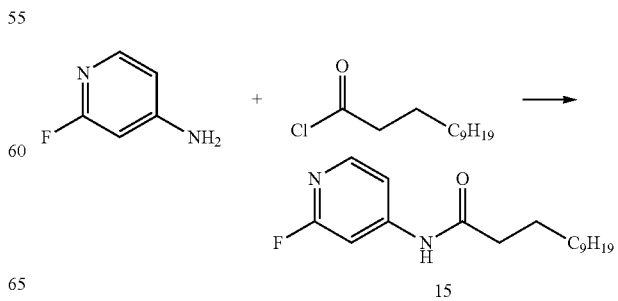

C12-4-amino-2-fluoropyridine (15): Prepared from 4-amino-2-fluoropyridine using general procedure B to furnish 15 in a 45% yield. HRMS (ESI-TOF) calculated for $C_{17}H_{28}FN_2O$ [M+H]$^+$: m/z 295.2186. found 295.2188; $^1$H NMR (500 MHz, CDCl$_3$) δ 8.09 (d, J=5.6 Hz, 1H), 7.40-7.31 (m, 2H), 7.17 (dt, J=5.7, 1.5 Hz, 1H), 2.40 (t, J=7.6 Hz, 2H), 1.72 (p, J=7.5 Hz, 2H), 1.26 (d, J=6.6 Hz, 16H), 0.87 (t, J=6.9 Hz, 3H); $^{13}$C NMR (125 MHz, CDCl$_3$) δ 171.9, 164.8 (d, J=236 Hz), 148.8 (d, J=12 Hz), 148.1 (d, J=17 Hz), 111.2 (d, J=4 Hz), 98.6 (d, J=43 Hz), 37.8, 31.9, 29.6, 29.6, 29.4, 29.3, 29.3, 29.1, 25.1, 22.7, 14.1.

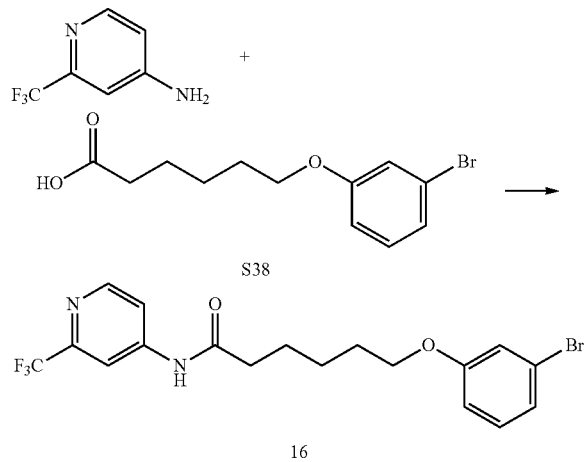

16

4-amino-2-trifluoromethylpyridine-C6-3-bromophenoxy-hybrid (16): Prepared from 4-amino-2-trifluoromethylpyridine and S38$^1$ using general procedure C to furnish 16 in a 42% yield. HRMS (ESI-TOF) calculated for $C_{18}H_{19}BrF_3N_2O_2$ [M+H]: m/z 431.0582. found 431.0571; $^1$H NMR (500 MHz, CDCl$_3$) δ 8.60 (d, J=5.5 Hz, 1H), 7.89 (d, J=2.1 Hz, 1H), 7.67 (dd, J=5.5, 2.1 Hz, 1H), 7.47 (s, 1H), 7.13 (t, J=8.1 Hz, 1H), 7.10-6.99 (m, 2H), 6.81 (ddd, J=8.2, 2.5, 1.1 Hz, 1H), 3.95 (t, J=6.2 Hz, 2H), 2.46 (t, J=7.4 Hz, 2H), 1.89-1.74 (m, 4H), 1.63-1.50 (m, 2H); $^{13}$C NMR (125 MHz, CDCl$_3$) δ 171.8, 159.7, 151.0, 149.3 (q, J=35 Hz), 146.1, 130.6, 124.7-117.9 (m), 123.7, 122.8, 117.6, 115.3, 113.4, 110.3 (q, J=3 Hz), 67.7, 37.5, 28.8, 25.6, 24.7.

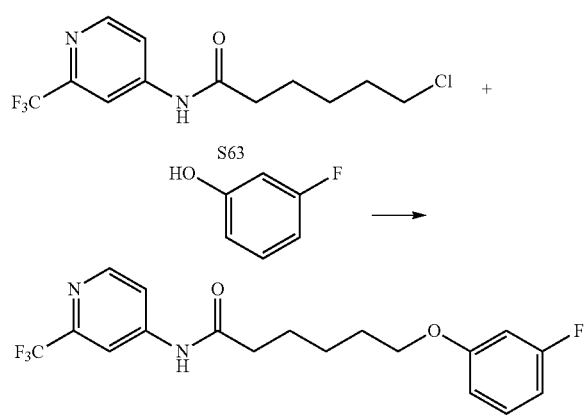

17

4-amino-2-trifluoromethylpyridine-C6-3-fluorophenoxy-hybrid (17): Prepared from 3-fluorophenol and S63 using general procedure D to furnish 17 in a 40% yield. HRMS (ESI-TOF) calculated for $C_{18}H_{19}F_4N_2O_2$ [M+H]: m/z 371.1383. found is 371.1367; $^1$H NMR (500 MHz, CDCl$_3$) δ 8.59 (s, 1H), 7.92 (s, 1H), 7.77 (s, 1H), 7.73-7.65 (m, 1H), 7.24-7.16 (m, 1H), 6.68-6.61 (m, 2H), 6.58 (dt, J=11.0, 2.4 Hz, 1H), 3.94 (t, J=6.2 Hz, 2H), 2.46 (t, J=7.4 Hz, 2H), 1.86-1.76 (m, 4H), 1.60-1.51 (m, 2H); $^{13}$C NMR (125 MHz, CDCl$_3$) δ 171.9, 163.6 (d, J=245 Hz), 160.3 (d, J=11 Hz), 150.9, 149.3 (q, J=35 Hz), 146.3, 130.2 (d, J=10 Hz), 121.3 (q, J=274 Hz), 115.4, 110.5-110.1 (m, 2C), 107.4 (d, J=21 Hz), 102.1 (d, J=25 Hz), 67.7, 37.5, 28.8, 25.7, 24.7.

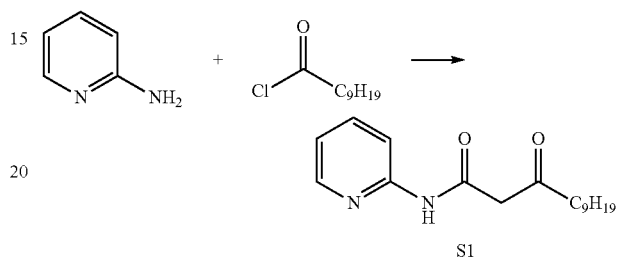

3OC12-2-aminopyridine (S1): Prepared from 2-aminopyridine using general procedure A to furnish S1 in a 60% yield. HRMS (ESI-TOF) calculated for $C_{17}H_{27}N_2O_2$ [M+H]$^+$: m/z 291.2073. found 291.2099; $^1$H NMR (500 MHz, CDCl$_3$) δ 9.55 (s, 1H), 8.30 (d, J=4.9 Hz, 1H), 8.15 (d, J=8.4 Hz, 1H), 7.69 (t, J=7.9 Hz, 1H), 7.10-7.00 (m, 1H), 3.57 (s, 2H), 2.58 (t, J=7.3 Hz, 2H), 1.60 (p, J=7.0 Hz, 2H), 1.46-1.14 (m, 12H), 0.87 (t, J=6.8 Hz, 3H); $^{13}$C NMR (125 MHz, CDCl$_3$) δ 205.9, 164.2, 151.0, 147.9, 138.3, 120.0, 114.3, 49.9, 44.0, 31.8, 29.4, 29.3, 29.2, 29.0, 23.3, 22.6, 14.1.

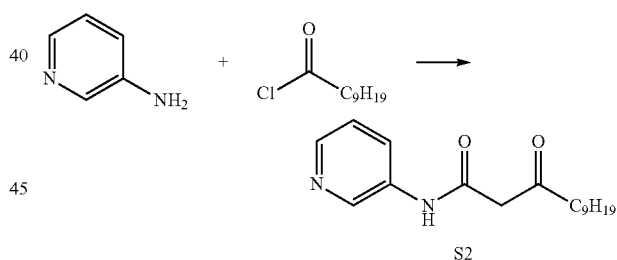

3OC12-3-aminopyridine (S2): Prepared from 3-aminopyridine using general procedure A to furnish S2 in a 65% yield. HRMS (ESI-TOF) calculated for $C_{17}H_{27}N_2O_2$ [M+H]$^+$: m/z 291.2073. found 291.2100; $^1$H NMR (500 MHz, CDCl$_3$) δ 9.48 (s, 1H), 8.66 (d, J=2.6 Hz, 1H), 8.37 (d, J=3.2 Hz, 1H), 8.13 (d, J=8.9 Hz, 1H), 7.28 (d, J=6.1 Hz, 1H), 3.60 (s, 2H), 2.59 (t, J=7.4 Hz, 2H), 1.71-1.52 (m, 2H), 1.39-1.17 (m, 12H), 0.88 (t, J=6.7 Hz, 3H); $^{13}$C NMR (125 MHz, CDCl$_3$) δ 208.1, 164.1, 145.5, 141.5, 134.3, 127.3, 123.7, 48.2, 44.3, 31.8, 29.3, 29.3, 29.2, 28.9, 23.3, 22.6, 14.1.

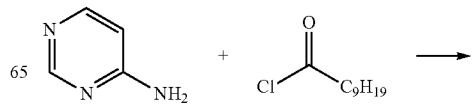

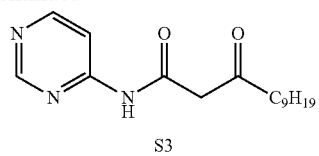

S3

3OC12-4-aminopyrimidine (S3): Prepared from 4-aminopyrimidine using general procedure A to furnish S3 in a 58% yield. HRMS (ESI-TOF) calculated for $C_{16}H_{26}N_3O_2$ [M+H]$^+$: m/z 292.2025. found 292.2020; $^1$H NMR (500 MHz, CDCl$_3$) δ 9.67 (s, 1H), 8.92-8.89 (m, 1H), 8.63 (d, J=5.7 Hz, 1H), 8.11 (d, J=5.7 Hz, 1H), 3.61 (s, 2H), 2.58 (t, J=7.4 Hz, 2H), 1.77-1.52 (m, 2H), 1.41-1.14 (m, 12H), 0.87 (t, J=6.8 Hz, 3H); $^{13}$C NMR (125 MHz, CDCl$_3$) δ 206.0, 165.0, 158.5, 158.5, 156.6, 110.5, 49.1, 44.3, 31.8, 29.3, 29.3, 29.2, 28.9, 23.3, 22.6, 14.1.

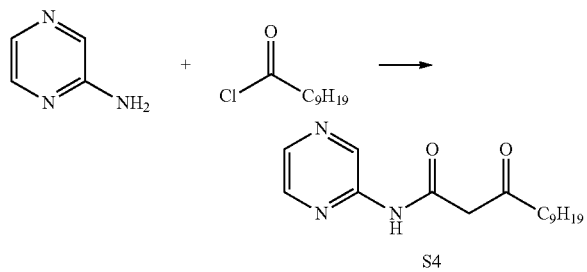

S4

3OC12-2-aminopyrazine (S4): Prepared from 2-aminopyrazine using general procedure A to furnish S4 in a 50% yield. HRMS (ESI-TOF) calculated for $C_{16}H_{26}N_3O_2$ [M+H]$^+$: m/z 292.2025. found 292.2016; $^1$H NMR (500 MHz, CDCl$_3$) δ 9.63 (s, 1H), 9.48 (s, 1H), 8.38-8.33 (m, 1H), 8.31-8.25 (m, 1H), 3.62 (s, 2H), 2.59 (t, J=7.4 Hz, 2H), 1.67-1.58 (m, 2H), 1.38-1.11 (m, 12H), 0.87 (t, J=6.9 Hz, 3H); $^{13}$C NMR (125 MHz, CDCl$_3$) δ 206.5, 164.0, 147.7, 142.3, 140.5, 137.2, 48.8, 44.3, 31.8, 29.4, 29.3, 29.2, 28.9, 23.3, 22.6, 14.1.

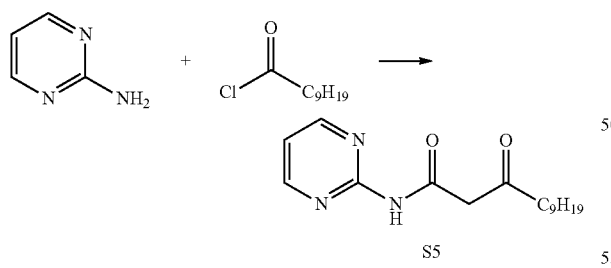

S5

3OC12-2-aminopyrimidine (S5): Prepared from 2-aminopyrimidine using general procedure A to furnish S5 in a 15% yield. HRMS (ESI-TOF) calculated for $C_{16}H_{26}N_3O_2$ [M+H]$^+$: m/z 292.2025. found 292.2024; $^1$H NMR (500 MHz, CDCl$_3$) δ 9.21 (s, 1H) 8.77-8.54 (m, 2H), 7.12-6.96 (m, 1H), 3.94 (s, 2H), 2.58 (t, J=7.4 Hz, 2H), 1.61 (p, J=7.3 Hz, 2H), 1.45-1.15 (m, 12H), 0.88 (t, J=6.9 Hz, 3H); $^{13}$C NMR (125 MHz, CDCl$_3$) δ 182.4, 171.5, 158.2, 157.1, 116.5, 51.4, 43.3, 31.8, 29.4, 29.4, 29.2, 29.1, 23.4, 22.6, 14.1.

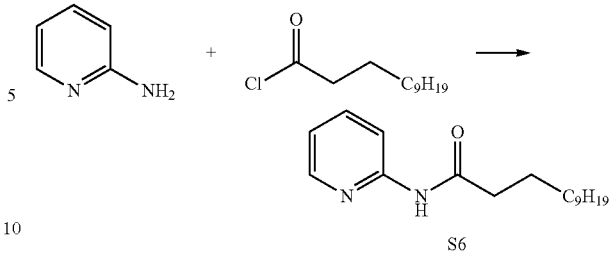

S6

C12-2-aminopyridine (S6): Prepared from 2-aminopyridine using general procedure B to furnish S6 in a 4% yield. HRMS (ESI-TOF) calculated for $C_{17}H_{29}N_2O$ [M+H]$^+$: m/z 277.2281. found 277.2284; $^1$H NMR (500 MHz, CDCl$_3$) δ 8.25 (ddd, J=4.9, 2.0, 0.9 Hz, 1H), 8.22 (d, J=8.3 Hz, 1H), 7.90 (s, 1H), 7.70 (ddd, J=8.7, 7.3, 1.9 Hz, 1H), 7.03 (ddd, J=7.4, 4.9, 1.1 Hz, 1H), 2.39 (t, J=7.6 Hz, 2H), 1.72 (p, J=7.5 Hz, 2H), 1.43-1.17 (m, 16H), 0.87 (t, J=6.9 Hz, 3H); $^{13}$C NMR (125 MHz, CDCl$_3$) δ 171.9, 151.4, 147.6, 138.5, 119.6, 114.0, 37.8, 31.9, 29.6, 29.6, 29.4, 29.3, 29.3, 29.2, 25.4, 22.7, 14.1.

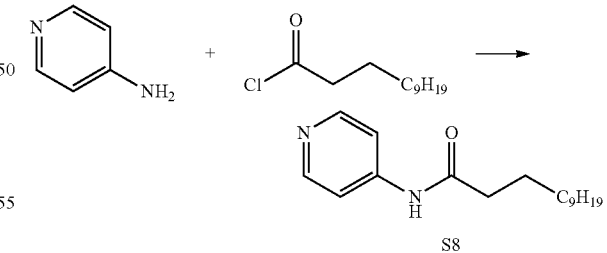

S7

C12-3-aminopyridine (S7): Prepared from 3-aminopyridine using general procedure B to furnish S7 in a 57% yield. HRMS (ESI-TOF) calculated for $C_{17}H_{29}N_2O$ [M+H]$^+$: m/z 277.2281. found 277.2277; $^1$H NMR (500 MHz, CDCl$_3$) δ 8.53 (d, J=2.6 Hz, 1H), 8.34 (dd, J=4.8, 1.5 Hz, 1H), 8.20 (dt, J=8.4, 2.0 Hz, 1H), 7.35 (s, 1H), 7.31-7.26 (m, 1H), 2.39 (t, J=7.6 Hz, 2H), 1.73 (p, J=7.5 Hz, 2H), 1.44-1.17 (m, 16H), 0.87 (t, J=6.9 Hz, 3H); $^{13}$C NMR (125 MHz, CDCl$_3$) δ 171.9, 145.2, 140.9, 134.7, 127.1, 123.7, 37.6, 31.9, 29.6, 29.6, 29.4, 29.3, 29.3, 29.2, 25.5, 22.7, 14.1.

S8

C12-4-aminopyridine (S8): Prepared from 4-aminopyridine using general procedure B to furnish S8 in a 69% yield. HRMS (ESI-TOF) calculated for $C_{17}H_{29}N_2O$ [M+H]$^+$: m/z 277.2281. found 277.2278; $^1$H NMR (500 MHz, CDCl$_3$) δ 8.57-8.44 (m, 2H), 7.55-7.46 (m, 2H), 7.44 (s, 1H), 2.39 (t, J=7.6 Hz, 2H), 1.72 (p, J=7.5 Hz, 2H), 1.41-1.17 (m, 16H), 0.87 (t, J=6.9 Hz, 3H); $^{13}$C NMR (125 MHz, CDCl$_3$) δ 172.1, 150.7, 144.9, 113.3, 37.9, 31.9, 29.6, 29.6, 29.4, 29.3, 29.3, 29.2, 25.3, 22.7, 14.1.

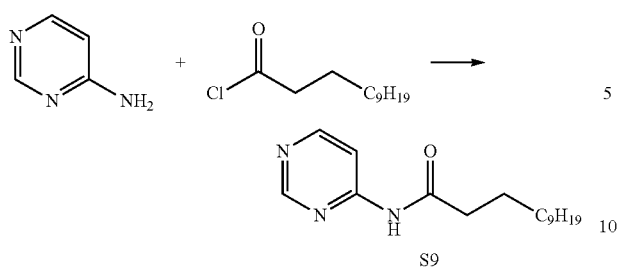
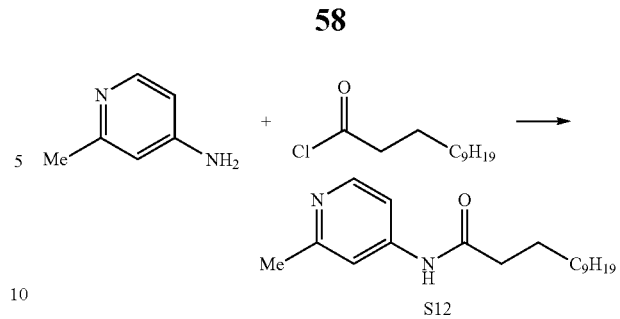

C12-4-aminopyrimidine (S9): Prepared from 4-aminopyrimidine using general procedure B to furnish S9 in a 69% yield. HRMS (ESI-TOF) calculated for $C_{16}H_{28}N_3O$ [M+H]$^+$: m/z 278.2232. found 278.2225; $^1$H NMR (500 MHz, CDCl$_3$) δ 8.85 (d, J=1.4 Hz, 1H), 8.62 (d, J=5.8 Hz, 1H), 8.18 (dd, J=5.8, 1.4 Hz, 1H), 7.91 (s, 1H), 2.42 (t, J=7.6 Hz, 2H), 1.72 (p, J=7.5 Hz, 2H), 1.44-1.17 (m, 16H), 0.87 (t, J=6.9 Hz, 3H); $^{13}$C NMR (125 MHz, CDCl$_3$) δ 172.5, 158.4, 158.3, 156.8, 110.1, 37.8, 31.9, 29.6, 29.6, 29.4, 29.3, 29.3, 29.1, 25.0, 22.7, 14.1.

C12-4-amino-2-methylpyridine (S12): Prepared from 4-amino-2-methylpyridine using general procedure B to furnish S12 in a 90% yield. HRMS (ESI-TOF) calculated for $C_{18}H_{31}N_2O$ [M+H]$^+$: m/z 291.2437. found 291.2431; $^1$H NMR (500 MHz, CDCl$_3$) δ 8.37 (d, J=5.6 Hz, 1H), 7.42 (s, 1H), 7.27 (s, 1H), 7.22 (dd, J=5.7, 2.1 Hz, 1H), 2.52 (s, 3H), 2.37 (t, J=7.6 Hz, 2H), 1.71 (p, J=7.5 Hz, 2H), 1.27 (d, J=19.0 Hz, 16H), 0.87 (t, J=6.9 Hz, 3H); $^{13}$C NMR (125 MHz, CDCl$_3$) δ 172.0, 159.7, 150.0, 145.1, 112.6, 110.7, 37.9, 31.9, 29.6, 29.6, 29.4, 29.3, 29.3, 29.2, 25.3, 24.6, 22.7, 14.1.

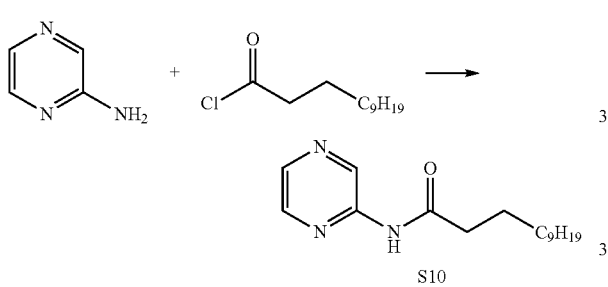
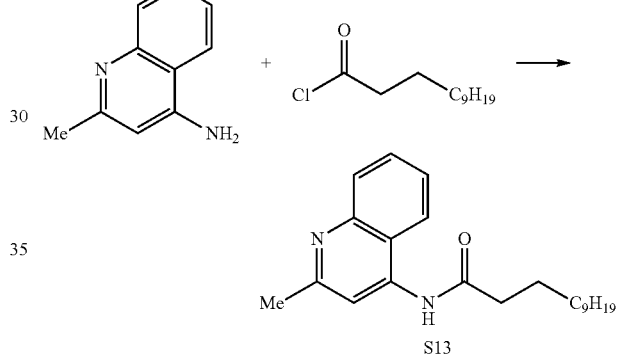

C12-2-aminopyrazine (S10): Prepared from 2-aminopyrazine using general procedure B to furnish S10 in a 15% yield. HRMS (ESI-TOF) calculated for $C_{16}H_{28}N_3O$ [M+H]$^+$: m/z 278.2232. found 278.2232; $^1$H NMR (500 MHz, CDCl$_3$) δ 9.56 (s, 1H), 8.34 (d, J=2.5 Hz, 1H), 8.22 (dd, J=2.7, 1.6 Hz, 1H), 7.92 (s, 1H), 2.44 (t, J=7.6 Hz, 2H), 1.74 (p, J=7.5 Hz, 2H), 1.26 (d, J=11.6 Hz, 16H), 0.87 (t, J=6.9 Hz, 3H); $^{13}$C NMR (125 MHz, CDCl$_3$) δ 171.6, 148.0, 141.8, 140.1, 137.0, 37.5, 31.9, 29.6, 29.6, 29.4, 29.3, 29.3, 29.1, 25.2, 22.7, 14.1.

C12-4-amino-2-methylquinoline (S13): Prepared from 4-amino-2-methylquinoline using general procedure B to furnish S13 in a 25% yield. HRMS (ESI-TOF) calculated for $C_{22}H_{33}N_2O$ [M+H]$^+$: m/z 341.2593. found 341.2593; $^1$H NMR (500 MHz, CDCl$_3$) δ 8.24 (s, 1H), 8.04 (d, J=8.4 Hz, 1H), 7.77 (s, 1H), 7.75-7.65 (m, 2H), 7.53 (t, J=7.6 Hz, 1H), 2.73 (s, 3H), 2.54 (t, J=7.6 Hz, 2H), 1.81 (p, J=7.4 Hz, 2H), 1.48-1.39 (m, 2H), 1.39-1.19 (m, 14H), 0.87 (t, J=6.8 Hz, 3H); $^{13}$C NMR (125 MHz, CDCl$_3$) δ 172.0, 160.2, 148.4, 140.1, 129.8, 129.4, 125.6, 118.5, 118.2, 111.4, 38.1, 31.9, 29.6, 29.6, 29.5, 29.4, 29.3, 29.2, 25.7, 25.5, 22.7, 14.1.

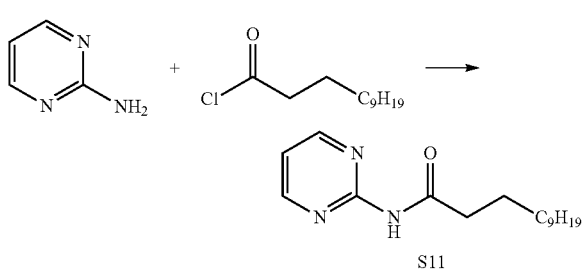
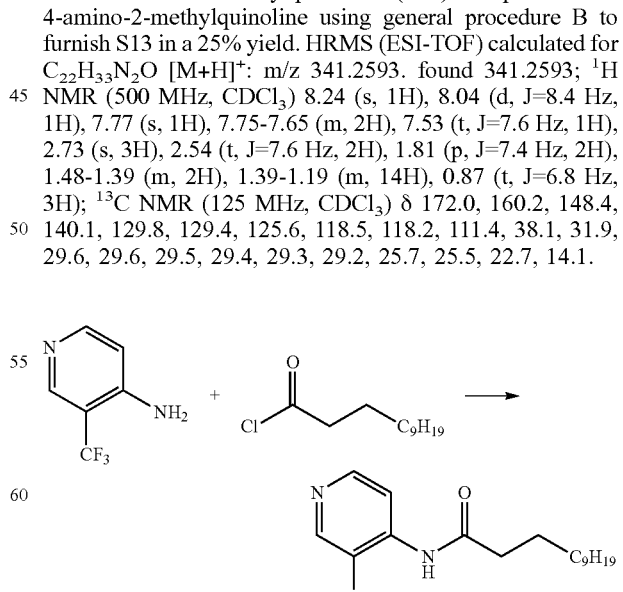

C12-2-aminopyrimidine (S11): Prepared from 2-aminopyrimidine using general procedure B to furnish S11 in a 5% yield. HRMS (ESI-TOF) calculated for $C_{16}H_{28}N_3O$ [M+H]$^+$: m/z 278.2232. found 278.2247. Spectra were consistent with those reported by Ref 2.

C12-4-amino-3-trifluoromethylpyridine (S14): Prepared from 4-amino-3-trifluoromethylpyridine using general procedure B to furnish S14 in a 56% yield. HRMS (ESI-TOF) calculated for $C_{18}H_{28}F_3N_2O$ [M+H]$^+$: m/z 345.2154. found 345.2146; $^1$H NMR (500 MHz, CDCl$_3$) δ 8.77 (s, 1H), 8.69 (d, J=5.9 Hz, 1H), 8.50 (d, J=5.8 Hz, 1H), 7.58 (s, 1H), 2.44 (t, J=7.5 Hz, 2H), 1.72 (p, J=7.4 Hz, 2H), 1.39-1.17 (m, 16H), 0.87 (t, J=6.8 Hz, 3H); $^{13}$C NMR (125 MHz, CDCl$_3$) δ 171.8, 164.3-161.7 (m), 154.4, 147.3 (q, J=6 Hz), 142.8, 128.2-119.4 (m), 115.0, 38.2, 31.9, 29.6, 29.5, 29.4, 29.3, 29.2, 29.0, 25.1, 22.7, 14.1.

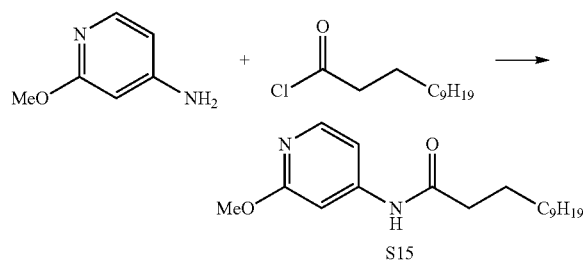

C12-4-amino-2-methoxypyridine (S15): Prepared from 4-amino-2-methoxypyridine using general procedure B to furnish S15 in a 93% yield. HRMS (ESI-TOF) calculated for $C_{18}H_{31}N_2O_2$ [M+H]$^+$: m/z 307.2386. found 307.2414; $^1$H NMR (500 MHz, CDCl$_3$) δ 8.05 (d, J=5.6 Hz, 1H), 7.16 (s, 1H), 7.04-6.96 (m, 2H), 3.92 (s, 3H), 2.36 (t, J=7.6 Hz, 2H), 1.71 (p, J=7.5 Hz, 2H), 1.26 (d, J=12.8 Hz, 16H), 0.87 (t, J=6.8 Hz, 3H); $^{13}$C NMR (125 MHz, CDCl$_3$) δ 171.9, 165.5, 147.7, 146.9, 108.0, 99.3, 53.6, 38.0, 32.0, 29.6, 29.6, 29.5, 29.4, 29.4, 29.2, 25.3, 22.7, 14.2.

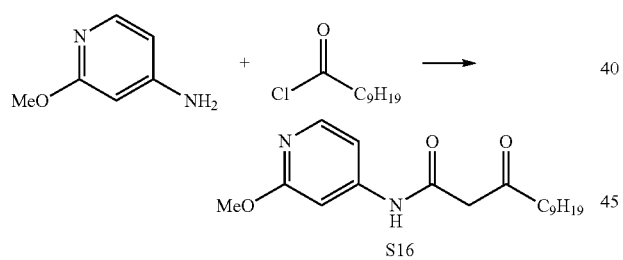

3OC12-4-amino-2-methoxypyridine (S16): Prepared from 4-amino-2-methoxypyridine using general procedure A to furnish S16 in a 43% yield. HRMS (ESI-TOF) calculated for $C_{18}H_{29}N_2O_3$ [M+H]: m/z 321.2178. found 321.2177; $^1$H NMR (500 MHz, CDCl$_3$) δ 9.53 (s, 1H), 8.05 (d, J=5.7 Hz, 1H), 7.08 (d, J=1.9 Hz, 1H), 7.00 (dd, J=5.7, 1.9 Hz, 1H), 3.91 (s, 3H), 3.56 (s, 2H), 2.57 (t, J=7.3 Hz, 2H), 1.71-1.49 (m, 2H), 1.38-1.06 (m, 12H), 0.86 (t, J=6.7 Hz, 3H); $^{13}$C NMR (125 MHz, CDCl$_3$) δ 207.9, 165.4, 164.0, 147.6, 146.4, 108.4, 99.9, 53.6, 48.4, 44.3, 31.8, 29.3, 29.3, 29.2, 28.9, 23.3, 22.6, 14.1.

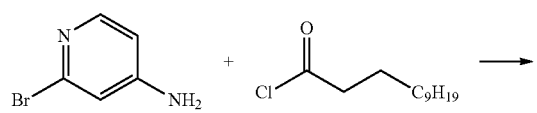

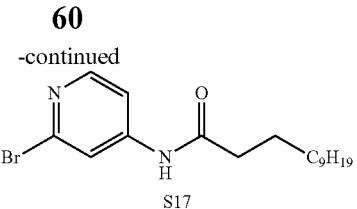

C12-4-amino-2-bromopyridine (S17): Prepared from 4-amino-2-bromopyridine using general procedure B to furnish S17 in a 52% yield. HRMS (ESI-TOF) calculated for $C_{17}H_{28}BrN_2O$ [M+H]: m/z 355.1385. found 355.1398; $^1$H NMR (500 MHz, CDCl$_3$) δ 8.23 (d, J=5.5 Hz, 1H), 7.78 (d, J=1.9 Hz, 1H), 7.39 (dd, J=5.6, 1.9 Hz, 1H), 7.26 (s, 1H), 2.43-2.36 (m, 2H), 1.71 (p, J=7.5 Hz, 2H), 1.35-1.16 (m, 16H), 0.87 (t, J=6.9 Hz, 3H); $^{13}$C NMR (125 MHz, CDCl$_3$) δ 171.9, 150.6, 146.5, 142.9, 116.9, 112.6, 37.8, 31.9, 29.6, 29.6, 29.4, 29.3, 29.3, 29.1, 25.1, 22.7, 14.1.

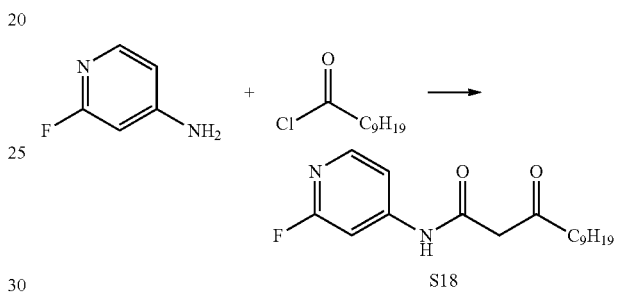

3OC12-4-amino-2-fluoropyridine (S18): Prepared from 4-amino-2-fluoropyridine using general procedure A to furnish S18 in a 42% yield. HRMS (ESI-TOF) calculated for $Ci7H26FN2O2$ [M+H]$^+$: m/z 309.1978. found 309.1978; $^1$H NMR (500 MHz, CDCl$_3$) δ 9.82 (s, 1H), 8.11 (d, J=5.6 Hz, 1H), 7.39-7.36 (m, 1H), 7.21 (d, J=5.6 Hz, 1H), 3.60 (s, 2H), 2.58 (t, J=7.3 Hz, 2H), 1.70-1.52 (m, 2H), 1.39-1.16 (m, 12H), 0.88 (t, J=6.7 Hz, 3H); $^{13}$C NMR (125 MHz, CDCl$_3$) δ 208.1, 164.7 (d, J=235 Hz), 164.2, 148.4 (d, J=11 Hz), 148.1 (d, J=17 Hz), 111.9 (d, J=4 Hz), 99.3 (d, J=43 Hz), 48.0, 44.4, 31.8, 29.3, 29.3, 29.2, 28.9, 23.3, 22.6, 14.1.

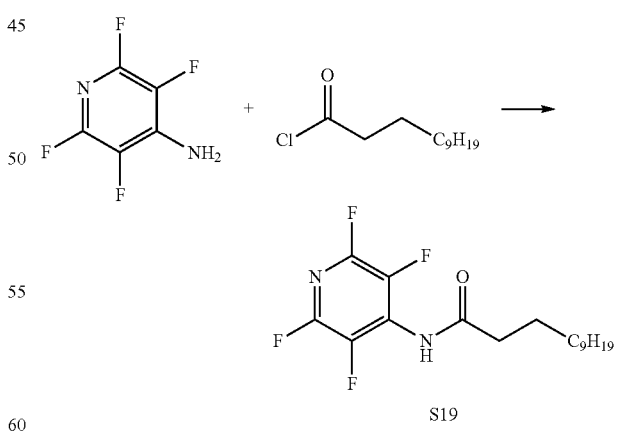

C12-4-amino-2,3,5,6-tetrafluoropyridine (S19): Prepared from 4-amino-2,3,5,6-tetrafluoropyridine using general procedure B to furnish S19 in a 10% yield. HRMS (ESI-TOF) calculated for $C_{17}H_{25}F_4N_2O$ [M+H]$^+$: m/z 349.1903. found 349.1879; $^1$H NMR (500 MHz, CDCl$_3$) 2.38 (t, J=7.5 Hz, 2H), 1.63-1.49 (m, 2H), 1.38-1.15 (m, 16H), 0.87 (t, J=6.9

Hz, 3H); $^{13}$C NMR (125 MHz, CDCl$_3$) δ 211.9, 42.8, 31.9, 29.6, 29.6, 29.5, 29.4, 29.3, 29.3, 23.9, 22.7, 14.1. The aryl signals were obscured by the C—F splitting.

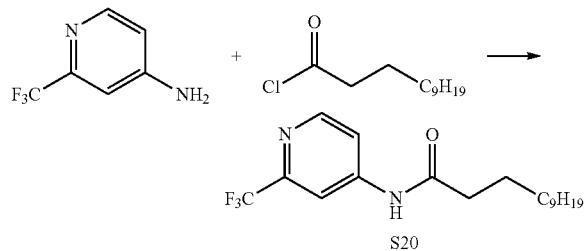

C12-4-amino-2-trifluoromethylpyridine (S20): Prepared from 4-amino-2-trifluoromethylpyridine using general procedure B to furnish S20 in a 92% yield. HRMS (ESI-TOF) calculated for C$_{18}$H$_{28}$F$_3$N$_2$O [M+H]$^+$: m/z 345.2154. found 345.2137; $^1$H NMR (500 MHz, CDCl$_3$) δ 8.76 (s, 1H), 8.52 (d, J=5.6 Hz, 1H), 7.97 (s, 1H), 7.76-7.66 (m, 1H), 2.40 (t, J=7.6 Hz, 2H), 1.69 (p, J=7.4 Hz, 2H), 1.52-0.99 (m, 16H), 0.85 (t, J=6.9 Hz, 3H); $^{13}$C NMR (125 MHz, CDCl$_3$) δ 173.3, 150.6, 148.9 (q, J=34 Hz), 147.0, 121.4 (q, J=274 Hz), 115.7, 110.7 (q, J=3 Hz), 37.6, 34.2, 31.9, 29.6, 29.5, 29.4, 29.2, 25.2, 24.9, 22.7, 14.1.

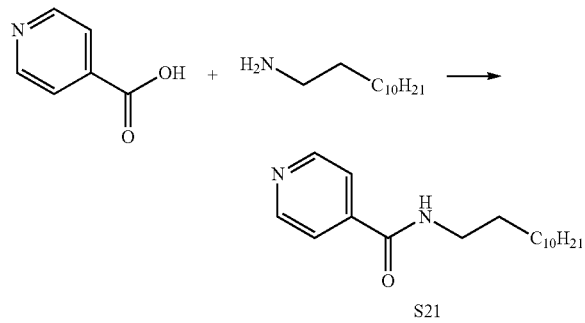

C12-isonicotinic amide (S21): Prepared from isonicotinic acid and dodecylamine using general procedure C. The crude product was purified by recrystallization from CH$_2$Cl$_2$/hexanes to provide S21 in a 40% yield. HRMS (ESI-TOF) calculated for C$_{18}$H$_{31}$N$_2$O [M+H]$^+$: m/z 291.2437. found 291.2425; $^1$H NMR (500 MHz, CDCl$_3$) δ 8.80-8.68 (m, 2H), 7.68-7.52 (m, 2H), 6.16 (s, 1H), 3.55-3.37 (m, 2H), 1.68-1.48 (m, 2H), 1.42-1.20 (m, 14H), 0.87 (t, J=6.9 Hz, 3H); $^{13}$C NMR (125 MHz, CDCl$_3$) δ 165.5, 150.6, 141.8, 120.8, 40.3, 31.9, 29.6, 29.6, 29.6, 29.5, 29.5, 29.3, 29.3, 26.9, 22.7, 14.1.

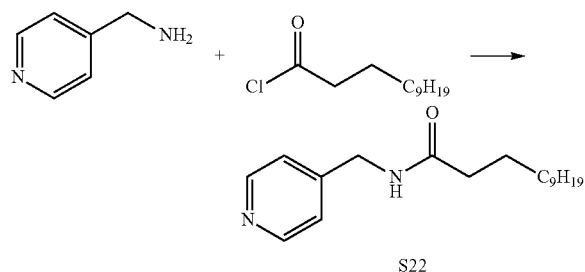

C12-4-(aminomethyl)pyridine (S22): Prepared from 4-(aminomethyl)pyridine using general procedure B to furnish S22 in a 10% yield. HRMS (ESI-TOF) calculated for C$_{18}$H$_{31}$N$_2$O [M+H]$^+$: m/z 291.2437. found 291.2434; $^1$H NMR (500 MHz, CDCl$_3$) δ 8.55 (d, J=5.0 Hz, 2H), 7.23-7.10 (m, 2H), 5.84 (s, 1H), 4.47 (d, J=6.1 Hz, 2H), 2.26 (t, J=8.0 Hz, 2H), 1.81-1.59 (m, 2H), 1.45-1.06 (m, 16H), 0.87 (t, J=6.7 Hz, 3H); $^{13}$C NMR (125 MHz, CDCl$_3$) δ 173.3, 150.0, 147.5, 122.3, 120.8, 42.2, 36.7, 31.9, 29.6, 29.6, 29.5, 29.3, 29.3, 25.7, 22.7, 14.1.

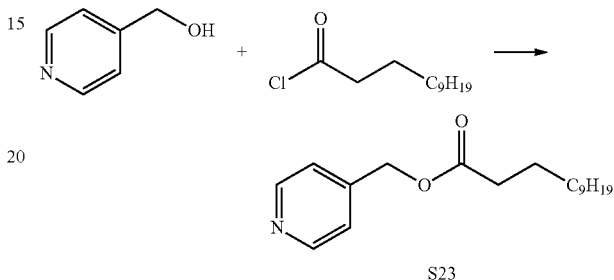

C12-4-(hydroxymethyl)pyridine (S23): Prepared from 4-(hydroxymethyl)pyridine using general procedure B to furnish S23 in a 66% yield. HRMS (ESI-TOF) calculated for C$_{18}$H$_{30}$NO$_2$ [M+H]$^+$: m/z 292.2277. found 292.2280; $^1$H NMR (500 MHz, CDCl$_3$) δ 8.61 (d, J=4.9 Hz, 2H), 7.25-7.23 (m, 2H), 5.12 (s, 2H), 2.40 (t, J=7.6 Hz, 2H), 1.66 (p, J=7.4 Hz, 2H), 1.38-1.15 (m, 16H), 0.87 (t, J=6.9 Hz, 3H); $^{13}$C NMR (125 MHz, CDCl$_3$) δ 173.4, 149.9, 145.1, 121.9, 64.0, 34.1, 31.9, 29.6, 29.6, 29.4, 29.3, 29.2, 29.1, 24.9, 22.7, 14.1.

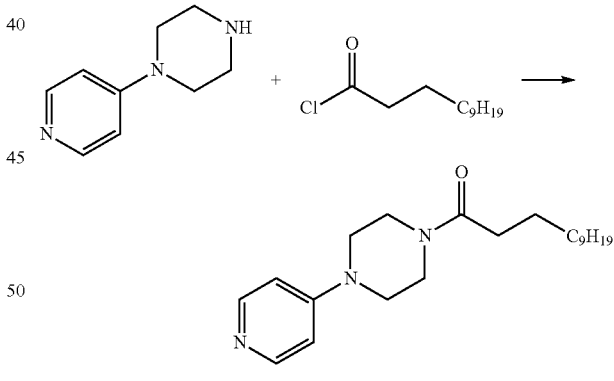

C12-4-(piperazine)pyridine (S24): Prepared from 4-(piperazine)pyridine using general procedure B to furnish S24 in a 24% yield. HRMS (ESI-TOF) calculated for C$_{21}$H$_{36}$N$_3$O [M+H]$^+$: m/z 346.2858. found 346.2851; $^1$H NMR (500 MHz, CDCl$_3$) δ 8.38-8.24 (m, 2H), 6.72-6.51 (m, 2H), 3.77 (t, J=5.4 Hz, 2H), 3.63 (t, J=5.3 Hz, 2H), 3.37 (t, J=5.3 Hz, 2H), 3.34 (t, J=5.4 Hz, 2H), 2.42-2.30 (m, 2H), 1.65 (p, J=7.5 Hz, 2H), 1.25 (m, 16H), 0.87 (t, J=6.9 Hz, 3H); $^{13}$C NMR (125 MHz, CDCl$_3$) δ 171.9, 154.5, 150.5, 108.5, 46.0, 44.8, 40.7, 33.3, 31.9, 29.6, 29.5, 29.5, 29.4, 29.3, 25.3, 22.7, 14.1.

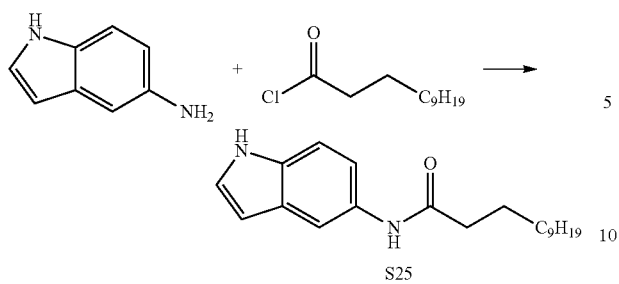

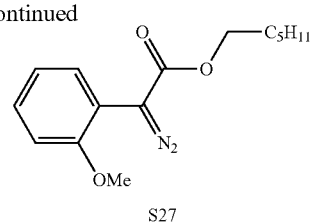

S27

Methoxyaryl diazoester (S27): S26 (0.12 g, 0.46 mmol, 1.0 equiv) was combined with 4-acetamidobenzenesulfonyl azide (0.27 g, 1.1 mmol, 2.4 equiv) in 2.4 mL CH$_3$CN. The reaction was cooled to 0° C. and 1,8-diazabiocyclo[5.4.0]undec-7-ene (0.28 mL, 1.9 mmol, 4.0 equiv). After stirring at room temperature for 24 h, the reaction was quenched with saturated aqueous NH$_4$Cl (3 mL) and extracted with diethyl ether (3×5 mL). The organic layer was dried over Na$_2$SO$_4$ and concentrated. Using a 20:1 petroleum ether/diethyl ether eluent, the crude product was purified by column chromatography to furnish S27 in a quantitative yield. $^1$H NMR (500 MHz, CDCl$_3$) δ 7.59-7.50 (m, 1H), 7.32-7.22 (m, 1H), 7.06-6.98 (m, 1H), 6.94-6.86 (m, 1H), 4.23 (t, J=6.7 Hz, 2H), 3.86 (s, 3H), 1.68 (p, J=7.0 Hz, 2H), 1.44-1.25 (m, 6H), 0.92-0.88 (m, 3H).

C12-5-aminoindole (S25): Prepared from 5-aminoindole using general procedure B to furnish S25 in an 89% yield. HRMS (ESI-TOF) calculated for C$_{20}$H$_{31}$N$_2$O [M+H]$^+$: m/z 315.2437. found 315.2415; $^1$H NMR (500 MHz, CDCl$_3$) δ 8.12 (s, 1H), 7.84 (s, 1H), 7.33 (d, J=8.7 Hz, 1H), 7.25-7.19 (m, 2H), 7.12 (s, 1H), 6.52 (s, 1H), 2.37 (t, J=7.5 Hz, 2H), 1.75 (p, J=7.6 Hz, 2H), 1.46-1.13 (m, 16H), 0.88 (t, J=6.8 Hz, 3H); $^{13}$C NMR (125 MHz, CDCl$_3$) δ 171.3, 133.1, 130.5, 128.0, 125.1, 116.3, 112.6, 111.1, 102.8, 37.8, 31.9, 29.6, 29.6, 29.5, 29.4, 29.3, 29.3, 25.8, 22.7, 14.1.

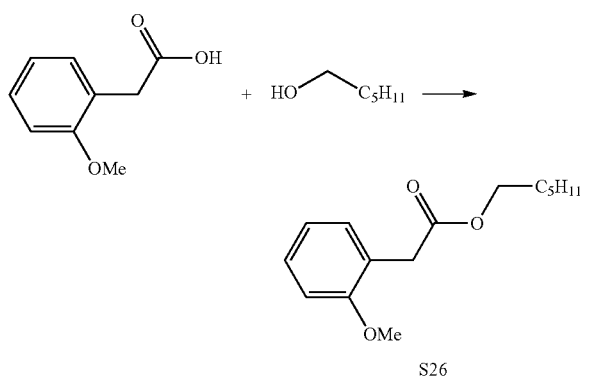

Methoxyarylester (S26): 2-Methoxyphenylacetic acid (0.10 g, 0.60 mmol, 1.0 equiv), n-hexanol (90 μL, 0.72 mmol, 1.2 equiv), diisopropylcarbodiimide (0.19 mL, 1.2 mmol, 1.7 equiv), dimethylaminopyridine (7.4 mg, 0.060 mmol, 0.01 equiv), and CH$_2$Cl$_2$ (8 mL) were combined. The reaction was stirred for 17 h, then poured onto water (5 mL) and extracted with CH$_2$Cl$_2$ (3×8 mL). The combined organic layer was washed sequentially with saturated NaHCO$_3$ (5 mL), water (5 mL), and brine (5 mL). The solution was then dried over Na$_2$SO$_4$ and concentrated. The crude product was purified by column chromatography to provide 0.12 g of S26 (78% yield); $^1$H NMR (500 MHz, CDCl$_3$) δ 7.30-7.22 (m, 1H), 7.21-7.15 (m, 1H), 6.92 (t, J=7.4 Hz, 1H), 6.87 (d, J=8.2 Hz, 1H), 4.09 (t, J=6.7 Hz, 2H), 3.81 (s, 3H), 3.62 (s, 2H), 1.60 (p, J=7.4 Hz, 2H), 1.36-1.20 (m, 6H), 0.88 (t, J=6.6 Hz, 3H); $^{13}$C NMR (125 MHz, CDCl$_3$) δ 172.0, 157.5, 130.8, 128.5, 123.2, 120.4, 110.3, 64.8, 55.3, 36.1, 31.4, 28.5, 25.5, 22.5, 14.0.

C6-dihydrobenzofuran ester (S28): Based on Ref. 3. To a flask containing Rh$_2$(S-DOSP)$_4$ (9.4 mg, 5.0×10$^{-3}$ mmol, 0.010 equiv) in 2.1 mL hexanes was added S27 (0.13 g, 0.48 mmol, 1.0 equiv) in mL hexanes over 3 h by syringe pump. After stirring for 72 h, the reaction mixture was concentrated and was purified by column chromatography to furnish a quantitative yield of S28. HRMS (ESI-TOF) calculated for C$_{15}$H$_{21}$O$_3$ [M+H]$^+$: m/z 249.1491. found 249.1489; $^1$H NMR (500 MHz, CDCl$_3$) δ 7.37 (d, J=7.6 Hz, 1H), 7.23-7.13 (m, 1H), 6.89 (td, J=7.5, 1.0 Hz, 1H), 6.82 (d, J=8.1 Hz, 1H), 4.94 (dd, J=9.2, 6.6 Hz, 1H), 4.67 (t, J=9.6 Hz, 1H), 4.33 (dd, J=9.8, 6.6 Hz, 1H), 4.16 (td, J=6.7, 2.7 Hz, 2H), 1.66 (p, J=6.7 Hz, 2H), 1.42-1.24 (m, 6H), 0.89 (t, J=6.7 Hz, 3H); $^{13}$C NMR (125 MHz, CDCl$_3$) δ 171.2, 159.7, 129.4, 125.3, 124.3, 120.6, 109.9, 72.4, 65.7, 47.2, 31.3, 28.5, 25.5, 22.5, 14.0.

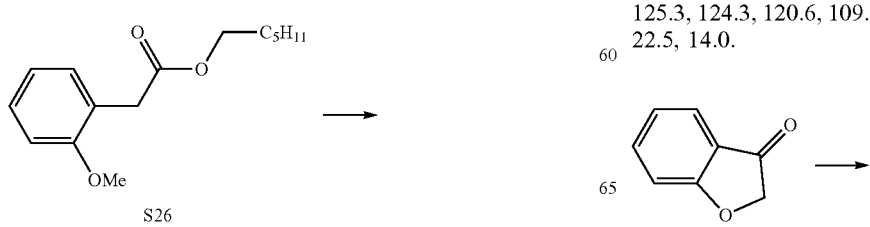

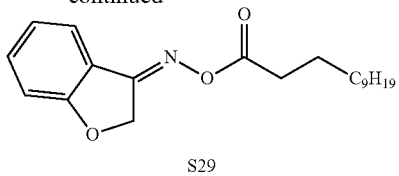

S29

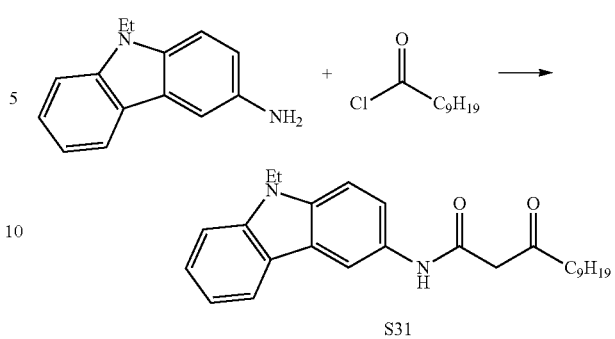

S31

C12-dihydrobenzofuran acylhydroxylamine (S29): 3-coumarone (50 mg, 0.37 mmol, 1.0 equiv), HONH$_2$.HCl (69 mg, 0.99 mmol, 2.7 equiv), and 0.75 mL pyridine were combined in a flame-dried flask and stirred for 3 h. The reaction was diluted with 3 mL EtOAc and washed sequentially with a 10% CuSO$_4$ solution (3×1 mL) and with brine (1×1 mL). The solution was dried over Na$_2$SO$_4$ and concentrated. The crude oxime was combined with 3.75 mL CH$_3$CN and Et$_3$N (0.16 mL, 1.1 mmol, 3.0 equiv). The reaction was cooled to 0° C., and dodecanoyl chloride (0.09 mL, 0.37 mmol, 1.0 equiv) was added dropwise. The reaction was allowed to return to room temperature over 4 h. The reaction was quenched with 2 mL saturated aqueous NaHCO$_3$ and extracted with CH$_2$Cl$_2$ (3×4 mL). The organic layer was washed with brine (5 mL), dried over Na$_2$SO$_4$, and concentrated. The crude product was purified by column chromatography to provide S29 in a 43% yield. HRMS (ESI-TOF) calculated for C$_{20}$H$_{30}$NO$_3$ [M+H]$^+$: m/z 332.2226. found 332.2231; $^1$H NMR (500 MHz, CDCl$_3$) δ 7.82 (d, J=7.8 Hz, 1H), 7.46 (t, J=7.9 Hz, 1H), 7.05 (t, J=7.6 Hz, 1H), 7.01 (d, J=8.5 Hz, 1H), 5.19 (d, J=2.3 Hz, 2H), 2.47 (t, J=7.6 Hz, 2H), 1.73 (p, J=7.0 Hz, 2H), 1.45-1.17 (m, 16H), 0.88 t, J=6.1 Hz, 3H); $^{13}$C NMR (125 MHz, CDCl$_3$) δ 170.8, 166.7, 164.4, 134.7, 123.7, 122.0, 117.9, 111.8, 70.9, 32.8, 31.9, 29.6, 29.6, 29.4, 29.3, 29.2, 29.1, 24.9, 22.7, 14.1.

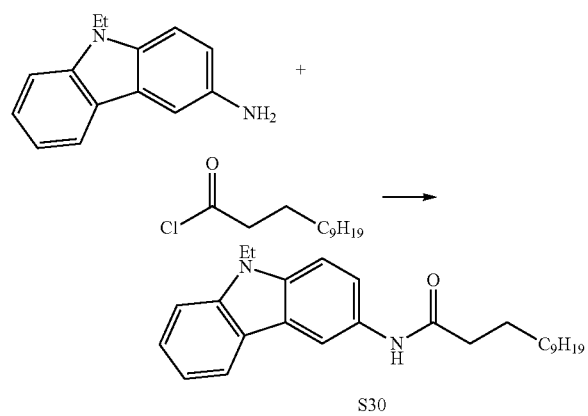

S30

C12-3-amino-1-ethylcarbazole (S30): Prepared from 3-amino-1-ethylcarbazole using general procedure B to furnish S30 in a 53% yield. HRMS (ESI-TOF) calculated for C$_{26}$H$_{37}$N$_2$O [M+H]$^+$: m/z 393.2906. found 393.2895; $^1$H NMR (500 MHz, CDCl$_3$) δ 8.30 (s, 1H), 8.03 (d, J=7.8 Hz, 1H), 7.60-7.51 (m, 1H), 7.48 (d, J=9.3 Hz, 1H), 7.44 (d, J=7.5 Hz, 1H), 7.37 (d, J=8.2 Hz, 1H), 7.31-7.24 (m, 1H), 7.18 (t, J=7.4 Hz, 1H), 4.34-4.24 (m, 2H), 2.39 (t, J=7.6 Hz, 2H), 1.77 (p, J=7.6 Hz, 2H), 1.56-1.04 (m, 19H), 0.89 (t, J=6.9 Hz, 3H); $^{13}$C NMR (125 MHz, CDCl$_3$) δ 171.7, 140.4, 137.1, 129.8, 125.8, 123.0, 122.8, 120.7, 119.6, 118.7, 112.9, 108.5, 108.4, 37.8, 37.6, 32.0, 29.7, 29.7, 29.6, 29.5, 29.4, 29.4, 25.9, 22.8, 14.2, 13.9

3OC12-3-amino-1-ethylcarbazole (S31): Prepared from 3-amino-1-ethylcarbazole using general procedure A to furnish S31 in a 17% yield. HRMS (ESI-TOF) calculated for C$_{26}$H$_{35}$N$_2$O$_2$ [M+H]$^+$: m/z 407.2699. found 407.2734; $^1$H NMR (500 MHz, CDCl$_3$) δ 9.22 (s, 1H), 8.33 (s, 1H), 8.08 (d, J=7.8 Hz, 1H), 7.55 (d, J=8.6 Hz, 1H), 7.46 (t, J=7.7 Hz, 1H), 7.39 (d, J=8.3 Hz, 1H), 7.35 (d, J=8.7 Hz, 1H), 7.21 (t, J=7.4 Hz, 1H), 4.35 (q, J=7.2 Hz, 2H), 3.62 (s, 2H), 2.62 (t, J=7.3 Hz, 2H), 1.70-1.60 (m, 2H), 1.42 (t, J=7.2 Hz, 3H), 1.38-1.06 (m, 12H), 0.88 (t, J=6.7 Hz, 3H); $^{13}$C NMR (125 MHz, CDCl$_3$) δ 208.4, 163.4, 140.4, 137.3, 129.3, 125.9, 123.0, 122.8, 120.8, 119.5, 118.8, 112.9, 108.6, 108.5, 48.8, 44.3, 37.6, 31.9, 29.4, 29.4, 29.3, 29.0, 23.4, 22.7, 14.2, 13.9.

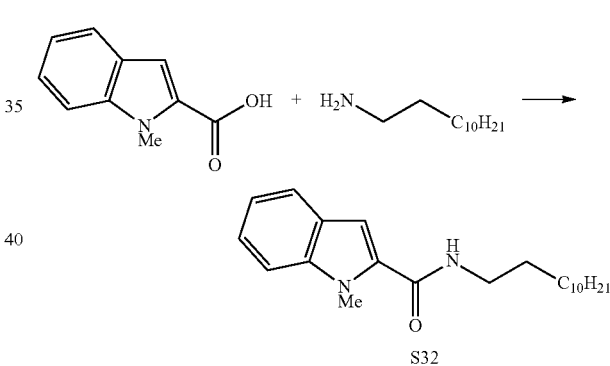

S32

C12-2-amido-1-methylindole (S32): Prepared from 1-methylindole-2-carboxylic acid and dodecylamine using general procedure C to furnish S32 in a 29% yield. HRMS (ESI-TOF) calculated for C$_{22}$H$_{35}$N$_2$O [M+H]$^+$: m/z 343.2749. found 343.2745; $^1$H NMR (500 MHz, CDCl$_3$) δ 7.65 (d, J=8.2 Hz, 1H), 7.42-7.29 (m, 2H), 7.22 (t, J=7.4 Hz, 1H), 6.83-6.75 (m, 1H), 4.05 (s, 3H), 3.54-3.47 (m, 2H), 1.71-1.62 (m, 2H), 1.50-1.08 (m, 18H), 0.87 (t, J=6.8 Hz, 3H); $^{13}$C NMR (125 MHz, CDCl$_3$) δ 160.7, 136.8, 125.2, 124.0, 121.7, 121.0, 120.5, 119.4, 110.3, 103.3, 77.3, 39.8, 32.0, 29.7, 29.6, 29.6, 29.5, 29.4, 29.3, 27.0, 22.7, 14.2.

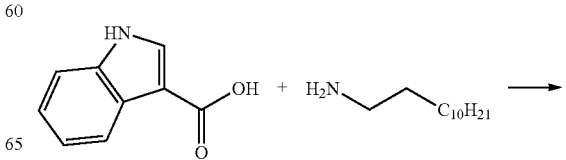

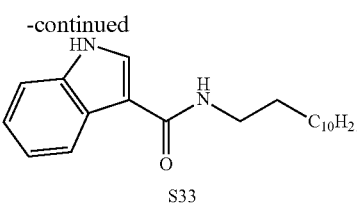

S33

C12-3-amidoindole (S33): Prepared from indole-3-carboxylic acid and dodecylamine using general procedure C to furnish S33 in a 47% yield. HRMS (ESI-TOF) calculated for $C_{21}H_{33}N_2O$ [M+H]$^+$: m/z 329.2593. found 329.2586; $^1$H NMR (500 MHz, CDCl$_3$) δ 9.32 (s, 1H), 7.98-7.85 (m, 1H), 7.74-7.69 (m, 1H), 7.47-7.41 (m, 1H), 7.26-7.22 (m, 2H), 6.08-6.00 (m, 1H), 3.55-3.47 (m, 2H), 1.65 (p, J=7.5 Hz, 2H), 1.49-1.13 (m, 18H), 0.87 (t, J=6.9 Hz, 3H); $^{13}$C NMR (125 MHz, CDCl$_3$) δ 165.6, 136.5, 128.2, 124.5, 122.8, 121.5, 119.6, 112.5, 112.2, 39.7, 32.0, 30.0, 29.7, 29.7, 29.7, 29.6, 29.4, 29.4, 27.1, 22.7, 14.2.

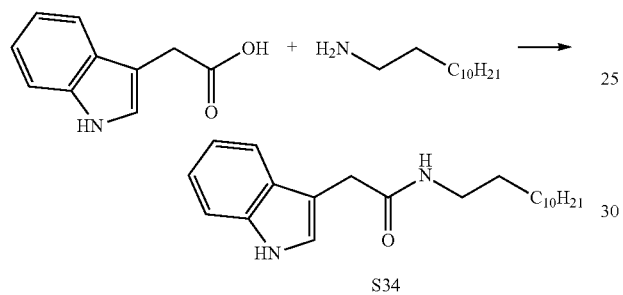

S34

C12-3-(methylamido)indole (S34): Prepared from 2-(1H-indol-3-yl)acetic acid and dodecylamine using general procedure C to furnish S34 in a 40% yield. HRMS (ESI-TOF) calculated for $C_{22}H_{35}N_2O$ [M+H]$^+$: m/z 343.2749. found 343.2740; $^1$H NMR (500 MHz, CDCl$_3$) δ 8.27 (s, 1H), 7.56 (d, J=7.9 Hz, 1H), 7.42 (d, J=8.2 Hz, 1H), 7.26-7.21 (m, 1H), 7.19-7.11 (m, 2H), 5.68 (s, 1H), 3.74 (s, 2H), 3.20-3.11 (m, 2H), 1.38-1.06 (m, 20H), 0.88 (t, J=6.9 Hz, 3H); $^{13}$C NMR (125 MHz, CDCl$_3$) δ 171.3, 136.4, 127.0, 123.7, 122.7, 120.2, 118.8, 111.4, 109.2, 39.6, 33.5, 32.0, 29.7, 29.7, 29.6, 29.5, 29.5, 29.4, 29.3, 26.8, 22.8, 14.2.

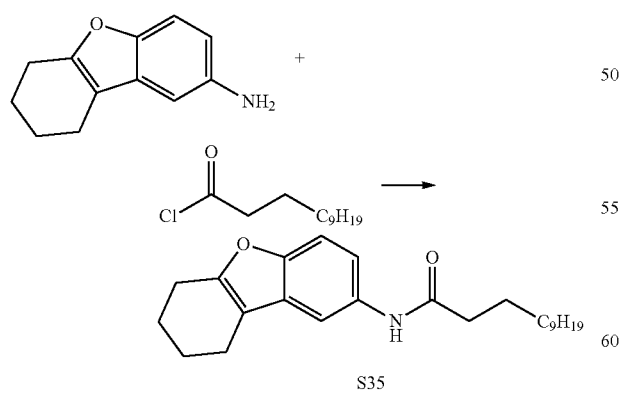

S35

C12-2-amino-tetrahydrodibenzofuran (S35): Prepared from 6,7,8,9-tetrahydrodibenzo[b,d]furan-2-amine using general procedure B to furnish S35 in a 68% yield. HRMS (ESI-TOF) calculated for $C_{24}H_{36}NO_2$ [M+H]$^+$: m/z 370.2746. found 370.2745; $^1$H NMR (500 MHz, CDCl$_3$) δ 7.75 (s, 1H), 7.40 (s, 1H), 7.30-7.22 (m, 1H), 7.09 (d, J=8.7 Hz, 1H), 2.76-2.67 (m, 2H), 2.63-2.50 (m, 2H), 2.35 (t, J=7.6 Hz, 2H), 1.96-1.86 (m, 2H), 1.84-1.78 (m, 2H), 1.73 (p, J=7.5 Hz, 2H), 1.50-1.08 (m, 16H), 0.87 (t, J=6.9 Hz, 3H); $^{13}$C NMR (125 MHz, CDCl$_3$) δ 171.6, 155.1, 151.2, 132.6, 129.3, 115.9, 113.2, 110.6, 37.8, 32.0, 29.7, 29.7, 29.6, 29.5, 29.4, 29.4, 29.1, 25.8, 23.5, 22.9, 22.7, 22.6, 20.4, 14.2

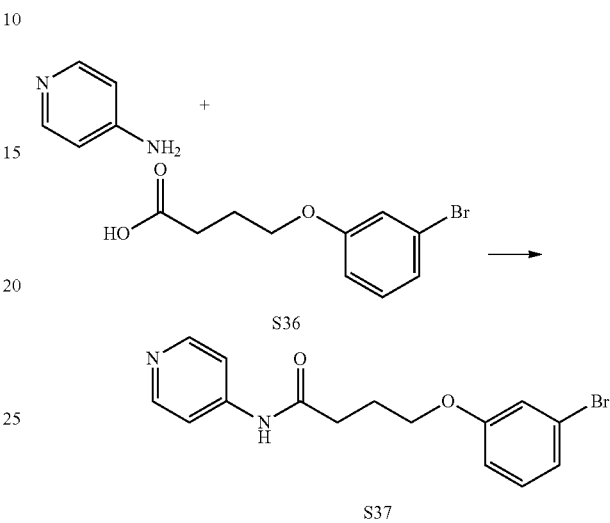

S37

4-aminopyridine-C4-3-bromophenoxyhybrid (S37): Prepared from 4-aminopyridine and S36[1] using general procedure C to furnish S37 in a 75% yield. HRMS (ESI-TOF) calculated for $C_{15}H_{16}BrN_2O_2$ [M+H]$^+$: m/z 335.0395. found 335.0388; $^1$H NMR (500 MHz, CDCl$_3$) δ 8.59-8.39 (m, 2H), 8.23 (s, 1H), 7.49 (d, J=5.4 Hz, 2H), 7.12 (t, J=8.0 Hz, 1H), 7.07 (d, J=8.2 Hz, 1H), 7.03-6.99 (m, 1H), 6.78 (dd, J=8.2, 2.4 Hz, 1H), 4.02 (t, J=5.8 Hz, 2H), 2.61 (t, J=7.1 Hz, 2H), 2.27-2.14 (m, 2H); $^{13}$C NMR (125 MHz, CDCl$_3$) δ 171.4, 159.3, 150.5, 145.1, 130.6, 124.0, 122.8, 117.7, 113.5, 113.2, 66.8, 33.9, 24.5.

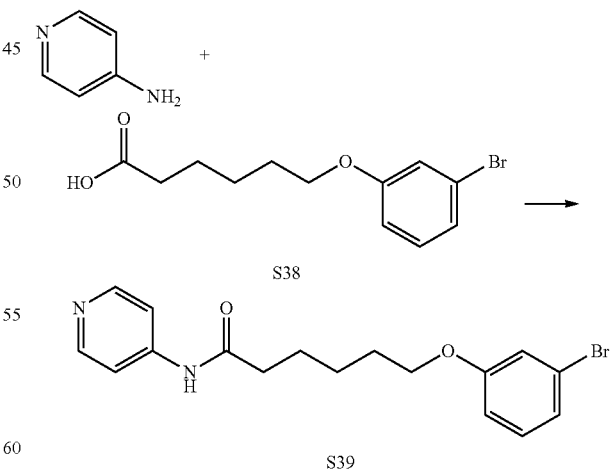

S39

4-aminopyridine-C6-3-bromophenoxyhybrid (S39): Prepared from 4-aminopyridine and S38[1] using general procedure C to furnish S39 in a 70% yield. HRMS (ESI-TOF) calculated for $C_{17}H_{20}BrN_2O_2$ [M+H]$^+$: m/z 363.0708. found 363.0710; $^1$H NMR (500 MHz, CDCl$_3$) δ 8.50 (s, 2H), 7.48

(d, J=5.3 Hz, 2H), 7.30 (s, 1H), 7.13 (t, J=8.1 Hz, 1H), 7.09-7.00 (m, 2H), 6.83-6.78 (m, 1H), 3.95 (t, J=6.3 Hz, 2H), 2.43 (t, J=7.5 Hz, 2H), 1.88-1.76 (m, 4H), 1.60-1.49 (m, 2H); $^{13}$C NMR (125 MHz, CDCl$_3$) δ 172.1, 159.7, 150.0, 145.6, 130.5, 123.7, 122.7, 117.6, 113.4, 113.4, 67.7, 37.5, 28.8, 25.6, 24.8.

Hz, 1H), 7.18 (dt, J=5.7, 1.6 Hz, 1H), 7.13 (t, J=8.1 Hz, 1H), 7.06 (ddd, J=7.9, 1.8, 1.0 Hz, 1H), 7.03 (t, J=2.1 Hz, 1H), 6.80 (ddd, J=8.2, 2.5, 1.1 Hz, 1H), 3.94 (1, J=6.2 Hz, 2H), 2.44 (t, J=7.4 Hz, 2H), 1.87-1.73 (m, 4H), 1.61-1.49 (m, 2H); $^{13}$C NMR (125 MHz, CDCl$_3$) δ 171.7, 164.8 (d, J=235 Hz), 159.7, 148.9 (d, J=12 Hz), 148.1 (d, J=17 Hz), 130.5, 123.7, 122.8, 117.6, 113.4, 111.3 (d, J=4 Hz), 98.7 (d, J=43 Hz), 67.7, 37.6, 28.8, 25.6, 24.7.

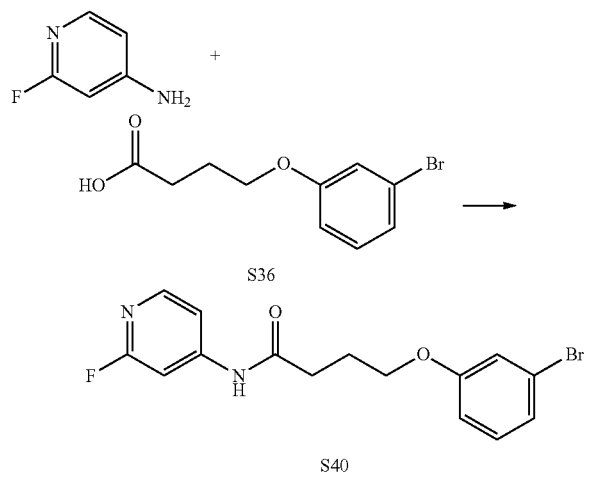

4-amino-2-fluoropyridine-C4-3-bromophenoxyhybrid (S40): Prepared from 4-amino-2-fluoropyridine and S36[1] using general procedure C to furnish S40 in a 48% yield. HRMS (ESI-TOF) calculated for C$_{15}$H$_{15}$BrFN$_2$O$_2$ [M+H]$^+$: m/z 353.0301. found 353.0290; $^1$H NMR (500 MHz, CDCl$_3$) δ 8.09 (d, J=5.7 Hz, 1H), 7.47 (s, 1H), 7.41-7.30 (m, 1H), 7.19-7.07 (m, 3H), 7.07-6.99 (m, 1H), 6.88-6.75 (m, 1H), 4.05 (t, J=5.7 Hz, 2H), 2.63 (t, J=7.0 Hz, 2H), 2.22 (p, J=6.8 Hz, 2H); $^{13}$C NMR (125 MHz, CDCl$_3$) δ 171.1, 164.8 (d, J=235 Hz), 159.3, 148.2 (d, J=17 Hz), 148.1, 130.7, 124.1, 122.9, 117.7, 113.3, 111.3, 98.7 (d, J=43 Hz), 66.7, 34.0, 24.4.

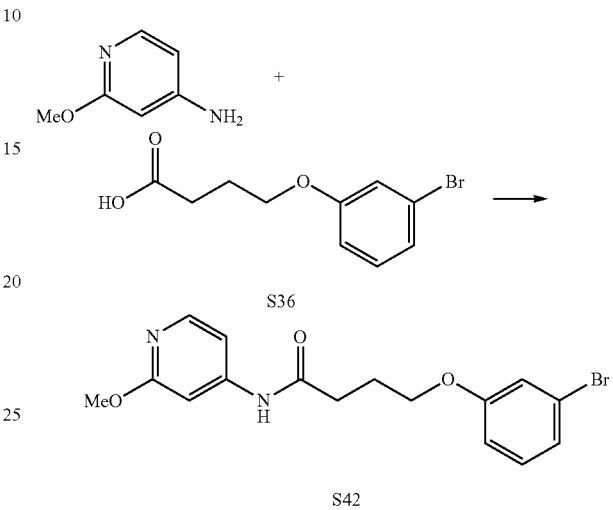

4-amino-2-methoxypyridine-C4-3-bromophenoxyhybrid (S42): Prepared from 4-amino-2-methoxypyridine and S36' using general procedure C to furnish S42 in a 72% yield. HRMS (ESI-TOF) calculated for C$_{16}$H$_{18}$BrN$_2$O$_3$ [M+H]$^+$: m/z 365.0501. found 365.0486; $^1$H NMR (500 MHz, CDCl$_3$) δ 8.04 (d, J=5.8 Hz, 1H), 7.13 (t, J=8.0 Hz, 1H), 7.08 (d, J=8.0 Hz, 1H), 7.05-6.99 (m, 2H), 6.97 (dd, J=5.8, 1.9 Hz, 1H), 6.81 (ddd, J=8.2, 2.5, 1.1 Hz, 1H), 4.03 (t, J=5.8 Hz, 2H), 3.91 (s, 3H), 2.59 (t, J=7.1 Hz, 2H), 2.29-2.14 (m, 2H); $^{13}$C NMR (125 MHz, CDCl$_3$) δ 171.0, 165.4, 159.3, 147.6, 146.7, 130.6, 124.0, 122.8, 117.7, 113.3, 107.9, 99.3, 66.8, 53.6, 34.0, 24.5.

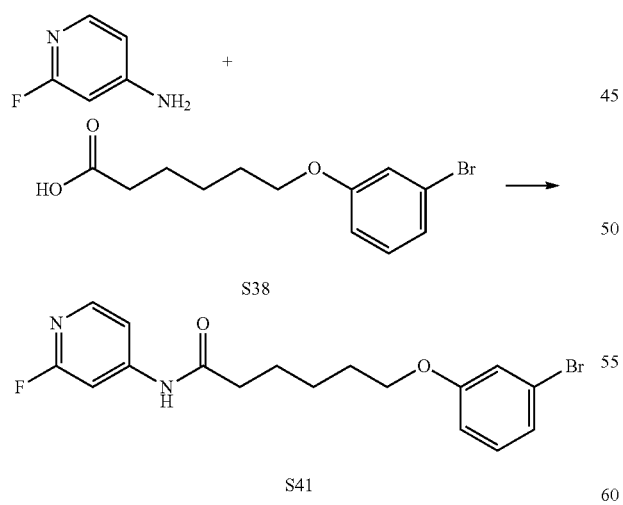

4-amino-2-fluoropyridine-C6-3-bromophenoxyhybrid (S41): Prepared from 4-amino-2-fluoropyridine and S38[1] using general procedure C to furnish S41 in a 14% yield. HRMS (ESI-TOF) calculated for C$_{17}$H$_{19}$BrFN$_2$O$_2$ [M+H]$^+$: m/z 381.0614. found 381.0595; $^1$H NMR (500 MHz, CDCl$_3$) δ 8.09 (d, J=5.7 Hz, 1H), 7.53 (s, 1H), 7.35 (d, J=1.8

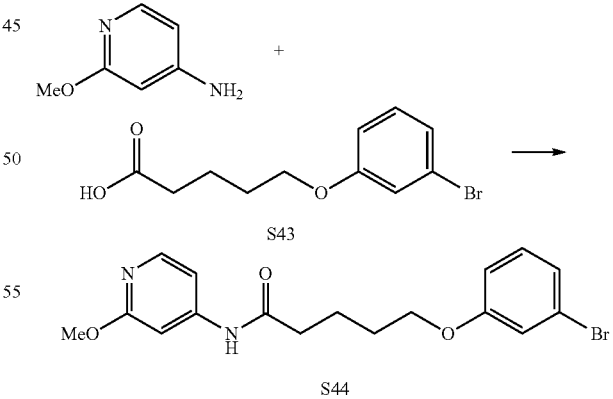

4-amino-2-methoxypyridine-C5-3-bromophenoxyhybrid (S44): Prepared from 4-amino-2-methoxypyridine and S43[1] using general procedure C to furnish S44 in a 58% yield. HRMS (ESI-TOF) calculated for C$_{17}$H$_{20}$BrN$_2$O$_3$ [M+1-1]': m/z 379.06573. found 379.0633; $^1$H NMR (500 MHz, CDCl$_3$) δ 8.05 (d, J=5.7 Hz, 1H), 7.13 (t, J=8.0 Hz, 1H), 7.10-7.05 (m, 1H), 7.05-6.96 (m, 3H), 6.81 (ddd, J=8.2, 2.5, 1.1 Hz, 1H), 3.98 (t, J=5.7 Hz, 2H), 3.92 (s, 3H), 2.46 (t, J=7.0 Hz, 2H), 2.02-1.81 (m, 4H); ¹³C NMR (125 MHz, CDCl₃) δ 171.2, 165.4, 159.5, 147.6, 146.8, 130.6, 123.8, 122.8, 117.6, 113.4, 107.9, 99.3, 67.7, 53.6, 37.2, 28.3, 22.0.

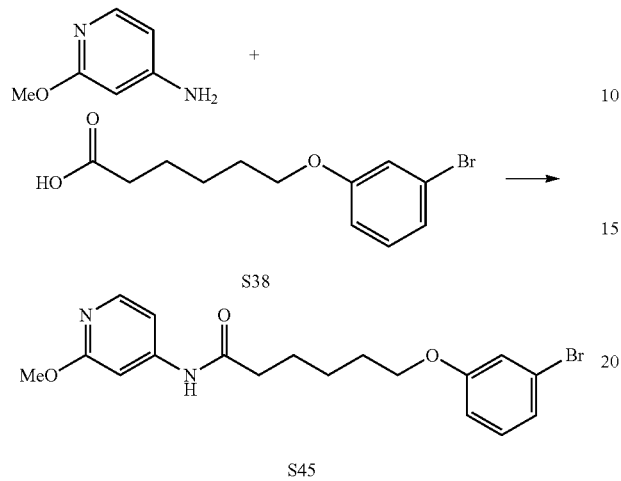

4-amino-2-methoxypyridine-C6-3-bromophenoxyhybrid (S45): Prepared from 4-amino-2-methoxypyridine and S38¹ using general procedure C to furnish S45 in a 13% yield. HRMS (ESI-TOF) calculated for C₁₈H₂₂BrN₂O₃ [M+H]⁺: m/z 393.0814. found 393.0805; ¹H NMR (500 MHz, CDCl₃) δ 8.11-7.98 (m, 1H), 7.18-7.09 (m, 2H), 7.07 (t, J=1.5 Hz, 1H), 7.06-6.97 (m, 3H), 6.81 (ddd, J=8.0, 2.4, 1.3 Hz, 1H), 3.95 (t, J=6.4 Hz, 2H), 3.92 (s, 3H), 2.41 (t, J=7.4 Hz, 2H), 1.88-1.72 (m, 4H), 1.63-1.48 (m, 3H); ¹³C NMR (125 MHz, CDCl₃) δ 171.4, 165.4, 159.7, 147.6, 146.8, 130.5, 123.7, 122.8, 117.6, 113.4, 107.9, 99.3, 67.7, 53.6, 37.7, 28.8, 25.6, 24.9.

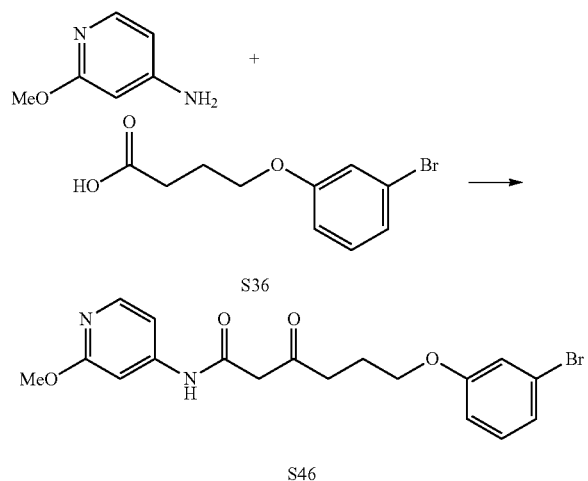

4-amino-2-methoxypyridine-3OC6-3-bromophenoxyhybrid (S46): S36¹ (0.83 g, 3.2 mmol, 1.0 equiv) was dissolved in 6.4 mL CH₂Cl₂. The reaction mixture was cooled to 0° C. and oxalylchloride (0.27 mL, 3.2 mmol, 1.0 equiv) was added dropwise. After 5 min, 1 drop of DMF was added to the reaction mixture. The reaction mixture was stirred at 0° C. for 30 min and then at room temperature for 90 min. The acid chloride was then used in general procedure A with 4-amino-2-methoxypyridine to furnish S46 in a 59% yield. HRMS (ESI-TOF) calculated for C₁₈H₂₀BrN₂O₄ [M+H]⁺: m/z 407.0606. found 407.0583; ¹H NMR (500 MHz, CDCl₃) δ 9.58 (s, 1H), 8.05 (d, J=5.7 Hz, 1H), 7.16 (s, 1H), 7.11 (t, J=8.0 Hz, 1H), 7.09-6.99 (m, 3H), 6.78 (d, J=8.1 Hz, 1H), 3.98 (t, J=5.9 Hz, 2H), 3.94 (s, 3H), 3.65 (s, 2H), 2.80 (t, J=7.0 Hz, 2H), 2.12 (p, J=6.0 Hz, 2H); ¹³C NMR (125 MHz, CDCl₃) δ 206.4, 165.0, 164.2, 159.3, 147.2, 146.7, 130.6, 124.1, 122.8, 117.6, 113.4, 108.5, 99.6, 66.6, 54.0, 49.1, 40.6, 23.0.

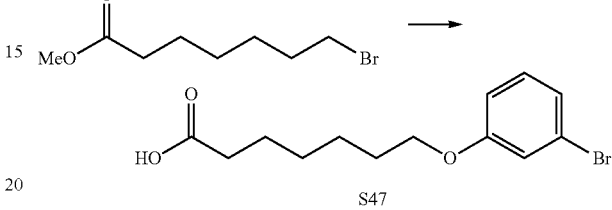

C7 acid (S47): Sodium hydride (60%, 22 mg, 0.49 mmol, 1.3 equiv) was added to 3-bromophenol (0.10 mL, 0.37 mmol, 1.0 equiv) in 0.50 mL DMF. The reaction was heated to 100° C. for 1 h. After cooling, methyl-7-bromoheptanoate (0.10 g, 0.45 mmol, 1.2 equiv), potassium iodide (7.4 mg, 0.045 mmol, 0.12 equiv), and potassium carbonate (0.18 g, 1.1 mmol, 3.0 equiv were added). After stirring at room temperature for 1 week, the reaction was diluted with 5 mL diethyl ether and washed sequentially with water (3×5 mL) and 2 M potassium hydroxide (3×5 mL). The organic layer was dried over Na₂SO₄ and concentrated. Column chromatography furnished the C7 aryl ester in a 55% yield. The ester (80 mg, 0.25 mmol, 1.0 equiv) was combined with lithium hydroxide monohydrate (57 mg, 1.3 mmol, 5 equiv) in 4:1 THF/H₂O (2.5 mL). The reaction was heated to 65° C. for 17 h or until complete. After cooling, the reaction was acidified with 1 M HCl. The aqueous layer was extracted with EtOAc (3×4 mL). The combined organic was washed with brine (5 mL), dried over Na₂SO₄, and concentrated to provide S47 in an 80% yield. The material was used without further purification. ¹H NMR (500 MHz, CDCl₃) δ 10.99 (bs, 1H), 7.13 (t, J=8.0 Hz, 1H), 7.09-7.01 (m, 2H), 6.86-6.78 (m, 1H), 3.92 (t, J=6.4 Hz, 2H), 2.38 (t, J=7.5 Hz, 2H), 1.83-1.73 (m, 2H), 1.67 (p, J=7.5 Hz, 2H), 1.55-1.37 (m, 4H).

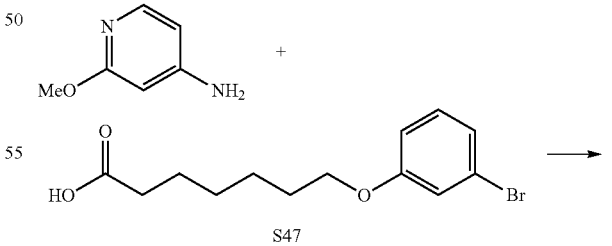

4-amino-2-methoxypyridine-C7-3-bromophenoxyhybrid (S48): Prepared from 4-amino-2-methoxypyridine and S47 using general procedure C to furnish S48 in a 21% yield. HRMS (ESI-TOF) calculated for $C_{19}H_{24}BrN_2O_3$ [M+H]$^+$: m/z 407.0970. found 407.0944; $^1$H NMR (500 MHz, CDCl$_3$) δ 8.05 (d, J=5.7, 1H), 7.18 (s, 1H), 7.12 (t, J=8.0 Hz, 1H), 7.08-6.95 (m, 4H), 6.81 (ddd, J=8.2, 2.5, 1.0 Hz, 1H), 3.95-3.89 (m, 5H), 2.38 (t, J=7.5 Hz, 2H), 1.87-1.69 (m, 4H), 1.54-1.37 (m, 4H); $^{13}$C NMR (125 MHz, CDCl$_3$) δ 171.6, 165.4, 159.8, 147.6, 146.8, 130.5, 123.6, 122.8, 117.6, 113.5, 107.9, 99.2, 67.9, 53.6, 37.7, 28.9, 28.8, 25.8, 25.1.

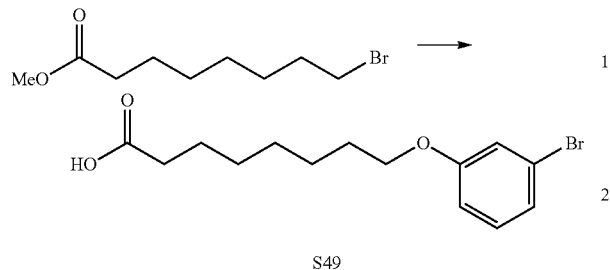

S49

C8 acid (S49): The acid was prepared using the same procedure as for S47, but starting with methyl-8-bromooctanoate to provide S49 in a quantitative yield. HRMS (ESI-TOF) calculated for $C_{14}H_{20}BrO_3$ [M+H]$^+$: m/z 315.0596. found 315.0607; $^1$H NMR (500 MHz, CDCl$_3$) δ 9.90 (bs, 1H), 7.12 (t, J=8.0 Hz, 1H), 7.08-7.02 (m, 2H), 6.82 (ddd, J=8.2, 2.4, 1.1 Hz, 1H), 3.92 (t, J=6.5 Hz, 2H), 2.37 (t, J=7.5 Hz, 2H), 1.81-1.73 (m, 2H), 1.70-1.62 (m, 2H), 1.50-1.42 (m, 2H), 1.42-0.34 (m, 4H); $^{13}$C NMR (125 MHz, CDCl$_3$) δ 177.9, 159.8, 130.5, 123.5, 122.7, 117.6, 113.5, 68.1, 33.6, 29.0, 28.9, 28.9, 25.8, 24.6.

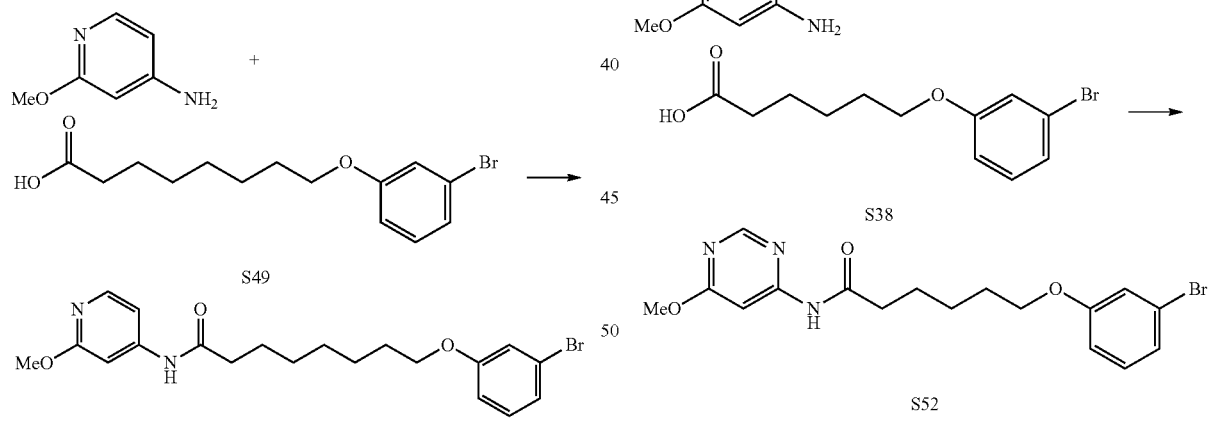

S49

S50

4-amino-2-methoxypyridine-C8-3-bromophenoxyhybrid (S50): Prepared from 4-amino-2-methoxypyridine and S49 using general procedure C to furnish S50 in a 36% yield. HRMS (ESI-TOF) calculated for $C_{20}H_{26}BrN_2O_3$ [M+H]$^+$: m/z 421.1127. found 421.1121; $^1$H NMR (500 MHz, CDCl$_3$) δ 8.08 (d, J=5.6 Hz, 1H), 7.21-7.13 (m, 2H), 7.13-6.98 (m, 4H), 6.85 (ddd, J=8.2, 2.5, 1.1 Hz, 1H), 4.03-3.91 (m, 5H), 2.41 (t, J=7.5 Hz, 2H), 1.86-1.71 (m, 4H), 1.54-1.37 (m, 6H); $^{13}$C NMR (125 MHz, CDCl$_3$) δ 171.7, 165.4, 159.8, 147.6, 146.8, 130.5, 123.6, 122.7, 117.6, 113.5, 107.9, 99.2, 68.0, 53.6, 37.8, 29.0, 29.0, 29.0, 25.8, 25.1.

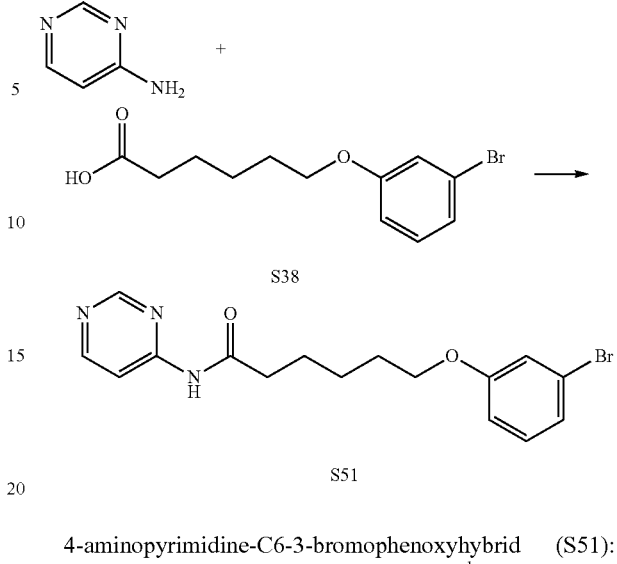

4-aminopyrimidine-C6-3-bromophenoxyhybrid (S51): Prepared from 4-aminopyrimidine and S38$^1$ using general procedure C to furnish S51 in a 48% yield. HRMS (ESI-TOF) calculated for $C_{16}H_{19}BrN_3O_2$ [M+H]$^+$: m/z 364.0661. found 364.0648; $^1$H NMR (500 MHz, CDCl$_3$) δ 8.85 (s, 1H), 8.63 (d, J=5.7 Hz, 1H), 8.27-8.09 (m, 2H), 7.12 (t, J=8.0 Hz, 1H), 7.09-7.01 (m, 2H), 6.84-6.78 (m, 1H), 3.95 (t, J=6.3 Hz, 2H), 2.47 (t, J=7.4 Hz, 2H), 1.88-1.77 (m, 4H), 1.61-1.49 (m, 2H); $^{13}$C NMR (125 MHz, CDCl$_3$) δ 172.2, 159.7, 158.5, 158.2, 156.9, 130.5, 123.7, 122.8, 117.6, 113.4, 110.2, 67.7, 37.6, 28.8, 25.6, 24.6

4-amino-6-methoxypyrimidine-C6-3-bromophenoxyhybrid (S52): Prepared from 4-amino-6-methoxypyrimidine and S38' using general procedure C to furnish S52 in a 23% yield. HRMS (ESI-TOF) calculated for $C_{17}H_{21}BrN_3O_3$ [M+H]: m/z 394.0766. found 394.0752; $^1$H NMR (500 MHz, CDCl$_3$) δ 8.45 (d, J=1.1 Hz, 1H), 7.82 (s, 1H), 7.56 (d, J=1.1 Hz, 1H), 7.12 (t, J=8.0 Hz, 1H), 7.09-7.01 (m, 2H), 6.81 (ddd, J=8.2, 2.5, 1.1 Hz, 1H), 3.97 (s, 3H), 3.94 (t, J=6.3 Hz, 2H), 2.43 (t, J=7.5 Hz, 2H), 1.87-1.73 (m, 4H), 1.59-1.49 (m, 2H); $^{13}$C NMR (125 MHz, CDCl$_3$) δ 171.9, 171.3, 159.7, 157.5, 157.4, 130.5, 123.7, 122.8, 117.6, 113.4, 95.0, 67.7, 54.2, 37.6, 28.8, 25.6, 24.7.

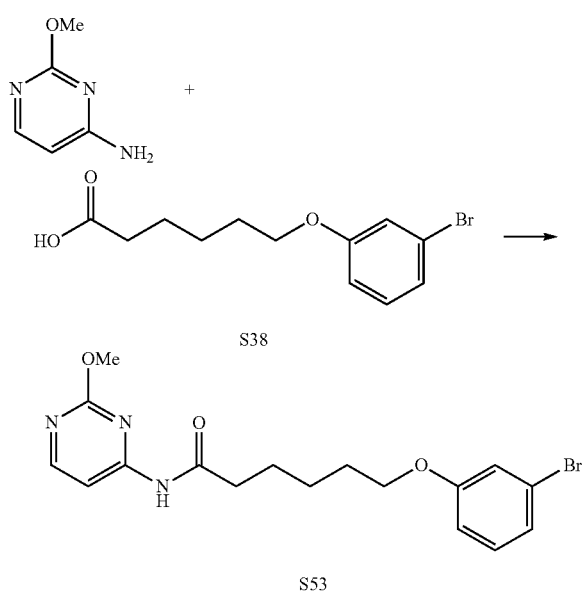

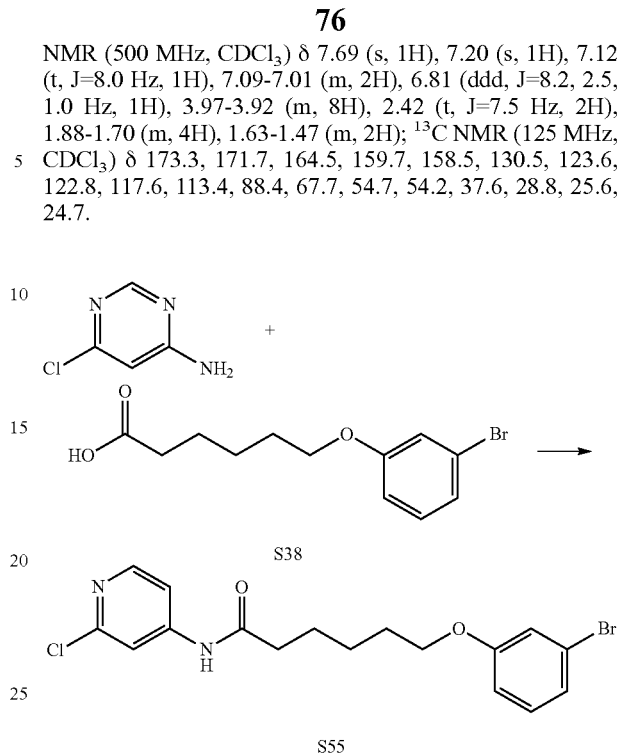

4-amino-2-methoxypyrimidine-C6-3-bromophenoxyhybrid (S53): Prepared from 4-amino-2-methoxypyrimidine and S38[1] using general procedure C to furnish S53 in a 14% yield. HRMS (ESI-TOF) calculated for $C_{17}H_{21}BrN_3O_3$ [M+H]: m/z 394.0766. found 394.0763; $^1$H NMR (500 MHz, CDCl$_3$) δ 8.41 (d, J=5.6 Hz, 1H), 7.86 (s, 1H), 7.79 (d, J=5.6 Hz, 1H), 7.12 (t, J=8.0 Hz, 1H), 7.09-7.00 (m, 2H), 6.81 (dd, J=8.2, 2.4 Hz, 1H), 4.01-3.89 (m, 5H), 2.45 (t, J=7.5 Hz, 2H), 1.87-1.75 (m, 4H), 1.57-1.50 (m, 2H); $^{13}$C NMR (125 MHz, CDCl$_3$) δ $^{13}$C NMR (126 MHz, CDCl$_3$) 172.1, 165.0, 160.5, 159.7, 158.9, 130.5, 123.7, 122.8, 117.7, 113.4, 103.9, 67.7, 54.8, 37.5, 28.8, 25.6, 24.6.

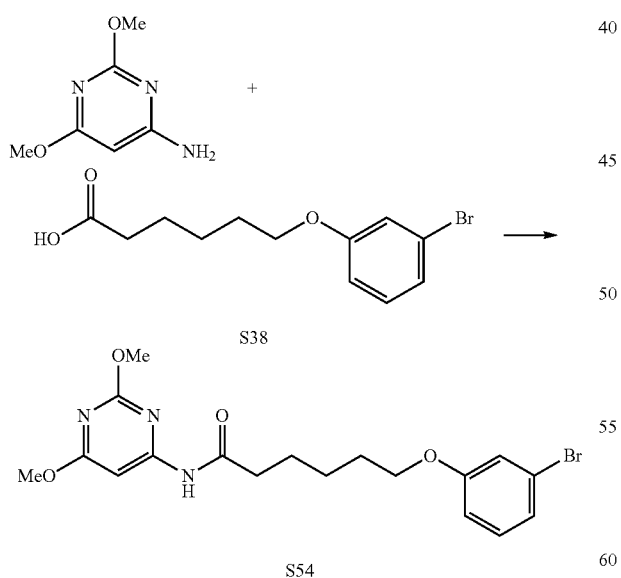

4-amino-2,6-dimethoxypyrimidine-C6-3-bromophenoxyhybrid (S54): Prepared from 4-amino-2,6-dimethoxypyrimidine and S38[1] using general procedure C to furnish S54 in a 13% yield. HRMS (ESI-TOF) calculated for $C_{18}H_{23}BrN_3O_4$ [M+H]$^+$: m/z 424.0872. found 424.0863; $^1$H NMR (500 MHz, CDCl$_3$) δ 7.69 (s, 1H), 7.20 (s, 1H), 7.12 (t, J=8.0 Hz, 1H), 7.09-7.01 (m, 2H), 6.81 (ddd, J=8.2, 2.5, 1.0 Hz, 1H), 3.97-3.92 (m, 8H), 2.42 (t, J=7.5 Hz, 2H), 1.88-1.70 (m, 4H), 1.63-1.47 (m, 2H); $^{13}$C NMR (125 MHz, CDCl$_3$) δ 173.3, 171.7, 164.5, 159.7, 158.5, 130.5, 123.6, 122.8, 117.6, 113.4, 88.4, 67.7, 54.7, 54.2, 37.6, 28.8, 25.6, 24.7.

4-amino-2-chloropyridine-C6-3-bromophenoxyhybrid (S55): Prepared from 4-amino-2-chloropyridine and S38[1] using general procedure C to furnish S55 in a 6.4% yield. HRMS (ESI-TOF) calculated for $C_{17}H_{19}BrClN_2O_2$ [M+H]$^+$: m/z 397.0318. found 397.0299; $^1$H NMR (500 MHz, CDCl$_3$) δ 8.26 (d, J=5.6 Hz, 1H), 7.64 (d, J=2.0 Hz, 1H), 7.41-7.35 (m, 1H), 7.34 (dd, J=5.7, 1.9 Hz, 1H), 7.13 (t, J=8.0 Hz, 1H), 7.10-7.05 (m, 1H), 7.03 (t, J=2.1 Hz, 1H), 6.81 (ddd, J=8.3, 2.5, 1.1 Hz, 1H), 3.95 (t, J=6.2 Hz, 2H), 2.43 (t, J=7.4 Hz, 2H), 1.89-1.74 (m, 4H), 1.65-1.48 (m, 2H); $^{13}$C NMR (125 MHz, CDCl$_3$) δ 171.6, 159.7, 152.5, 150.2, 146.8, 130.5, 123.7, 122.9, 117.6, 113.4, 113.3, 112.2, 67.7, 37.6, 28.8, 25.6, 24.7.

4-amino-2-trifluoromethylpyridine-C4-3-bromophenoxyhybrid (S56): Prepared from 4-amino-2-trifluoromethylpyridine and S36[1] using general procedure C to furnish S56 in a 4.0% yield. HRMS (ESI-TOF) calculated for $C_{16}H_{15}BrF_3N_2O_2$ [M+H]$^+$: m/z 403.0269. found 403.0259; $^1$H NMR (500 MHz, CDCl$_3$) δ 8.60 (d, J=5.5 Hz, 1H), 7.87 (d, J=2.0 Hz, 1H), 7.70-7.57 (m, 2H), 7.14 (t, J=8.0 Hz, 1H), 7.09 (dt, J=8.0, 1.4 Hz, 1H), 7.03 (t, J=2.1 Hz, 1H), 6.80 (ddd, J=8.1, 2.5, 1.0 Hz, 1H), 4.05 (t, J=5.8 Hz, 2H), 2.65 (t, J=7.0 Hz, 2H), 2.27-2.18 (m, 2H); $^{13}$C NMR (125 MHz, CDCl$_3$) δ 171.3, 159.2, 151.1, 149.9-148.7 (m), 146.0, 130.7, 124.5-118.0 (m), 124.2, 122.9, 117.7, 115.3, 113.3, 110.4-110.2 (m), 66.7, 34.0, 24.4.

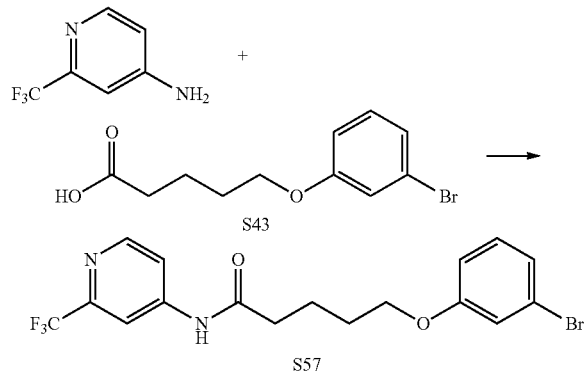

4-amino-2-trifluoromethylpyridine-C5-3-bromophenoxyhybrid (S57): Prepared from 4-amino-2-trifluoromethylpyridine and S43[1] using general procedure C to furnish S57 in a 6.1% yield. HRMS (ESI-TOF) calculated for $C_{17}H_{17}BrF_3N_2O_2$ [M+H]$^+$: m/z 417.0425. found 417.0431; $^1$H NMR (500 MHz, CDCl$_3$) δ 8.60 (d, J=5.6 Hz, 1H), 7.87 (d, J=2.1 Hz, 1H), 7.66 (dd, J=5.5, 2.1 Hz, 1H), 7.46 (d, J=2.7 Hz, 1H), 7.13 (t, J=8.0 Hz, 1H), 7.08 (dt, J=7.9, 1.3 Hz, 1H), 7.04 (t, J=2.1 Hz, 1H), 6.81 (ddd, J=8.2, 2.5, 1.1 Hz, 1H), 4.00 (t, J=5.7 Hz, 2H), 2.52 (t, J=7.0 Hz, 2H), 2.04-1.82 (m, 4H); $^{13}$C NMR (125 MHz, CDCl$_3$) δ 171.6, 159.4, 151.0, 149.3 (q, J=35 Hz), 146.0, 130.6, 123.9, 122.8, 117.6, 121.3 (q, J=274 Hz), 115.3, 113.4, 110.3-110.2 (m), 67.7, 37.1, 28.3, 21.9.

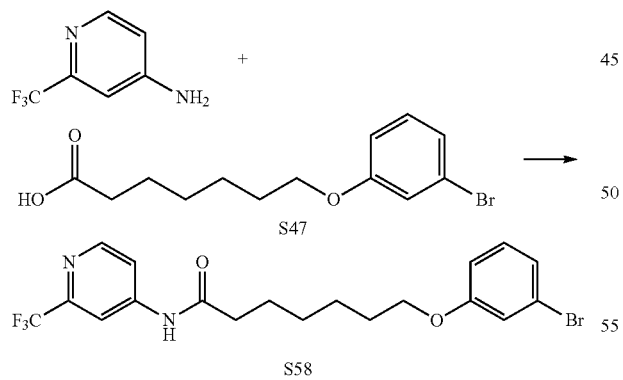

4-amino-2-trifluoromethylpyridine-C7-3-bromophenoxyhybrid (S58): Prepared from 4-amino-2-trifluoromethylpyridine and S47[1] using general procedure C to furnish S58 in a 17% yield. HRMS (ESI-TOF) calculated for $C_{19}H_{21}BrF_3N_2O_2$ [M+H]: m/z 445.0738. found 445.0719; $^1$H NMR (500 MHz, CDCl$_3$) δ 8.61 (d, J=5.5 Hz, 1H), 7.93 (d, J=2.0 Hz, 1H), 7.70 (dd, J=5.6, 2.1 Hz, 1H), 7.57 (s, 1H), 7.12 (t, J=8.0 Hz, 1H), 7.09-7.00 (m, 2H), 6.81 (ddd, J=8.2, 2.4, 1.1 Hz, 1H), 3.92 (t, J=6.4 Hz, 2H), 2.38 (t, J=7.4 Hz, 2H), 1.84-1.72 (m, 2H), 1.67 (p, J=7.5 Hz, 2H), 1.55-1.37 (m, 4H); $^{13}$C NMR (125 MHz, CDCl$_3$) δ 178.9, 177.4, 159.8, 151.0, 149.5-148.9 (m), 130.5, 124.8-116.7 (m), 123.6, 122.7, 117.6, 115.6, 113.5, 110.7-110.5 (m), 68.0, 33.7, 28.9, 28.7, 25.7, 24.5.

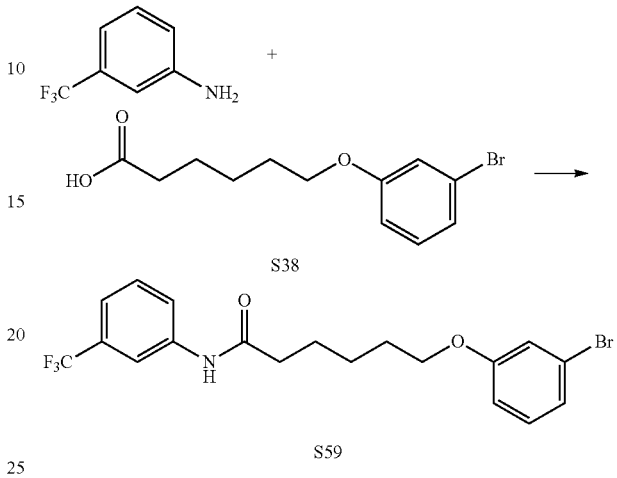

1-amino-3-trifluoromethyl-C6-3-bromophenoxyhybrid (S59): Prepared from 3-(trifluoromethyl)aniline and S38[1] using general procedure C to furnish S59 in a 70% yield. HRMS (ESI-TOF) calculated for $C_{19}H_{20}BrF_3NO_2$ [M+H]$^+$: m/z 430.0630. found 430.0595; $^1$H NMR (500 MHz, CDCl$_3$) δ 7.83 (s, 1H), 7.71 (d, J=8.1 Hz, 1H), 7.44 (t, J=8.1 Hz, 1H), 7.39-7.32 (m, 1H), 7.28 (s, 1H), 7.12 (t, J=8.3 Hz, 1H), 7.09-7.00 (m, 2H), 6.81 (d, J=8.3 Hz, 1H), 3.95 (t, J=6.4 Hz, 2H), 2.42 (t, J=7.5 Hz, 2H), 1.93-1.76 (m, 4H), 1.64-1.52 (m, 2H); $^{13}$C NMR (125 MHz, CDCl$_3$) δ 171.2, 159.7, 138.3, 131.3 (q, J=32 Hz), 130.5, 129.5, 127.1-120.3 (m), 123.7, 122.8, 122.7, 120.8-120.7 (m), 117.6, 116.4-116.3 (m), 113.4, 67.7, 37.5, 28.9, 25.7, 25.0.

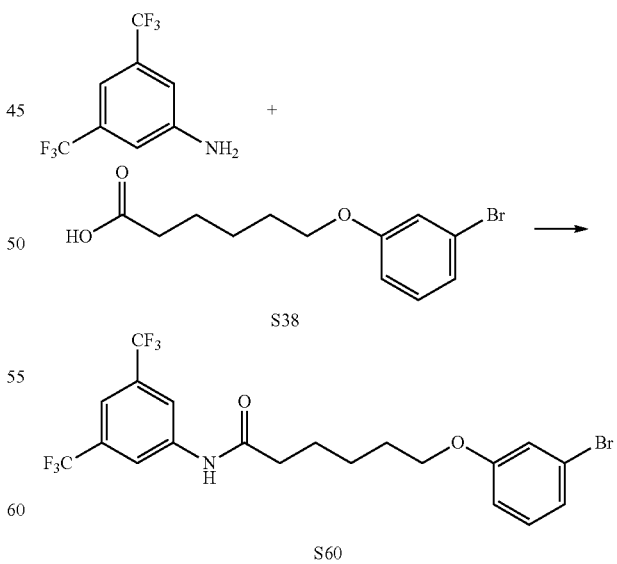

1-amino-3,5-bis(trifluoromethyl)-C6-3-bromophenoxyhybrid (S60): Prepared from 3,5-bis(trifluoromethyl)aniline and S38[1] using general procedure C to furnish S60 in a 22% yield. HRMS (ESI-TOF) calculated for $C_{20}H_{19}BrF_6NO_2$

[M+H]+: m/z 498.0503. found 498.0488; 1H NMR (500 MHz, CDCl3) δ 8.04 (s, 2H), 7.60 (s, 1H), 7.36 (s, 1H), 7.13 (t, J=8.1 Hz, 1H), 7.10-6.99 (m, 2H), 6.81 (ddd, J=8.2, 2.5, 1.1 Hz, 1H), 3.95 (t, J=6.3 Hz, 2H), 2.45 (t, J=7.4 Hz, 2H), 1.89-1.74 (m, 4H), 1.64-1.50 (m, 2H); 13C NMR (125 MHz, CDCl3) δ 171.3, 159.7, 139.1, 132.3 (q, J=33 Hz), 130.5, 123.7, 122.8 (t, J=137 Hz), 122.8, 119.4-119.1 (m), 117.6, 117.6-117.4 (m), 113.4, 67.7, 37.4, 28.8, 25.7, 24.9.

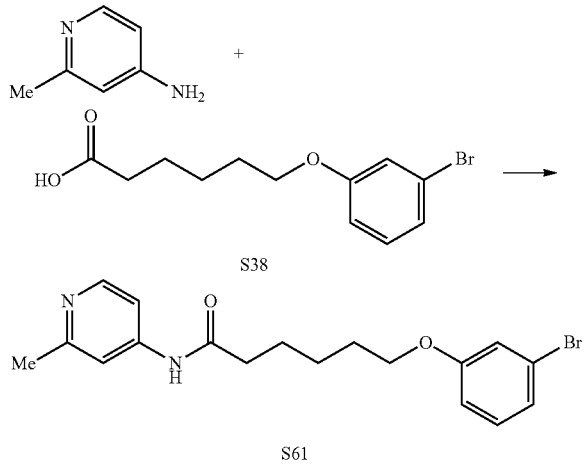

4-amino-2-methylpyridine-C6-3-bromophenoxyhybrid (S61): Prepared from 4-amino-2-methylpyridine and S38[1] using general procedure C to furnish S61 in a 52% yield. HRMS (ESI-TOF) calculated for $C_{18}H_{22}BrN_2O_2$ [M+H]+: m/z 377.0865. found 377.0871; 1H NMR (500 MHz, CDCl3) δ 8.31 (d, J=5.8 Hz, 1H), 8.20 (s, 1H), 7.62 (s, 1H), 7.46-7.37 (m, 1H), 7.12 (t, J=8.0 Hz, 1H), 7.06 (dt, J=7.9, 1.2 Hz, 1H), 7.02 (t, J=2.1 Hz, 1H), 6.85-6.76 (m, 1H), 3.94 (t, J=6.3 Hz, 2H), 2.56 (s, 3H), 2.48 (t, J=7.4 Hz, 2H), 1.87-1.72 (m, 4H), 1.62-1.49 (m, 2H); 13C NMR (125 MHz, CDCl3) δ 172.2, 160.6, 159.7, 158.4, 147.8, 130.5, 123.7, 122.8, 117.6, 113.4, 113.1, 111.2, 67.7, 37.6, 28.8, 25.6, 24.8, 23.6.

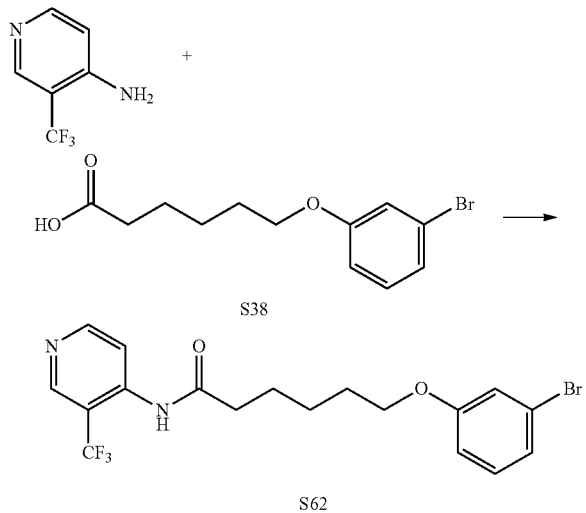

4-amino-3-trifluoromethylpyridine-C6-3-bromophenoxy-hybrid (S62): Prepared from 4-amino-3-trifluoromethylpyridine and S38[1] using general procedure C to furnish S62 in a 44% yield. HRMS (ESI-TOF) calculated for $C_{18}H_{19}BrF_3N_2O_2$ [M+H]+: m/z 431.0582. found 431.0573. 1H NMR (500 MHz, CDCl3) δ 8.90-8.64 (m, 2H), 8.50 (d, J=5.3 Hz, 1H), 7.57 (s, 1H), 7.13 (t, J=8.0 Hz, 1H), 7.09-6.99 (m, 2H), 6.81 (ddd, J=8.3, 2.5, 1.0 Hz, 1H), 3.95 (t, J=6.3 Hz, 2H), 2.49 (t, J=7.4 Hz, 2H), 1.89-1.76 (m, 4H), 1.64-1.49 (m, 2H). 13C NMR (125 MHz, CDCl3) δ 171.4, 159.7, 154.3, 147.4-147.0 (m), 142.7, 130.5, 127.0-120.1 (m, 2C), 123.7, 122.7, 117.6, 115.4-115.1 (m), 113.4, 67.6, 38.0, 28.8, 25.5, 24.7.

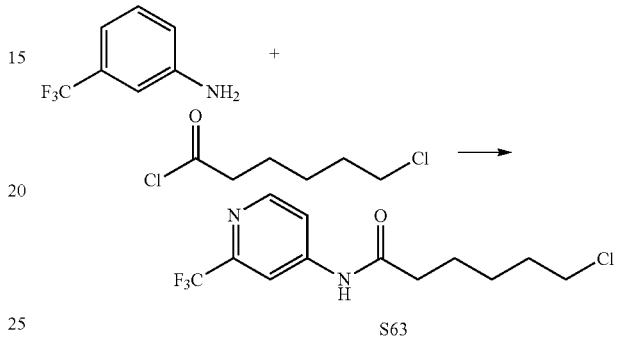

6-chloro-N-(2-(trifluoromethyl)pyridin-4-yl)hexanamide (S63): Pyridine (0.30 mL, 3.7 mmol, 1.0 equiv) was added to a mixture of 4-amino-2-trifluoromethylpyridine (0.60 g, 3.7 mmol, 1.0 equiv) in CH2Cl2 (25 mL). After cooling the reaction to 0° C., 6-chlorohexanoyl chloride[4] (0.45 mL, 3.7 mmol, 1.0 equiv) was added dropwise. The reaction mixture was allowed to warm to room temperature overnight. The reaction was quenched with saturated aqueous NH4Cl (10 mL) and was extracted with CH2Cl2 (3×25 mL). The combined organic layers were washed sequentially with 1 M HCl (3×25 mL) and brine (1×25 mL), dried over Na2SO4, and concentrated to provide S63 in an 80% yield. S63 was used without further purification. HRMS (ESI-TOF) calculated for $C_{12}H_{15}ClF_3N_2O$ [M+H]+: m/z 295.0825. found 295.0823; 1H NMR: (500 MHz, CDCl3) δ 8.57 (d, J=5.6 Hz, 1H), 7.98 (s, 1H), 7.93 (d, J=2.1 Hz, 1H), 7.69 (dd, J=5.5, 2.0 Hz, 1H), 3.54 (t, J=6.5 Hz, 2H), 2.44 (t, J=7.4 Hz, 2H), 1.96-1.66 (m, 4H), 1.59-1.46 (m, 2H); 13C NMR: (125 MHz, CDCl3) δ 172.1, 150.8, 149.2 (q, J=35 Hz), 146.5, 121.4 (q, J=274 Hz), 115.5, 110.5 (q, J=3 Hz), 44.8, 37.4, 32.2, 26.3, 24.3.

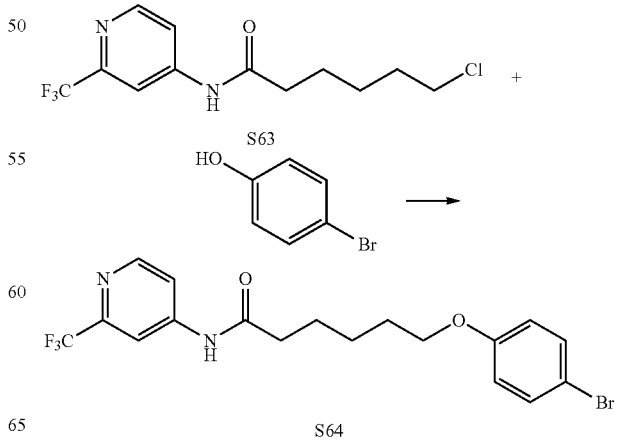

4-amino-2-trifluoromethylpyridine-C6-4-bromophenoxy-hybrid (S64): Prepared from 4-bromophenol and S63 using general procedure D to furnish S64 in a 24% yield. HRMS (ESI-TOF) calculated for $C_{18}H_{19}BrF_3N_2O_2$ [M+H]$^+$: m/z 431.0582. found 431.0580; $^1$H NMR (500 MHz, CDCl$_3$) δ 8.60 (d, J=5.4 Hz, 1H), 7.90 (s, 1H), 7.73-7.66 (m, 1H), 7.54 (s, 1H), 7.42-7.31 (m, 2H), 6.85-6.65 (m, 2H), 3.94 (t, J=6.2 Hz, 2H), 2.46 (t, J=7.4 Hz, 2H), 1.93-1.72 (m, 4H), 1.66-1.47 (m, 2H); $^{13}$C NMR (125 MHz, CDCl$_3$) δ 172.0, 158.0, 149.3 (q, J=34 Hz), 148.8, 146.3, 132.2, 121.3 (q, J=274 Hz), 116.2, 115.4, 112.7, 110.4 (q, J=3 Hz), 67.7, 37.5, 28.8, 25.6, 24.7.

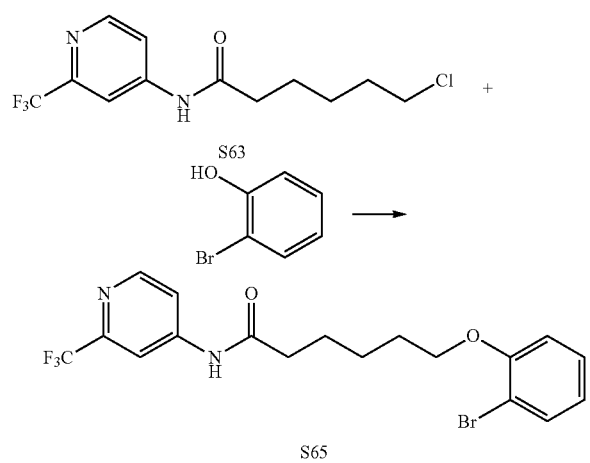

S65

4-amino-2-trifluoromethylpyridine-C6-2-bromophenoxy-hybrid (S65): Prepared from 2-bromophenol and S63 using general procedure D to furnish S65 in a 38% yield. HRMS (ESI-TOF) calculated for $C_{18}H_{19}BrF_3N_2O_2$ [M+H]$^+$: m/z 431.0582. found 431.0562; $^1$H NMR (500 MHz, CDCl$_3$) δ 8.58 (d, J=5.5 Hz, 1H), 7.90 (s, 1H), 7.72 (s, 1H), 7.68 (dd, J=5.6, 2.1 Hz, 1H), 7.52 (dd, J=7.9, 1.6 Hz, 1H), 7.26-7.22 (m, 1H), 6.87 (dd, J=8.3, 1.4 Hz, 1H), 6.83 (td, J=7.6, 1.4 Hz, 1H), 4.04 (t, J=6.0 Hz, 2H), 2.48 (t, J=7.5 Hz, 2H), 1.93-1.80 (m, 4H), 1.68-1.58 (m, 2H); $^{13}$C NMR (125 MHz, CDCl$_3$) δ 172.0, 155.1, 150.9, 149.2 (q, J=35 Hz), 146.2, 133.3, 128.5, 121.8, 121.2 (q, J=274 Hz), 115.4, 113.1, 112.0, 110.4-110.3 (m), 68.7, 37.6, 28.6, 25.8, 24.7.

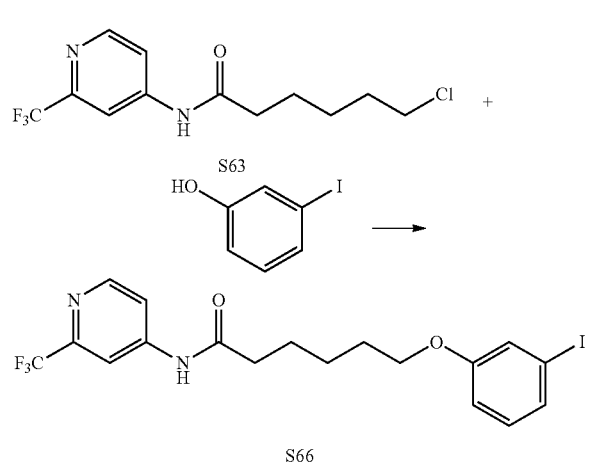

S66

4-amino-2-trifluoromethylpyridine-C6-3-iodophenoxy-hybrid (S66): Prepared from 3-iodophenol and S63 using general procedure D to furnish S66 in a 34% yield. HRMS (ESI-TOF) calculated for $C_{18}H_{19}F_3IN_2O_2$ [M+H]$^+$: m/z 479.0443. found 479.04262; $^1$H NMR (500 MHz, CDCl$_3$) δ 8.59 (d, J=5.2 Hz, 1H), 7.92 (s, 1H), 7.77-7.58 (m, 2H), 7.29-7.25 (m, 1H), 7.24-7.20 (m, 1H), 6.98 (t, J=8.0 Hz, 1H), 6.84 (dd, J=8.4, 2.4 Hz, 1H), 3.93 (t, J=6.2 Hz, 2H), 2.46 (t, J=7.4 Hz, 2H), 1.87-1.76 (m, 4H), 1.60-1.50 (m, 2H); $^{13}$C NMR (125 MHz, CDCl$_3$) δ 172.0, 159.5, 150.9, 149.2 (q, J=34 Hz), 146.3, 130.8, 129.8, 123.6, 121.3 (q, J=274 Hz), 115.4, 114.1, 110.4 (q, J=3 Hz), 94.3, 67.6, 37.5, 28.8, 25.6, 24.7.

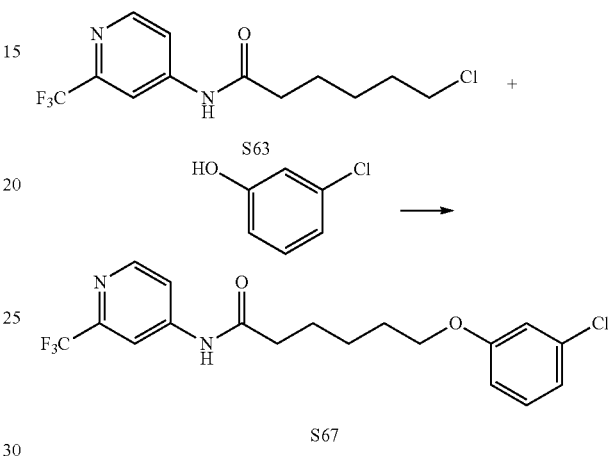

S67

4-amino-2-trifluoromethylpyridine-C6-3-chlorophenoxy-hybrid (S67): Prepared from 3-chlorophenol and S63 using general procedure D to furnish S67 in a 46% yield. HRMS (ESI-TOF) calculated for $C_{18}H_{19}ClF_3N_2O_2$ [M+H]$^+$: m/z 387.1087. found 387.1079; $^1$H NMR (500 MHz, CDCl$_3$) δ 8.59 (d, J=5.5 Hz, 1H), 7.91 (s, 1H), 7.75-7.60 (m, 2H), 7.18 (t, J=8.1 Hz, 1H), 6.95-6.89 (m, 1H), 6.89-6.85 (m, 1H), 6.76 (dd, J=8.2, 2.4 Hz, 1H), 3.95 (t, J=6.2 Hz, 2H), 2.46 (t, J=7.4 Hz, 2H), 1.89-1.75 (m, 4H), 1.62-1.50 (m, 2H); $^{13}$C NMR (125 MHz, CDCl$_3$) δ 171.9, 159.6, 150.9, 149.3 (q, J=35 Hz), 146.2, 134.8, 130.2, 120.8, 121.3 (q, J=274 Hz), 115.4, 114.7, 112.9, 110.5-110.3 (m), 67.7, 37.5, 28.8, 25.6, 24.7.

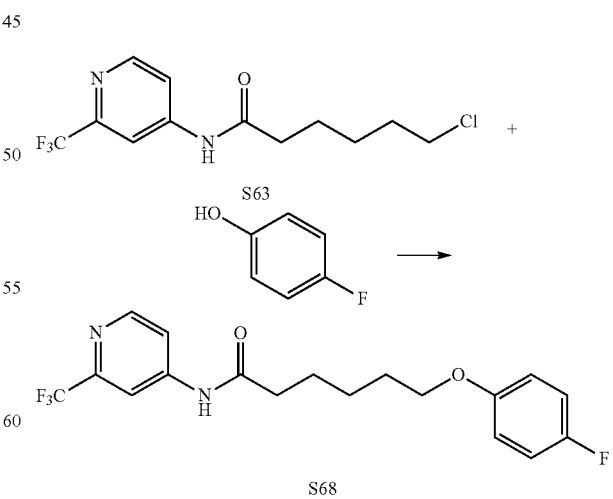

S68

4-amino-2-trifluoromethylpyridine-C6-4-fluorophenoxy-hybrid (S68): Prepared from 4-fluorophenol and S63 using general procedure D to furnish S68 in a 17% yield. HRMS (ESI-TOF) calculated for $C_{18}H_{19}F_4N_2O_2$ [M+H]$^+$: m/z 371.1383. found 371.1364; $^1$H NMR (500 MHz, CDCl$_3$) δ 8.60 (d, J=5.5 Hz, 1H), 7.90-7.86 (m, 1H), 7.79-7.61 (m, 1H), 7.48 (s, 1H), 7.00-6.92 (m, 2H), 6.84-6.79 (m, 2H), 3.93 (t, J=6.2 Hz, 2H), 2.46 (t, J=7.4 Hz, 2H), 1.87-1.76 (m, 4H), 1.59-1.52 (m, 2H); $^{13}$C NMR (125 MHz, CDCl$_3$) δ 171.8, 158.1, 155.6 (d, J=152 Hz), 151.0, 149.3 (q, J=35 Hz), 146.0, 121.3 (q, J=274 Hz), 115.8 (d, J=23 Hz), 115.4-115.2 (m, 2C), 110.3 (q, J=3 Hz), 68.1, 37.6, 29.0, 25.7, 24.7.

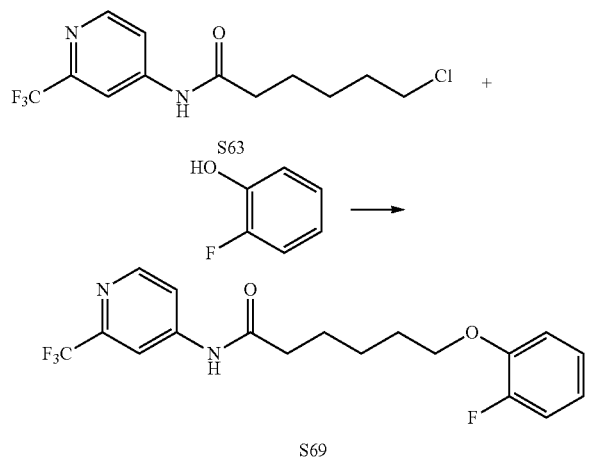

4-amino-2-trifluoromethylpyridine-C6-2-fluorophenoxyhybrid (S69): Prepared from 2-fluorophenol and S63 using general procedure D to furnish S69 in a 37% yield. HRMS (ESI-TOF) calculated for $C_{18}H_{19}F_4N_2O_2$ [M+H]$^+$: m/z 371.1383. found 371.1377; $^1$H NMR (500 MHz, CDCl$_3$) δ 8.58 (d, J=5.5 Hz, 1H), 7.93-7.84 (m, 1H), 7.78-7.62 (m, 2H), 7.12-7.01 (m, 2H), 6.99-6.92 (m, 1H), 6.92-6.85 (m, 1H), 4.05 (t, J=6.1 Hz, 2H), 2.46 (t, J=7.5 Hz, 2H), 1.93-1.77 (m, 4H), 1.64-1.55 (m, 2H); $^{13}$C NMR (125 MHz, CDCl$_3$) δ 172.1, 152.6 (d, J=244 Hz), 151.0, 149.2 (q, J=35 Hz), 146.9 (d, J=11 Hz), 146.2, 124.4 (d, J=4 Hz), 121.3 (q, J=275 Hz), 121.0 (d, J=7 Hz), 116.1 (d, J=18 Hz), 115.4, 114.6 (d, J=2 Hz), 110.4 (q, J=3 Hz), 68.9, 37.5, 28.6, 25.7, 24.8.

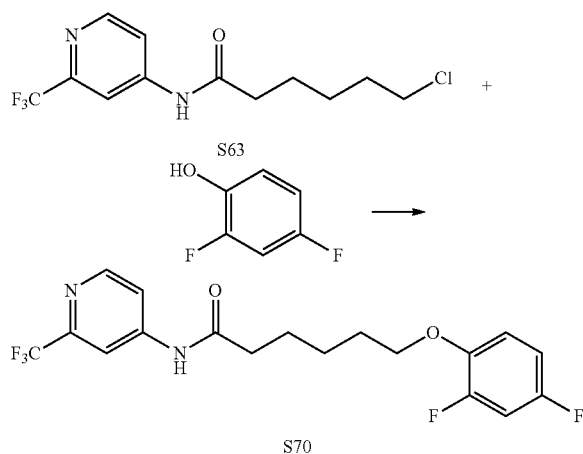

4-amino-2-trifluoromethylpyridine-C6-2,4-bisfluorophenoxyhybrid (S70): Prepared from 2,4-bisfluorophenol and S63 using general procedure D to furnish S70 in a 49% yield. HRMS (ESI-TOF) calculated for $C_{18}H_{18}F_5N_2O_2$ [M-ql]$^f$: m/z 389.1288. found 389.1288; $^1$H NMR (500 MHz, CDCl$_3$) δ 8.58 (d, J=5.5 Hz, 1H), 7.91 (d, J=2.1 Hz, 1H), 7.81 (s, 1H), 7.68 (dd, J=5.6, 2.1 Hz, 1H), 6.93-6.81 (m, 2H), 6.80-6.74 (m, 1H), 4.00 (t, J=6.2 Hz, 2H), 2.46 (t, J=7.4 Hz, 2H), 1.89-1.77 (m, 4H), 1.62-1.53 (m, 2H); $^{13}$C NMR (125 MHz, CDCl$_3$) δ 172.0, 156.3 (dd, J=242, 10 Hz), 152.4 (dd, J=248, 12 Hz), 150.93, 149.2 (q, J=34 Hz), 146.2, 143.4 (dd, J=11, 4 Hz), 121.3 (q, J=274 Hz), 115.5-115.2 (m, 2C), 110.6-110.2 (m, 2C), 104.8 (dd, J=27, 22 Hz), 69.7, 37.5, 28.8, 25.6, 24.7.

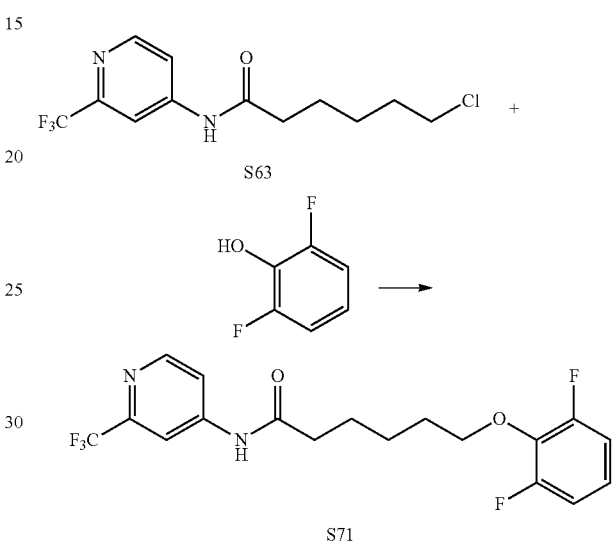

4-amino-2-trifluoromethylpyridine-C6-2,6-bisfluorophenoxyhybrid (S71): Prepared from 2,6-bisfluorophenol and S63 using general procedure D to furnish S71 in a 47% yield. HRMS (ESI-TOF) calculated for $C_{18}H_{18}F_5N_2O_2$ m/z 389.1288. found 389.1290; $^1$H NMR (500 MHz, CDCl$_3$) δ 8.58 (d, J=5.5 Hz, 1H), 7.89 (d, J=2.0 Hz, 1H), 7.74 (s, 1H), 7.69 (dd, J=5.6, 2.0 Hz, 1H), 7.00-6.92 (m, 1H), 6.91-6.82 (m, 2H), 4.13 (t, J=6.2 Hz, 2H), 2.46 (t, J=7.4 Hz, 2H), 1.92-1.76 (m, 4H), 1.64-1.56 (m, 2H); $^{13}$C NMR (125 MHz, CDCl$_3$) δ 172.1, 156.2 (dd, J=248, 6 Hz), 151.0, 149.2 (q, J=34 Hz), 146.2, 136.4-134.5 (m), 122.8 (t, J=9 Hz), 121.3 (q, J=274 Hz), 115.4, 112.5-111.9 (m), 110.3, 74.5, 37.6, 29.5, 25.3, 24.7.

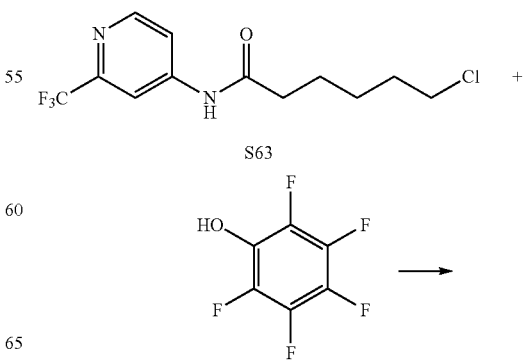

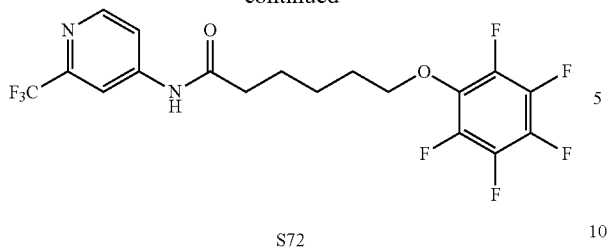

S72

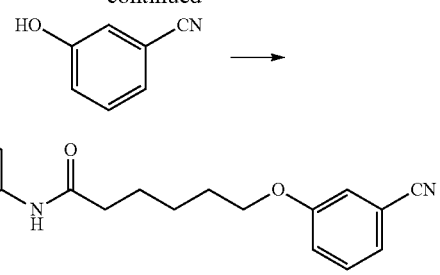

4-amino-2-trifluoromethylpyridine-C6-perfluorophenoxyhybrid (S72): Prepared from pentafluorophenol and S63 using general procedure D to furnish S72 in a 57% yield. HRMS (ESI-TOF) calculated for $C_{18}H_{15}F_8N_2O_2$ [M+H]: m/z 443.1006. found 443.1007; $^1$H NMR (500 MHz, CDCl$_3$) δ 8.59 (d, J=5.5 Hz, 1H), 7.91 (d, J=2.1 Hz, 1H), 7.74 (s, 1H), 7.69 (dd, J=5.6, 2.1 Hz, 1H), 4.15 (t, J=6.2 Hz, 2H), 2.47 (t, J=7.4 Hz, 2H), 1.93-1.75 (m, 4H), 1.62-1.53 (m, 2H); $^{13}$C NMR (125 MHz, CDCl$_3$) δ 171.8, 151.0, 149.3 (q, J=35 Hz), 146.2, 121.3 (d, J=274 Hz), 115.3, 110.3 (q, J=3 Hz), 75.3, 37.4, 29.5, 25.2, 24.5. The aryl signals of the perfluoronated aryl phenol were obscured by the C—F splitting.

4-amino-2-trifluoromethylpyridine-C6-3-cyanophenoxyhybrid (S74): Prepared from 3-cyanophenol and S63 using general procedure D to furnish S74 in a 22% yield. HRMS (ESI-TOF) calculated for $C_{19}H_{19}F_3N_3O_2$ [M+H]$^+$: m/z 378.1429. found 378.1413; $^1$H NMR (300 MHz, CD$_3$OD) δ 8.52 (d, J=5.6 Hz, 1H), 8.11 (d, J=2.0 Hz, 1H), 7.77 (dd, J=5.6, 2.1 Hz, 1H), 7.49-7.37 (m, 1H), 7.31-7.14 (m, 3H), 4.04 (t, J=6.3 Hz, 2H), 2.48 (t, J=7.4 Hz, 2H), 1.92-1.72 (m, 4H), 1.65-1.49 (m, 2H); $^{13}$C NMR (125 MHz, acetone-d6) δ 173.4, 160.3, 151.9, 149.3 (q, J=34 Hz), 148.4, 131.6, 125.1, 132.2-118.7 (m), 120.9, 119.3, 118.0, 116.2, 114.2, 110.8-110.5 (m), 69.0, 37.7, 29.6, 26.3, 25.5.

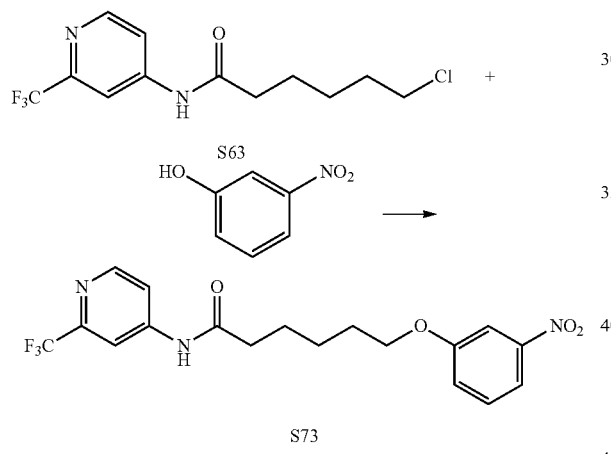

S73

4-amino-2-trifluoromethylpyridine-C6-3-nitrophenoxyhybrid (S73): Prepared from 3-nitrophenol and S63 using general procedure D to furnish S73 in a 25% yield. HRMS (ESI-TOF) calculated for $C_{18}H_{19}F_3N_3O_4$ [M+H]$^+$: m/z 398.1328. found 398.1300; $^1$H NMR (500 MHz, CDCl$_3$) δ 8.59 (d, J=5.5 Hz, 1H), 7.93 (s, 1H), 7.84-7.73 (m, 2H), 7.72-7.67 (m, 2H), 7.41 (t, J=8.2 Hz, 1H), 7.20 (dd, J=8.4, 2.5 Hz, 1H), 4.04 (t, J=6.2 Hz, 2H), 2.48 (t, J=7.4 Hz, 2H), 1.97-1.70 (m, 4H), 1.67-1.51 (m, 2H); $^{13}$C NMR (125 MHz, CDCl$_3$) δ 171.8, 159.4, 151.0, 149.2 (q, J=40.0 Hz), 149.1, 146.1, 130.0, 121.6, 121.3 (q, J=274 Hz), 115.7, 115.3, 110.3 (q, J=3 Hz), 108.6, 68.2, 37.5, 28.7, 25.6, 24.6.

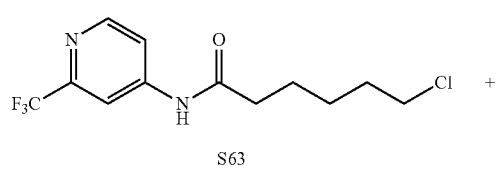

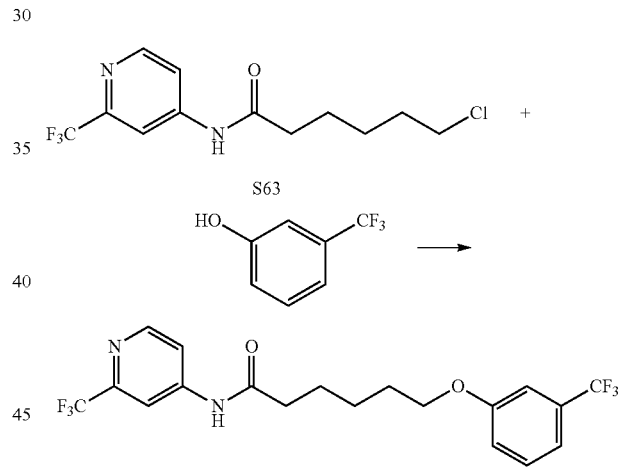

S75

4-amino-2-trifluoromethylpyridine-C6-3-trifluoromethylphenoxyhybrid (S75): Prepared from 3-trifluoromethylphenol and S63 using general procedure D to furnish S75 in a 16% yield. HRMS (ESI-TOF) calculated for $C_{19}H_{19}F_6N_2O_2$ [M+H]$^+$: m/z 421.1351. found 421.1353. $^1$H NMR (500 MHz, CDCl$_3$) δ 8.60 (d, J=5.5 Hz, 1H), 7.90 (d, J=2.1 Hz, 1H), 7.68 (dd, J=5.6, 2.1 Hz, 1H), 7.52 (s, 1H), 7.37 (t, J=8.0 Hz, 1H), 7.19 (d, J=7.7 Hz, 1H), 7.12-7.08 (m, 1H), 7.06-7.02 (m, 1H), 4.00 (t, J=6.2 Hz, 2H), 2.47 (t, J=7.4 Hz, 2H), 1.97-1.75 (m, 4H), 1.65-1.53 (m, 2H). $^{13}$C NMR (125 MHz, CDCl$_3$) δ 171.7, 159.0, 151.0, 149.3 (q, J=34 Hz), 146.1, 131.7 (q, J=32 Hz), 130.00, 125.7 (q, J=183 Hz), 121.3 (q, J=274 Hz), 117.9-117.8 (m), 117.3 (q, J=4 Hz), 115.3, 111.1 (q, J=4 Hz), 110.3 (d, J=3 Hz), 67.7, 37.5, 28.8, 25.6, 24.7.

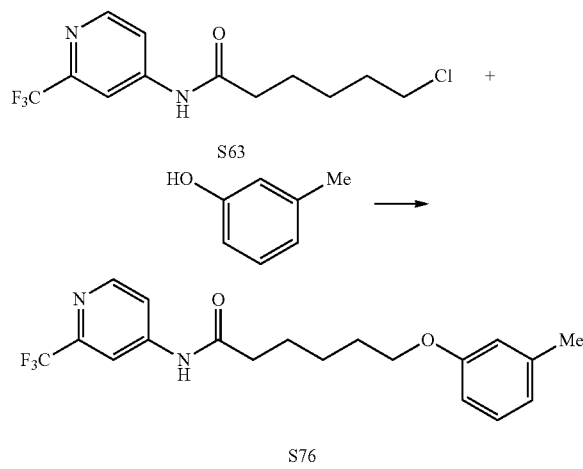

S76

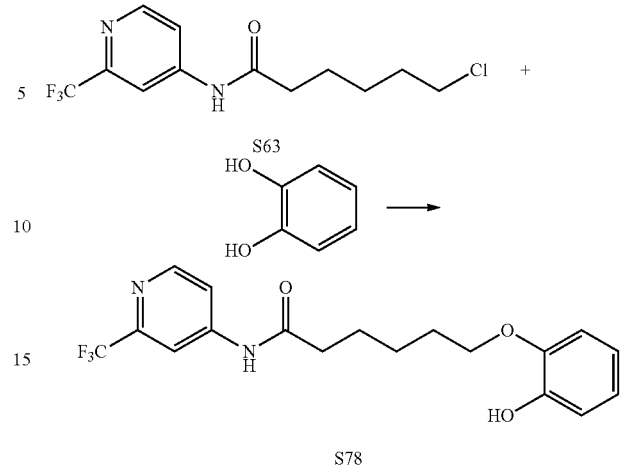

S78

4-amino-2-trifluoromethylpyridine-C6-3-methylphenoxyhybrid (S76): Prepared from 3-methylphenol and S63 using general procedure D to furnish S76 in a 30% yield. HRMS (ESI-TOF) calculated for $C_{19}H_{22}F_3N_2O_2$ [M+1-1]': m/z 367.1633. found 367.1618; $^1$H NMR (500 MHz, CDCl$_3$) δ 8.58 (d, J=5.4 Hz, 1H), 7.89 (d, J=2.0 Hz, 1H), 7.73-7.62 (m, 2H), 7.16 (t, J=7.8 Hz, 1H), 6.76 (d, J=7.6 Hz, 1H), 6.72-6.64 (m, 2H), 3.96 (t, J=6.2 Hz, 2H), 2.45 (t, J=7.4 Hz, 2H), 2.32 (s, 3H), 1.88-1.76 (m, 4H), 1.62-1.50 (m, 2H); $^{13}$C NMR (125 MHz, CDCl$_3$) δ 172.0, 158.8, 151.0, 149.3 (q, J=34 Hz), 146.1, 139.5, 129.2, 121.5, 121.3 (q, J=274 Hz), 115.9, 115.3, 111.2, 110.3 (q, J=3.0 Hz), 67.3, 37.6, 28.9, 25.7, 24.8, 21.5.

4-amino-2-trifluoromethylpyridine-C6-2-hydroxyphenoxyhybrid (S78): Prepared from 1,2-dihydroxybenzene and S63 using general procedure D to furnish S78 in an 18% yield. HRMS (ESI-TOF) calculated for $C_{18}H_{20}F_3N_2O_3$ [M+H]$^+$: m/z 369.1426. found 369.1415; $^1$H NMR (500 MHz, CDCl$_3$) δ 8.59 (d, J=5.5 Hz, 1H), 7.89 (d, J=2.0 Hz, 1H), 7.69 (dd, J=5.6, 2.1 Hz, 1H), 7.64 (s, 1H), 6.96-6.91 (m, 1H), 6.90-6.80 (m, 3H), 5.73 (s, 1H), 4.06 (t, J=6.2 Hz, 2H), 2.46 (t, J=7.4 Hz, 2H), 1.97-1.73 (m, 4H), 1.62-1.51 (m, 2H); $^{13}$C NMR (125 MHz, CDCl$_3$) δ 171.8, 151.0, 149.3 (q, J=34 Hz), 146.1, 145.7, 145.6, 125.0-117.3 (m) 121.4, 120.2, 115.4, 114.6, 111.6, 110.3 (q, J=3 Hz), 68.3, 37.4, 28.8, 25.6, 24.6.

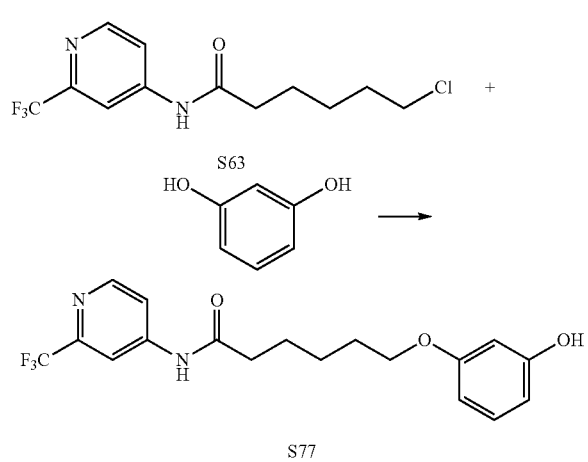

S77

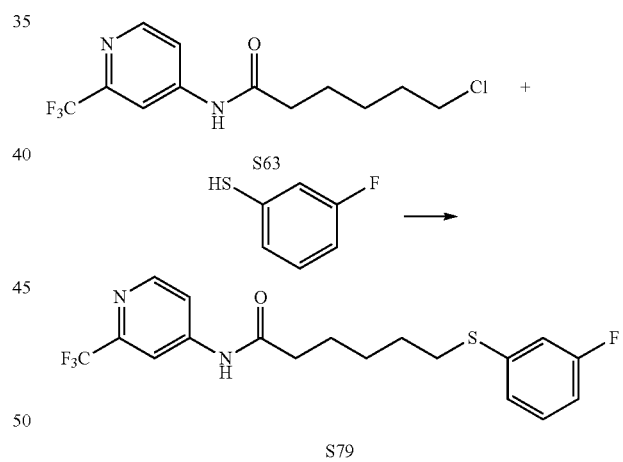

S79

4-amino-2-trifluoromethylpyridine-C6-3-hydroxyphenoxyhybrid (S77): Prepared from 1,3-dihydroxybenzene and S63 using general procedure D to furnish S77 in a 4% yield. HRMS (ESI-TOF) calculated for $C_{18}H_{20}F_3N_2O_3$ [M+H]$^+$: m/z 369.1426. found 369.1398; $^1$H NMR (500 MHz, CD$_3$OD) δ 8.52 (d, J=5.6 Hz, 1H), 8.11 (d, J=2.0 Hz, 1H), 7.78 (dd, J=5.6, 2.0 Hz, 1H), 7.02 (t, J=8.0 Hz, 1H), 6.42-6.28 (m, 3H), 3.94 (t, J=6.3 Hz, 2H), 2.48 (t, J=7.4 Hz, 2H), 1.87-1.71 (m, 4H), 1.64-1.48 (m, 2H); $^{13}$C NMR (125 MHz, CD$_3$OD) δ 175.6, 161.9, 159.8, 152.0, 151.4-150.6 (m), 149.4, 131.0, 125.8-118.1 (m), 117.0, 111.6 (m), 108.8, 106.8, 102.9, 68.6, 38.1, 30.3, 27.0, 26.2.

4-amino-2-trifluoromethylpyridine-C6-3-fluoroarylsulfide hybrid (S79): Prepared from 3-fluorothiophenol and S63 using general procedure D to furnish S79 in a 55% yield. HRMS (ESI-TOF) calculated for $C_{18}H_{19}F_4N_2OS$ [M+H]$^+$: m/z 387.1154. found 387.1139; $^1$H NMR (500 MHz, CDCl$_3$) δ 8.58 (d, J=5.5 Hz, 1H), 7.90 (d, J=2.0 Hz, 1H), 7.76 (s, 1H), 7.67 (dd, J=5.6, 2.1 Hz, 1H), 7.25-7.19 (m, 1H), 7.07-7.01 (m, 1H), 6.97 (dt, J=9.6, 2.2 Hz, 1H), 6.84 (td, J=8.4, 2.5 Hz, 1H), 2.93 (t, J=7.2 Hz, 2H), 2.42 (t, J=7.4 Hz, 2H), 1.80-1.65 (m, 4H), 1.58-1.42 (m, 2H); NMR (125 MHz, CDCl$_3$) δ 171.8, 162.8 (d, J=247 Hz), 150.9, 149.2 (q, J=34 Hz), 146.2, 139.1 (d, J=8 Hz), 130.1 (d, J=9 Hz), 123.8 (d, J=3 Hz), 121.3 (q, J=274 Hz), 115.4, 114.9 (d, J=23 Hz), 112.4 (d, J=24 Hz), 110.3 (q, J=3 Hz). 37.4, 32.8, 28.5, 28.1, 24.4.

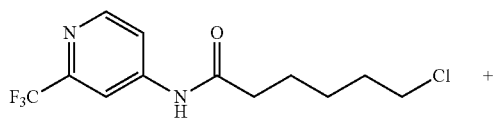

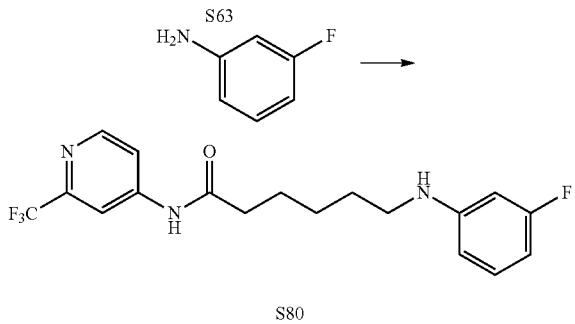

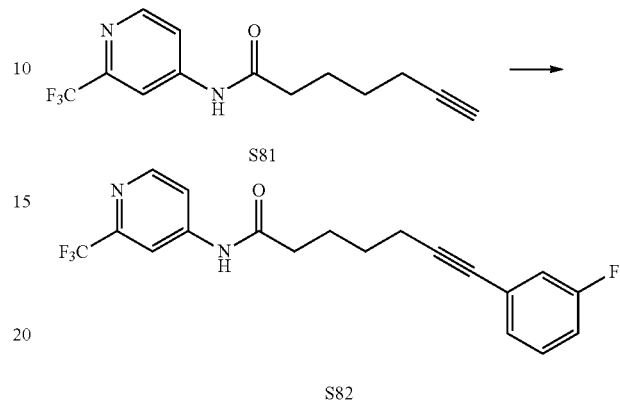

J=7.5 Hz, 2H), 2.27-2.18 (m, 2H), 1.99-1.93 (m, 1H), 1.84 (p, J=7.5 Hz, 2H), 1.58 (p, J=7.1 Hz, 2H); $^{13}$C NMR: (125 MHz, CDCl$_3$) 172.3, 150.7, 149.0 (q, J=36 Hz), 146.6, 121.3 (q, J=274 Hz), 115.6, 110.6-110.4 (m), 83.7, 68.9, 36.9, 27.6, 24.0, 18.1.

4-amino-2-trifluoromethylpyridine-C6-3-fluoroaniline hybrid (S80): Prepared from 3-fluoroaniline and S63 using general procedure D to furnish S80 in a 23% yield. HRMS (ESI-TOF) calculated for C$_{18}$H$_{20}$F$_4$N$_3$O [M+H]$^+$: m/z 370.1543. found 370.1528; $^1$H NMR (500 MHz, CDCl$_3$) δ 8.59 (d, J=5.5 Hz, 1H), 7.90 (d, J=2.1 Hz, 1H), 7.67 (dd, J=5.5, 2.1 Hz, 1H), 7.58 (s, 1H), 7.12-7.04 (m, 1H), 6.41-6.32 (m, 2H), 6.27 (dt, J=11.7, 2.3 Hz, 1H), 3.79 (s, 1H), 3.11 (t, J=7.0 Hz, 2H), 2.44 (t, J=7.3 Hz, 2H), 1.79 (p, J=7.5 Hz, 2H), 1.71-1.61 (m, 2H), 1.53-1.43 (m, 2H); $^{13}$C NMR (125 MHz, CDCl$_3$) δ 171.8, 164.1 (d, J=243 Hz), 151.0, 150.0 (d, J=11 Hz), 149.3 (q, J=34 Hz), 146.1, 130.3 (d, J=10 Hz), 121.3 (q, J=274 Hz), 115.3, 110.3 (q, J=3 Hz), 108.6 (d, J=2 Hz), 103.6 (d, J=22 Hz), 99.1 (d, J=25 Hz), 43.4, 37.5, 29.0, 26.5, 24.7.

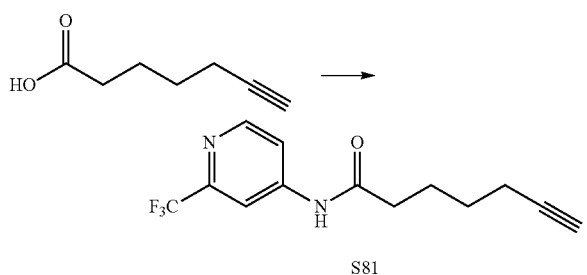

N-(2-(trifluoromethyl)pyridin-4-yl)hept-6-ynamide (S81): 6-Heptynoic acid (0.10 mL, 0.79 mmol, 1.0 equiv) was dissolved in CH$_2$Cl$_2$ (1.6 mL). Then oxalyl chloride (0.40 mL, 4.8 mmol, 6.1 equiv) was added dropwise. The reaction mixture was heated at reflux for 1 hour, or until complete. The reaction mixture was concentrated, and then dissolved in CH$_2$Cl$_2$ (5 mL). 4-Amino-2-(trifluoromethyl) pyridine (0.12 g, 0.79 mmol, 1.0 equiv) and pyridine (60 µL, 0.79 mmol, 1.0 equiv) were added to the solution. The reaction mixture was stirred for 12 h, and was then quenched with NH$_4$Cl (10 mL). The aqueous layer was extracted with CH$_2$Cl$_2$ (3×10 mL). The combined organic layer was washed sequentially with 1 M HCl (2×10 mL) and brine (20 mL), dried over Na$_2$SO$_4$ and concentrated, providing S81 in a 75% yield over two steps. S81 was taken onward without further purification. HRMS (ESI-TOF) calculated for C$_{13}$H$_{14}$F$_3$N$_2$O [M+H]$^+$: m/z 271.1058. found 271.1048; $^1$H NMR: (500 MHz, CDCl$_3$) δ 8.54 (d, J=5.5 Hz, 1H), 8.51-8.32 (m, 1H), 7.97-7.93 (m, 1H), 7.71-7.67 (m, 1H), 2.45 (t, 7-(3-fluorophenyl)-N-(2-(trifluoromethyl)pyridin-4-yl) hept-6-ynamide (S82): S81 (40 mg, 0.15 mmol, 1.5 equiv), 1-bromo-3-fluorobenzene (12 pt, 0.10 mmol, 1.0 equiv), bis(triphenylphosphine)palladium(II) dichloride (4.0 mg, 5 mol %), triphenylphosphine (1.0 mg, 2.5 mol %), and triethylamine (20 µL, 0.15 mmol, 1.5 equiv) were dissolved in THF (1 mL). The reaction mixture was stirred for 20 minutes at room temperature, and then copper(I) iodide (1.0 mg, 2 mol %) was added. After 16 hours, the reaction mixture was filtered through Celite and concentrated. The crude product was purified using flash chromatography to furnish S82 in a 22% yield. HRMS (ESI-TOF) calculated for C$_{19}$H$_{17}$F$_4$N$_2$O [M+H]$^+$: m/z 365.1277. found 365.1251; $^1$H NMR (500 MHz, CDCl$_3$) δ 8.58 (d, J=5.5 Hz, 1H), 7.87 (d, J=2.0 Hz, 1H), 7.74-7.61 (m, 2H), 7.26-7.20 (m, 1H), 7.18-7.13 (m, 1H), 7.10-7.04 (m, 1H), 7.02-6.95 (m, 1H), 2.53-2.44 (m, 4H), 1.92 (p, J=7.6 Hz, 2H), 1.80-1.59 (m, 2H); $^{13}$C NMR (125 MHz, CDCl$_3$) δ 171.7, 162.3 (d, J=246 Hz), 151.0, 149.3 (q, J=34 Hz), 146.1, 129.8 (d, J=9 Hz), 127.4, 125.4 (d, J=10 Hz), 121.3 (q, J=274 Hz), 118.3 (d, J=23 Hz), 115.3, 115.1 (d, J=21 Hz), 110.3 (q, J=3 Hz), 90.5, 80.1, 37.0, 27.7, 24.2, 19.1

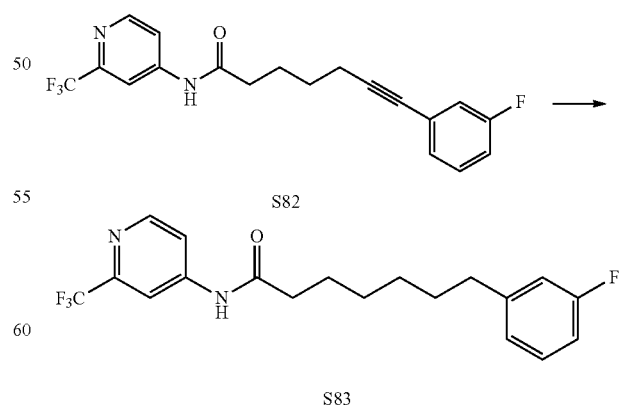

7-(3-fluorophenyl)-N-(2-(trifluoromethyl)pyridin-4-yl) heptanamide (S83): S82 (12 mg, 0.033 mmol) was dissolved in methanol (1 mL). Palladium on carbon (2.0 mg, 10 wt %)

was added to the solution, and a hydrogen balloon was added. After 12 h, the reaction mixture was filtered through Celite, concentrated, and purified using flash chromatography to give an 89% yield of S83. HRMS (ESI-TOF) calculated for $C_{19}H_{21}F_4N_2O$ [M+H]$^+$: m/z $C_{19}H_{21}F_4N_2O$. found 369.1578; $^1$H NMR (500 MHz, CDCl$_3$) δ 8.58 (d, J=5.5 Hz, 1H), 7.90 (d, J=2.1 Hz, 1H), 7.75-7.53 (m, 2H), 7.25-7.18 (m, 1H), 6.93 (d, J=7.4 Hz, 1H), 6.90-6.82 (m, 2H), 2.59 (t, J=7.7 Hz, 2H), 2.40 (t, J=7.5 Hz, 2H), 1.72 (p, J=7.5 Hz, 2H), 1.62 (p, J=7.7 Hz, 2H), 1.49-1.30 (m, 4H); $^{13}$C NMR (125 MHz, CDCl$_3$) δ 172.1, 162.8 (d, J=245 Hz), 151.0, 149.3 (q, J=35 Hz), 146.2, 145.1 (d, J=7 Hz), 129.6 (d, J=8 Hz), 124.0 (d, J=3 Hz), 121.3 (q, J=274 Hz), 115.2, 115.1 (d, J=21 Hz), 112.5 (d, J=21 Hz), 110.3 (q, J=3 Hz), 37.6, 35.5, 30.9, 28.9, 28.8, 24.9.

TABLE 7

Genes down-regulated by mBTL in the wild-type strain determined through microarray analysis. The ratio of gene expression in untreated cells to that of mBTL treated cells (fold down-regulation) is displayed for genes that exhibited changes greater than 2-fold. Additional columns indicate the genes that are also downregulated in the lasR and rhlR null strains. Ratios are the average of three independent experiments.

| Gene locus | Gene name | Description | Ratio | LasR-regulated | RhlR-regulated |
| --- | --- | --- | --- | --- | --- |
| PA14_20020 | hasAp | heme acquisition protein HasAp | 13.6 | * | * |
| PA14_21530 | | ankyrin domain-containing protein | 9.2 | * | * |
| PA14_54840 | | tRNA-Gly | 7.6 | * | * |
| PA14_53300 | | alkyl hydroperoxide reductase | 7.5 | * | * |
| PA14_30720 | | tRNA-Cys | 7.0 | * | * |
| PA14_39420 | | hypothetical protein | 6.6 | * | * |
| PA14_07470 | | tRNA-Met | 6.5 | * | * |
| PA14_03090 | | hypothetical protein | 6.5 | * | * |
| PA14_39960 | phzB2 | phenazine biosynthesis protein | 6.2 | | * |
| PA14_26990 | | hypothetical protein | 5.9 | * | * |
| PA14_14570 | | tRNA-Leu | 5.7 | * | * |
| PA14_58710 | | tRNA-Thr | 5.7 | * | * |
| PA14_27190 | | tRNA-Ser | 5.6 | * | |
| PA14_39970 | phzA2 | phenazine biosynthesis protein | 5.6 | | * |
| PA14_30420 | | tRNA-Ser | 5.5 | * | * |
| PA14_62790 | | tRNA-Met | 5.5 | * | * |
| PA14_51830 | | DNA-binding stress protein | 5.5 | * | * |
| PA14_52320 | | tRNA-Met | 5.5 | * | * |
| PA14_24870 | | tRNA-Pro | 5.4 | * | * |
| PA14_51230 | | tRNA-Ser | 5.4 | * | * |
| PA14_09150 | katA | catalase | 5.3 | * | * |
| PA14_68150 | | tRNA-Thr | 5.0 | * | * |
| PA14_06810 | norC | nitric-oxide reductase subunit C | 4.9 | * | * |
| PA14_61830 | | tRNA-Met | 4.9 | * | * |
| PA14_60160 | | tRNA-Pro | 4.8 | * | * |
| PA14_22320 | | hypothetical protein | 4.8 | * | * |
| PA14_18590 | | hypothetical protein | 4.7 | * | * |
| PA14_51420 | pqsB | PqsB | 4.6 | | |
| PA14_41330 | | tRNA-His | 4.5 | * | * |
| PA14_27330 | | phospho-2-dehydro-3-deoxyheptonate aldolase | 4.3 | * | * |
| PA14_28190 | | tRNA-Val | 4.1 | * | * |
| PA14_05860 | | hypothetical protein | 4.0 | * | * |
| PA14_18800 | | hypothetical protein | 4.0 | * | * |
| PA14_06830 | norB | nitric-oxide reductase subunit B | 3.9 | * | * |
| PA14_23570 | | tRNA-Ala | 3.8 | * | * |
| PA14_06875 | | rsmYregulatoryRNA | 3.7 | * | * |
| PA14_01490 | | hemolysin | 3.7 | | * |
| PA14_48060 | aprA | alkaline metalloproteinase | 3.6 | * | * |
| PA14_28660 | infC | translation initiation factor IF-3 | 3.5 | | |
| PA14_01710 | ahpC | alkyl hydroperoxide reductase | 3.4 | * | * |
| PA14_36330 | hcnA | hydrogen cyanide synthase HcnA | 3.4 | | * |
| PA14_20500 | | tRNA-Arg | 3.4 | * | * |
| PA14_51410 | pqsC | PqsC | 3.3 | | |
| PA14_28740 | | tRNA-Pro | 3.3 | | * |
| PA14_13950 | | hypothetical protein | 3.2 | | |
| PA14_50290 | fliC | flagellin type B | 3.2 | | |
| PA14_08900 | rplV | 50S ribosomal protein L22 | 3.2 | | |
| PA14_08220 | | hypothetical protein | 3.2 | | |
| PA14_58040 | | hypothetical protein | 3.1 | * | * |
| PA14_15990 | trmD | tRNA (guanine-N(1)-)-methyltransferase | 3.1 | | |
| PA14_01720 | ahpF | alkyl hydroperoxide reductase | 3.1 | * | * |
| PA14_51610 | | hypothetical protein | 3.1 | | |
| PA14_53290 | trxB2 | thioredoxin reductase 2 | 3.1 | * | * |
| PA14_09470 | phzB1 | phenazine biosynthesis protein | 3.1 | | * |
| PA14_26980 | | hypothetical protein | 3.0 | * | * |
| PA14_63460 | | tRNA-Sec | 3.0 | | * |
| PA14_41340 | | tRNA-Arg | 3.0 | * | * |
| PA14_28720 | ihfA | integration host factor subunit alpha | 3.0 | | |
| PA14_08930 | rpmC | 50S ribosomal protein L29 | 3.0 | | |
| PA14_59230 | | colicin immunity protein | 3.0 | | |

TABLE 7-continued

Genes down-regulated by mBTL in the wild-type strain determined through microarray analysis. The ratio of gene expression in untreated cells to that of mBTL treated cells (fold down-regulation) is displayed for genes that exhibited changes greater than 2-fold. Additional columns indicate the genes that are also downregulated in the lasR and rhlR null strains. Ratios are the average of three independent experiments.

| Gene locus | Gene name | Description | Ratio | LasR-regulated | RhlR-regulated |
|---|---|---|---|---|---|
| PA14_39470 | | hypothetical protein | 3.0 | | |
| PA14_69200 | trxA | thioredoxin | 3.0 | * | * |
| PA14_61040 | katB | catalase | 2.9 | * | * |
| PA14_60480 | | hypothetical protein | 2.9 | | |
| PA14_08880 | rplB | 50S ribosomal protein L2 | 2.9 | | |
| PA14_14560 | | hypothetical protein | 2.9 | | |
| PA14_08660 | | tRNA-Gly | 2.9 | * | * |
| PA14_36320 | hcnB | hydrogen cyanide synthase HcnB | 2.8 | | * |
| PA14_03410 | | tRNA-Arg | 2.8 | * | * |
| PA14_28670 | rpmI | 50S ribosomal protein L35 | 2.8 | | |
| PA14_53610 | | hypothetical protein | 2.8 | | |
| PA14_09130 | rplQ | 50S ribosomal protein L17 | 2.7 | | |
| PA14_07680 | | hypothetical protein | 2.7 | | |
| PA14_41320 | | tRNA-Leu | 2.7 | * | |
| PA14_68030 | | tRNA-Phe | 2.7 | * | * |
| PA14_62680 | | hypothetical protein | 2.7 | | |
| PA14_38180 | | hypothetical protein | 2.7 | | |
| PA14_10230 | adh | 2,3-butanediol dehydrogenase | 2.6 | | |
| PA14_58010 | | hypothetical protein | 2.6 | | |
| PA14_20290 | | DNA binding-protein | 2.6 | | |
| PA14_09080 | rpsM | 30S ribosomal protein S13 | 2.6 | | |
| PA14_49520 | pyoS3A | pyocin killing protein | 2.6 | | |
| PA14_55940 | | hypothetical protein | 2.6 | * | * |
| PA14_70190 | rpmB | 50S ribosomal protein L28 | 2.6 | | |
| PA14_09540 | mexG | hypothetical protein | 2.6 | | * |
| PA14_58000 | sodM | superoxide dismutase | 2.5 | | |
| PA14_51380 | pqsE | quinolone signal response protein | 2.5 | | |
| PA14_35840 | | hypothetical protein | 2.5 | | |
| PA14_18690 | | peroxidase | 2.5 | | |
| PA14_49030 | | hypothetical protein | 2.5 | | |
| PA14_28680 | rplT | 50S ribosomal protein L20 | 2.5 | | |
| PA14_48140 | | hypothetical protein | 2.5 | * | * |
| PA14_23410 | orfJ | glycosyl transferase family protein | 2.5 | | |
| PA14_58030 | fumC | fumarate hydratase | 2.5 | | |
| PA14_18070 | | periplasrnic metal-binding protein | 2.5 | * | * |
| PA14_51390 | pqsD | 3-oxoacyl-ACP synthase | 2.5 | | |
| PA14_23330 | rpsA | 30S ribosomal protein S1 | 2.5 | | |
| PA14_24650 | rmf | ribosome modulation factor | 2.5 | | |
| PA14_14300 | | zinc-binding oxidoreductase | 2.5 | | |
| PA14_49470 | nrdB | ribonucleotide-diphosphate reductase subunit beta | 2.5 | | |
| PA14_57460 | | cell division protein MraZ | 2.5 | | |
| PA14_08820 | fusA1 | elongation factor G | 2.4 | | |
| PA14_17480 | rpoS | RNA polymerase sigma factor RpoS | 2.4 | * | |
| PA14_09090 | rpsK | 30S ribosomal protein S11 | 2.4 | | |
| PA14_35160 | | hypothetical protein | 2.4 | | * |
| PA14_62690 | | hypothetical protein | 2.4 | * | |
| PA14_19590 | | molybdopterin-binding protein | 2.4 | | * |
| PA14_57950 | | hypothetical protein | 2.4 | | |
| PA14_23360 | wzz | O-antigen chain length regulator | 2.4 | | |
| PA14_20050 | | outer membrane protein | 2.4 | * | |
| PA14_41230 | clpX | ATP-dependent protease ATP-binding subunit ClpX | 2.4 | | |
| PA14_59430 | | hypothetical protein | 2.4 | | |
| PA14_50880 | | hypothetical protein | 2.4 | | |
| PA14_06750 | nirS | nitrite reductase | 2.4 | * | * |
| PA14_49510 | pyoS3I | immunity protein S3I structureal gene | 2.4 | | |
| PA14_64500 | | transcriptional regulator | 2.4 | * | * |
| PA14_28780 | | hypothetical protein | 2.3 | | |
| PA14_30210 | clpS | ATP-dependent Clp protease adaptor protein ClpS | 2.3 | | |
| PA14_69370 | algP | alginate regulatory protein AlgP | 2.3 | | |
| PA14_41570 | oprF | major porin and structural outer membrane porin OprF precursor | 2.3 | | |
| PA14_09270 | pchE | dihydroaeruginoic acid synthetase | 2.3 | | * |
| PA14_08790 | rpsL | 30S ribosomal protein S12 | 2.3 | | |
| PA14_35760 | | hypothetical protein | 2.3 | | |
| PA14_53590 | | hypothetical protein | 2.3 | | |
| PA14_19110 | rhlB | rhamnosyltransferase chain B | 2.3 | | * |
| PA14_13940 | | S-type pyocin protein | 2.3 | | |
| PA14_35850 | | hypothetical protein | 2.3 | | |
| PA14_08810 | rpsG | 30S ribosomal protein S7 | 2.3 | | |
| PA14_09340 | fptA | Fe(III)-pyochelin outer membrane receptor | 2.3 | | |
| PA14_65180 | rpsF | 30S ribosomal protein S6 | 2.2 | | |

TABLE 7-continued

Genes down-regulated by mBTL in the wild-type strain determined through microarray analysis. The ratio of gene expression in untreated cells to that of mBTL treated cells (fold down-regulation) is displayed for genes that exhibited changes greater than 2-fold. Additional columns indicate the genes that are also downregulated in the lasR and rhlR null strains. Ratios are the average of three independent experiments.

| Gene locus | Gene name | Description | Ratio | LasR-regulated | RhlR-regulated |
|---|---|---|---|---|---|
| PA14_48040 | aprI | alkaline proteinase inhibitor AprI | 2.2 | * | * |
| PA14_68940 | | hypothetical protein | 2.2 | | * |
| PA14_51430 | pqsA | coenzyme A ligase | 2.2 | | |
| PA14_29570 | | hypothetical protein | 2.2 | | |
| PA14_08720 | rplK | 50S ribosomal protein L11 | 2.2 | | |
| PA14_08910 | rpsC | 30S ribosomal protein S3 | 2.2 | | |
| PA14_59400 | | hypothetical protein | 2.2 | | |
| PA14_09210 | pchA | salicylate biosynthesis isochorismate synthase | 2.2 | | |
| PA14_59610 | | hypothetical protein | 2.2 | | |
| PA14_59190 | | hypothetical protein | 2.2 | | |
| PA14_14750 | | iron-binding protein IscA | 2.2 | | * |
| PA14_56070 | mvaT | transcriptional regulator MvaT, P16 subunit | 2.2 | | |
| PA14_08690 | | tRNA-Trp | 2.2 | | * |
| PA14_19100 | rhlA | rhamnosyltransferase chain A | 2.2 | | * |
| PA14_33750 | | outer membrane protein | 2.2 | * | * |
| PA14_08840 | rpsJ | 30S ribosomal protein S10 | 2.2 | | |
| PA14_45960 | lasR | transcriptional regulator LasR | 2.2 | * | |
| PA14_60960 | | hypothetical protein | 2.2 | | |
| PA14_68340 | arcB | ornithine carbamoyltransferase | 2.2 | | |
| PA14_19490 | | antioxidant protein | 2.2 | | * |
| PA14_61760 | | tRNA-Gln | 2.2 | * | * |
| PA14_25630 | rpmF | 50S ribosomal protein L32 | 2.2 | | |
| PA14_23400 | | hypothetical protein | 2.2 | | |
| PA14_70180 | rpmG | 50S ribosomal protein L33 | 2.2 | | |
| PA14_51810 | | hypothetical protein | 2.2 | | |
| PA14_08730 | rplA | 50S ribosomal protein L1 | 2.2 | | |
| PA14_23390 | orfE | polysaccharide biosynthesis protein | 2.2 | | |
| PA14_30190 | icd | isocitrate dehydrogenase | 2.2 | | |
| PA14_15850 | | hypothetical protein | 2.2 | | |
| PA14_10560 | | hypothetical protein | 2.2 | | * |
| PA14_23340 | ihfB | integration host factor subunit beta | 2.2 | | |
| PA14_53070 | hpd | 4-hydroxyphenylpyruvate dioxygenase | 2.2 | | |
| PA14_20010 | hasR | heme uptake outer membrane receptor HasR | 2.2 | | |
| PA14_41250 | tig | trigger factor | 2.2 | | |
| PA14_08850 | rplC | 50S ribosomal protein L3 | 2.2 | | |
| PA14_08960 | rplX | 50S ribosomal protein L24 | 2.2 | | |
| PA14_51350 | phnB | anthranilate synthase component II | 2.2 | | |
| PA14_09115 | rpoA | DNA-directed RNA polymerase subunit alpha | 2.2 | | |
| PA14_59390 | | hypothetical protein | 2.1 | | * |
| PA14_67190 | | hypothetical protein | 2.1 | | |
| PA14_37520 | | hypothetical protein | 2.1 | | |
| PA14_61380 | | hypothetical protein | 2.1 | * | |
| PA14_17440 | truD | tRNA pseudouridine synthase D | 2.1 | | |
| PA14_20530 | | hypothetical protein | 2.1 | | |
| PA14_08890 | rpsS | 30S ribosomal protein S19 | 2.1 | | |
| PA14_14730 | iscS | cysteine desulfurase | 2.1 | | |
| PA14_73300 | atpE | F0F1 ATP synthase subunit C | 2.1 | | |
| PA14_54490 | | hypothetical protein | 2.1 | * | |
| PA14_09480 | phzA1 | phenazine biosynthesis protein | 2.1 | | |
| PA14_12260 | | hypothetical protein | 2.1 | | |
| PA14_59620 | | hypothetical protein | 2.1 | | |
| PA14_28710 | pheT | phenylalanyl-tRNA synthetase subunit beta | 2.1 | | |
| PA14_20610 | lecB | fucose-binding lectin PA-IIL | 2.1 | | * |
| PA14_08970 | rplE | 50S ribosomal protein L5 | 2.1 | | |
| PA14_56780 | sodB | superoxide dismutase | 2.1 | | |
| PA14_31350 | | hypothetical protein | 2.1 | | * |
| PA14_16830 | | hypothetical protein | 2.1 | | |
| PA14_52990 | phhA | phenylalanine 4-monooxygenase | 2.1 | | |
| PA14_49200 | oprH | PhoP/Q and low Mg2+ inducible outer membrane prote | 2.1 | | |
| PA14_53340 | | hypothetical protein | 2.1 | | |
| PA14_49860 | | hypothetical protein | 2.1 | | |
| PA14_08750 | rplL | 50S ribosomal protein L7/L12 | 2.1 | | |
| PA14_13460 | | RNA polymerase sigma factor | 2.1 | * | * |
| PA14_07480 | | reverse transcriptase | 2.0 | | |
| PA14_08870 | rplW | 50S ribosomal protein L23 | 2.0 | | |
| PA14_09220 | pchB | isochorismate-pyruvate lyase | 2.0 | | |
| PA14_59590 | | hypothetical protein | 2.0 | | |
| PA14_62720 | rpsO | 30S ribosomal protein S15 | 2.0 | * | * |
| PA14_66875 | phaF | polyhydroxyalkanoate synthesis protein PhaF | 2.0 | | |
| PA14_04300 | | hypothetical protein | 2.0 | | |
| PA14_37420 | | transmembrane sensor protein | 2.0 | | |

TABLE 7-continued

Genes down-regulated by mBTL in the wild-type strain determined through microarray analysis. The ratio of gene expression in untreated cells to that of mBTL treated cells (fold down-regulation) is displayed for genes that exhibited changes greater than 2-fold. Additional columns indicate the genes that are also downregulated in the lasR and rhlR null strains. Ratios are the average of three independent experiments.

| Gene locus | Gene name | Description | Ratio | LasR-regulated | RhlR-regulated |
|---|---|---|---|---|---|
| PA14_14740 | | scaffold protein | 2.0 | | * |
| PA14_55810 | | two-component response regulator | 2.0 | | |
| PA14_41210 | hupB | DNA-binding protein HU | 2.0 | | * |
| PA14_10490 | | hypothetical protein | 2.0 | | * |
| PA14_16910 | | hypothetical protein | 2.0 | | |
| PA14_57010 | groEL | chaperonin GroEL | 2.0 | | |
| PA14_02260 | | two-component response regulator | 2.0 | * | |
| PA14_50280 | | hypothetical protein | 2.0 | | |
| PA14_09000 | rplF | 50S ribosomal protein L6 | 2.0 | | |
| PA14_66620 | pilQ | type 4 fimbrial biogenesis outer membrane protein PilQ precursor | 2.0 | | |
| PA14_59380 | | hypothetical protein | 2.0 | | |
| PA14_09020 | rpsE | 30S ribosomal protein S5 | 2.0 | | |

TABLE 8

Genes down-regulated by disruption of the lasR gene determined through microarray analysis. The ratio of gene expression of the wild-type strain to that of the lasR null strain (fold down-regulation) is displayed for genes that exhibited changes greater than 2-fold. Ratios are the average of three independent experiments.

| Gene locus | Gene name | Description | Ratio |
|---|---|---|---|
| PA14_45960 | lasR | transcriptional regulator LasR | 81.7 |
| PA14_06810 | norC | nitric-oxide reductase subunit C | 74.5 |
| PA14_22320 | | hypothetical protein | 52.0 |
| PA14_20020 | hasAp | heme acquisition protein HasAp | 34.9 |
| PA14_21530 | | ankyrin domain-containing protein | 33.1 |
| PA14_33290 | | hypothetical protein | 28.1 |
| PA14_45950 | rsaL | regulatory protein RsaL | 23.4 |
| PA14_01720 | ahpF | alkyl hydroperoxide reductase | 23.3 |
| PA14_26990 | | hypothetical protein | 21.5 |
| PA14_53290 | trxB2 | thioredoxin reductase 2 | 20.9 |
| PA14_09150 | katA | catalase | 16.7 |
| PA14_03090 | | hypothetical protein | 15.8 |
| PA14_53300 | | alkyl hydroperoxide reductase | 15.3 |
| PA14_06830 | norB | nitric-oxide reductase subunit B | 15.3 |
| PA14_40260 | | hypothetical protein | 12.8 |
| PA14_01710 | ahpC | alkyl hydroperoxide reductase | 12.8 |
| PA14_52320 | | tRNA-Met | 12.4 |
| PA14_62790 | | tRNA-Met | 12.3 |
| PA14_10380 | | hypothetical protein | 11.8 |
| PA14_58710 | | tRNA-Thr | 11.2 |
| PA14_39420 | | hypothetical protein | 11.1 |
| PA14_06875 | | rsmYregulatoryRNA | 11.1 |
| PA14_68150 | | tRNA-Thr | 11.0 |
| PA14_18590 | | hypothetical protein | 9.7 |
| PA14_51230 | | tRNA-Ser | 8.7 |
| PA14_30420 | | tRNA-Ser | 8.7 |
| PA14_05860 | | hypothetical protein | 8.6 |
| PA14_72370 | | hypothetical protein | 7.9 |
| PA14_27330 | | phospho-2-dehydro-3-deoxyheptonate aldolase | 7.5 |
| PA14_55940 | | hypothetical protein | 7.3 |
| PA14_20500 | | tRNA-Arg | 7.3 |
| PA14_07470 | | tRNA-Met | 7.2 |
| PA14_39780 | | hypothetical protein | 6.8 |
| PA14_48060 | aprA | alkaline metalloproteinase | 6.4 |
| PA14_54840 | | tRNA-Gly | 6.3 |
| PA14_28190 | | tRNA-Val | 6.2 |
| PA14_41340 | | tRNA-Arg | 5.9 |
| PA14_24870 | | tRNA-Pro | 5.7 |
| PA14_51830 | | DNA-binding stress protein | 5.7 |
| PA14_18800 | | hypothetical protein | 5.6 |
| PA14_61040 | katB | catalase | 5.4 |
| PA14_14570 | | tRNA-Leu | 5.2 |

TABLE 8-continued

Genes down-regulated by disruption of the lasR gene determined through microarray analysis. The ratio of gene expression of the wild-type strain to that of the lasR null strain (fold down-regulation) is displayed for genes that exhibited changes greater than 2-fold. Ratios are the average of three independent experiments.

| Gene locus | Gene name | Description | Ratio |
|---|---|---|---|
| PA14_09900 | prpL | Pvds-regulated endoprotease, lysyl class | 5.1 |
| PA14_26980 | | hypothetical protein | 5.0 |
| PA14_03410 | | tRNA-Arg | 4.8 |
| PA14_52560 | | tRNA-Ser | 4.7 |
| PA14_60160 | | tRNA-Pro | 4.4 |
| PA14_23570 | | tRNA-Ala | 4.1 |
| PA14_64500 | | transcriptional regulator | 4.0 |
| PA14_36820 | | hypothetical protein | 4.0 |
| PA14_08670 | | tRNA-Thr | 4.0 |
| PA14_41330 | | tRNA-His | 4.0 |
| PA14_40240 | | ABC transporter ATP-binding protein/permease | 4.0 |
| PA14_36560 | | hypothetical protein | 3.9 |
| PA14_01290 | coxB | cytochrome c oxidase subunit II | 3.9 |
| PA14_27190 | | tRNA-Ser | 3.8 |
| PA14_48040 | aprI | alkaline proteinase inhibitor AprI | 3.8 |
| PA14_40230 | | secretion protein | 3.8 |
| PA14_16720 | | hypothetical protein | 3.7 |
| PA14_35340 | | 2-ketogluconate kinase | 3.7 |
| PA14_61380 | | hypothetical protein | 3.7 |
| PA14_28600 | | hypothetical protein | 3.6 |
| PA14_48610 | | sparagine synthase | 3.6 |
| PA14_72360 | | hypothetical protein | 3.6 |
| PA14_61760 | | tRNA-Gln | 3.5 |
| PA14_13390 | | hypothetical protein | 3.5 |
| PA14_17980 | glpF | glycerol uptake facilitator protein | 3.5 |
| PA14_22100 | | hypothetical protein | 3.5 |
| PA14_01780 | | nucleoside 2-deoxyribosyltransferase | 3.5 |
| PA14_49130 | dctA | C4-dicarboxylate transporter DctA | 3.4 |
| PA14_72060 | | hypothetical protein | 3.3 |
| PA14_24860 | snr1 | cytochrome c Snr1 | 3.3 |
| PA14_46750 | | hypothetical protein | 3.3 |
| PA14_62720 | rpsO | 30S ribosomal protein S15 | 3.2 |
| PA14_01300 | coxA | cytochrome c oxidase subunit I | 3.2 |
| PA14_28620 | | hypothetical protein | 3.2 |
| PA14_56910 | | hypothetical protein | 3.1 |
| PA14_66880 | | hypothetical protein | 3.1 |
| PA14_55790 | | hypothetical protein | 3.0 |
| PA14_06750 | nirS | nitrite reductase | 3.0 |
| PA14_61830 | | tRNA-Met | 3.0 |
| PA14_01320 | coIII | cytochrome c oxidase subunit III | 2.9 |
| PA14_01350 | | hypothetical protein | 2.9 |
| PA14_00300 | plcB | phospholipase C, PlcB | 2.8 |
| PA14_62810 | secG | preprotein translocase subunit SecG | 2.7 |
| PA14_22880 | | Fe—S protein | 2.7 |
| PA14_13350 | | hypothetical protein | 2.7 |
| PA14_13460 | | RNA polymerase sigma factor | 2.7 |
| PA14_62870 | rrmJ | cell division protein FtsJ | 2.7 |
| PA14_68030 | | tRNA-Phe | 2.7 |
| PA14_69200 | trxA | thioredoxin | 2.7 |
| PA14_53250 | cpbD | chitin-binding protein CbpD | 2.7 |
| PA14_58040 | | hypothetical protein | 2.6 |
| PA14_57030 | fxsA | FxsA protein | 2.6 |
| PA14_08660 | | tRNA-Gly | 2.6 |
| PA14_53630 | | hypothetical protein | 2.6 |
| PA14_17480 | rpoS | RNA polymerase sigma factor RpoS | 2.6 |
| PA14_33050 | | hypothetical protein | 2.6 |
| PA14_54490 | | hypothetical protein | 2.5 |
| PA14_02500 | exbB1 | transport protein ExbB | 2.5 |
| PA14_20050 | | outer membrane protein | 2.5 |
| PA14_62860 | ftsH | cell division protein FtsH | 2.5 |
| PA14_06770 | nirQ | regulatory protein NirQ | 2.5 |
| PA14_53840 | | hypothetical protein | 2.5 |
| PA14_38550 | maiA | maleylacetoacetate isomerase | 2.5 |
| PA14_00790 | prlC | oligopeptidase A | 2.5 |
| PA14_18070 | | periplasmic metal-binding protein | 2.5 |
| PA14_07890 | | ABC transporter permease | 2.4 |
| PA14_38825 | pqqA | coenzyme PQQ synthesis protein PqqA | 2.4 |
| PA14_55920 | | type II secretion system protein | 2.4 |
| PA14_13380 | | hypothetical protein | 2.4 |
| PA14_20770 | | hypothetical protein | 2.4 |

TABLE 8-continued

Genes down-regulated by disruption of the lasR gene determined through microarray analysis. The ratio of gene expression of the wild-type strain to that of the lasR null strain (fold down-regulation) is displayed for genes that exhibited changes greater than 2-fold. Ratios are the average of three independent experiments.

| Gene locus | Gene name | Description | Ratio |
|---|---|---|---|
| PA14_22310 | | hypothetical protein | 2.4 |
| PA14_63170 | | transcriptional regulator | 2.4 |
| PA14_47190 | cyoB | cytochrome o ubiquinol oxidase subunit I | 2.3 |
| PA14_02510 | exbD1 | transport protein ExbD | 2.3 |
| PA14_67770 | pgm | phosphoglyceromutase | 2.3 |
| PA14_62690 | | hypothetical protein | 2.3 |
| PA14_26020 | | aminopeptidase | 2.3 |
| PA14_61060 | | oxidoreductase | 2.3 |
| PA14_30720 | | tRNA-Cys | 2.3 |
| PA14_48140 | | hypothetical protein | 2.3 |
| PA14_36920 | | hypothetical protein | 2.3 |
| PA14_25180 | psrA | transcriptional regulator PsrA | 2.3 |
| PA14_58070 | | hypothetical protein | 2.3 |
| PA14_53160 | | hypothetical protein | 2.3 |
| PA14_42200 | | hypothetical protein | 2.3 |
| PA14_35980 | | acyl-CoA dehydrogenase | 2.3 |
| PA14_49050 | | hypothetical protein | 2.3 |
| PA14_12130 | lis | lipoyl synthase | 2.3 |
| PA14_40250 | | outer membrane protein | 2.3 |
| PA14_60750 | pra | protein activator | 2.3 |
| PA14_05020 | | hypothetical protein | 2.2 |
| PA14_13370 | | hypothetical protein | 2.2 |
| PA14_23680 | ibpA | heat-shock protein IbpA | 2.2 |
| PA14_20480 | | hypothetical protein | 2.2 |
| PA14_11510 | ribA | GTP cyclohydrolase II | 2.2 |
| PA14_53210 | | hypothetical protein | 2.2 |
| PA14_41320 | | tRNA-Leu | 2.2 |
| PA14_35360 | | hypothetical protein | 2.1 |
| PA14_36980 | | hypothetical protein | 2.1 |
| PA14_72870 | | aminotransferase | 2.1 |
| PA14_20780 | | two-component response regulator | 2.1 |
| PA14_63480 | | amino acid permease | 2.1 |
| PA14_54430 | algU | RNA polymerase sigma factor AlgU | 2.1 |
| PA14_33060 | | hypothetical protein | 2.1 |
| PA14_28140 | | hypothetical protein | 2.1 |
| PA14_72170 | | citrate transporter | 2.1 |
| PA14_53040 | | lysozyme inhibitor | 2.1 |
| PA14_11610 | | ABC transporter permease | 2.1 |
| PA14_02260 | | two-component response regulator | 2.1 |
| PA14_61020 | | hypothetical protein | 2.1 |
| PA14_19870 | ldh | leucine dehydrogenase | 2.1 |
| PA14_72970 | tonB | TonB protein | 2.1 |
| PA14_33750 | | outer membrane protein | 2.1 |
| PA14_34330 | | hypothetical protein | 2.1 |
| PA14_00480 | | hypothetical protein | 2.1 |
| PA14_60500 | fklB | peptidyl-prolyl cis-trans isomerase FklB | 2.1 |
| PA14_09700 | | monooxygenase | 2.1 |
| PA14_16250 | lasB | elastase LasB | 2.0 |
| PA14_49460 | nrdA | ribonucleotide-diphosphate reductase subunit alpha | 2.0 |
| PA14_72140 | | hypothetical protein | 2.0 |
| PA14_35370 | ptxS | transcriptional regulator PtxS | 2.0 |
| PA14_66550 | hemE | uroporphyrinogen decarboxylase | 2.0 |
| PA14_12030 | | hypothetical protein | 2.0 |
| PA14_70490 | | lipoprotein | 2.0 |
| PA14_38060 | | hypothetical protein | 2.0 |
| PA14_73230 | atpC | F0F1 ATP synthase subunit epsilon | 2.0 |
| PA14_72770 | | hypothetical protein | 2.0 |
| PA14_47530 | | hypothetical protein | 2.0 |
| PA14_66400 | | potassium efflux protein KefA | 2.0 |
| PA14_37410 | | hypothetical protein | 2.0 |
| PA14_44700 | alkB2 | alkane-1 monooxygenase | 2.0 |

TABLE 9

Genes down-regulated by disruption of the rhlR gene determined through microarray analysis. The ratio of gene expression of the wild-type strain to that of the rhlR null strain (fold down-regulation) is displayed for genes that exhibited changes greater than 2-fold. Ratios are the average of three independent experiments.

| Gene locus | Gene name | Description | Ratio |
|---|---|---|---|
| PA14_10360 | | hypothetical protein | 54.5 |
| PA14_22320 | | hypothetical protein | 47.2 |
| PA14_34870 | chiC | chitinase | 44.6 |
| PA14_15350 | | integrase | 43.8 |
| PA14_18800 | | hypothetical protein | 42.7 |
| PA14_15600 | | hypothetical protein | 35.7 |
| PA14_01720 | ahpF | alkyl hydroperoxide reductase | 34.7 |
| PA14_53250 | cpbD | chitin-binding protein CbpD | 33.7 |
| PA14_21530 | | ankyrin domain-containing protein | 32.7 |
| PA14_20610 | lecB | fucose-binding lectin PA-IIL | 29.6 |
| PA14_53290 | trxB2 | thioredoxin reductase 2 | 26.8 |
| PA14_19100 | rhlA | rhamnosyltransferase chain A | 24.4 |
| PA14_06810 | norC | nitric-oxide reductase subunit C | 23.6 |
| PA14_01490 | | hemolysin | 23.2 |
| PA14_15480 | merR | transcriptional regulator MerR | 23.1 |
| PA14_15610 | | hypothetical protein | 22.7 |
| PA14_26990 | | hypothetical protein | 22.6 |
| PA14_53300 | | alkyl hydroperoxide reductase | 19.6 |
| PA14_11140 | | nonribosomal peptide synthetase | 18.4 |
| PA14_09540 | mexG | hypothetical protein | 16.3 |
| PA14_01710 | ahpC | alkyl hydroperoxide reductase | 16.0 |
| PA14_40310 | | acyl carrier protein | 15.9 |
| PA14_03090 | | hypothetical protein | 15.6 |
| PA14_28360 | | hypothetical protein | 15.2 |
| PA14_38270 | | hypothetical protein | 15.1 |
| PA14_37745 | | carbamoyl transferase | 14.3 |
| PA14_16250 | lasB | elastase LasB | 14.2 |
| PA14_06830 | norB | nitric-oxide reductase subunit B | 13.9 |
| PA14_09150 | katA | catalase | 13.6 |
| PA14_15560 | | hypothetical protein | 11.1 |
| PA14_51230 | | tRNA-Ser | 10.5 |
| PA14_09530 | mexH | RND efflux membrane fusion protein | 10.3 |
| PA14_05860 | | hypothetical protein | 9.9 |
| PA14_54840 | | tRNA-Gly | 9.8 |
| PA14_03510 | | hypothetical protein | 9.7 |
| PA14_68940 | | hypothetical protein | 9.7 |
| PA14_39420 | | hypothetical protein | 9.2 |
| PA14_31290 | pa1L | PA-I galactophilic lectin | 9.0 |
| PA14_19590 | | molybdopterin-binding protein | 8.7 |
| PA14_16100 | | hypothetical protein | 8.4 |
| PA14_68150 | | tRNA-Thr | 8.2 |
| PA14_52320 | | tRNA-Met | 8.1 |
| PA14_62790 | | tRNA-Met | 7.7 |
| PA14_15520 | trbJ | conjugal transfer protein TrbJ | 7.3 |
| PA14_40290 | lasA | LasA protease | 7.2 |
| PA14_30720 | | tRNA-Cys | 7.1 |
| PA14_58710 | | tRNA-Thr | 6.6 |
| PA14_03520 | | hypothetical protein | 6.4 |
| PA14_31360 | | hypothetical protein | 6.4 |
| PA14_24870 | | tRNA-Pro | 6.2 |
| PA14_15580 | | Type II restriction enzyme, methylase subunit | 6.2 |
| PA14_32950 | | hypothetical protein | 6.1 |
| PA14_51830 | | DNA-binding stress protein | 6.1 |
| PA14_53840 | | hypothetical protein | 6.0 |
| PA14_18590 | | hypothetical protein | 5.8 |
| PA14_34880 | | GntR family transcriptional regulator | 5.6 |
| PA14_28190 | | tRNA-Val | 5.5 |
| PA14_49760 | rhlC | rhamnosyltransferase 2 | 5.5 |
| PA14_10490 | | hypothetical protein | 5.4 |
| PA14_68210 | rmlC | dTDP-4-dehydrorhamnose 3,5-epimerase | 5.4 |
| PA14_59390 | | hypothetical protein | 5.3 |
| PA14_30420 | | tRNA-Ser | 5.3 |
| PA14_21030 | | ATP-dependent Clp protease proteolytic subunit | 5.3 |
| PA14_09520 | mexI | RND efflux transporter | 5.2 |
| PA14_41330 | | tRNA-His | 5.2 |
| PA14_55940 | | hypothetical protein | 5.1 |
| PA14_63210 | | two-component response regulator | 5.0 |
| PA14_20500 | | tRNA-Arg | 4.9 |
| PA14_27330 | | phospho-2-dehydro-3-deoxyheptonate aldolase | 4.9 |
| PA14_16720 | | hypothetical protein | 4.9 |
| PA14_34750 | | taurine catabolism dioxygenase | 4.9 |

TABLE 9-continued

Genes down-regulated by disruption of the rhlR gene determined through microarray analysis. The ratio of gene expression of the wild-type strain to that of the rhlR null strain (fold down-regulation) is displayed for genes that exhibited changes greater than 2-fold. Ratios are the average of three independent experiments.

| Gene locus | Gene name | Description | Ratio |
|---|---|---|---|
| PA14_15400 | | replication protein, RepC | 4.9 |
| PA14_23570 | | tRNA-Ala | 4.9 |
| PA14_49130 | dctA | C4-dicarboxylate transporter DctA | 4.8 |
| PA14_20020 | hasAp | heme acquisition protein HasAp | 4.7 |
| PA14_15360 | | hypothetical protein | 4.7 |
| PA14_56590 | | hypothetical protein | 4.6 |
| PA14_15460 | merA | mercuric reductase | 4.6 |
| PA14_48040 | aprI | alkaline proteinase inhibitor AprI | 4.5 |
| PA14_27190 | | tRNA-Ser | 4.5 |
| PA14_61040 | katB | catalase | 4.4 |
| PA14_68190 | rmlD | dTDP-4-dehydrorhamnose reductase | 4.3 |
| PA14_11130 | | short chain dehydrogenase | 4.3 |
| PA14_36330 | hcnA | hydrogen cyanide synthase HcnA | 4.3 |
| PA14_31350 | | hypothetical protein | 4.2 |
| PA14_41340 | | tRNA-Arg | 4.2 |
| PA14_36320 | hcnB | hydrogen cyanide synthase HcnB | 4.2 |
| PA14_52560 | | tRNA-Ser | 4.1 |
| PA14_09500 | opmD | outer membrane protein | 4.0 |
| PA14_19110 | rhlB | rhamnosyltransferase chain B | 4.0 |
| PA14_61830 | | tRNA-Met | 4.0 |
| PA14_26980 | | hypothetical protein | 3.9 |
| PA14_34780 | | ABC transporter ATP-binding protein | 3.9 |
| PA14_09470 | phzB1 | phenazine biosynthesis protein | 3.9 |
| PA14_60160 | | tRNA-Pro | 3.9 |
| PA14_06875 | | rsmY regulatory RNA | 3.9 |
| PA14_18680 | | hypothetical protein | 3.9 |
| PA14_03410 | | tRNA-Arg | 3.8 |
| PA14_15590 | | hypothetical protein | 3.8 |
| PA14_13460 | | RNA polymerase sigma factor | 3.8 |
| PA14_39960 | phzB2 | phenazine biosynthesis protein | 3.8 |
| PA14_43040 | | hypothetical protein | 3.8 |
| PA14_02500 | exbB1 | transport protein ExbB | 3.8 |
| PA14_61060 | | oxidoreductase | 3.6 |
| PA14_62390 | | hypothetical protein | 3.6 |
| PA14_15510 | traJ | conjugal transfer relaxosome component TraJ | 3.6 |
| PA14_17980 | glpF | glycerol uptake facilitator protein | 3.6 |
| PA14_15500 | | oriT-binding protein, Trak | 3.6 |
| PA14_50740 | | hypothetical protein | 3.6 |
| PA14_45950 | rsaL | regulatory protein RsaL | 3.5 |
| PA14_15450 | merD | transcriptional regulator MerD | 3.5 |
| PA14_19540 | | hypothetical protein | 3.5 |
| PA14_48140 | | hypothetical protein | 3.5 |
| PA14_40860 | | hypothetical protein | 3.4 |
| PA14_03490 | | hypothetical protein | 3.4 |
| PA14_33290 | | hypothetical protein | 3.3 |
| PA14_15490 | | hypothetical protein | 3.3 |
| PA14_68170 | rmlB | dTDP-D-glucose 4,6-dehydratase | 3.3 |
| PA14_00640 | phzH | potential phenazine-modifying enzyme | 3.3 |
| PA14_62860 | ftsH | cell division protein FtsH | 3.3 |
| PA14_55580 | nemO | heme oxygenase | 3.3 |
| PA14_69200 | trxA | thioredoxin | 3.3 |
| PA14_35160 | | hypothetical protein | 3.3 |
| PA14_31170 | | hypothetical protein | 3.3 |
| PA14_72060 | | hypothetical protein | 3.3 |
| PA14_66460 | | hypothetical protein | 3.2 |
| PA14_14570 | | tRNA-Leu | 3.2 |
| PA14_07470 | | tRNA-Met | 3.1 |
| PA14_30620 | | AraC family transcriptional regulator | 3.1 |
| PA14_38825 | pqqA | coenzyme PQQ synthesis protein PqqA | 3.1 |
| PA14_64930 | | hypothetical protein | 3.1 |
| PA14_61760 | | tRNA-Gln | 3.1 |
| PA14_10350 | | secretion protein | 3.1 |
| PA14_53040 | | lysozyme inhibitor | 3.1 |
| PA14_02510 | exbD1 | transport protein ExbD | 3.0 |
| PA14_19530 | | NAD(P)H-dependent FMN reductase | 3.0 |
| PA14_28050 | | chemotaxis transducer | 3.0 |
| PA14_72970 | tonB | TonB protein | 3.0 |
| PA14_62810 | secG | preprotein translocase subunit SecG | 2.9 |
| PA14_25180 | psrA | transcriptional regulator PsrA | 2.9 |
| PA14_35170 | | redox-sensing activator of soxS | 2.9 |
| PA14_08670 | | tRNA-Thr | 2.9 |

TABLE 9-continued

Genes down-regulated by disruption of the rhlR gene determined through microarray analysis. The ratio of gene expression of the wild-type strain to that of the rhlR null strain (fold down-regulation) is displayed for genes that exhibited changes greater than 2-fold. Ratios are the average of three independent experiments.

| Gene locus | Gene name | Description | Ratio |
|---|---|---|---|
| PA14_66550 | hemE | uroporphyrinogen decarboxylase | 2.9 |
| PA14_58040 | | hypothetical protein | 2.9 |
| PA14_06750 | nirS | nitrite reductase | 2.9 |
| PA14_41210 | hupB | DNA-binding protein HU | 2.9 |
| PA14_00790 | prlC | oligopeptidase A | 2.8 |
| PA14_68930 | | permease | 2.8 |
| PA14_62720 | rpsO | 30S ribosomal protein S15 | 2.8 |
| PA14_34730 | | XRE family transcriptional regulator | 2.8 |
| PA14_57030 | fxsA | FxsA protein | 2.8 |
| PA14_64500 | | transcriptional regulator | 2.8 |
| PA14_09490 | phzM | phenazine-specific methyltransferase | 2.8 |
| PA14_53160 | | hypothetical protein | 2.8 |
| PA14_32520 | | hypothetical protein | 2.8 |
| PA14_14710 | | Rrf2 family protein | 2.8 |
| PA14_06770 | nirQ | regulatory protein NirQ | 2.7 |
| PA14_12970 | tauD | taurine dioxygenase | 2.7 |
| PA14_23980 | xcpP | secretion protein XcpP | 2.7 |
| PA14_24860 | snr1 | cytochrome c Snr1 | 2.7 |
| PA14_43050 | | hypothetical protein | 2.7 |
| PA14_38550 | maiA | maleylacetoacetate isomerase | 2.7 |
| PA14_34770 | | ABC transporter substrate-binding protein | 2.7 |
| PA14_30410 | | hypothetical protein | 2.7 |
| PA14_19490 | | antioxidant protein | 2.6 |
| PA14_26780 | | hypothetical protein | 2.6 |
| PA14_39800 | | ECF subfamily RNA polymerase sigma-70 factor | 2.6 |
| PA14_30670 | pgsA | CDP-diacylglycerol--glycerol-3-phosphate 3-phosphatidyltransferase | 2.6 |
| PA14_10330 | | outer membrane protein | 2.6 |
| PA14_06180 | | RNA polymerase sigma factor | 2.6 |
| PA14_12920 | | taurine ABC transporter periplasmic protein | 2.6 |
| PA14_28620 | | hypothetical protein | 2.6 |
| PA14_60030 | | hypothetical protein | 2.6 |
| PA14_40260 | | hypothetical protein | 2.6 |
| PA14_39780 | | hypothetical protein | 2.6 |
| PA14_36820 | | hypothetical protein | 2.6 |
| PA14_71900 | | hypothetical protein | 2.5 |
| PA14_34460 | | hypothetical protein | 2.5 |
| PA14_19520 | | ABC transporter ATP-binding protein | 2.5 |
| PA14_13210 | | hypothetical protein | 2.5 |
| PA14_09270 | pchE | dihydroaeruginoic acid synthetase | 2.5 |
| PA14_08660 | | tRNA-Gly | 2.5 |
| PA14_06130 | | hypothetical protein | 2.5 |
| PA14_05020 | | hypothetical protein | 2.5 |
| PA14_62800 | | tRNA-Leu | 2.5 |
| PA14_31370 | | hypothetical protein | 2.5 |
| PA14_15370 | | hypothetical protein | 2.5 |
| PA14_60750 | pra | protein activator | 2.5 |
| PA14_37470 | | flavin-dependent oxidoreductase | 2.5 |
| PA14_03080 | | acetyltransferase | 2.4 |
| PA14_06580 | | hypothetical protein | 2.4 |
| PA14_37990 | | RNA polymerase sigma factor | 2.4 |
| PA14_68200 | rmlA | glucose-1-phosphate thymidylyltransferase | 2.4 |
| PA14_30550 | | periplasmic aliphatic sulfonate-binding protein | 2.4 |
| PA14_12130 | lis | lipoyl synthase | 2.4 |
| PA14_58580 | | hydroxylase | 2.4 |
| PA14_15110 | | hypothetical protein | 2.4 |
| PA14_11010 | | hypothetical protein | 2.4 |
| PA14_00800 | | hypothetical protein | 2.4 |
| PA14_18070 | | periplasmic metal-binding protein | 2.3 |
| PA14_41930 | | hypothetical protein | 2.3 |
| PA14_28250 | | secreted acid phosphatase | 2.3 |
| PA14_09370 | | hypothetical protein | 2.3 |
| PA14_10560 | | hypothetical protein | 2.3 |
| PA14_10500 | | cbb3-type cytochrome c oxidase subunit I | 2.3 |
| PA14_31700 | | CDP-alcohol phosphatidyltransferase | 2.3 |
| PA14_72870 | | aminotransferase | 2.3 |
| PA14_21260 | | hypothetical protein | 2.3 |
| PA14_22880 | | Fe—S protein | 2.3 |
| PA14_26190 | | hypothetical protein | 2.3 |
| PA14_23090 | | keto-hydroxyglutarate-aldolase/keto-deoxy-phosphogluconate aldolase | 2.3 |

TABLE 9-continued

Genes down-regulated by disruption of the rhlR gene determined through microarray analysis. The ratio of gene expression of the wild-type strain to that of the rhlR null strain (fold down-regulation) is displayed for genes that exhibited changes greater than 2-fold. Ratios are the average of three independent experiments.

| Gene locus | Gene name | Description | Ratio |
|---|---|---|---|
| PA14_37440 | | MFS transporter | 2.3 |
| PA14_52250 | | two-component response regulator | 2.3 |
| PA14_08690 | | tRNA-Trp | 2.2 |
| PA14_13140 | | hypothetical protein | 2.2 |
| PA14_16110 | | hypothetical protein | 2.2 |
| PA14_63460 | | tRNA-Sec | 2.2 |
| PA14_20770 | | hypothetical protein | 2.2 |
| PA14_28740 | | tRNA-Pro | 2.2 |
| PA14_40510 | ccoN-2 | cbb3-type cytochrome c oxidase subunit I | 2.2 |
| PA14_60540 | | hypothetical protein | 2.2 |
| PA14_38060 | | hypothetical protein | 2.2 |
| PA14_35340 | | 2-ketogluconate kinase | 2.2 |
| PA14_39970 | phzA2 | phenazine biosynthesis protein | 2.2 |
| PA14_72550 | | adhesin | 2.2 |
| PA14_42200 | | hypothetical protein | 2.2 |
| PA14_68030 | | tRNA-Phe | 2.2 |
| PA14_33750 | | outer membrane protein | 2.2 |
| PA14_56910 | | hypothetical protein | 2.2 |
| PA14_41450 | | hypothetical protein | 2.2 |
| PA14_52130 | | hypothetical protein | 2.2 |
| PA14_62870 | rrmJ | cell division protein FtsJ | 2.2 |
| PA14_52690 | aruG | arginine/ornithine succinyltransferase AII subunit | 2.2 |
| PA14_36310 | hcnC | hydrogen cyanide synthase HcnC | 2.2 |
| PA14_49800 | | oxidoreductase | 2.2 |
| PA14_34820 | | regulatory protein | 2.1 |
| PA14_43520 | | hypothetical protein | 2.1 |
| PA14_38220 | | hypothetical protein | 2.1 |
| PA14_15570 | | hypothetical protein | 2.1 |
| PA14_40240 | | ABC transporter ATP-binding protein/permease | 2.1 |
| PA14_31050 | | hypothetical protein | 2.1 |
| PA14_47190 | cyoB | cytochrome o ubiquinol oxidase subunit I | 2.1 |
| PA14_34830 | | regulatory protein | 2.1 |
| PA14_14750 | | iron-binding protein IscA | 2.1 |
| PA14_58690 | | hypothetical protein | 2.1 |
| PA14_12940 | | taurine ABC transporter ATP-binding protein | 2.1 |
| PA14_68070 | | periplasmic binding protein | 2.1 |
| PA14_19120 | rhlR | transcriptional regulator RhlR | 2.1 |
| PA14_40630 | | hypothetical protein | 2.1 |
| PA14_37770 | | hydrolase | 2.1 |
| PA14_02530 | | hypothetical protein | 2.1 |
| PA14_64940 | | hypothetical protein | 2.1 |
| PA14_09290 | pchG | pyochelin biosynthetic protein PchG | 2.1 |
| PA14_06170 | | transmembrane sensor | 2.0 |
| PA14_48060 | aprA | alkaline metalloproteinase | 2.0 |
| PA14_15540 | | mating pair formation protein TrbL | 2.0 |
| PA14_34510 | | hypothetical protein | 2.0 |
| PA14_65320 | miaA | tRNA delta(2)-isopentenylpyrophosphate transferase | 2.0 |
| PA14_52700 | aruF | arginine/ornithine succinyltransferase AI subunit | 2.0 |
| PA14_13000 | | transcriptional regulator | 2.0 |
| PA14_19370 | | asparagine synthetase | 2.0 |
| PA14_14740 | | scaffold protein | 2.0 |
| PA14_30630 | pqsH | FAD-dependent monooxygenase | 2.0 |

TABLE 10

Genes up-regulated by mBTL in the wild-type strain determined through microarray analysis. The ratio of gene expression in mBTL treated cells to that of untreated cells (fold up-regulation) is displayed for genes that exhibited changes greater than 2-fold. Ratios are the average of three independent experiments.

| Gene locus | Gene name | Description | Ratio |
|---|---|---|---|
| PA14_10380 | | hypothetical protein | 2.6 |
| PA14_31290 | pa1L | PA-I galactophilic lectin | 2.4 |
| PA14_10370 | | hypothetical protein | 2.3 |
| PA14_61200 | | hypothetical protein | 2.3 |
| PA14_49300 | | lipoxygenase | 2.3 |
| PA14_10350 | | secretion protein | 2.2 |
| PA14_31840 | | hypothetical protein | 2.2 |
| PA14_52000 | | hypothetical protein | 2.2 |

TABLE 10-continued

Genes up-regulated by mBTL in the wild-type strain determined through microarray analysis. The ratio of gene expression in mBTL treated cells to that of untreated cells (fold up-regulation) is displayed for genes that exhibited changes greater than 2-fold. Ratios are the average of three independent experiments.

| Gene locus | Gene name | Description | Ratio |
|---|---|---|---|
| PA14_45310 | ccmF | cytochrome C-type biogenesis protein CcmF | 2.1 |
| PA14_37070 | | hypothetical protein | 2.1 |
| PA14_31280 | | integrase | 2.1 |
| PA14_31890 | | RND efflux transporter | 2.0 |
| PA14_20640 | | hypothetical protein | 2.0 |

TABLE 11

Genes down-regulated by mBTL in the lasR mutant determined through microarray analysis. The ratio of gene expression in untreated cells to that of mBTL treated cells (fold down-regulation) is displayed for genes that exhibited changes greater than 2-fold. Ratios are the average of three independent experiments.

| Gene locus | Gene name | Description | Ratio |
|---|---|---|---|
| PA14_33810 | pvdA | L-ornithine N5-oxygenase | 18.4 |
| PA14_09490 | phzM | phenazine-specific methyltransferase | 12.8 |
| PA14_33510 | | hypothetical protein | 12.6 |
| PA14_33820 | pvdQ | penicillin acylase-related protein | 11.0 |
| PA14_33610 | | peptide synthase | 10.9 |
| PA14_51380 | pqsE | quinolone signal response protein | 7.8 |
| PA14_09480 | phzA1 | phenazine biosynthesis protein | 7.7 |
| PA14_51420 | pqsB | PqsB | 6.7 |
| PA14_09470 | phzB1 | phenazine biosynthesis protein | 6.6 |
| PA14_49720 | | hypothetical protein | 5.7 |
| PA14_33730 | | dipeptidase | 5.4 |
| PA14_51410 | pqsC | PqsC | 5.4 |
| PA14_33280 | pvdL | peptide synthase | 5.1 |
| PA14_33650 | pvdD | pyoverdine synthetase D | 4.6 |
| PA14_51430 | pqsA | coenzyme A ligase | 4.5 |
| PA14_36320 | hcnB | hydrogen cyanide synthase HcnB | 4.4 |
| PA14_28470 | | hypothetical protein | 4.4 |
| PA14_51390 | pqsD | 3-oxoacyl-ACP synthase | 4.2 |
| PA14_36330 | hcnA | hydrogen cyanide synthase HcnA | 4.1 |
| PA14_51350 | phnB | anthranilate synthase component II | 4.0 |
| PA14_39970 | phzA2 | phenazine biosynthesis protein | 3.9 |
| PA14_39960 | phzB2 | phenazine biosynthesis protein | 3.9 |
| PA14_33690 | pvdE | pyoverdine biosynthesis protein PvdE | 3.8 |
| PA14_09400 | phzS | hypothetical protein | 3.7 |
| PA14_10960 | | ferredoxin oxidoreductase subunit | 3.7 |
| PA14_54910 | | thioesterase | 3.6 |
| PA14_03370 | | hypothetical protein | 3.5 |
| PA14_25640 | plsX | glycerol-3-phosphate acyltransferase PlsX | 3.5 |
| PA14_21020 | | non-ribosomal peptide synthetase | 3.5 |
| PA14_34490 | | hypothetical protein | 3.5 |
| PA14_29560 | | hypothetical protein | 3.4 |
| PA14_33760 | | ABC transporter ATP-binding protein/permease | 3.3 |
| PA14_52800 | acsA | acetyl-CoA synthetase | 3.3 |
| PA14_19710 | | alpha/beta hydrolase | 3.3 |
| PA14_53230 | | oxidoreductase | 3.3 |
| PA14_67190 | | hypothetical protein | 3.3 |
| PA14_02970 | | hypothetical protein | 3.2 |
| PA14_33630 | pvdJ | protein PvdJ | 3.1 |
| PA14_30720 | | tRNA-Cys | 3.1 |
| PA14_08220 | | hypothetical protein | 3.1 |
| PA14_54870 | | hypothetical protein | 3.0 |
| PA14_55110 | | hypothetical protein | 3.0 |
| PA14_14560 | | hypothetical protein | 3.0 |
| PA14_59410 | | hypothetical protein | 3.0 |
| PA14_29250 | | hypothetical protein | 2.9 |
| PA14_55550 | | ECF subfamily RNA polymerase sigma-70 factor | 2.9 |
| PA14_68040 | | short-chain dehydrogenase | 2.9 |
| PA14_41800 | | transcriptional regulator | 2.9 |
| PA14_51610 | | hypothetical protein | 2.9 |
| PA14_55360 | exbB2 | transport protein ExbB2 | 2.9 |
| PA14_51920 | | acylphosphatase | 2.8 |

TABLE 11-continued

Genes down-regulated by mBTL in the lasR mutant determined through microarray analysis. The ratio of gene expression in untreated cells to that of mBTL treated cells (fold down-regulation) is displayed for genes that exhibited changes greater than 2-fold. Ratios are the average of three independent experiments.

| Gene locus | Gene name | Description | Ratio |
|---|---|---|---|
| PA14_33270 | pvdG | protein PvdG | 2.8 |
| PA14_34420 | | maltose/mannitol ABC transporter substrate-binding prote | 2.8 |
| PA14_69550 | | hypothetical protein | 2.8 |
| PA14_50050 | | MFS family transporter | 2.8 |
| PA14_63070 | | GntR family transcriptional regulator | 2.7 |
| PA14_48950 | | hypothetical protein | 2.7 |
| PA14_18350 | | bifunctional UDP-glucuronic acid decarboxylase/UDP-4-al | 2.7 |
| PA14_32790 | | hypothetical protein | 2.7 |
| PA14_20330 | phpE | phosphonate ABC transporter permease | 2.7 |
| PA14_35880 | | gamma-aminobutyraldehyde dehydrogenase | 2.7 |
| PA14_33700 | pvdF | pyoverdine synthetase F | 2.7 |
| PA14_57460 | | cell division protein MraZ | 2.7 |
| PA14_18150 | | acetyl-coa synthetase | 2.7 |
| PA14_23080 | pgl | 6-phosphogluconolactonase | 2.7 |
| PA14_33250 | | hypothetical protein | 2.7 |
| PA14_68380 | nudE | ADP-ribose diphosphatase NudE | 2.6 |
| PA14_01600 | | aldehyde dehydrogenase | 2.6 |
| PA14_41740 | | hypothetical protein | 2.6 |
| PA14_49010 | | hypothetical protein | 2.6 |
| PA14_38170 | | hypothetical protein | 2.6 |
| PA14_09660 | | acyl-CoA synthetase | 2.6 |
| PA14_19960 | | hypothetical protein | 2.6 |
| PA14_35950 | | dehydrogenase | 2.6 |
| PA14_50310 | | sugar nucleotidyltransferase | 2.5 |
| PA14_19750 | | hypothetical protein | 2.5 |
| PA14_23670 | | hypothetical protein | 2.5 |
| PA14_63330 | | glycerolphosphodiesterase | 2.5 |
| PA14_42910 | | hypothetical protein | 2.5 |
| PA14_51850 | | hypothetical protein | 2.5 |
| PA14_69430 | | hypothetical protein | 2.5 |
| PA14_59590 | | hypothetical protein | 2.5 |
| PA14_35390 | pvcD | pyoverdine biosynthesis protein PvcD | 2.5 |
| PA14_38420 | | hypothetical protein | 2.5 |
| PA14_58900 | | large exoprotein | 2.5 |
| PA14_57770 | hisC1 | histidinol-phosphate aminotransferase | 2.4 |
| PA14_33560 | | adhesion protein | 2.4 |
| PA14_22550 | | LysR family transcriptional regulator | 2.4 |
| PA14_55160 | toxR | transcriptional regulator ToxR | 2.4 |
| PA14_67350 | hutU | urocanate hydratase | 2.4 |
| PA14_21680 | | hypothetical protein | 2.4 |
| PA14_47650 | cobS | cobalamin synthase | 2.4 |
| PA14_33740 | pvdP | protein PvdP | 2.4 |
| PA14_51050 | | aldehyde dehydrogenase | 2.4 |
| PA14_52720 | argD | bifunctional N-succinyldiaminopimelate-aminotransferase/ | 2.4 |
| PA14_01250 | | sulfate transporter | 2.4 |
| PA14_72980 | | G3E family GTPase | 2.4 |
| PA14_10130 | | short chain dehydrogenase | 2.4 |
| PA14_29390 | | hypothetical protein | 2.4 |
| PA14_61620 | | MerR family transcriptional regulator | 2.4 |
| PA14_20950 | fabH2 | 3-oxoacyl-ACP synthase | 2.4 |
| PA14_05890 | | stomatin-like protein | 2.3 |
| PA14_54740 | | hypothetical protein | 2.3 |
| PA14_72960 | | MFS dicarboxylate transporter | 2.3 |
| PA14_36310 | hcnC | hydrogen cyanide synthase HunC | 2.3 |
| PA14_04030 | | hypothetical protein | 2.3 |
| PA14_61170 | | transmembrane protein | 2.3 |
| PA14_33550 | | ABC transporter ATP-binding protein | 2.3 |
| PA14_46170 | | LysR family transcriptional regulator | 2.3 |
| PA14_46000 | | hypothetical protein | 2.3 |
| PA14_63605 | fdnG | formate dehydrogenase-O, major subunit | 2.3 |
| PA14_72230 | | hypothetical protein | 2.3 |
| PA14_35940 | | acyl-CoA synthetase | 2.3 |
| PA14_28630 | | hydrolase | 2.3 |
| PA14_05430 | | chemotaxis protein | 2.3 |
| PA14_22600 | | glycosyl transferase family protein | 2.3 |
| PA14_34320 | | DszC family monooxygenase | 2.3 |
| PA14_51020 | | hypothetical protein | 2.3 |
| PA14_29500 | | type II secretion system protein | 2.3 |
| PA14_18880 | nth | endonuclease III | 2.3 |
| PA14_29050 | | molybdopterin oxidoreductase | 2.3 |
| PA14_54110 | | transporter | 2.3 |

TABLE 11-continued

Genes down-regulated by mBTL in the lasR mutant determined through microarray analysis. The ratio of gene expression in untreated cells to that of mBTL treated cells (fold down-regulation) is displayed for genes that exhibited changes greater than 2-fold. Ratios are the average of three independent experiments.

| Gene locus | Gene name | Description | Ratio |
|---|---|---|---|
| PA14_52900 | | acyl-CoA dehydrogenase | 2.3 |
| PA14_42100 | | hypothetical protein | 2.3 |
| PA14_33720 | pvdN | protein PvdN | 2.3 |
| PA14_20130 | | LysR family transcriptional regulator | 2.2 |
| PA14_03265 | | hypothetical protein | 2.2 |
| PA14_33240 | | hypothetical protein | 2.2 |
| PA14_73000 | | hypothetical protein | 2.2 |
| PA14_27410 | | outer membrane protein | 2.2 |
| PA14_41020 | | Orn/Arg/Lys decarboxylase | 2.2 |
| PA14_58110 | | Maf-like protein | 2.2 |
| PA14_32650 | | glutathione S-transferase | 2.2 |
| PA14_03250 | | hypothetical protein | 2.2 |
| PA14_27700 | | transcriptional regulator | 2.2 |
| PA14_26810 | | two-component sensor | 2.2 |
| PA14_67540 | | hypothetical protein | 2.2 |
| PA14_31740 | | hypothetical protein | 2.2 |
| PA14_33770 | | hypothetical protein | 2.2 |
| PA14_33570 | | hypothetical protein | 2.2 |
| PA14_03320 | | hypothetical protein | 2.2 |
| PA14_22060 | | hypothetical protein | 2.2 |
| PA14_17260 | dnaE | DNA polymerase III subunit alpha | 2.2 |
| PA14_03360 | | hypothetical protein | 2.2 |
| PA14_14630 | secD | preprotein translocase subunit SecD | 2.2 |
| PA14_34250 | | glycerophosphoryl diester phosphodiesterase | 2.2 |
| PA14_66700 | | nuclease | 2.2 |
| PA14_53740 | | hypothetical protein | 2.2 |
| PA14_20480 | | hypothetical protein | 2.1 |
| PA14_55390 | | hypothetical protein | 2.1 |
| PA14_34460 | | hypothetical protein | 2.1 |
| PA14_69890 | | multidrug efflux protein NorA | 2.1 |
| PA14_43510 | | hypothetical protein | 2.1 |
| PA14_61340 | | hypothetical protein | 2.1 |
| PA14_00560 | exoT | exoenzyme T | 2.1 |
| PA14_33710 | pvdO | protein PvdO | 2.1 |
| PA14_13330 | | hypothetical protein | 2.1 |
| PA14_27450 | | hypothetical protein | 2.1 |
| PA14_43100 | | Rhs family protein | 2.1 |
| PA14_72750 | | hypothetical protein | 2.1 |
| PA14_54890 | | hypothetical protein | 2.1 |
| PA14_40900 | | short-chain dehydrogenase | 2.1 |
| PA14_41780 | | hypothetical protein | 2.1 |
| PA14_31770 | | oxidoreductase | 2.1 |
| PA14_50570 | | hypothetical protein | 2.1 |
| PA14_33580 | | hypothetical protein | 2.1 |
| PA14_45830 | | hypothetical protein | 2.1 |
| PA14_34510 | | hypothetical protein | 2.1 |
| PA14_10600 | | MFS transporter | 2.1 |
| PA14_08630 | | pantothenate kinase | 2.1 |
| PA14_26890 | pyrF | orotidine 5'-phosphate decarboxylase | 2.1 |
| PA14_33540 | | ABC transporter permease | 2.1 |
| PA14_37380 | | flavin-binding monooxygenase | 2.1 |
| PA14_06650 | nirN | c-type cytochrome | 2.1 |
| PA14_28020 | | hypothetical protein | 2.1 |
| PA14_17650 | | hypothetical protein | 2.1 |
| PA14_23640 | | hypothetical protein | 2.1 |
| PA14_46290 | | TetR family transcriptional regulator | 2.1 |
| PA14_65390 | | hypothetical protein | 2.1 |
| PA14_68740 | argA | N-acetylglutamate synthase | 2.1 |
| PA14_55000 | | ABC transporter periplasmic protein | 2.1 |
| PA14_28660 | infC | translation initiation factor IF-3 | 2.1 |
| PA14_33530 | | hypothetical protein | 2.1 |
| PA14_51540 | | transposase | 2.1 |
| PA14_29000 | | hypothetical protein | 2.1 |
| PA14_58980 | | hypothetical protein | 2.1 |
| PA14_55040 | | ferric enterobactin transporter ATP-binding protein | 2.1 |
| PA14_33500 | pvdH | diaminobutyrate--2-oxoglutarate aminotransferase | 2.1 |
| PA14_59940 | | hypothetical protein | 2.1 |
| PA14_26610 | | hypothetical protein | 2.1 |
| PA14_59540 | | hypothetical protein | 2.1 |
| PA14_08620 | birA | biotin--protein ligase | 2.1 |
| PA14_38020 | | ntibiotic biosynthesis monooxygenase | 2.1 |

TABLE 11-continued

Genes down-regulated by mBTL in the lasR mutant determined through microarray analysis. The ratio of gene expression in untreated cells to that of mBTL treated cells (fold down-regulation) is displayed for genes that exhibited changes greater than 2-fold. Ratios are the average of three independent experiments.

| Gene locus | Gene name | Description | Ratio |
|---|---|---|---|
| PA14_06030 | | acyltransferase | 2.0 |
| PA14_40790 | | transcriptional regulator | 2.0 |
| PA14_28170 | | formate/nitrate transporter | 2.0 |
| PA14_36090 | | porin | 2.0 |
| PA14_36400 | | hypothetical protein | 2.0 |
| PA14_22350 | actP | acetate permease | 2.0 |
| PA14_63380 | | hypothetical protein | 2.0 |
| PA14_46010 | | ABC transporter ATP-binding protein | 2.0 |
| PA14_44480 | | hypothetical protein | 2.0 |
| PA14_52080 | | hypothetical protein | 2.0 |
| PA14_51360 | phnA | anthranilate synthase component I | 2.0 |
| PA14_73100 | | hypothetical protein | 2.0 |
| PA14_26390 | | hypothetical protein | 2.0 |
| PA14_64580 | | two-component sensor | 2.0 |
| PA14_41563 | cobA | uroporphyrin-III C-methyltransferase | 2.0 |
| PA14_20940 | | acyl carrier protein | 2.0 |
| PA14_26070 | | hypothetical protein | 2.0 |
| PA14_67260 | | histidine/phenylalanine ammonia-lyase | 2.0 |

TABLE 12

Genes down-regulated by mBTL in the rhlR mutant determined through microarray analysis. The ratio of gene expression in untreated cells to that of mBTL treated cells (fold down-regulation) is displayed for genes that exhibited changes greater than 2-fold. Ratios are the average of three independent experiments.

| Gene locus | Gene name | Description | Ratio |
|---|---|---|---|
| PA14_58970 | | hypothetical protein | 3.0 |
| PA14_33360 | | hypothetical protein | 2.2 |
| PA14_52320 | | tRNA-Met | 2.0 |
| PA14_62790 | | tRNA-Met | 2.0 |

TABLE 13

Genes up-regulated by mBTL in a rhlI null strain determined through microarray analysis. The ratio of gene expression in mBTL treated cells to that of untreated cells (fold up-regulation) is displayed for genes that exhibited changes greater than 2-fold. Additional columns indicate the genes that are down-regulated in the lasR and rhlR null strains. Ratios are the average of three independent experiments.

| Gene locus | Gene name | Description | Ratio | LasR-regulated | RhlR-regulated |
|---|---|---|---|---|---|
| PA14_10360 | | hypothetical protein | 39.5 | | * |
| PA14_53250 | cpbD | chitin-binding protein CbpD | 10.1 | * | * |
| PA14_01710 | ahpC | alkyl hydroperoxide reductase | 94 | * | * |
| PA14_06810 | norC | nitric-oxide reductase subunit C | 5.8 | * | * |
| PA14_10380 | | hypothetical protein | 4.9 | * | |
| PA14_11140 | | nonribosomal peptide synthetase | 4.7 | | * |
| PA14_28360 | | hypothetical protein | 4.2 | | * |
| PA14_66720 | priA | primosome assembly protein PriA | 3.9 | | |
| PA14_03520 | | hypothetical protein | 3.8 | | * |
| PA14_58040 | | hypothetical protein | 3.7 | * | * |
| PA14_14710 | | Rrf2 family protein | 3.5 | | * |
| PA14_17690 | | hypothetical protein | 3.4 | | |
| PA14_46450 | aceK | bifunctional isocitrate dehydrogenase kinase/phosphatase | 3.3 | | |
| PA14_35730 | | hypothetical protein | 3.1 | | |
| PA14_22320 | | hypothetical protein | 3.0 | * | * |
| PA14_38270 | | hypothetical protein | 3.0 | | * |
| PA14_16250 | lasB | elastase LasB | 2.9 | * | * |
| PA14_18800 | | hypothetical protein | 2.9 | | |
| PA14_53290 | trxB2 | thioredoxin reductase 2 | 2.9 | * | * |
| PA14_19640 | | short chain dehydrogenase | 2.8 | | |
| PA14_52380 | | cytochrome b561 | 2.7 | | |

TABLE 13-continued

Genes up-regulated by mBTL in a rhlI null strain determined through microarray analysis. The ratio of gene expression in mBTL treated cells to that of untreated cells (fold up-regulation) is displayed for genes that exhibited changes greater than 2-fold. Additional columns indicate the genes that are down-regulated in the lasR and rhlR null strains. Ratios are the average of three independent experiments.

| Gene locus | Gene name | Description | Ratio | LasR-regulated | RhlR regulated |
|---|---|---|---|---|---|
| PA14_33360 | | hypothetical protein | 2.5 | | |
| PA14_26990 | | hypothetical protein | 2.5 | * | * |
| PA14_40290 | lasA | LasA protease | 2.5 | | * |
| PA14_03490 | | hypothetical protein | 2.5 | | * |
| PA14_03510 | | hypothetical protein | 2.4 | | * |
| PA14_03770 | speB1 | agmatinase | 2.4 | | |
| PA14_06830 | norB | nitric-oxide reductase subunit B | 2.3 | * | * |
| PA14_44140 | | hypothetical protein | 2.3 | | |
| PA14_56110 | | hypothetical protein | 2.3 | | |
| PA14_05860 | | hypothetical protein | 2.2 | * | * |
| PA14_06990 | | hypothetical protein | 2.2 | | |
| PA14_17510 | | hypothetical protein | 2.2 | | |
| PA14_64390 | ureC | urease subunit alpha | 2.2 | | |
| PA14_01720 | ahpF | alkyl hydroperoxide reductase | 2.1 | * | * |
| PA14_51830 | | DNA-binding stress protein | 2.1 | * | * |
| PA14_71840 | | hypothetical protein | 2.1 | | |
| PA14_05660 | | transcriptional regulator | 2.1 | | |
| PA14_60480 | | hypothetical protein | 2.1 | | |
| PA14_18860 | | hypothetical protein | 2.0 | | |
| PA14_19210 | | hypothetical protein | 2.0 | | |
| PA14_46420 | | short chain dehydrogenase | 2.0 | | |
| PA14_24440 | | lipoprotein | 2.0 | | |
| PA14_14740 | | scaffold protein | 2.0 | | * |

The invention claimed is:

1. A compound having the formula:

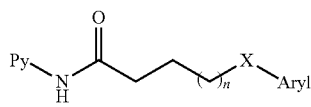

wherein

Py is a pyridine ring attached in the 2, 3, or 4 position and substituted with one or more additional substituents selected from the group consisting of alkyl, trifluoromethyl, methoxy, F, Cl and Br;

Aryl is a benzene ring with one or more additional substituents selected from the group consisting of methyl, trifluoromethyl, cyano, nitro, F, Cl, Br and methoxy;

X is O, NH, S or $CH_2$; and n is 0 to 4 —$CH_2$— units.

2. A compound having the formula:

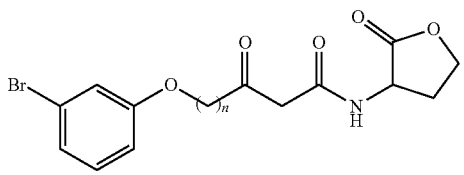

where n=1 or 3.

3. A composition comprising the compound of claim 1 or 2.

4. A method for inhibiting gram negative bacteria biofilm production, virulence factor production, pyocyanin production, or quorum sensing, the method comprising the steps of:

providing a composition comprising a compound of claim 1 or 2; and contacting at least one gram negative bacteria with the composition.

5. The method of claim 4, wherein the gram negative bacteria is selected from Pseudomonas, Burkholderia cepaci C. violaceum, V. harveyi, Neisseria gonorrhoeae, Neisseria meningitidis, Bordetella pertussis, Haemophilus influenzae, Legionella pneumophila, Brucella, Francisella, Xanthomonas, Agrobacterium, Escherichia coli, Salmonella, Shigella, Proteus, or Yersinia pestisi.

6. The method of claim 5, wherein the Pseudomonas is P. aeruginosa.

7. The method of claim 4, wherein the composition inhibits the f LasR/RhlR receptor signaling of the at least one gram negative bacteria.

8. The method of claim 4, wherein the subject is selected from a cow, a pig, a horse, a chicken, a cat, a dog, or a human.

9. The method of claim 4, wherein the subject has an infection selected from a respiratory illness, pulmonary tract infection, a urinary tract infection, a catheter-associated infection, a blood infection, a middle ear infection, dental plaque, gingivitis, chronic sinusitis, endocarditis, eye infections, eye infections resulting from contact lens use, implanted device infection, a medical device infection, a central nervous infection, a gastrointestinal tract infection, a bone infection, a joint infection, an ear infection, an eye infection, a burn, a wound, an antibiotic resistant infection, is immunocompromised, is immunosuppressed, or has an opportunistic infection.

10. The method of claim 9, wherein the medical device infection occurs in a patient having a catheter, a stent, a joint prosthesis, a prosthetic cardiac valve, on a ventilator or an intrauterine device.

11. The method of claim 9, wherein the pulmonary tract infection is pneumonia.

12. The method of claim 9, wherein the respiratory illness is Cystic Fibrosis.

13. The method of claim 12, wherein the patient has both Cystic Fibrosis and pneumonia.

14. The method of claim 4, wherein the composition is administered therapeutically.

15. The method of claim 4, wherein the composition is administered prophylactically.

16. The method of claim 15, wherein the subject is undergoing surgery, implantation of medical devices, or dental procedures.

17. The method of claim 4, wherein the composition is co-administered with one or more additional drugs or other therapeutic agents.

18. The method according to claim 17, wherein said one or more additional drugs or other therapeutic agents comprise one or more antibiotics.

19. The method of claim 4, wherein the composition is administered topically.

20. The method of claim 4, wherein the composition is administered intravenously.

21. The method of claim 4, wherein the composition is administered intranasally.

22. The method of claim 4, wherein the composition is used in an industrial setting.

23. The method of claim 22, wherein the industrial setting is a work area, a medical instrument, a medical device, a chemical unit operation, a pipe, a sewage system, a pipeline, a tubing, or a filtration device.

24. The method of claim 23, wherein the medical device is a catheter, a joint prosthesis, a prosthetic cardiac valve, a ventilator, a stent, or an intrauterine device.

25. The method of claim 23, wherein the chemical unit operation comprises a microfluidic platform, a microelectromechanical system, a 3D printer, or a system for coating nanoparticle surfaces.

* * * * *